(12) United States Patent
Ledoussal et al.

(10) Patent No.: US 9,994,509 B2
(45) Date of Patent: Jun. 12, 2018

(54) INHIBITORS OF VIRAL REPLICATION, THEIR PROCESS OF PREPARATION AND THEIR THERAPEUTICAL USES

(71) Applicant: HIVIH, Paris (FR)

(72) Inventors: Benoit Ledoussal, Pommerit Jaudy (FR); Frédéric Le Strat, Gagny (FR); Sophie Chasset, Nandy (FR); Julien Barbion, Sannois (FR); Julie Brias, Paris (FR); Audrey Caravano, Enghien les Bains (FR); Fabien Faivre, Drancy (FR); Sophie Vomscheid, Paris (FR)

(73) Assignee: HIVIH, Paris (FR)

( * ) Notice: Subject to any disclaimer, the term of this patent is extended or adjusted under 35 U.S.C. 154(b) by 0 days. days.

(21) Appl. No.: 14/902,955

(22) PCT Filed: Jul. 7, 2014

(86) PCT No.: PCT/EP2014/064446
§ 371 (c)(1),
(2) Date: Jan. 5, 2016

(87) PCT Pub. No.: WO2015/001125
PCT Pub. Date: Jan. 8, 2015

(65) Prior Publication Data
US 2016/0152543 A1 Jun. 2, 2016

(30) Foreign Application Priority Data
Jul. 5, 2013 (EP) .................................. 13305965

(51) Int. Cl.
| | |
|---|---|
| *C07C 59/13* | (2006.01) |
| *C07D 311/04* | (2006.01) |
| *A61K 31/352* | (2006.01) |
| *C07D 491/052* | (2006.01) |
| *A61K 31/4741* | (2006.01) |
| *C07D 405/10* | (2006.01) |
| *A61K 31/4184* | (2006.01) |
| *A61K 31/192* | (2006.01) |
| *C07D 405/04* | (2006.01) |
| *A61K 31/4709* | (2006.01) |
| *C07D 409/10* | (2006.01) |
| *A61K 31/381* | (2006.01) |
| *A61K 45/06* | (2006.01) |
| *C07D 311/58* | (2006.01) |

(52) U.S. Cl.
CPC ............ *C07C 59/13* (2013.01); *A61K 31/192* (2013.01); *A61K 31/352* (2013.01); *A61K 31/381* (2013.01); *A61K 31/4184* (2013.01); *A61K 31/4709* (2013.01); *A61K 31/4741* (2013.01); *A61K 45/06* (2013.01); *C07D 311/04* (2013.01); *C07D 311/58* (2013.01); *C07D 405/04* (2013.01); *C07D 405/10* (2013.01); *C07D 409/10* (2013.01); *C07D 491/052* (2013.01); *C07C 2601/02* (2017.05); *C07C 2601/08* (2017.05)

(58) Field of Classification Search
None
See application file for complete search history.

(56) References Cited

U.S. PATENT DOCUMENTS

| | | | |
|---|---|---|---|
| 2,842,559 | A | 7/1958 | Johnson |
| 4,736,057 | A | 4/1988 | Guildford et al. |
| 4,872,918 | A | 10/1989 | Podraza et al. |
| 6,339,097 | B1 | 1/2002 | Festal et al. |
| 7,939,545 | B2 | 5/2011 | Tsantrizos et al. |
| 7,956,068 | B2 | 6/2011 | Carson et al. |
| 8,337,960 | B2 | 12/2012 | Shimazu et al. |
| 8,338,441 | B2 | 12/2012 | Yoakim et al. |
| 8,377,960 | B2 | 2/2013 | Tsantrizos et al. |
| 8,461,180 | B2 | 6/2013 | Tsantrizos et al. |
| 8,710,230 | B2 | 4/2014 | Tsantrizos et al. |
| 8,785,638 | B2 | 7/2014 | Bardiot et al. |
| 8,906,906 | B2 | 12/2014 | Chaltin et al. |
| 9,006,229 | B2 | 4/2015 | Mitchell et al. |
| 9,199,959 | B2 | 12/2015 | Iwaki et al. |
| 9,409,871 | B2 | 8/2016 | He et al. |
| 2006/0079696 | A1 | 4/2006 | Masson et al. |
| 2007/0244155 | A1 | 10/2007 | Sharma et al. |
| 2010/0168225 | A1 | 7/2010 | Jean et al. |
| 2012/0142771 | A1 | 6/2012 | Iwama et al. |
| 2013/0190491 | A1 | 7/2013 | Tsantrizos et al. |
| 2013/0203727 | A1 | 8/2013 | Babaoglu et al. |
| 2013/0210801 | A1 | 8/2013 | Babaoglu et al. |
| 2014/0031338 | A1 | 1/2014 | Chasset et al. |
| 2014/0249306 | A1 | 9/2014 | Iwaki et al. |

(Continued)

FOREIGN PATENT DOCUMENTS

| | | |
|---|---|---|
| EP | 0015776 | 9/1980 |
| GB | 942663 | 11/1963 |
| JP | 55-127347 | 10/1980 |

(Continued)

OTHER PUBLICATIONS

Seco et al. disclose in Tetrahedron Letters (1994), 35(18), 2921-2924.*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Cervia, et al., "Enfuvirtide (T-20): A Novel Human Immunodeficiency Virus Type 1 Fusion Inhibitor", 2003, pp. 1102-1106, vol. 37, No. 8, Reviews of Anti-Infective Agents.
Hughes, et al., "New treatment options for HIV salvage patients: An overview of second generation PIs, NNRTIs, integrase inhibitors and CCR5 antagonists", 2008, pp. 1-10, vol. 57, No. 1, Journal of Infection.
Daar, et al, "Emerging Resistance Profiles of Newly Approved Antiretroviral Drugs", Oct./Nov. 2008, vol. 16, No. 4, Emerging Resistance Profiles.

(Continued)

*Primary Examiner* — Dennis Heyer
(74) *Attorney, Agent, or Firm* — B. Aaron Schulman, Esq.; Stites & Harbison, PLLC

(57) ABSTRACT

The present invention relates to compounds, their use in the treatment or the prevention of viral disorders, including HIV.

17 Claims, No Drawings

(56) References Cited

U.S. PATENT DOCUMENTS

2015/0274718 A1  10/2015  Benarous et al.

FOREIGN PATENT DOCUMENTS

| JP | 2002-501064 | 1/2002 | | |
|----|-------------|--------|---|---|
| WO | WO-9937639 | 7/1999 | | |
| WO | WO 2012/140243 | * | 10/2012 | ........... C07D 311/58 |

OTHER PUBLICATIONS

De Clercq, Erik, "Emerging antiviral drugs", 2008, vol. 13, No. 3, Expert Opinion. Emerging Drugs.
Lopez-Verges et al: "Tail-interacting protein TIP47 is a connector between Gag and Env and is required for Env incorporation into HIV-1 virions", PNAS, U S A., (Oct. 3, 2006), vol. 103, No. 40, pp. 14947-14952.
Christ et al: "Rational design of small-molecule inhibitors of the LEDGF/p75-integrase interaction and HIV replication"; May 16, 2010, pp. 1-7, Nature Chemical Biology.
Gregg S. Jones et al: "Preclinical Evaluation of GS-9160, a Novel Inhibitor of Human Immunodificiency Virus Type 1 Integrase", Mar. 2009, vol. 53, No. 3, pp. 1194-1203, Antimicrobial Agents and Chemotherapy.
Adachi et al: "Production of acquired immunodeficiency syndrome-associated retrovirus in human and nonhuman cells transfected with an infectious molecular clone", Aug. 1986, vol. 59, No. 2, pp. 284-291, Journal of Virology, American Society for Microbiology.
Bradsher, et al., "Aromatic Cyclodehydration. XXVIII. 9,10-Dialkylphenanthrenes by Cyclization of Ketones", Aug. 20, 2014, pp. 4140-4143, vol. 76, XP-002669325.
Daly, et al., "Synthesis and Metabolism of 6-Hydroxycatecholamines", Nov. 1965, vol. 4, No. 11, Biochemistry.
Wei, et al., "Organolithium additions to styrene derivatives—III. Enantioselective routes to 2-arylalkanoic acids", 1997, pp. 665-668, vol. 8, No. 5, Tetrahedron: Asymmetry.
Wang, et al., "Versatile Pd(II)-Catalyzed C-H Activation/Aryl-Aryl Coupling of Benzoic and Phenyl Acetic Acids", 2008, 17676-17677, vol. 130, J. Am. Chem. Soc.
Carlsson, et al., "148. In den Catecholamin-Metabolismus eingreifende Substanzen. 3. 2,3-Dihydroxyphenylacetamide and verwandte Verbindugen", pp. 1340-1349, vol. 47, No. 148, Helvetica Chima Acta.
Nicolaou, et al., "Total Synthesis of Sporolide B and 9-epi-Sporolide B", 2010, pp. 11350-11363, vol. 132, J. Am. Chem. Soc.
Assy, et al., "The synthesis of pyridazine and fused pyridazine", XP-002669328.
XP-002669330.
XP-002669332.
XP-002669333.
XP-002669334.
XP-002669331.
Ryabukhin, et al., "Chlorotrimethylsilane-Mediated Friedlander Synthesis of Polysubstituted Quinolines", 2007, pp. 1214-1224, No. 8, Synthesis, XP-002669327.
Butera, et al., "Computer-Assisted Design and Synthesis of Novel Aldose Reductase Inhibitors", 1989, pp. 757-765, vol. 32, No. 4, Journal of Medicinal Chemistry, XP-002669323.
Newman, et al., "The Synthesis of 5-Methylchrysene and Related Compounds", Apr. 1940, pp. 870-874, vol. 62, XP-002669324.
Gutsche, et al., "The Stereochemistry of the 2-Phenylcyclohexanecarboxylic Acids and the β-(2-Phenylcyclonhexane)-propionic Acids", Dec. 1948, pp. 4150-4154, vol. 70, XP-002663384.
Suginome, et al., "Photoinduced Transformations. Part 38. Photoreactions of 17-Ethoxycarbonylemthylene-etiojerva-5,13(17)- and -5,16-diene-3β,20$_\xi$ -triol 3,20-Diacetate 11-Nitrites", 1978, pp. 612-618, XP-02669321.
Touzin, Anne Marie, "Reaction D'Hydroxyalkylation Des Enolates D'Ester α Heterosustitutes Synthese D'Steers D'Enol D'α Cetoestes et de β Cetoesters a Alkoxyles" 1975, pp. 1477-1480, No. 18, Tetrahedron Letters, XP-002669320.
Medarde, et al., "Synthesis and evaluation of cardiotonic activity of simple butenolides II", 1993, pp. 887-892, vol. 28, Eur J Med Chem, XP-002669322.
Iida, et al., "Stereochemical Studies of Alkyl Methylcyclohexaneacetates with 13C NMR Spectroscopy in Relation to Their Attractiveness to the German Cockroach", 1981, pp. 1553-1559, vol. 45, No. 7, Agric. Biol. Chem., XP-002663385.
Turner, et al., "Cyclized Products from the Stobbe Condensation with _-Keto-esters", Mar. 1951, pp. 1284-1287, XP-002663383.
Turner, et al., "The Structure and Total Synthesis of Cassaic Acid", Apr. 20, 1966, pp. 1766-1775, vol. 88, No. 8, Journal of the American Chemical Society, XP-002663382.
Dostert, et al., "211. Synthese d'analogues partiellement satures des neuroleptiques tricycliques clothiapine et octoclothepine", 1970, pp. 1813-1827, vol. 53, No. 7, XP-002663381.
Buchta, et al., "Uber Tri Tetra-Und Pentacyclische Verbindungen, Die in Beziehung Zum Steranthren Stehen", pp. 129-152.
Sayer, et al, "Conformational Effects in the Hydrolyses of Rigid Benzylic Epoxides: Implications for Diol Epoxides of Polycyclic Hydrocarbons", 1982, pp. 1972-1978, vol. 104, J. Am. Chem. Soc.
Parmar, et al., "Synthesis, antimicrobial and antiviral activities of novel polyphenolic compounds", Mar. 1996, pp. 220-232, vol. 35B, Indian Journal of Chemistry, XP-001022822.
Berlin, et al., "Olivomycin and related antibodies. XXVI. Absolute configuration of olivine and chromomycinone", XP-002663377.
Berlin, et al., "Olivomycin and related antibodies. XXXI. Stereochemistr of chromomycinone", XP-002663378.
Lutsenko, V.V., "Some. Alpha-methozyacetic acids of cyclohexane and 3-cyclohexane series", XP-002663376.
Singh, G., XP-002663375.
XP-002663375.
Zhang, et al., A new compound from Forsythia suspense (Thunb.) Vanl with antiviral effect on RSV, XP-002663386.
International Search Report for PCT/EP2014/064446 dated Sep. 16, 2014.
Jing, et al., "The Steps in HIV Replication and the Targets for Inhibitors", 1997, pp. 247-250, vol. 4, No. 4, Pharmaceutical Biotechnology.

* cited by examiner

INHIBITORS OF VIRAL REPLICATION, THEIR PROCESS OF PREPARATION AND THEIR THERAPEUTICAL USES

The present invention relates to compounds, their use in the treatment or in the prevention of viral disorders, including HIV-related disorders. The present invention also relates to methods for the preparation of such compounds. The present invention also relates to pharmaceutical compositions comprising such compounds. The present invention also relates to the treatment of viral infections by the administration of a therapeutically efficient amount of such compounds.

The Acquired Immuno Deficiency Syndrome (AIDS) is a disease due to infection by the Human Immunodeficiency Virus (HIV). HIV is a retrovirus, belonging to the subclass of primate lentiviruses. Two types of HIV have been identified, HIV-1 and HIV-2. HIV-1 is responsible for the larger part of the AIDS global epidemic in the world, with virtually every country reporting cases. Currently HIV infected patients are treated with Highly Active Antiretroviral Therapies (HAART) that rely on a combination of several drugs belonging to different classes. Up to 2003, all approved anti-HIV drugs were inhibitors of the catalytic activity of two viral enzymes, Reverse Transcriptase (RT) inhibitors and Protease (PR) inhibitors. Reverse Transcriptase inhibitors include two different classes, Nucleoside/Nucleotide RT Inhibitors (NRTI) and Non Nucleoside RT Inhibitors (NNRTI). In 2003 a new class of Anti-retroviral drug (ARV), Fusion inhibitor (Enfuvirtide) was introduced (Cervia et al, Clin Infec Dis., 2003, 37(8):1102-6). And lately, in 2007, two other classes of ARV were approved, Entry inhibitors (Maraviroc (Pfizer)) targeting the CCR5 co-receptor, and Integrase inhibitors (Raltegravir (Merck)) (Hughes et al, J Infect., 2008, 57(1):1-10.). Although these three novel drugs were very useful to treat patients in therapeutic failure due to multiresistance to RT and PR inhibitors, resistance mutations against these drugs have already been reported.

Although the development of these potent anti-HIV drugs, has allowed HIV-infected people to live longer and to benefit of a higher quality of life, it is clear that these drugs do not cure the HIV infection. Moreover, their prolonged use often results in significant toxicity and in the emergence of drug-resistant viruses. Importantly, the ability of HIV to establish latent reservoirs early in the course of infection ensures the persistence of the virus even in the face of intensive drug therapy and vigorous antiviral immune response.

Thus, there is a continuous need for the development of novel anti-HIV therapies or agents to overcome the problems of resistance to the existing drugs and to improve treatment efficiency (Daar E S, Top HIV Med., 2008; 16(4): 110-116; De Clercq E., Expert Opinion on Emerging Drugs 2008; 13(3):393-416).

WO 2012/003497, WO 2012/003498 and WO 2012/145728 respectively describe quinoline derivatives, napthyl derivatives and benzothiazole derivatives as anti-HIV agents. WO 2012/140243 and WO 2013/062028 describe phenyl derivatives as anti-HIV agents.

Surprisingly, the inventors have identified and prepared new compounds having an improved antiviral activity, in particular antiretroviral activity especially on HIV in comparison with prior art compounds.

The invention encompasses compounds which are inhibitors of HIV replication as assessed by HIV-1 replication assay as herein-detailed. The invention also encompasses compounds that are thus useful agents for treating or preventing infection and disease due to a virus, in particular a retrovirus (orthoretrovirinae), more particularly a lentivirus, such as HIV, or other viral pathogenic diseases or disorders, notably by inhibiting replication of the virus into the host infected cells, or at the time of infection occurrence or progression Therefore, the invention encompasses compounds that constitute a useful class of new potent antiviral compounds that can be used in the treatment and/or in the prevention of viral, in particular antiretroviral, more particularly antilentiviral infections in patients, in particular mammals and humans, more specifically for the treatment and/or for the prevention of HIV infection or related disease in humans.

The present invention further relates to such compounds for their use as a medicament, to the use of such compounds as medicament, more specifically as antiviral agents, and to their use for the manufacture of medicament for treating and/or for preventing viral infections and related diseases, in particular retroviral, especially lentiviral infections and related diseases such as, but not limited to, HIV and related diseases in humans.

The invention also relates to pharmaceutical compositions comprising such compounds in an antiviral effective amount, optionally in combination with at least one further antiviral agent.

The present invention further relates to such a pharmaceutical composition for its use as a medicament, especially for use in the treatment of an HIV infection in a mammal being infected or having a risk of being infected by the HIV.

The present invention also relates to a method of treatment or of prevention of viral infections and related diseases, in particular retroviral infections and related diseases, more particularly lentiviral infections and related diseases, such as, but not limited to HIV infections and related diseases in humans, by the administration of one or more such compounds, optionally in combination with one or more other antiviral agents, to a patient in need thereof.

The present invention also relates to a method of inhibiting the replication of HIV by comprising exposing the virus to an effective amount of one or more such compounds under conditions where replication of HIV is inhibited.

In a first aspect, the invention provides compounds comprising a 6-membered carbocycle, said compounds having a structure according to formula (I):

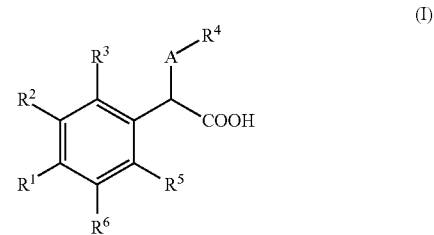

wherein:
$R^1$ and $R^6$, non-substituted or substituted by at least one $T^1$, identical or different, independently represent a hydrogen atom; —CN; —OH; —NH$_2$; —CF$_3$; a halogen atom; a linear or branched $C_1$-$C_8$ alkyl; a linear or branched $C_2$-$C_8$ alkenyl; a linear or branched $C_2$-$C_8$ alkynyl; —Z—C(O)$_2$R$^7$; —Z—OC(O)$_2$R$^7$; —Z—OR$^8$; —Z—SR$^8$; —Z—S(O)R$^8$; —Z—S(O)$_2$R$^8$; —Z—NR$^7$R$^8$; —Z—OC(O)R$^8$; —Z—C(O)R$^8$; —Z—C(O)NR$^7$R$^8$; —Z—NR$^8$C(O)R$^8$; —Z—NR$^8$C (O)NR$^7$R$^8$; Z—NR$^8$S(O)$_2$R$^8$; Z—NR$^8$S(O)$_2$NR$^7$R$^8$; —Z—OC(O)NR$^7$R$^8$; —Z—NR$^8$C(O)$_2$R$^7$; —Z—S(O)$_2$NR$^7$R$^8$; a saturated, partially or totally unsaturated or aromatic 3-, 4-, 5-, 6- or 7-membered carbocycle; a C$_1$-C$_8$ alkyl-(saturated, partially or totally unsaturated or aromatic 3-, 4-, 5-, 6- or 7-membered carbocycle); a saturated, partially or totally unsaturated or aromatic 3-, 4-, 5-, 6- or 7-membered carbocycle fused with a saturated, partially or totally unsaturated or aromatic 3-, 4-, 5-, 6- or 7-membered carbocycle; a C$_1$-C$_8$ alkyl-(saturated, partially or totally unsaturated or aromatic 3-, 4-, 5-, 6- or 7-membered carbocycle fused with a saturated, partially or totally unsaturated or aromatic 3-, 4-, 5-, 6- or 7-membered carbocycle); a saturated, partially or totally unsaturated or aromatic 3-, 4-, 5-, 6- or 7-membered carbocycle fused with a saturated, partially or totally unsaturated or aromatic 4-, 5-, 6- or 7-membered heterocycle; a C$_1$-C$_8$ alkyl-(saturated, partially or totally unsaturated or aromatic 3-, 4-, 5-, 6- or 7-membered carbocycle fused with a saturated, partially or totally unsaturated or aromatic 4-, 5-, 6- or 7-membered heterocycle); a saturated, partially or totally unsaturated or aromatic 4-, 5-, 6- or 7-membered heterocycle; a C$_1$-C$_8$ alkyl-(saturated, partially or totally unsaturated or aromatic 4-, 5-, 6- or 7-membered heterocycle); a saturated, partially or totally unsaturated or aromatic 4-, 5-, 6- or 7-membered heterocycle fused with a saturated, partially or totally unsaturated or aromatic 3-, 4-, 5-, 6- or 7-membered carbocycle; a C$_1$-C$_8$ alkyl-(saturated, partially or totally unsaturated or aromatic 4-, 5-, 6- or 7-membered heterocycle fused with a saturated, partially or totally unsaturated or aromatic 3-, 4-, 5-, 6- or 7-membered carbocycle); a saturated, partially or totally unsaturated or aromatic 4-, 5-, 6- or 7-membered heterocycle fused with a saturated, partially or totally unsaturated or aromatic 4-, 5-, 6- or 7-membered heterocycle; or a C$_1$-C$_8$ alkyl-(saturated, partially or totally unsaturated or aromatic 4-, 5-, 6- or 7-membered heterocycle fused with a saturated, partially or totally unsaturated or aromatic 4-, 5-, 6- or 7-membered heterocycle);

R$^2$, non-substituted or substituted by at least one T$^1$, represents a linear or branched C$_2$-C$_8$ alkyl; a linear or branched C$_2$-C$_8$ alkenyl; a linear or branched C$_1$-C$_8$ heteroalkyl; a linear or branched C$_2$-C$_8$ heteroalkenyl; a C$_3$-C$_7$ cycloalkyl; a C$_1$-C$_8$ alkyl-(C$_3$-C$_7$ cycloalkyl); a C$_1$-C$_8$ heteroalkyl-(C$_3$-C$_7$ cycloalkyl); a C$_1$-C$_8$ alkyl-(partially or totally unsaturated or aromatic C$_3$-C$_7$ carbocycle); a C$_1$-C$_8$ heteroalkyl-(partially unsaturated C$_3$-C$_7$ carbocycle); a C$_4$-C$_7$ heterocycloalkyl; a C$_1$-C$_8$ alkyl-(C$_4$-C$_7$ heterocycloalkyl); a C$_1$-C$_8$ heteroalkyl-(C$_4$-C$_7$ heterocycloalkyl); a C$_1$-C$_8$ alkyl-(partially or totally unsaturated or aromatic C$_4$-C$_7$ heterocycle); or a C$_1$-C$_8$ heteroalkyl-(partially or totally unsaturated or aromatic C$_4$-C$_7$ heterocycle);

R$^3$, non-substituted or substituted by at least one T$^2$, represents a saturated, partially or totally unsaturated or aromatic 5-, 6- or 7-membered carbocycle; a saturated, partially or totally unsaturated or aromatic 5-, 6- or 7-membered carbocycle fused with a saturated, partially or totally unsaturated or aromatic 3-, 4-, 5-, 6- or 7-membered carbocycle; a saturated, partially or totally unsaturated or aromatic 5-, 6- or 7-membered carbocycle fused with a saturated, partially or totally unsaturated or aromatic 4-, 5-, 6- or 7-membered heterocycle; a saturated, partially or totally unsaturated or aromatic 5-, 6- or 7-membered carbocycle fused with a saturated, partially or totally unsaturated or aromatic 3-, 4-, 5-, 6- or 7-membered carbocycle and further fused with a saturated, partially or totally unsaturated or aromatic 4-, 5-, 6- or 7-membered heterocycle; a saturated, partially or totally unsaturated or aromatic 5-, 6- or 7-membered carbocycle fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a saturated, partially or totally unsaturated or aromatic 5-, 6- or 7-membered carbocycle fused with a saturated, partially or totally unsaturated or aromatic 3-, 4-, 5-, 6- or 7-membered carbocycle and further fused with a saturated, partially or totally unsaturated or aromatic 3-, 4-, 5-, 6- or 7-membered carbocycle; a saturated, partially or totally unsaturated or aromatic 5-, 6- or 7-membered carbocycle fused with a saturated, partially or totally unsaturated or aromatic 4-, 5-, 6- or 7-membered heterocycle and further fused with a saturated, partially or totally unsaturated or aromatic 3-, 4-, 5-, 6- or 7-membered carbocycle; a saturated, partially or totally unsaturated or aromatic 5-, 6- or 7-membered heterocycle; a saturated, partially or totally unsaturated or aromatic 5-, 6- or 7-membered heterocycle fused with a saturated, partially or totally unsaturated or aromatic 3-, 4-, 5-, 6- or 7-membered carbocycle; a saturated, partially or totally unsaturated or aromatic 5-, 6- or 7-membered heterocycle fused with a saturated, partially or totally unsaturated or aromatic 4-, 5-, 6- or 7-membered heterocycle; a saturated, partially or totally unsaturated or aromatic 5-, 6- or 7-membered heterocycle fused with a saturated, partially or totally unsaturated or aromatic 3-, 4-, 5-, 6- or 7-membered carbocycle and further fused with a saturated, partially or totally unsaturated or aromatic 4-, 5-, 6- or 7-membered heterocycle; a saturated, partially or totally unsaturated or aromatic 5-, 6- or 7-membered heterocycle fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a saturated, partially or totally unsaturated or aromatic 5-, 6- or 7-membered heterocycle fused with a saturated, partially or totally unsaturated or aromatic 4-, 5-, 6- or 7-membered heterocycle and further fused with a saturated, partially or totally unsaturated or aromatic 3-, 4-, 5-, 6- or 7-membered carbocycle; or a saturated, partially or totally unsaturated or aromatic 5-, 6- or 7-membered heterocycle fused with a saturated, partially or totally unsaturated or aromatic 3-, 4-, 5-, 6- or 7-membered carbocycle and further fused with a saturated, partially or totally unsaturated or aromatic 3-, 4-, 5-, 6- or 7-membered carbocycle;

A represents a —CH$_2$; —CH═; —O— or —S—;

R$^4$, substituted or non-substituted by at least one T$^3$, represents a linear or branched C$_2$-C$_6$ alkyl; a linear or branched C$_2$-C$_6$ alkenyl; a linear or branched C$_1$-C$_6$ fluoroalkyl; a C$_3$-C$_6$ cycloalkyl; or a C$_1$-C$_3$ alkyl-(C$_3$-C$_6$ cycloalkyl);

R$^5$ represents a halogen atom; —CF$_3$; a linear or branched C$_1$-C$_6$ alkyl; a linear or branched C$_2$-C$_6$ alkenyl; a linear or branched C$_2$-C$_6$ alkynyl; a linear or branched fluoroalkyl; a C$_3$-C$_6$ cycloalkyl; —CH$_2$OH; or —CH$_2$—O—CH$_3$;

$R^5$ and $R^6$ may form, with the carbon atoms of the phenyl ring of formula (I) to which they are bonded, an aryl or may form, with the carbon atoms of the phenyl ring of formula (I) to which they are bonded, a heteroaryl comprising at least one N atom;

$R^7$ and $R^8$, identical or different, independently represent a hydrogen atom; a linear or branched $C_1$-$C_8$ alkyl; a linear or branched $C_2$-$C_8$ alkenyl; a linear or branched $C_2$-$C_8$ alkynyl; a linear or branched $C_1$-$C_8$ heteroalkyl; a linear or branched fluoroalkyl; a linear or branched fluoroalkenyl; a linear or branched fluoroalkynyl; —$(X)_x$—$(CT^6T^7)_y$$NT^4T^5$; —$(X)_x$—$(CT^6T^7)_y$C(O)$NT^4T^5$; —$(X)_x$—$(CT^6T^7)_y$OT$^4$; —$(X)_x$—$(CT^6T^7)_y$NT$^4$C(O)OT$^5$; a $C_3$-$C_7$ cycloalkyl; a $C_4$-$C_7$ heterocycloalkyl; a partially or totally unsaturated or aromatic $C_4$-$C_7$ carbocycle; a partially or totally unsaturated or aromatic $C_5$-$C_7$ heterocycle; a $C_1$-$C_8$ alkyl-($C_3$-$C_7$ cycloalkyl); a $C_1$-$C_8$ alkyl-($C_4$-$C_7$ heterocycloalkyl); a $C_1$-$C_8$ alkyl-(partially or totally unsaturated or aromatic $C_4$-$C_7$ carbocycle); or a $C_1$-$C_8$ alkyl-(partially or totally unsaturated or aromatic $C_5$-$C_7$ heterocycle);

$R^7$ and $R^8$ may form, with the nitrogen atom to which they are bonded, a saturated or partially unsaturated 4-, 5-, 6- or 7-membered heterocycle, the said heterocycle could further comprise at least one supplementary heteroatom;

$T^1$ independently represents a halogen atom; an alkyl; —$(X)_x$—$C_1$-$C_6$ alkyl; a linear or branched fluoroalkyl; a linear or branched —O—$C_1$-$C_3$ fluoroalkyl; —$(X)_x$—$C_3$-$C_6$ cycloalkyl; —$(X)_x$—$C_4$-$C_6$ heterocycle; —$(X)_x$—$(CT^6T^7)_y$CN; —$(X)_x$—$(CT^6T^7)_y$OT$^4$; —$(X)_x$—$(CT^6T^7)_y$ST$^4$; —$(X)_x$—$(CT^6T^7)_y$S(O)T$^4$; —$(X)_x$—$(CT^6T^7)_y$S(O)$_2$T$^4$; —$(X)_x$—$(CT^6T^7)_y$NT$^4$T$^5$; —$(X)_x$—$(CT^6T^7)_y$C(O)T$^4$; —$(X)_x$—$(CT^6T^7)_y$C(O)—$(CT^6T^7)_y$OT$^4$; —$(X)_x$—$(CT^6T^7)_y$C(O)OT$^4$; —$(X)_x$—$(CT^6T^7)_y$C(O)NT$^4$T$^5$; —$(X)_x$—$(CT^6T^7)_y$NT$^4$C(O)NT$^4$T$^5$; —$(X)_x$—$(CT^6T^7)_y$NT$^4$C(O)T$^5$; —$(X)_x$—$(CT^6T^7)_y$NT$^4$C(O)OT$^5$; —$(X)_x$—$(CT^6T^7)_y$OC(O)NT$^4$T$^5$; —$(X)_x$—$(CT^6T^7)_y$S(O)$_2$NT$^4$T$^5$; or —$(X)_x$—$(CT^6T^7)_y$NT$^4$S(O)$_2$T$^5$;

$T^2$ independently represents a halogen atom; a linear or branched —O—($C_1$-$C_3$ alkyl); a linear or branched $C_1$-$C_3$ fluoroalkyl; a linear or branched —O—($C_1$-$C_3$ fluoroalkyl); a linear or branched $C_1$-$C_3$ alkyl; a $C_3$-$C_6$ cycloalkyl; or —CN;

two geminal $T^2$ may form with the carbon atom to which they are bonded, a $C_3$-$C_7$ cycloalkyl;

$T^3$ independently represents a linear $C_1$-$C_2$ alkyl; or a fluor atom;

$T^4$ and $T^5$, identical or different, independently represent a hydrogen atom; a branched or linear $C_1$-$C_6$ alkyl; or a $C_3$-$C_6$ cycloalkyl;

$T^4$, $T^5$ and the nitrogen atom to which they are bonded, may form a saturated or partially unsaturated 4-, 5-, 6- or 7-membered heterocycle, the said heterocycle could further comprise at least one supplementary heteroatom;

$T^6$ and $T^7$, identical or different, independently represent a hydrogen atom; a fluorine atom; a linear or branched $C_1$-$C_3$ alkyl; or a $C_3$-$C_6$ cycloalkyl;

$T^6$, $T^7$ and the carbon atom to which they are bonded may form a $C_3$-$C_6$ cycloalkyl;

$T^8$ independently represents a hydrogen atom, a linear or branched $C_1$-$C_3$ alkyl; or a $C_3$-$C_6$ cycloalkyl;

X independently represents an oxygen atom; a sulphur atom; NT$^8$; S=O; or S(O)$_2$;

Z independently represents a single bond; or a linear or branched $C_1$-$C_8$ alkyl;

x represents 0 or 1;

y represents 0, 1, 2 or 3;

and a racemate, enantiomer, stereoisomer, atropisomer or diastereoisomer or a pharmaceutically acceptable salt thereof.

Even if described in particular or preferred embodiments, the present invention is not to be understood as being limited to such particular or preferred embodiments.

The term "heteroalkyl", as used herein, either alone or in combination with another radical, refers to a saturated hydrocarbon radical comprising at least one heteroatom and/or substituting by at least one heteroatom.

The term "halogen", as used herein, either alone or used in combination with another radical, refers to a fluorine atom, a chlorine atom, a bromine atom and a iodide atom, notably a fluorine atom.

The term "cycloalkyl", as used herein, either alone or in combination with another radical, refers to a monocyclic or polycyclic saturated hydrocarbon radical.

The term "heterocycloalkyl", as used herein, either alone or in combination with another radical, refers to a monocyclic or polycyclic saturated hydrocarbon radical comprising at least one heteroatom.

The term "aryl", as used herein, either alone or in combination with another radical, refers to a carbocyclic aromatic monocyclic group containing 6 carbon atoms which can be fused with at least another saturated, partially or totally unsaturated or aromatic carbocycle or heterocycle.

The term "heteroaryl", as used herein, either alone or in combination with another radical, refers to a heterocyclic aromatic monocyclic group containing 5 carbon atoms and one heteroatom which can be fused with at least another saturated, partially or totally unsaturated or aromatic carbocycle or heterocycle.

The terms "alkyl-cycloalkyl", "alkyl-carbocycle" or "alkyl-heterocycle" as used herein, alone or in combination with another radical, refer to a, alkyl radical in which one of the hydrogen atoms bonded to a carbon atom, is replaced respectively by a cycloalkyl radical, a saturated, partially or totally unsaturated or aromatic carbocycle radical or a saturated, partially or totally unsaturated or aromatic heterocycle radical.

The terms "heteroalkyl-cycloalkyl", "heteroalkyl-carbocycle" or "heteroalkyl-heterocycle" as used herein, alone or in combination with another radical, refer to a heteroalkyl radical in which one of the hydrogen atoms bonded to a carbon atom, is replaced respectively by a cycloalkyl radical, a saturated, partially or totally unsaturated or aromatic carbocycle radical or a saturated, partially or totally unsaturated or aromatic heterocycle radical.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which comprises a basic or an acidic moiety, by conventional chemical methods. Furthermore, the term "pharmaceutically acceptable salt" refers to relatively non-toxic, inorganic and organic acid or base addition salts of the compounds of the present invention. These salts can be prepared in situ during the final isolation and purification of the compounds. In particular, the acid addition salts can be prepared by separately reacting the purified compound in its purified form with an organic or inorganic acid and by isolating the salt thus formed. Among the examples of acid addition salts are the hydrobromide, hydrochloride, hydroiodide, sulfamate, sulfate, bisulfate, phosphate, nitrate, acetate, propionate, succinate, oxalate, valerate, oleate, palmitate, stearate, laurate, borate, benzoate, lactate, tosylate, citrate, maleate, fumarate, tartrate, naphthylate, mesylate, glucoheptanate, glucoronate, glutamate, lactobionate, malonate, salicylate, methylenebis-b-hydroxynaphthoate, gentisic acid, isethionate, di-p-toluoyltartrate, ethanesulfonate, benzenesulfonate, cyclohexyl sulfamate, quinateslaurylsulfonate salts, and the like. Examples of base addition salts include ammonium salts such as tromethamine, meglumine, epolamine, etc., metal salts such as sodium, lithium, potassium, calcium, zinc or magnesium, salts with organic bases such as dicyclohexylamine salts, N-methyl-D-glucamine. Lists of suitable salts are found in *Remington's Pharmaceutical Sciences,* 17$^{th}$ ed., Mack Publishing Company, Easton, Pa., 1985, p. 1418, the disclosure of which is hereby incorporated by reference, and in S. M. Berge et al. "Pharmaceutical Salts" *J. Pharm. Sci,* 66: p. 1-19 (1977), the disclosure of which is hereby incorporated by reference.

The term "stereoisomer" is employed herein to refer to compounds which have identical chemical linker sequence and differ each to one other by the three-dimensional orientations of their functional groups in space.

The term "enantiomer" is employed herein to refer to one of the two specific stereoisomers which is a non-superimposable mirror image with one other but is related to one other by reflection.

The term "diastereoisomer" is employed herein to refer to one of the stereoisomers which is a non-superimposable mirror image with one other but is not related to one other by reflection.

The term "racemate" is employed herein to refer to an equal amount of two specific enantiomers.

The term "atropisomer" is employed herein to refer to stereoisomer obtained by a sterically hindered single bond whereby the free rotation of functional groups on either side of this bond is not allowed.

The term "prevention" as used herein is intended to mean the administration of a compound or composition according to the invention in order to prevent infection by a virus or to prevent occurrence of related diseases.

The term "treatment" as used herein is intended to mean in particular the administration of a compound or composition according to the present invention to alleviate or eliminate symptoms of HIV infection, and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, especially to prevent the appearance of symptoms of the disease and/or to prevent the virus from reaching detectable levels in the blood, and the administration of a compound or composition according to the present invention to prevent perinatal transmission of virus, e.g. HIV from mother to baby, by administration to the mother before giving birth and to the child within the first days of life. The term "treatment" also refers to the treatment of a disease-state in a patient include inhibiting or ameliorating the disease-state in a patient, for example arresting or developing its development; or relieving the disease-state in a patient such as, causing regression or cure if the disease-state. In the case of HIV, treatment includes reducing the level of HIV viral load in a patient.

The term "patient" means a person or an animal at risk of being infected by a virus or, a person or an animal being infected with a viral, preferably a retroviral and more preferably an HIV virus.

The expression "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skilled in the art having regard to its own knowledge, the state of the art, and this disclosure.

The expression "pharmaceutically acceptable carrier" is employed for any excipient, solvent, dispersion medium, absorption retardant, diluent or adjuvant etc., such as preserving or antioxidant agents, fillers, binder, disintegrating agents, wetting agents, emulsifying agents, suspending agents, solvents, dispersion media, coatings, antibacterial and antifungal agents, isotonic and absorption delaying agents and the like, that does not produce a secondary reaction, for example an allergic reaction, in humans or animals.

Pharmaceutically acceptable carriers are well known to a person skilled in the art, and include those described in "Remington's Pharmaceutical Sciences" (Mack Publishing Company, Easton, USA, 1985). Except insofar as any conventional media or adjuvant is incompatible with the active ingredient, its use in the therapeutic compositions is contemplated.

The term "combination" refers to the administration of a compound of formula (I) with at least one other antiviral agent. This encompasses at least two active principles in one composition or in separate compositions which are administered separately or concomitantly.

The term "HIV" as used herein encompasses HIV-1 and HIV-2.

The invention may be further defined as applicable to HIV-1 or to HIV-2.

The term "mammal" as used herein is intended to encompass humans, as well as non-human mammals which are susceptible to infection by HIV or non human equivalents of HIV. Non-human mammals include but are not limited to domestic animals, such as cats, and non-domestic animals such as primates.

The invention primarily provides compounds of formula (I) as herein defined.

The invention provides a compound of formula (I) wherein:
A represents —$CH_2$—; or —O—;
$R^1$, $R^2$, $R^3$, $R^4$, $R^5$, $R^6$, $R^7$, $R^8$, $T^1$, $T^2$, $T^3$, $T^4$, $T^5$, $T^6$, $T^7$, $T^8$, X, Z, x and y are defined as for the compound of formula (I) according to the invention.

Preferably, the invention provides a compound of formula (I) wherein
$R^4$ represents a cyclopropyl;
$R^1$, $R^2$, $R^3$, $R^5$, $R^6$, $R^7$, $R^8$, $T^1$, $T^2$, $T^3$, $T^4$, $T^5$, $T^6$, $T^7$, $T^8$, A, X, Z, x and y are defined as for the compound of formula (I) according to the invention.

Preferably, the invention provides a compound of formula (I) wherein
$R^4$ represents a tert-butyl;
$R^1$ and $R^6$ represent simultaneously a hydrogen atom;
$R^2$, $R^3$, $R^5$, $R^7$, $R^8$, $T^1$, $T^2$, $T^3$, $T^4$, $T^5$, $T^6$, $T^7$, $T^8$, A, X, Z, x and y are defined as for the compound of formula (I) according to the invention.

The invention provides compounds comprising a 6-membered carbocycle, said compounds having a structure according to formula (I):
wherein:
$R^1$ and $R^6$, non-substituted or substituted by at least one $T^1$, identical or different, independently represent a hydrogen atom; —CN; —OH; —$CF_3$; a halogen atom; a linear or branched $C_1$-$C_8$ alkyl; a linear or branched $C_2$-$C_8$ alkenyl; a linear or branched $C_2$-$C_8$ alkynyl; —Z—C(O)O$R^7$; —Z—S(O)O$R^7$; —Z—OC(O)O$R^7$; —Z—O$R^8$; —Z—S$R^8$; —Z—N$R^7R^8$; —Z—OC(O)$R^8$; —Z—C(O)$R^8$; —Z—C(O)N$R^7R^8$; —Z—N$R^8$C(O)$R^8$; —Z—OC(O)N$R^7R^8$; —Z—N$R^8$C(O)O$R^7$; —Z—S(O)N$R^7R^8$; a saturated, partially or totally unsaturated or aromatic 3-, 4-, 5-, 6- or 7-membered carbocycle; a saturated, partially or totally unsaturated or aromatic 3-, 4-, 5-, 6- or 7-membered carbocycle fused with a saturated, partially or totally unsaturated or aromatic 3-, 4-, 5-, 6- or 7-membered carbocycle; a saturated, partially or totally unsaturated or aromatic 5-, 6- or 7-membered carbocycle fused with a saturated, partially or totally unsaturated or aromatic 4-, 5-, 6- or 7-membered heterocycle; a saturated, partially or totally unsaturated or aromatic 4-, 5-, 6- or 7-membered heterocycle; a saturated, partially or totally unsaturated or aromatic 4-, 5-, 6- or 7-membered heterocycle fused with a saturated, partially or totally unsaturated or aromatic 3-, 4-, 5-, 6- or 7-membered carbocycle; a saturated, partially or totally unsaturated or aromatic 4-, 5-, 6- or 7-membered heterocycle fused with a saturated, partially or totally unsaturated or aromatic 4-, 5-, 6- or 7-membered heterocycle;
$R^2$, non-substituted or substituted by at least one $T^1$, represents a linear or branched $C_2$-$C_8$ alkyl; a linear or branched $C_2$-$C_8$ alkenyl; a linear or branched $C_1$-$C_8$ heteroalkyl; a linear or branched $C_2$-$C_8$ heteroalkenyl; a $C_3$-$C_7$ cycloalkyl; a partially unsaturated $C_4$ carbocycle; a $C_1$-$C_8$ alkyl-($C_3$-$C_7$ cycloalkyl); a $C_1$-$C_8$ heteroalkyl-($C_3$-$C_7$ cycloalkyl); a $C_1$-$C_8$ alkyl-(partially or totally unsaturated or aromatic $C_3$-$C_7$ carbocycle); a $C_1$-$C_8$ heteroalkyl-(partially $C_3$-$C_7$ carbocycle); a $C_4$-$C_7$ heterocycloalkyl; a $C_1$-$C_8$ alkyl-($C_4$-$C_7$ heterocycloalkyl); a $C_1$-$C_8$ heteroalkyl-($C_4$-$C_7$ heterocycloalkyl); a $C_1$-$C_8$ alkyl-(partially or totally unsaturated or aromatic $C_4$-$C_7$ heterocycle); a $C_1$-$C_8$ heteroalkyl-(partially or totally unsaturated or aromatic $C_4$-$C_7$ heterocycle);
$R^3$, non-substituted or substituted by at least one $T^2$, represents a saturated, partially or totally unsaturated or aromatic 5-, 6- or 7-membered carbocycle; a saturated, partially or totally unsaturated or aromatic 5-, 6- or 7-membered carbocycle fused with a saturated, partially or totally unsaturated or aromatic 3-, 4-, 5-, 6- or 7-membered carbocycle; a saturated, partially or totally unsaturated or aromatic 5-, 6- or 7-membered carbocycle fused with a saturated, partially or totally unsaturated or aromatic 4-, 5-, 6- or 7-membered heterocycle; a saturated, partially or totally unsaturated or aromatic 5-, 6- or 7-membered carbocycle fused with a saturated, partially or totally unsaturated or aromatic 3-, 4-, 5-, 6- or 7-membered carbocycle and further fused with a saturated, partially or totally unsaturated or aromatic 4-, 5-, 6- or 7-membered heterocycle; a saturated, partially or totally unsaturated or aromatic 5-, 6- or 7-membered carbocycle fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a saturated, partially or totally unsaturated or aromatic 5-, 6- or 7-membered carbocycle fused with a saturated, partially or totally unsaturated or aromatic 3-, 4-, 5-, 6- or 7-membered carbocycle and further fused with a saturated, partially or totally unsaturated or aromatic 3-, 4-, 5-, 6- or 7-membered carbocycle; a saturated, partially or totally unsaturated or aromatic 5-, 6- or 7-membered heterocycle; a saturated, partially or totally unsaturated or aromatic 5-, 6- or 7-membered heterocycle fused with a saturated, partially or totally unsaturated or aromatic 3-, 4-, 5-, 6- or 7-membered carbocycle; a saturated, partially or totally unsaturated or aromatic 5-, 6- or 7-membered heterocycle fused with a saturated, partially or totally unsaturated or aromatic 4-, 5-, 6- or 7-membered heterocycle; a saturated, partially or totally unsaturated or aromatic 5-, 6- or 7-membered heterocycle fused with a saturated, partially or totally unsaturated or aromatic 3-, 4-, 5-, 6- or 7-membered carbocycle and further fused with a saturated, partially or totally unsaturated or aromatic 4-, 5-, 6- or 7-membered heterocycle; a saturated, partially or totally unsaturated or aromatic 5-, 6- or 7-membered heterocycle fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a saturated, partially or totally unsaturated or aromatic 5-, 6- or 7-membered heterocycle fused with a saturated, partially or totally unsaturated or aromatic 3-, 4-, 5-, 6- or 7-membered carbocycle and further fused with a saturated, partially or totally unsaturated or aromatic 3-, 4-, 5-, 6- or 7-membered carbocycle;
$R^4$, substituted or non-substituted by at least one $T^3$, represents a linear or branched $C_2$-$C_8$ alkyl; a linear or branched $C_1$-$C_8$ fluoroalkyl or a $C_3$-$C_8$ cycloalkyl;
$R^5$ represents a halogen atom; —$CF_3$; a linear or branched $C_1$-$C_6$ alkyl; a linear or branched $C_2$-$C_8$ alkenyl; a linear or branched $C_2$-$C_8$ alkynyl; a linear or branched fluoroalkyl; a $C_3$-$C_8$ cycloalkyl, —$CH_2OH$; —$CH_2$—O—$CH_3$;

R⁵ and R⁶ form, with the carbon atoms to which they are bonded, an aryl or form, with the carbon atoms to which they are bonded, a heteroaryl comprising at least one N atom;

R⁷ and R⁸, identical or different, independently represent a hydrogen atom; a linear or branched $C_1$-$C_8$ alkyl; a linear or branched $C_2$-$C_8$ alkenyl; a linear or branched $C_2$-$C_8$ alkynyl; a linear or branched fluoroalkyl; a linear or branched fluoroalkenyl; a linear or branched fluoroalkynyl; a $C_3$-$C_7$ cycloalkyl; a $C_4$-$C_7$ heterocycloalkyl; a partially or totally unsaturated or aromatic $C_4$-$C_7$ carbocycle; a partially or totally unsaturated or aromatic $C_5$-$C_7$ heterocycle; a $C_1$-$C_8$ alkyl-($C_3$-$C_7$ cycloalkyl); a $C_1$-$C_8$ alkyl-($C_4$-$C_7$ heterocycloalkyl); a $C_1$-$C_8$ alkyl-(partially or totally unsaturated or aromatic $C_4$-$C_7$ carbocycle); a $C_1$-$C_8$ alkyl-(partially or totally unsaturated or aromatic $C_5$-$C_7$ heterocycle);

R⁷ and R⁸ form, with the nitrogen atom to which they are bonded, a saturated, partially or totally unsaturated 4-, 5-, 6- or 7-membered heterocycle comprising at least one N atom;

$T^1$ independently represents a halogen atom; an alkyl; —(X)$_x$—$C_1$-$C_6$ alkyl; a linear or branched fluoroalkyl; a linear or branched —O—$C_1$-$C_3$ fluoroalkyl; —(X)$_x$—$C_3$-$C_6$ cycloalkyl; —(X)$_x$—$C_4$-$C_6$ heterocycle; —(X)$_x$—(CT⁶T⁷)$_y$CN; —(X)$_x$—(CT⁶T⁷)$_y$OT⁴; —(X)$_x$—(CT⁶T⁷)$_y$ST⁴; —(X)$_x$—(CT⁶T⁷)$_y$S(O)T⁴; —(X)$_x$—(CT⁶T⁷)$_y$S(O)$_2$T⁴; —(X)$_x$—(CT⁶T⁷)$_y$NT⁴T⁵; —(X)$_x$—(CT⁶T⁷)$_y$C(O)T⁴; —(X)$_x$—(CT⁶T⁷)$_y$C(O)OT⁴; —(X)$_x$—(CT⁶T⁷)$_y$C(O)NT⁴T⁵; —(X)$_x$—(CT⁶T⁷)$_y$NT⁴C(O)NT⁴T⁵; —(X)$_x$—(CT⁶T⁷)$_y$NT⁴C(O)T⁵; —(X)$_x$—(CT⁶T⁷)$_y$NT⁴C(O)OT⁵; —(X)$_x$—(CT⁶T⁷)$_y$OC(O)NT⁴T⁵; —(X)$_x$—(CT⁶T⁷)$_y$S(O)$_2$NT⁴T⁵; —(X)$_x$—(CT⁶T⁷)$_y$NT⁴S(O)$_2$T⁵;

$T^2$ independently represents a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; a $C_3$-$C_6$ cycloalkyl; —CN;

two geminal $T^2$ form with the carbon atom to which they are bonded, a $C_3$-$C_7$ cycloalkyl;

$T^3$ independently represents a linear or branched $C_1$-$C_2$ alkyl; a fluor atom;

$T^4$ and $T^5$, identical or different, independently represent a hydrogen atom; a branched or linear $C_1$-$C_6$ alkyl; a $C_3$-$C_6$ cycloalkyl;

$T^4$, $T^5$ and the nitrogen atom to which they are bonded, form a $C_4$-$C_6$ heterocycloalkyl;

$T^6$ and $T^7$, identical or different, independently represent a hydrogen atom; a fluorine atom; a linear or branched $C_1$-$C_3$ alkyl; a $C_3$-$C_6$ cycloalkyl;

$T^6$, $T^7$ and the carbon atom to which they are bonded form a $C_3$-$C_6$ cycloalkyl;

X independently represents an oxygen atom; a sulphur atom; NT³; S=O or S(O)$_2$;

Z independently represents a single bond; a linear or branched $C_2$-$C_8$ alkyl;

x represents 0 or 1;

y represents 0, 1, 2 or 3;

and a racemate, enantiomer, stereoisomer, atropisomer or diastereoisomer or a pharmaceutically acceptable salt thereof.

The invention also provides compounds of formula (A), (B), (C), (D), (E), (F), (G), (H), (J), (K) or (L):

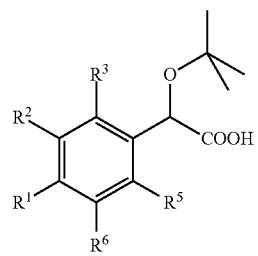

(A)

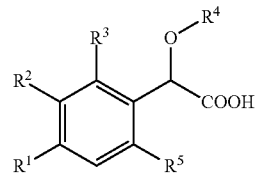

(B)

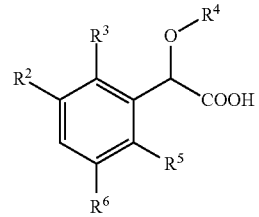

(C)

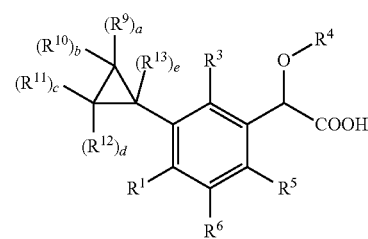

(D)

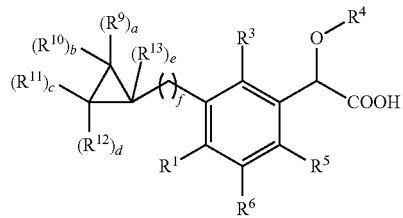

(E)

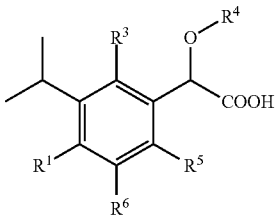

(F)

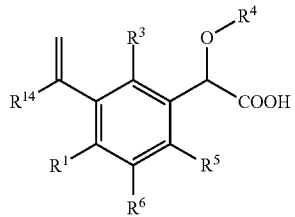

(G)

-continued

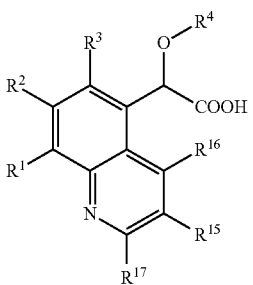

(H)

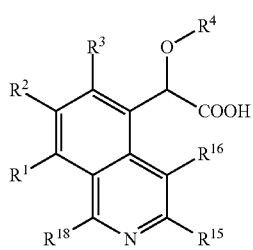

(J)

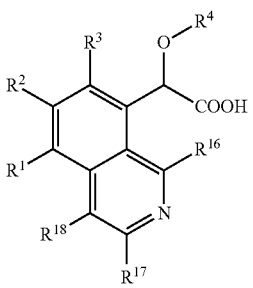

(K)

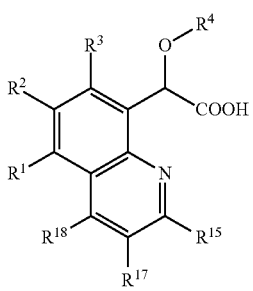

(L)

wherein, $R^9$, $R^{10}$, $R^{11}$, $R^{12}$, $R^{13}$, identical or different, independently represent a hydrogen atom; a halogen atom; an alkyl; or a $C_3$-$C_6$ cycloalkyl;

$R^{15}$, $R^{16}$, $R^{17}$, $R^{18}$, identical or different, independently represent a hydrogen atom; a halogen atom; an alkyl; —$(X)_x$-$C_1$-$C_6$ alkyl; a linear or branched fluoroalkyl; a linear or branched —O—$C_1$-$C_3$ fluoroalkyl; —$(X)_x$—$C_3$-$C_6$ cycloalkyl; —$(X)_x$—$C_4$-$C_6$ heterocycle; —$(X)_x$—$(CT^6T^7)_y$-aryl; —$(X)_x$—$(CT^6T^7)_y$CN; —$(X)_x$—$(CT^6T^7)_y$OT$^4$; —$(X)_x$—$(CT^6T^7)_y$ST$^4$; —$(X)_x$—$(CT^6T^7)_y$S(O)T$^4$; —$(X)_x$—$(CT^6T^7)_y$S(O)$_2$T$^4$; —$(X)_x$—$(CT^6T^7)_y$NT$^4$T$^5$; —$(X)_x$—$(CT^6T^7)_y$C(O)T$^4$; —$(X)_x$—$(CT^6T^7)_y$C(O)—$(CT^6T^7)_y$OT$^4$; —$(X)_x$—$(CT^6T^7)_y$C(O)OT$^4$; —$(X)_x$—$(CT^6T^7)_y$C(O)NT$^4$T$^5$; —$(X)_x$—$(CT^6T^7)_y$NT$^4$C(O)NT$^4$T$^5$; —$(X)_x$—$(CT^6T^7)_y$NT$^4$C(O)T$^5$; —$(X)_x$—$(CT^6T^7)_y$NT$^4$C(O)OT$^5$; —$(X)_x$—$(CT^6T^7)_y$OC(O)NT$^4$T$^5$; —$(X)_x$—$(CT^6T^7)_y$S(O)$_2$NT$^4$T$^5$; or —$(X)_x$—$(CT^6T^7)_y$NT$^4$S(O)$_2$T$^5$;

$R^{14}$ represents a hydrogen atom; a $C_3$-$C_6$ cycloalkyl; or an alkyl;

a, b, c, d, e, identical or different, independently represent 0 or 1;

f represents 1, 2, 3, 4, 5, or 6;

$R^1$, $R^2$, $R^3$, $R^4$, $R^5$, $R^6$, $R^7$, $R^8$, $T^1$, $T^2$, $T^3$, $T^4$, $T^5$, $T^6$, $T^7$, $T^8$, X, Z, x and y are defined as for the compound of formula (I) according to the invention.

In another embodiment, the invention also provides a compound of formula (D), (E), (F) or (G):

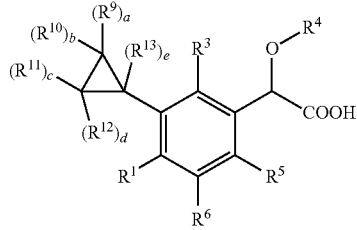

(D)

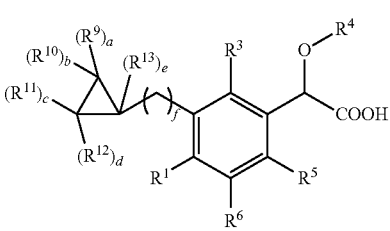

(E)

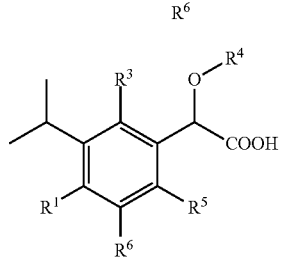

(F)

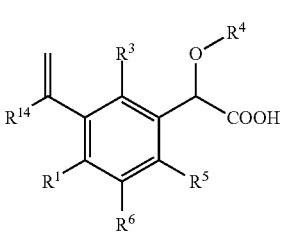

(G)

wherein, $R^9$, $R^{10}$, $R^{11}$, $R^{12}$, $R^{13}$, identical or different, independently represent a hydrogen atom; a halogen atom; an alkyl; or a $C_3$-$C_6$ cycloalkyl;

$R^{14}$ represents a hydrogen atom; a $C_3$-$C_6$ cycloalkyl; or an alkyl;

a, b, c, d, e, identical or different, independently represent 0 or 1;

f represents 1, 2, 3, 4, 5, or 6;

$R^1$, $R^2$, $R^3$, $R^4$, $R^5$, $R^6$, $R^7$, $R^8$, $T^1$, $T^2$, $T^3$, $T^4$, $T^5$, $T^6$, $T^7$, $T^8$, X, Z, x and y are defined as for the compound of formula (I) according to the invention.

Preferably, the invention provides a compound of formula (D):

(D)

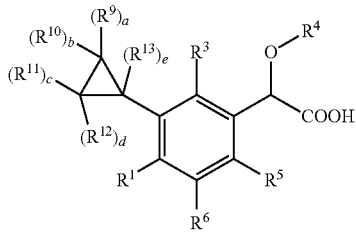

wherein,
R$^9$, R$^{10}$, R$^{11}$, R$^{12}$, R$^{13}$, identical or different, independently represent a hydrogen atom; a halogen atom; an alkyl; or a C$_3$-C$_6$ cycloalkyl;
a, b, c, d, e, identical or different, independently represent 0 or 1;
R$^1$, R$^3$, R$^4$, R$^5$, R$^6$, R$^7$, R$^8$, T$^1$, T$^2$, T$^3$, T$^4$, T$^5$, T$^6$, T$^7$, T$^8$, X, Z, x and y are defined as for the compound of formula (I) according to the invention.

The invention also provides a compound of formula (DA), (EA), (FA) or (GA):

(DA)

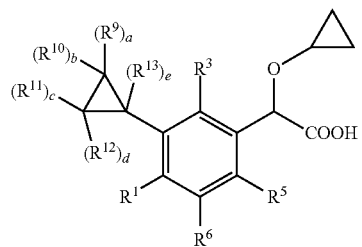

(EA)

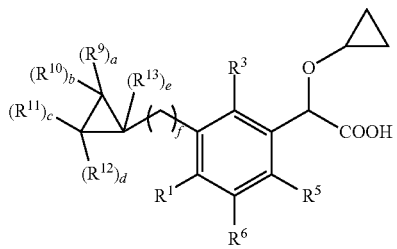

(FA)

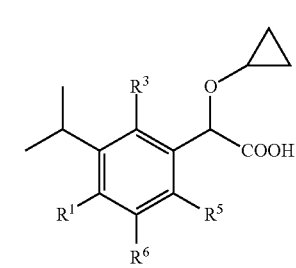

(GA)

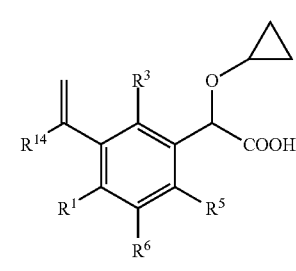

wherein,
R$^9$, R$^{10}$, R$^{11}$, R$^{12}$, R$^{13}$, identical or different, independently represent a hydrogen atom; a halogen atom; an alkyl; or a C$_3$-C$_6$ cycloalkyl;
R$^{14}$ represents a hydrogen atom; a C$_3$-C$_6$ cycloalkyl; or an alkyl;
a, b, c, d, e, identical or different, independently represent 0 or 1;
f represents 1, 2, 3, 4, 5, or 6;
R$^1$, R$^2$, R$^3$, R$^5$, R$^6$, R$^7$, R$^8$, T$^1$, T$^2$, T$^3$, T$^4$, T$^5$, T$^6$, T$^7$, T$^8$, X, Z, x and y are defined as for the compound of formula (I) according to the invention.

The invention also provides a compound of formula (AB), (AC), (AD), (AE), (AF), (AG), (BC), (BD), (BE), (BF), (BG), (CD), (CE), (CF), (CG), (HA), (HC) or (HD):

(AB)

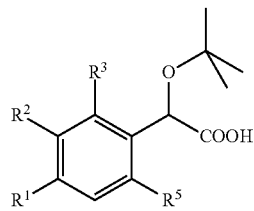

(AC)

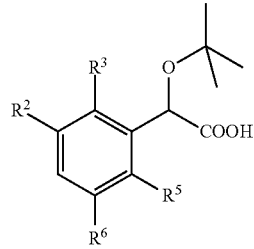

(AD)

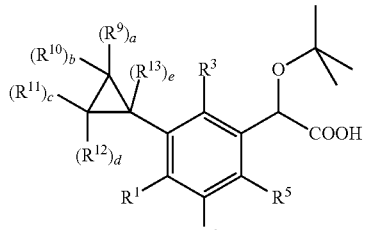

(AE)

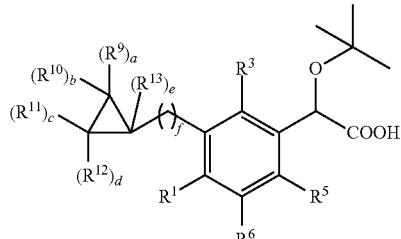

(AF)

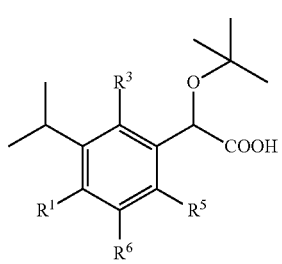

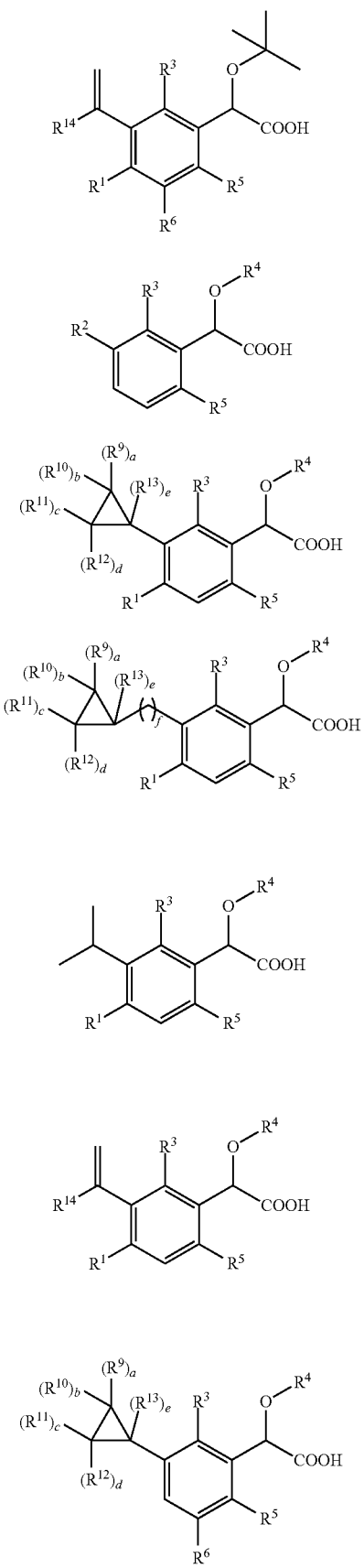
(AG)
(BC)
(BD)
(BE)
(BF)
(BG)
(CD)
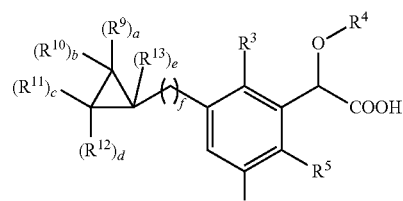
(CE)
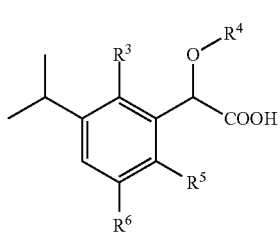
(CF)
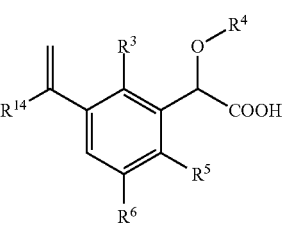
(CG)
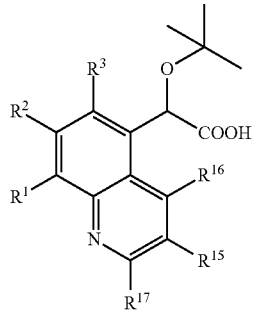
(HA)
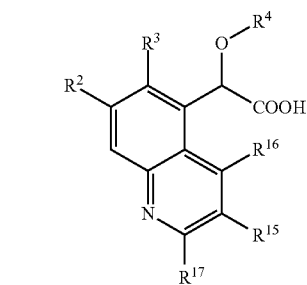
(HC)
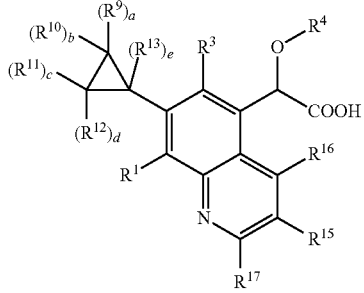
(HD)

wherein, $R^9$, $R^{19}$, $R^{11}$, $R^{12}$, $R^{13}$, identical or different, independently represent a hydrogen atom; a halogen atom; an alkyl; or a $C_3$-$C_6$ cycloalkyl;

$R^{15}$, $R^{16}$, $R^{17}$, identical or different, independently represent a hydrogen atom; a halogen atom; an alkyl; —$(X)_x$-$C_1$-$C_6$ alkyl; a linear or branched fluoroalkyl; a linear or branched —O—$C_1$-$C_3$ fluoroalkyl; —$(X)_x$—$C_3$-$C_6$ cycloalkyl; —$(X)_x$—$C_4$-$C_6$ heterocycle; —$(X)_x$—$(CT^6T^7)_y$-aryl; —$(X)_x$—$(CT^6T^7)_y$CN; —$(X)_x$—$(CT^6T^7)_y$OT$^4$; —$(X)_x$—$(CT^6T^7)_y$ST$^4$; —$(X)_x$—$(CT^6T^7)_y$S(O)T$^4$; —$(X)_x$—$(CT^6T^7)_y$S(O)$_2$T$^4$; —$(X)_x$—$(CT^6T^7)_y$NT$^4$T$^5$; —$(X)_x$—$(CT^6T^7)_y$C(O)T$^4$; —$(X)_x$—$(CT^6T^7)_y$C(O)—$(CT^6T^7)_y$OT$^4$; —$(X)_x$—$(CT^6T^7)_y$C(O)OT$^4$; —$(X)_x$—$(CT^6T^7)_y$C(O)NT$^4$T$^5$; —$(X)_x$—$(CT^6T^7)_y$NT$^4$C(O)NT$^4$T$^5$; —$(X)_x$—$(CT^6T^7)_y$NT$^4$C(O)T$^5$; —$(X)_x$—$(CT^6T^7)_y$NT$^4$C(O)OT$^5$; —$(X)_x$—$(CT^6T^7)_y$OC(O)NT$^4$T$^5$; —$(X)_x$—$(CT^6T^7)_y$S(O)$_2$NT$^4$T$^5$; or —$(X)_x$—$(CT^6T^7)_y$NT$^4$S(O)$_2$T$^5$;

$R^{14}$ represents a hydrogen atom; a $C_3$-$C_6$ cycloalkyl; or an alkyl;

a, b, c, d, e, identical or different, independently represent 0 or 1;

f represents 1, 2, 3, 4, 5, or 6;

$R^1$, $R^2$, $R^3$, $R^4$, $R^5$, $R^6$, $R^7$, $R^8$, $T^1$, $T^2$, $T^3$, $T^4$, $T^5$, $T^6$, $T^7$, $T^8$, X, Z, x and y are defined as for the compound of formula (I) according to the invention.

The invention also provides compounds of formula (ABC), (ABD), (ABE), (ABF), (ABG), (BCD), (BCE), (BCF), (BCG), (HAC) or (HAD):

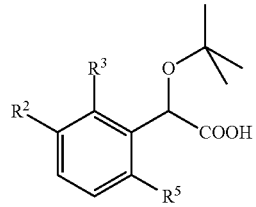
(ABC)

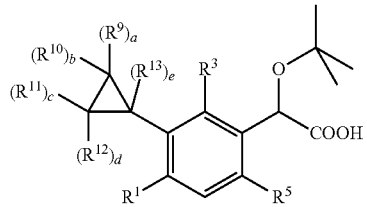
(ABD)

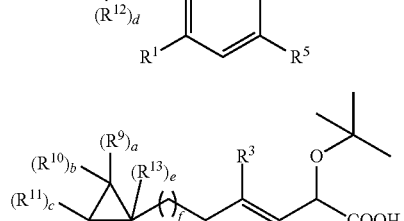
(ABE)

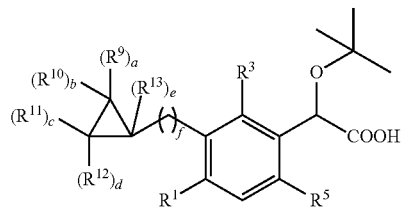
(ABF)

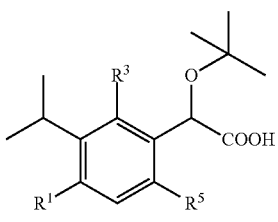
(ABG)

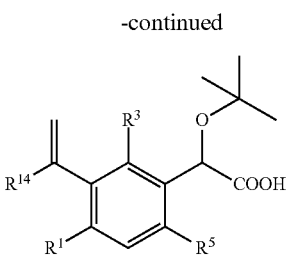
(BCD)

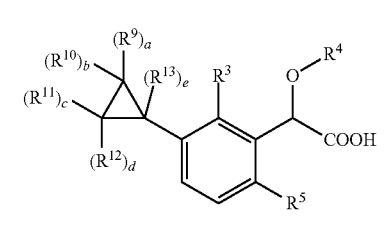
(BCE)

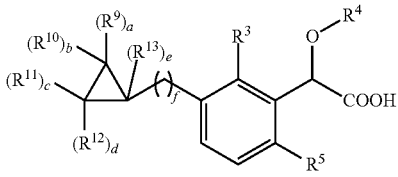
(BCF)

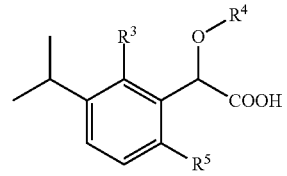
(BCG)

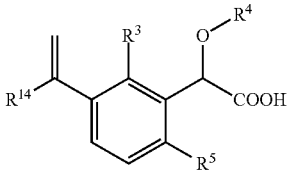
(HAC)

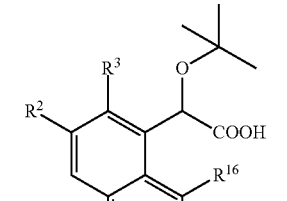

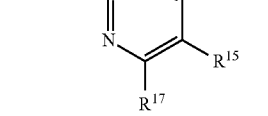

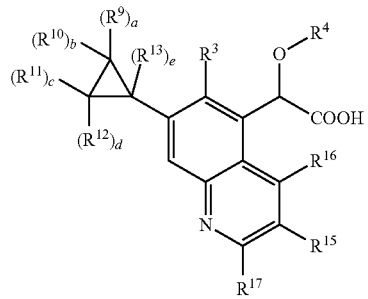
(HAD)

wherein,
$R^9$, $R^{19}$, $R^{11}$, $R^{12}$, $R^{13}$, identical or different, independently represent a hydrogen atom; a halogen atom; an alkyl; or a $C_3$-$C_6$ cycloalkyl;

$R^{15}$, $R^{16}$, $R^{17}$ when present in the formula, identical or different, independently represent a hydrogen atom; a halogen atom; an alkyl; —$(X)_x$-$C_1$-$C_6$ alkyl; a linear or branched fluoroalkyl; a linear or branched —O—$C_1$-$C_3$ fluoroalkyl; —$(X)_x$—$C_3$-$C_6$ cycloalkyl; —$(X)_x$—$C_4$-$C_6$ heterocycle; —$(X)_x$—$(CT^6T^7)_y$-aryl; —$(X)_x$—$(CT^6T^7)_y$CN; —$(X)_x$—$(CT^6T^7)_y$OT$^4$; —$(X)_x$—$(CT^6T^7)_y$ST$^4$; —$(X)_x$—$(CT^6T^7)_y$S(O)T$^4$; —$(X)_x$—$(CT^6T^7)_y$S(O)$_2$T$^4$; —$(X)_x$—$(CT^6T^7)_y$NT$^4$T$^5$; —$(X)_x$—$(CT^6T^7)_y$C(O)T$^4$; —$(X)_x$—$(CT^6T^7)_y$C(O)—$(CT^6T^7)_y$OT$^4$; —$(X)_x$—$(CT^6T^7)_y$C(O)OT$^4$; —$(X)_x$—$(CT^6T^7)_y$C(O)NT$^4$T$^5$; —$(X)_x$—$(CT^6T^7)_y$NT$^4$C(O)NT$^4$T$^5$; —$(X)_x$—$(CT^6T^7)_y$NT$^4$C(O)T$^5$; —$(X)_x$—$(CT^6T^7)_y$NT$^4$C(O)OT$^5$; —$(X)_x$—$(CT^6T^7)_y$OC(O)NT$^4$T$^5$; —$(X)_x$—$(CT^6T^7)_y$S(O)$_2$NT$^4$T$^5$; or —$(X)_x$—$(CT^6T^7)_y$NT$^4$S(O)$_2$T$^5$;

$R^{14}$ represents a hydrogen atom; a $C_3$-$C_6$ cycloalkyl; or an alkyl;

a, b, c, d, e, when present in the formula, identical or different, independently represent 0 or 1;

f represents 1, 2, 3, 4, 5, or 6;

$R^1$, $R^2$, $R^3$, $R^4$, $R^5$, $R^6$, $R^7$, $R^8$, $T^1$, $T^2$, $T^3$, $T^4$, $T^5$, $T^6$, $T^7$, $T^8$, X, Z, x and y are defined as for the compound of formula (I) according to the invention.

The invention also provides compounds of formula (ABCD), (ABCE), (ABCF), (ABCG) or (HACD):

(ABCD)
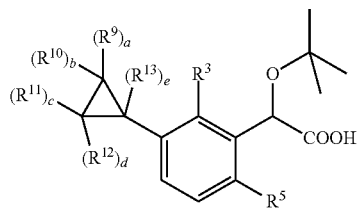

(ABCE)
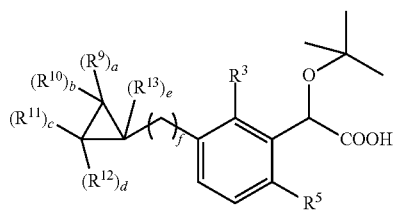

(ABCF)
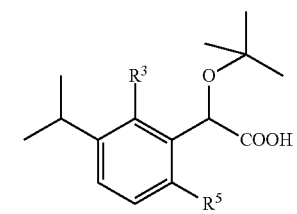

(ABCG)
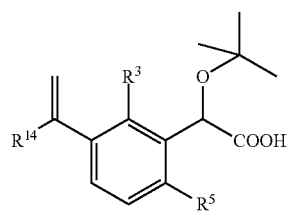

(HACD)
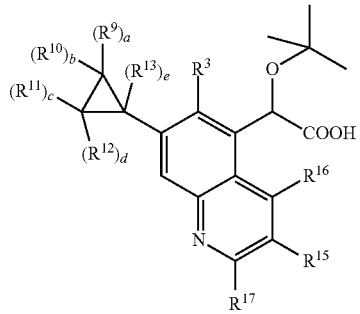

wherein,
$R^9$, $R^{10}$, $R^{11}$, $R^{12}$, $R^{13}$, identical or different, independently represent a hydrogen atom; a halogen atom; an alkyl; or a $C_3$-$C_6$ cycloalkyl;

$R^{15}$, $R^{16}$, $R^{17}$, identical or different, independently represent a hydrogen atom; a halogen atom; an alkyl; —$(X)_x$-$C_1$-$C_6$ alkyl; a linear or branched fluoroalkyl; a linear or branched —O—$C_1$-$C_3$ fluoroalkyl; —$(X)_x$—$C_3$-$C_6$ cycloalkyl; —$(X)_x$—$C_4$-$C_6$ heterocycle; —$(X)_x$—$(CT^6T^7)_y$-aryl; —$(X)_x$—$(CT^6T^7)_y$CN; —$(X)_x$—$(CT^6T^7)_y$OT$^4$; —$(X)_x$—$(CT^6T^7)_y$ST$^4$; —$(X)_x$—$(CT^6T^7)_y$S(O)T$^4$; —$(X)_x$—$(CT^6T^7)_y$S(O)$_2$T$^4$; —$(X)_x$—$(CT^6T^7)_y$NT$^4$T$^5$; —$(X)_x$—$(CT^6T^7)_y$C(O)T$^4$; —$(X)_x$—$(CT^6T^7)_y$C(O)—$(CT^6T^7)_y$OT$^4$; —$(X)_x$—$(CT^6T^7)_y$C(O)OT$^4$; —$(X)_x$—$(CT^6T^7)_y$C(O)NT$^4$T$^5$; —$(X)_x$—$(CT^6T^7)_y$NT$^4$C(O)NT$^4$T$^5$; —$(X)_x$—$(CT^6T^7)_y$NT$^4$C(O)T$^5$; —$(X)_x$—$(CT^6T^7)_y$NT$^4$C(O)OT$^5$; —$(X)_x$—$(CT^6T^7)_y$OC(O)NT$^4$T$^5$; —$(X)_x$—$(CT^6T^7)_y$S(O)$_2$NT$^4$T$^5$; or —$(X)_x$—$(CT^6T^7)_y$NT$^4$S(O)$_2$T$^5$;

$R^{14}$ represents a hydrogen atom; a $C_3$-$C_6$ cycloalkyl; or an alkyl;

a, b, c, d, e, identical or different, independently represent 0 or 1;

f represents 1, 2, 3, 4, 5, or 6;

$R^1$, $R^2$, $R^3$, $R^4$, $R^5$, $R^6$, $R^7$, $R^8$, $T^1$, $T^2$, $T^3$, $T^4$, $T^5$, $T^6$, $T^7$, $T^8$, X, Z, x and y are defined as for the compound of formula (I) according to the invention.

Preferably, the invention provides a compound selected from the group consisting of compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF), (ABCG) or (HACD) wherein, $R^1$ and $R^6$, non-substituted or substituted by at least one $T^1$, identical or different, independently represent a hydrogen atom; —CN; —NH$_2$; —OH; —CF$_3$; —OCF$_3$; —Z—OR$^8$; Z—NR$^8$SO$_2$R$^8$; —Z—NR$^8$C(O)R$^8$; —Z—NR$^7$R$^8$; a halogen atom; a linear or branched $C_1$-$C_4$ alkyl; a linear or branched $C_1$-$C_4$ fluoroalkyl; a linear or branched $C_1$-$C_4$ heteroalkyl; a linear or branched $C_2$-$C_8$ alkenyl; a linear or branched $C_2$-$C_8$ alkynyl; a $C_3$-$C_4$ cycloalkyl; a saturated, partially or totally unsaturated or aromatic 3-, 4-, 5-, 6- or 7-membered carbocycle; a saturated, partially or totally unsaturated or aromatic 4-, 5-, 6- or 7-membered heterocycle; or a saturated, partially or totally unsaturated or aromatic 4-, 5-, 6- or 7-membered heterocycle fused with a saturated, partially or totally unsaturated or aromatic 3-, 4-, 5-, 6- or 7-membered carbocycle; or $R^2$, non-substituted or substituted by at least one $T^1$, represents a linear or branched $C_2$-$C_8$ alkyl; a linear or branched $C_2$-$C_8$ alkenyl; a linear or branched $C_1$-$C_8$ heteroalkyl; a $C_3$-$C_7$ cycloalkyl; a $C_1$-$C_8$ alkyl-($C_3$-$C_7$ cycloalkyl); a $C_4$-$C_7$ heterocycloalkyl; or a $C_1$-$C_8$ alkyl-($C_4$-$C_7$ heterocycloalkyl); or $R^3$, non-substituted or substituted by at least one $T^2$, represents when present in the formula, an aryl; a heteroaryl; a partially unsaturated 5-, 6-, 7-membered carbocycle; a saturated or partially unsaturated 5-, 6-, 7-membered heterocycle; a partially unsaturated 5-, 6, 7-membered carbocycle fused with a saturated, partially or totally unsaturated or aromatic 4-, 5-, 6-, 7-membered heterocycle; a saturated or partially unsaturated 5-, 6-, 7-membered heterocycle fused with a saturated, partially or totally unsaturated or aromatic 4-, 5-, 6- or 7-membered carbocycle; an aryl fused with a partially or totally unsaturated or aromatic 4-, 5-, 6-, 7-membered heterocycle; or an aryl fused with a 6-membered heteroaryl and fused with a partially unsaturated 6-membered heterocycle; an heteroaryl fused with a partially or totally unsaturated or aromatic 4-, 5-, 6-, 7-membered carbocycle; or $R^4$, non-substituted or substituted by at least one $T^3$, represents a linear or branched $C_2$-$C_4$ alkyl; a linear or branched $C_2$-$C_6$ alkenyl; a linear or branched $C_2$-$C_4$ fluoroalkyl; a $C_3$-$C_4$ cycloalkyl; or a $C_1$-$C_3$ alkyl-($C_3$-$C_6$ cycloalkyl); or $R^5$ represents —$CH_3$; —$CH_2F$; —$CHF_2$; —$CF_3$; —$CH_2OH$; or —$CH_2OCH_3$; or $R^5$ and $R^6$ may form, with the carbon atoms of the phenyl ring of formula (I) to which they are bonded, a heteroaryl comprising at least one N atom; or A when present in the formula, represents —$CH_2$; or —O;
$R^7, R^8, R^9, R^{10}, R^{11}, R^{12}, R^{13}, R^{14}, R^{15}, R^{16}, R^{17}, R^{18}, T^1, T^2, T^3, T^4, T^5, T^6, T^7, T^8$, X, Z, a, b, c, d, e, f, x and y are defined as for the compound of formula (I), (A), (B), (C), (D), (E), (F), (G), (H), (J), (K) or (L) according to the invention.

Preferably, the invention provides a compound selected from the group consisting of compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF), (ABCG) or (HACD) wherein, $R^1$ and $R^6$, non-substituted or substituted by at least one $T^1$, identical or different, independently represent a hydrogen atom; —CN; —$NH_2$; —OH; —$CF_3$; —$OCF_3$; Z—$NR^8SO_2R^8$; —Z—$NR^8C(O)R^8$; —Z—$NR^7R^8$; a halogen atom; a linear or branched $C_1$-$C_4$ alkyl; a linear or branched $C_1$-$C_4$ fluoroalkyl; a linear or branched $C_2$-$C_8$ alkenyl; a linear or branched $C_2$-$C_8$ alkynyl; a linear or branched $C_1$-$C_4$ heteroalkyl; a $C_3$-$C_4$ cycloalkyl; a saturated, partially or totally unsaturated or aromatic 3-, 4-, 5-, 6- or 7-membered carbocycle; a saturated, partially or totally unsaturated or aromatic 4-, 5-, 6- or 7-membered heterocycle; or a saturated, partially or totally unsaturated or aromatic 4-, 5-, 6- or 7-membered heterocycle fused with a saturated, partially or totally unsaturated or aromatic 3-, 4-, 5-, 6- or 7-membered carbocycle; and $R^2$, non-substituted or substituted by at least one $T^1$, represents a linear or branched $C_2$-$C_8$ alkyl; a linear or branched $C_2$-$C_8$ alkenyl; a linear or branched $C_1$-$C_8$ heteroalkyl; a $C_3$-$C_7$ cycloalkyl; a $C_1$-$C_8$ alkyl-($C_3$-$C_7$ cycloalkyl); a $C_4$-$C_7$ heterocycloalkyl; or a $C_1$-$C_8$ alkyl-($C_4$-$C_7$ heterocycloalkyl); and $R^3$, non-substituted or substituted by at least one $T^2$, represents when present in the formula, an aryl; a heteroaryl; a partially unsaturated 5-, 6-, 7-membered carbocycle; a saturated or partially unsaturated 5-, 6-, 7-membered heterocycle; a partially unsaturated 5-, 6, 7-membered carbocycle fused with a saturated, partially or totally unsaturated or aromatic 4-, 5-, 6-, 7-membered heterocycle; a saturated or partially unsaturated 5-, 6-, 7-membered heterocycle fused with a saturated, partially or totally unsaturated or aromatic 4-, 5-, 6- or 7-membered carbocycle; an aryl fused with a partially or totally unsaturated or aromatic 4-, 5-, 6-, 7-membered heterocycle; or an aryl fused with a 6-membered heteroaryl and fused with a partially unsaturated 6-membered heterocycle; an heteroaryl fused with a partially or totally unsaturated or aromatic 4-, 5-, 6-, 7-membered carbocycle; and $R^4$, non-substituted or substituted by at least one $T^3$, represents a linear or branched $C_2$-$C_4$ alkyl; a linear or branched $C_2$-$C_6$ alkenyl; a linear or branched $C_2$-$C_4$ fluoroalkyl; a $C_3$-$C_4$ cycloalkyl; or a $C_1$-$C_3$ alkyl-($C_3$-$C_6$ cycloalkyl); and $R^5$ represents —$CH_3$; —$CH_2F$; —$CHF_2$; —$CF_3$; —$CH_2OH$; or —$CH_2OCH_3$; and $R^5$ and $R^6$ may form, with the carbon atoms of the phenyl ring of formula (I) to which they are bonded, a heteroaryl comprising at least one N atom; and A when present in the formula, represents —$CH_2$; or —O;
$R^7, R^8, R^9, R^{10}, R^{11}, R^{12}, R^{13}, R^{14}, R^{15}, R^{16}, R^{17}, R^{18}, T^1, T^2, T^3, T^4, T^5, T^6, T^7, T^8$, X, Z, a, b, c, d, e, f, x and y are defined as for the compound of formula (I), (A), (B), (C), (D), (E), (F), (G), (H), (J), (K) or (L) according to the invention.

More preferably, the invention provides a compound selected in the group consisting of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD) wherein, $R^1$ and $R^6$, non-substituted or substituted by at least one $T^1$, identical or different, independently represent a hydrogen atom; a methyl; an ethyl; a methoxy; a methanesulfonamido; a phenyl; an acetamido; a N,N-dimethylamino; a N-methyl-N-hydroxyethylamino; a cyclohexylmethylsulfonylamino; or a benzimidazolyl; or $R^2$, non-substituted or substituted by at least one $T^1$, a cyclopropyl; a cyclobutyl; a cyclopentyl; a isopropyl; a isopropenyl; a methoxy; a methylenecyclopropyl; an ethyl; an ethylenyl; a propyl; or $R^4$, non-substituted or substituted by at least one $T^3$, represents a tert-butyl; an ethyl; a propyl; a propenyl; a cyclopropyl; a methylenecyclopropyl; a 2,2,2-trifluoroethyl; an isopropyl; a cyclobutyl; a 2,2-difluoroethyl; or a 2-fluoroethyl; or $R^5$ represents —$CH_3$; or —$CF_3$; or A represents —$CH_2$; or —O;
$R^3, R^7, R^8, R^9, R^{10}, R^{11}, R^{12}, R^{13}, R^{14}, R^{15}, R^{16}, R^{17}, R^{18}, T^1, T^2, T^3, T^4, T^5, T^6, T^7, T^8$, X, Z, a, b, c, d, e, f, x and y, are defined as for compound of formula (I), (A), (B), (C), (D), (E), (F), (G), (H), (J), (K) or (L) according to the invention.

More preferably, the invention provides a compound selected in the group consisting of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF), (ABCG) or (HACD) wherein,

- $R^1$ and $R^6$, non-substituted or substituted by at least one $T^1$, identical or different, independently represent a hydrogen atom; a methyl; an ethyl; a methoxy; a methanesulfonamido; a phenyl; an acetamido; a N,N-dimethylamino; a N-methyl-N-hydroxyethylamino; a cyclohexylmethylsulfonamino; or a benzimidazolyl; and
- $R^2$, non-substituted or substituted by at least one $T^1$, a cyclopropyl; a cyclobutyl; a cyclopentyl; a isopropyl; a isopropenyl; a methoxy; a methylenecyclopropyl; an ethyl; an ethylenyl; a propyl; and
- $R^4$, non-substituted or substituted by at least one $T^3$, represents a tert-butyl; an ethyl; a propyl; a propenyl; a cyclopropyl; a methylenecyclopropyl; a 2,2,2-trifluoroethyl; an isopropyl; a cyclobutyl; a 2,2-difluoroethyl; or a 2-fluoroethyl; and
- $R^5$ represents —$CH_3$; or —$CF_3$; and
- A represents —$CH_2$; or —O;
- $R^3, R^7, R^8, R^9, R^{10}, R^{11}, R^{12}, R^{13}, R^{14}, R^{15}, R^{16}, R^{17}, R^{18}, T^1, T^2, T^3, T^4, T^5, T^6, T^7, T^8, X, Z, a, b, c, d, e, f, x$ and $y$, are defined as for compound of formula (I), (A), (B), (C), (D), (E), (F), (G), (H), (J), (K) or (L) according to the invention.

As an example of compounds of formula (AB), the invention provides a compound:
2-[4-(1H-1,3-benzodiazol-2-yl)-2-(3,4-dihydro-2H-1-benzopyran-6-yl)-3-methoxy-6-(trifluoromethyl)phenyl]-2-(tert-butoxy)acetic acid.

As examples of compounds of formula (ABC), the invention provides compounds selected in the group consisting of:
2-(tert-butoxy)-2-[3-(cyclopentyl)-2-(3,4-dihydro-2H-1-benzopyran-6-yl)-6-(trifluoromethyl)phenyl]acetic acid;
2-(tert-butoxy)-2-[2-(3,4-dihydro-2H-1-benzopyran-6-yl)-3-ethyl-6-(trifluoromethyl)phenyl]acetic acid;
tert-butoxy-(2-chroman-6-yl-3-cyclobutyl-6-methyl-phenyl)-acetic acid.

As examples of compounds of formulae (ABCD), the invention provides compounds selected from the group consisting of:
2-(tert-butoxy)-2-[3-cyclopropyl-2-(3,4-dihydro-2H-1-benzopyran-6-yl)-6-methylphenyl]acetic acid;
2-(tert-butoxy)-2-[3-cyclopropyl-2-(3,4-dihydro-2H-1-benzopyran-6-yl)-6-(trifluoromethyl)phenyl]acetic acid;
2-(tert-butoxy)-2-[3-cyclopropyl-2-(2,3-dihydropyrano[4,3,2-de]quinolin-7-yl)-6-methylphenyl]acetic acid;
2-(tert-butoxy)-2-(6-cyclopropyl-4'-methoxy-3-methyl-biphenyl-2-yl]acetic acid;
(S)-2-(tert-butoxy)-2-[3-cyclopropyl-2-(3,4-dihydro-2H-1-benzopyran-6-yl)-6-methylphenyl]acetic acid;
2-(tert-butoxy)-2-(6-cyclopropyl-3,4'-dimethyl-biphenyl-2-yl)-acetic acid;
2-(tert-butoxy)-2-(6-cyclopropyl-4'-fluoro-3-methyl-biphenyl-2-yl)-acetic acid;
2-(tert-butoxy)-2-[3-cyclopropyl-6-methyl-2-(5-methyl-chroman-6-yl)-phenyl]acetic acid;
(trans-3-bicyclopropyl-2-yl-2-chroman-6-yl-6-methyl-phenyl)-tert-butoxy-acetic acid;
2-(tert-butoxy)-2-[3-cyclopropyl-2-(4,4-dimethyl-cyclohex-1-enyl)-6-methyl-phenyl]acetic acid;
2-(tert-butoxy)-2-(4'-chloro-6-cyclopropyl-3-methyl-biphenyl-2-yl)acetic acid;
tert-butoxy-[3-cyclopropyl-2-(8-fluoro-5-methyl-chroman-6-yl)-6-methyl-phenyl]-acetic acid;
tert-butoxy-[2-chroman-6-yl-6-methyl-3-(1-methyl-cyclopropyl)-phenyl]-acetic acid;
tert-Butoxy-[2-chroman-6-yl-6-methyl-3-(cis-2-methyl-cyclopropyl)-phenyl]-acetic acid;
(S)-tert-butoxy-[3-cyclopropyl-6-methyl-2-(5-methyl-chroman-6-yl)-phenyl]-acetic acid;
(S)-tert-butoxy-[3-cyclopropyl-2-(8-fluoro-5-methyl-chroman-6-yl)-6-methyl-phenyl]-acetic acid.

As an example of compounds of formula (ABCE), the invention provides a compound:
tert-Butoxy-(2-chroman-6-yl-3-cyclopropylmethyl-6-methyl-phenyl)-acetic acid.

As examples of compounds of formula (ABCF), the invention provides compounds selected in the group consisting of:
2-(tert-butoxy)-2-[2-(3,4-dihydro-2H-1-benzopyran-6-yl)-3-isopropyl-6-methylphenyl]acetic acid;
2-(tert-butoxy)-2-[2-(3,4-dihydro-2H-1-benzopyran-6-yl)-3-(propan-2-yl)-6-(trifluoromethyl)phenyl]acetic acid.

As examples of compounds of formula (ABCG), the invention provides compounds selected in the group consisting of:
2-(tert-butoxy)-2-[2-(3,4-dihydro-2H-1-benzopyran-6-yl)-3-isopropenyl-6-methylphenyl]acetic acid;
2-(tert-butoxy)-2-[2-(3,4-dihydro-2H-1-benzopyran-6-yl)-3-(prop-1-en-2-yl)-6-(trifluoromethyl)phenyl]acetic acid;
2-(tert-butoxy)-2-[2-(3,4-dihydro-2H-1-benzopyran-6-yl)-3-ethenyl-6-(trifluoromethyl)phenyl]acetic acid.

As example of compounds of formula (BC), the invention provides a compound:
2-chroman-6-yl-6-methyl-3-propyl-phenyl)-isopropoxy-acetic acid.

As examples of compounds of formula (BCD), the invention provides compounds selected in the group consisting of:
2-(2-chroman-6-yl-3-cyclopropyl-6-methyl-phenyl)-2-ethoxy-acetic acid;
(2-chroman-6-yl-3-cyclopropyl-6-methyl-phenyl)-propoxy-acetic acid;
(2-chroman-6-yl-3-cyclopropyl-6-methyl-phenyl)-cyclopropyl methoxy-acetic acid;
(2-chroman-6-yl-3-cyclopropyl-6-methyl-phenyl)-(2,2,2-trifluoro-ethoxy)-acetic acid;
(2-chroman-6-yl-3-cyclopropyl-6-methyl-phenyl)-cyclobutoxy-acetic acid;
(2-chroman-6-yl-3-cyclopropyl-6-methyl-phenyl)-(2,2-difluoro-ethoxy)-acetic acid;
(2-chroman-6-yl-3-cyclopropyl-6-methyl-phenyl)-(2-fluoro-ethoxy)-acetic acid;
(2-chroman-6-yl-3-cyclopropyl-6-methyl-phenyl)-isopropoxy-acetic acid;
(2-chroman-6-yl-3-cyclopropyl-6-methyl-phenyl)-(1-methyl-cyclopropoxy)-acetic acid;
2-[3-cyclopropyl-2-(3,4-dihydro-2H-1-benzopyran-6-yl)-6-methylphenyl]pent-4-enoic acid.

As examples of compounds of formula (DA), the invention provides compounds selected in the group consisting of:
2-[3-cyclopropyl-2-(3,4-dihydro-2H-1-benzopyran-6-yl)-6-methylphenyl]-2-cyclopropoxyacetic acid;
(S)-2-[3-cyclopropyl-2-(3,4-dihydro-2H-1-benzopyran-6-yl)-6-methylphenyl]-2-cyclopropoxyacetic acid;
(2-chroman-6-yl-3-cyclopropyl-6-trifluoromethyl-phenyl)-cyclopropoxy-acetic acid;

cyclopropoxy-[3-cyclopropyl-6-methyl-2-(5-methyl-chroman-6-yl)-phenyl]-acetic acid;
cyclopropoxy-[3-cyclopropyl-2-(8-fluoro-5-methyl-chroman-6-yl)-6-methyl-phenyl]-acetic acid;
(S)-cyclopropoxy-[3-cyclopropyl-6-methyl-2-(5-methyl-chroman-6-yl)-phenyl]-acetic acid;
(S)-cyclopropoxy-[3-cyclopropyl-2-(8-fluoro-5-methyl-chroman-6-yl)-6-methyl-phenyl]-acetic acid;
(2-chroman-6-yl-3-cyclopropyl-6-methyl-phenyl)-(2,2-difluoro-cyclopropoxy)-acetic acid;
2-[2-chroman-6-yl-3-cyclopropyl-5-(methanesulfonamido)-6-methyl-phenyl]-2-(cyclopropoxy)acetic acid;
2-(5-acetamido-2-chroman-6-yl-3-cyclopropyl-6-methyl-phenyl)-2-(cyclopropoxy)acetic acid;
2-[2-chroman-6-yl-3-cyclopropyl-5-(dimethylamino)-6-methyl-phenyl]-2-(cyclopropoxy)acetic acid;
2-[2-chroman-6-yl-3-cyclopropyl-5-[2-hydroxyethyl(methyl)amino]-6-methyl-phenyl]-2-(cyclopropoxy)acetic acid;
(2-chroman-6-yl-3-cyclopropyl-4-methanesulfonylamino-6-methyl-phenyl)-cyclopropoxy-acetic acid;
(4-acetylamino-2-chroman-6-yl-3-cyclopropyl-6-methyl-phenyl)-cyclopropoxy-acetic acid;
(3-chroman-6-yl-2-cyclopropyl-5-methyl-biphenyl-4-yl)-cyclopropoxy-acetic acid;
(2-chroman-6-yl-3-cyclopropyl-4-ethyl-6-methyl-phenyl)-cyclopropoxy-acetic acid;
(2-chroman-6-yl-3-cyclopropyl-4-methoxy-6-methyl-phenyl)-cyclopropoxy-acetic acid;
2-(2-chroman-6-yl-3-cyclopropyl-5-ethyl-6-methyl-phenyl)-2-(cyclopropoxy)acetic acid;
2-(2-chroman-6-yl-3-cyclopropyl-5-ethyl-6-methyl-phenyl)-2-(cyclopropoxy)acetic acid;
(2-chroman-6-yl-3-cyclopropyl-4,6-dimethyl-phenyl)-cyclopropoxy-acetic acid;
2-[2-chroman-6-yl-5-(cyclohexylmethylsulfonylamino)-3-cyclopropyl-6-methyl-phenyl]-2-(cyclopropoxy)acetic acid.

As an example of compounds of formula (HACD), the invention provides a compound:
tert-butoxy-(6-chroman-6-yl-7-cyclopropyl-quinolin-5-yl)-acetic acid.

As examples of compounds of formula (I), the invention provides compounds selected in the group consisting of:
3-cyclopropyl-2-[3-cyclopropyl-2-(3,4-dihydro-2H-1-benzopyran-6-yl)-6-methylphenyl]propanoic acid;
2-[3-cyclopropyl-2-(3,4-dihydro-2H-1-benzopyran-6-yl)-6-methylphenyl]-4-methylpentanoic acid.

More preferably, the invention provides compounds selected in the group consisting of:
2-[4-(1H-1,3-benzodiazol-2-yl)-2-(3,4-dihydro-2H-1-benzopyran-6-yl)-3-methoxy-6-(trifluoromethyl)phenyl]-2-(tert-butoxy)acetic acid;
2-(tert-butoxy)-2-[3-(cyclopentyl)-2-(3,4-dihydro-2H-1-benzopyran-6-yl)-6-(trifluoromethyl)phenyl]acetic acid;
2-(tert-butoxy)-2-[2-(3,4-dihydro-2H-1-benzopyran-6-yl)-3-(prop-1-en-2-yl)-6-(trifluoromethyl)phenyl]acetic acid;
2-(tert-butoxy)-2-[2-(3,4-dihydro-2H-1-benzopyran-6-yl)-3-ethenyl-6-(trifluoromethyl)phenyl]acetic acid;
2-(tert-butoxy)-2-[2-(3,4-dihydro-2H-1-benzopyran-6-yl)-3-ethyl-6-(trifluoromethyl)phenyl]acetic acid;
tert-butoxy-(2-chroman-6-yl-3-cyclobutyl-6-methyl-phenyl)-acetic acid;
2-(tert-butoxy)-2-[3-cyclopropyl-2-(3,4-dihydro-2H-1-benzopyran-6-yl)-6-methylphenyl]acetic acid;
2-(tert-butoxy)-2-[3-cyclopropyl-2-(3,4-dihydro-2H-1-benzopyran-6-yl)-6-(trifluoromethyl)phenyl]acetic acid;
2-(tert-butoxy)-2-[3-cyclopropyl-2-(2,3-dihydropyrano[4,3,2-de]quinolin-7-yl)-6-methylphenyl]acetic acid;
2-(tert-butoxy)-2-(6-cyclopropyl-4'-methoxy-3-methyl-biphenyl-2-yl]acetic acid;
(S)-2-(tert-butoxy)-2-[3-cyclopropyl-2-(3,4-dihydro-2H-1-benzopyran-6-yl)-6-methylphenyl]acetic acid;
2-(tert-butoxy)-2-(6-cyclopropyl-3,4'-dimethyl-biphenyl-2-yl)-acetic acid;
2-(tert-butoxy)-2-(6-cyclopropyl-4'-fluoro-3-methyl-biphenyl-2-yl)-acetic acid;
2-(tert-butoxy)-2-[3-cyclopropyl-6-methyl-2-(5-methyl-chroman-6-yl)-phenyl]acetic acid;
(trans-3-bicyclopropyl-2-yl-2-chroman-6-yl-6-methyl-phenyl)-tert-butoxy-acetic acid;
2-(tert-butoxy)-2-[3-cyclopropyl-2-(4,4-dimethyl-cyclohex-1-enyl)-6-methyl-phenyl]acetic acid;
2-(tert-butoxy)-2-(4'-chloro-6-cyclopropyl-3-methyl-biphenyl-2-yl)acetic acid;
tert-butoxy-[3-cyclopropyl-2-(8-fluoro-5-methyl-chroman-6-yl)-6-methyl-phenyl]-acetic acid;
tert-butoxy-[2-chroman-6-yl-6-methyl-3-(1-methyl-cyclopropyl)-phenyl]-acetic acid;
tert-Butoxy-[2-chroman-6-yl-6-methyl-3-(cis-2-methyl-cyclopropyl)-phenyl]-acetic acid;
(S)-tert-butoxy-[3-cyclopropyl-6-methyl-2-(5-methyl-chroman-6-yl)-phenyl]-acetic acid;
(S)-tert-butoxy-[3-cyclopropyl-2-(8-fluoro-5-methyl-chroman-6-yl)-6-methyl-phenyl]-acetic acid;
tert-Butoxy-(2-chroman-6-yl-3-cyclopropylmethyl-6-methyl-phenyl)-acetic acid;
2-(tert-butoxy)-2-[2-(3,4-dihydro-2H-1-benzopyran-6-yl)-3-isopropyl-6-methylphenyl]acetic acid;
2-(tert-butoxy)-2-[2-(3,4-dihydro-2H-1-benzopyran-6-yl)-3-(propan-2-yl)-6-(trifluoromethyl)phenyl]acetic acid;
2-(tert-butoxy)-2-[2-(3,4-dihydro-2H-1-benzopyran-6-yl)-3-isopropenyl-6-methylphenyl]acetic acid;
2-chroman-6-yl-6-methyl-3-propyl-phenyl)-isopropoxy-acetic acid;
2-(2-chroman-6-yl-3-cyclopropyl-6-methyl-phenyl)-2-ethoxy-acetic acid;
2-[3-cyclopropyl-2-(3,4-dihydro-2H-1-benzopyran-6-yl)-6-methylphenyl]-2-cyclopropoxyacetic acid;
(S)-2-[3-cyclopropyl-2-(3,4-dihydro-2H-1-benzopyran-6-yl)-6-methylphenyl]-2-cyclopropoxyacetic acid;
(2-chroman-6-yl-3-cyclopropyl-6-methyl-phenyl)-propoxy-acetic acid;
(2-chroman-6-yl-3-cyclopropyl-6-methyl-phenyl)-cyclopropyl methoxy-acetic acid;
(2-chroman-6-yl-3-cyclopropyl-6-methyl-phenyl)-(2,2,2-trifluoro-ethoxy)-acetic acid;
(2-chroman-6-yl-3-cyclopropyl-6-methyl-phenyl)-cyclobutoxy-acetic acid;
(2-chroman-6-yl-3-cyclopropyl-6-methyl-phenyl)-(2,2-difluoro-ethoxy)-acetic acid;
(2-chroman-6-yl-3-cyclopropyl-6-methyl-phenyl)-(2-fluoro-ethoxy)-acetic acid;
(2-chroman-6-yl-3-cyclopropyl-6-methyl-phenyl)-isopropoxy-acetic acid;
cyclopropoxy-[3-cyclopropyl-2-(8-fluoro-5-methyl-chroman-6-yl)-6-methyl-phenyl]-acetic acid;
(2-chroman-6-yl-3-cyclopropyl-6-methyl-phenyl)-(1-methyl-cyclopropoxy)-acetic acid;
(S)-cyclopropoxy-[3-cyclopropyl-6-methyl-2-(5-methyl-chroman-6-yl)-phenyl]-acetic acid;
(2-chroman-6-yl-3-cyclopropyl-6-trifluoromethyl-phenyl)-cyclopropoxy-acetic acid;

cyclopropoxy-[3-cyclopropyl-6-methyl-2-(5-methyl-chroman-6-yl)-phenyl]-acetic acid;
(S)-cyclopropoxy-[3-cyclopropyl-2-(8-fluoro-5-methyl-chroman-6-yl)-6-methyl-phenyl]-acetic acid;
(2-chroman-6-yl-3-cyclopropyl-6-methyl-phenyl)-(2,2-difluoro-cyclopropoxy)-acetic acid;
2-[2-chroman-6-yl-3-cyclopropyl-5-(methanesulfonamido)-6-methyl-phenyl]-2-(cyclopropoxy)acetic acid;
2-(5-acetamido-2-chroman-6-yl-3-cyclopropyl-6-methyl-phenyl)-2-(cyclopropoxy)acetic acid;
2-[2-chroman-6-yl-3-cyclopropyl-5-(dimethylamino)-6-methyl-phenyl]-2-(cyclopropoxy)acetic acid;
2-[2-chroman-6-yl-3-cyclopropyl-5-[2-hydroxyethyl(methyl)amino]-6-methyl-phenyl]-2-(cyclopropoxy)acetic acid;
(2-chroman-6-yl-3-cyclopropyl-4-methanesulfonylamino-6-methyl-phenyl)-cyclopropoxy-acetic acid;
(4-acetylamino-2-chroman-6-yl-3-cyclopropyl-6-methyl-phenyl)-cyclopropoxy-acetic acid;
(3-chroman-6-yl-2-cyclopropyl-5-methyl-biphenyl-4-yl)-cyclopropoxy-acetic acid;
(2-chroman-6-yl-3-cyclopropyl-4-ethyl-6-methyl-phenyl)-cyclopropoxy-acetic acid;
(2-chroman-6-yl-3-cyclopropyl-4-methoxy-6-methyl-phenyl)-cyclopropoxy-acetic acid;
2-(2-chroman-6-yl-3-cyclopropyl-5-ethyl-6-methyl-phenyl)-2-(cyclopropoxy)acetic acid;
2-(2-chroman-6-yl-3-cyclopropyl-5-ethyl-6-methyl-phenyl)-2-(cyclopropoxy)acetic acid;
(2-chroman-6-yl-3-cyclopropyl-4,6-dimethyl-phenyl)-cyclopropoxy-acetic acid;
2-[2-chroman-6-yl-5-(cyclohexylmethylsulfonylamino)-3-cyclopropyl-6-methyl-phenyl]-2-(cyclopropoxy)acetic acid;
tert-butoxy-(6-chroman-6-yl-7-cyclopropyl-quinolin-5-yl)-acetic acid;
3-cyclopropyl-2-[3-cyclopropyl-2-(3,4-dihydro-2H-1-benzopyran-6-yl)-6-methylphenyl]propanoic acid;
2-[3-cyclopropyl-2-(3,4-dihydro-2H-1-benzopyran-6-yl)-6-methylphenyl]-4-methylpentanoic acid;
2-[3-cyclopropyl-2-(3,4-dihydro-2H-1-benzopyran-6-yl)-6-methylphenyl]pent-4-enoic acid.

In a second aspect, the invention also provides a process for the preparation of the compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG), or (HACD). The person skilled in the art is able to prepare the compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD) for example, by application or adaptation of the methods described in the prior art, or variations thereon as appreciated by the skilled person. The appropriate modifications and substitutions will be readily apparent and well known or readily obtainable from the scientific literature to those skilled in the art. After preparing the compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD), the person skilled in the art is able to recover the compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD) under their pure forms from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD) can, if desired, be further purified by various well-known techniques, such as recrystallization, reprecipitation or the various chromatography techniques, notably column chromatography or preparative thin layer chromatography. Further, the compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD) may contain one or more asymmetrically substituted carbon atom(s). The person skilled in the art is also able to isolate optically active or racemic forms of the compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD) by using well-known and standard techniques. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

In a third aspect, the invention provides a pharmaceutical composition comprising a compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD) as an active ingredient and at least one pharmaceutically acceptable carrier.

The pharmaceutical composition according to the invention may be prepared in the desired form by any of the methods well-known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000.

Preferred pharmaceutical composition in which a compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD) according to the invention, is formulated for oral or parenteral administration.

For oral administration, the pharmaceutical composition is under the form of tablets, pills, powders, capsules, troches, losenges or the like.

Other forms for the oral administration of the pharmaceutical composition is chosen among syrup, elixir or solution.

For parenteral administration, the pharmaceutical composition is under the form of sterile aqueous or non-aqueous solutions, suspensions, or emulsions.

The preferred dosage of compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF), (ABCG) or (HACD) in the pharmaceutical composition according to the invention to be administered is likely depending on such variables as the type and extent of progression of the viral infection, notably the HIV infection or related diseases, the overall health status of the particular patient, the relative biological efficacy of the compound selected, the formulation of the compound, the route of administration, the pharmacokinetic properties of the compound by the chosen delivery route, and the speed (bolus or continuous infusion) and schedule of administrations (number of repetitions in a given period of time).

In this embodiment, the pharmaceutical composition under a solid form for oral administration is normally formulated in unit dose and the pharmaceutical composition according to the invention provides from about 1 to 1000 mg of the compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD) according to the invention per unit dose. Some examples of dosages are 1 mg, 10 mg, 100 mg, 250 mg, 500 mg, and 1000 mg.

In this embodiment, the pharmaceutical composition under a liquid form for the oral and/or parenteral administration, is normally formulated in unit dose ranging from about 1 to 100 mg/mL of the compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF), (ABCG) or (HACD) according to the invention per dose and per day. Some examples of dosages are 1 mg/mL, 10 mg/mL, 25 mg/mL, 50 mg/mL, and 100 mg/mL.

In this embodiment, the pharmaceutical composition could further comprise at least one other antiviral agent. The antiviral agent is chosen among a compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD) different from the compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF) (ABCG) or (HACD) being administered with the antiviral agent; an HIV integrase catalytic site inhibitor such as, raltegravir (ISENTRESS®; Merck), elvitegravir (Gilead), soltegravir (dolutegravir, GSK; ViiV) and GSK 1265744 (GSK; ViiV); an HIV nucleoside reverse transcriptase inhibitor such as, abacavir (ZIAGEN®; GSK), didanosine (VIDEX®; BMS), tenofovir (VIREAD®; Gilead), emtricitabine (EMTRIVA®; Gilead), lamivudine (EPIVIR®; GSK/Shire), stavudine (ZERIT®; BMS), zidovudine (RETROVIR®; GSK), elvucitabine (Achillion), festinavir (Oncolys); an HIV non-nucleoside reverse transcriptase inhibitor such as, neviparine (VIRAMUNE®; BI), efavirenz (SUSTIVA®; BMS), etravirine (INTELENCE®; J&J), rilpivirine TMC278, R278474; J&J), fosdevirine (GSK/ViiV), lersivirine (Pfizer/ViiV); an HIV protease inhibitor such as, atazanavir (REYATAZ®; BMS), darunavir (PREZISTA®; J&J), indinavir (CRIXIVAN®; Merck), lopinavir (KELETRA®; Abbott), nelfinavir (VIRACEPT®; Pfizer), saquinavir (INVIRASE®; Hoffmann-La-Roche), tipranavir (APTIVUS®; BI), ritonavir (NORVIR®; Abbott), fosamprenavir (LEXIVA®; GSK/Vertex); an HIV entry inhibitor such as, maraviroc (SELZENTRY®; Pfizer), enfuvirtide (FUZEON®; Trimeris), BMS-663038 (BMS); an HIV maturation inhibitor such as, bevirimat (Myriad Genetics).

Generally, the at least one further antiviral agent will be present in a unit range similar to agents of that class used in therapy. Typically, this is 0.25-1000 mg per unit dose when the pharmaceutical composition according to the invention is under a solid form for the oral administration. Typically, this is 1-100 mg/mL per unit dose when the pharmaceutical composition according to the invention is under a liquid form for the oral and/or parenteral administration.

In a fourth aspect, the invention provides a use of a compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF), (ABCG) or (HACD) as a medicament to prevent or to treat a viral infection or related diseases, preferably to prevent or to treat a retroviral infection or related diseases, more preferably to prevent or to treat HIV infection or related diseases.

In a fifth aspect, the invention provides a method for the treatment or the prevention of a viral infection or related diseases, preferably a retroviral infection or related diseases and more preferably an HIV infection or related diseases, in a patient comprising the administration of a therapeutically effective amount of a compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF), (ABCG), or (HACD) or a racemate, enantiomer, stereoisomer, atropisomer or diastereoisomer or a pharmaceutically acceptable salt thereof, with a pharmaceutically acceptable carrier.

In a sixth aspect, the invention also provides a method for the treatment or the prevention of a viral infection or related diseases, preferably a retroviral infection or related diseases and more preferably HIV infection or related diseases, in a patient comprising the administration of a therapeutically effective amount of a compound of formula (I), (A), (B), (C), (D), (E), (F), (G), (H), (J), (K), (L), (AB), (AC), (AD), (AE), (AF), (AG), (BC), (BD), (BE), (BF), (BG), (CD), (CE), (CF), (CG), (HA), (HC), (HD), (DA), (EA), (FA), (GA), (ABC), (ABD), (ABE), (ABF), (ABG), (BCD), (BCE), (BCF), (BCG), (HAD), (HAC), (ABCD), (ABCE), (ABCF), (ABCG) or (HACD) or a racemate, enantiomer, stereoisomer, atropisomer or diastereoisomer or a pharmaceutically acceptable salt thereof, in combination with a therapeutically effective amount of at least one other antiviral agent as above-described with a pharmaceutically acceptable carrier.

EXAMPLES

The following examples are provided for the purpose of illustrating the present invention and by no means should be interpreted to limit the scope of the present invention. The first part represents the preparation of the compounds (intermediates and final compounds) whereas the second part describes the evaluation of antiviral activity of compounds according to the invention.

Preparation of the Compounds
Abbreviations or symbols used herein include:
DMSO: dimethylsulfoxide
MS: Mass Spectrometry
NMR: Nuclear Magnetic Resonance Spectroscopy
s: singlet
bs: broad singlet
d: doublet
t: triplet
q: quadruplet
dd: doubled doublet
ddd: doubled doubled doublet
dt: doubled triplet
m: massif
TLC: Thin Layer Chromatography Example 1

Synthesis of 2-(tert-butoxy)-2-[3-cyclopropyl-2-(3,4-dihydro-2H-1-benzopyran-6-yl)-6-methylphenyl]acetic acid

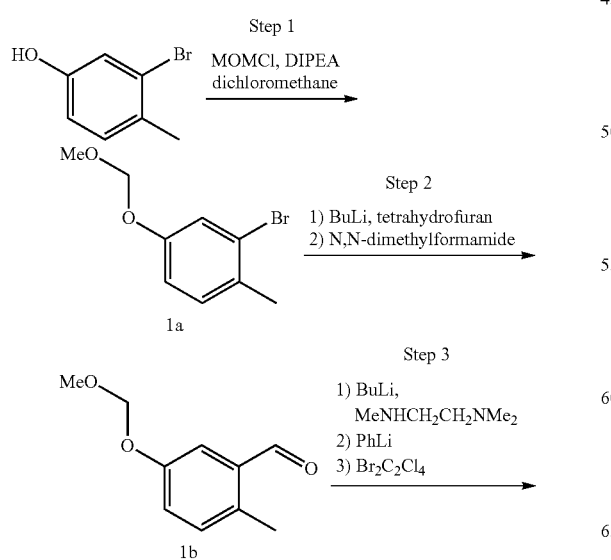

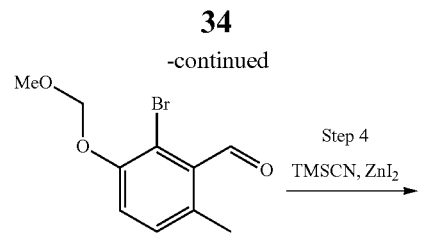

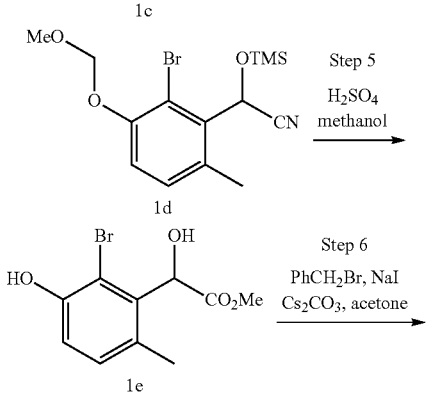

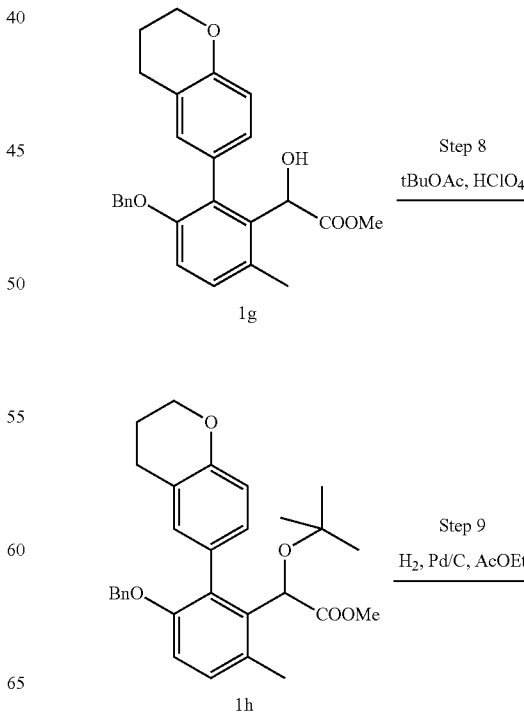

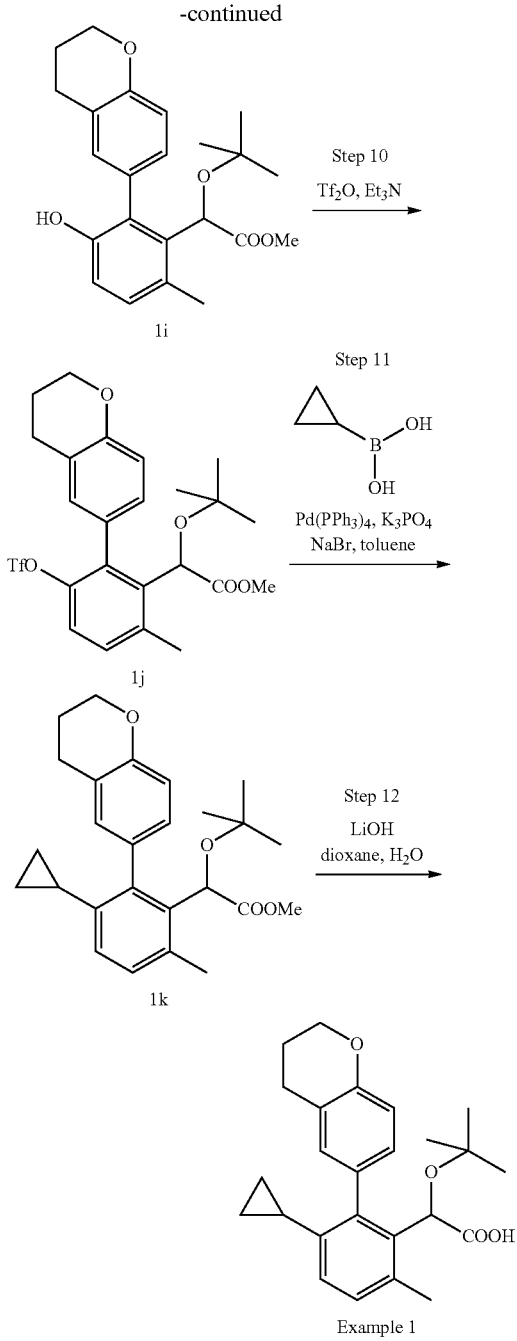

Example 1 provide 2-bromo-4-methoxymethoxy-1-methyl-benzene (1a) (4.55 g, 19.7 mmol, 95%) as a yellow oil.

$^1$H NMR (400 MHz, CDCl$_3$) δ 2.33 (s, 3H), 3.46 (s, 3H), 5.13 (s, 2H), 6.89 (dd, J=2.4 Hz, J=8.4 Hz, 1H), 7.12 (d, J=8.4 Hz, 1H), 7.25 (d, J=2.4 Hz, 1H).

Step 2: Preparation of Intermediate 5-methoxymethox-2-methyl-benzaldehyde (1b)

To a solution of 2-bromo-4-methoxymethoxy-1-methyl-benzene (1a) (4.54 g, 19.6 mmol) in anhydrous (100 mL) under nitrogen atmosphere at −78° C. was dropwise added a 1.6 M n-butyllithium solution in hexanes (15.3 mL, 24.5 mmol). The mixture was stirred at −78° C. for 30 minutes and N,N-dimethylformamide (2.3 mL, 29.7 mmol) was added. After 30 minutes at −78° C., water was added (100 mL). The layers were separated. The aqueous layer was extracted with ethyl acetate (2×50 mL). The combined organic layers were washed with brine (50 mL), dried over sodium sulfate and concentrated in vacuo to provide 5-methoxymethox-2-methyl-benzaldehyde (1b) (3.29 g, 18.2 mmol, 93%) as a yellow oil.

$^1$H NMR (300 MHz, CDCl$_3$) δ0.60 (s, 3H), 3.48 (s, 3H), 5.20 (s, 2H), 7.14-7.20 (m, 2H), 7.47 (s, 1H), 10.24 (s, 1H).

Step 3: Preparation of Intermediate 2-bromo-3-methoxymethox-6-methyl-benzaldehyde (1c)

To a solution of N,N',N'-trimethylethylenediamine (2.6 mL, 20 mmol) in anhydrous toluene (30 mL) at 0° C. under nitrogen atmosphere was dropwise added a 1.6 M n-butyllithium solution in hexanes (12 mL, 19.2 mmol). The mixture was stirred at room temperature for 15 minutes before adding a solution of 5-methoxymethox-2-methyl-benzaldehyde (1b) (3.28 g, 18.2 mmol) in anhydrous toluene (10 mL). After 15 minutes at room temperature, the mixture was cooled with an ice bath and a 1.8 M phenyllithium solution in dibutyl ether (30 mL, 54 mmol) was dropwise added. The mixture was stirred at room temperature overnight. Anhydrous (50 mL) was added to the resulting suspension and the mixture was cooled at −78° C. Dibromotetrachloroethane (17.8 g, 54.6 mmol) was portionwise added. The mixture was stirred at room temperature for 90 minutes before adding water (100 mL). The layers were separated. The aqueous layer was extracted with ethyl acetate (2×100 mL). The combined organic layers were washed with 1 M hydrochloric acid (100 mL), brine (100 mL), dried over sodium sulfate and concentrated in vacuo. The residue was purified by flash chromatography on silica gel (dichloromethane/ethyl acetate: 30/70) to provide 2-bromo-3-methoxymethox-6-methyl-benzaldehyde (1c) (2.78 g, 10.7 mmol, 59%) as a yellow solid.

$^1$H NMR (300 MHz, CDCl$_3$) δ 2.50 (s, 3H), 3.53 (s, 3H), 5.25 (s, 2H), 7.13 (d, J=8.4 Hz, 1H), 7.23 (d, J=8.4 Hz, 1H), 10.55 (s, 1H).

MS m/z ([M+H]$^+$) 259/261.

Step 4: Preparation of Intermediate 2-(2-bromo-3-methoxymethoxy-6-methylphenyl)-2-trimethylsilanyloxy-acetonitrile (1d)

To a solution of 2-bromo-3-methoxymethox-6-methyl-benzaldehyde (1c) (2.78 g, 10.7 mmol) in anhydrous dichloromethane (40 mL) at 0° C. older nitrogen atmosphere, were successively added zinc iodide (685 mg, 2.15 mmol) and trimethylsilylcyanide (2.0 mL, 16.1 mmol). The mixture was Step 1: Preparation of Intermediate 2-bromo-4-methoxymethoxy-1-methyl-benzene (1a)

To a solution of 3-bromo-4-methylphenol (3.87 g, 20.7 mmol) in anhydrous dichloromethane (40 mL) under nitrogen atmosphere at 0° C. were successively added diisopropylethylamine (5.4 mL, 31.0 mmol) and chloromethyl methyl ether (2.0 mL, 26.9 mmol). The mixture was stirred at 0° C. for 3 hours before adding water (40 mL). Layers were separated and the aqueous one was extracted with dichloromethane (40 mL). The combined organic layers were washed with a 2 M sodium hydroxide solution (30 mL), dried over sodium sulfate and concentrated in vacuo to stirred at 0° C. for 90 minutes before adding a saturated solution of sodium hydrogenocarbonate (40 mL). The layers were separated. The aqueous layer was extracted with dichloromethane (40 mL). The combined organic layers were dried over sodium sulfate and concentrated in vacuo to provide 2-(2-bromo-3-methoxymethoxy-6-methyl-phenyl)-2-trimethylsilanyloxy-acetonitrile (1 d) (3.78 g, 10.5 mmol, 98%) as a yellow oil.

$^1$H NMR (300 MHz, CDCl$_3$) δ 0.20 (s, 9H), 2.61 (s, 3H), 3.51 (s, 3H), 5.22 (s, 2H), 6.40 (s, 1H), 7.08 (d, J=8.4 Hz, 1H), 7.13 (d, J=8.4 Hz, 1H).

Step 5: Preparation of Intermediate methyl 2-(2-bromo-3-hydroxy-6-methylphenyl)-2-hydroxyacetate (1e)

To a solution of 2-(2-bromo-3-methoxymethoxy-6-methyl-phenyl)-2-trimethylsilanyloxy-acetonitrile (1d) (3.78 g, 10.5 mmol) in anhydrous methanol (50 mL) at 0° C. under nitrogen atmosphere was dropwise added sulfuric acid (23 mL). The mixture was refluxed overnight then cooled at room temperature and poured in water (150 mL). The aqueous layer was extracted with diethyl ether (2×50 mL) then with ethyl acetate (2×50 mL). The combined organic layers were washed with a saturated solution of sodium hydrogenocarbonate (100 mL), brine (100 mL), dried over sodium sulfate and concentrated in vacuo to provide methyl 2-(2-bromo-3-hydroxy-6-methyl-phenyl)-2-hydroxyacetate (1e) (2.58 g, 9.38 mmol, 89%) as a brown oil.

$^1$H NMR (300 MHz, CDCl$_3$) δ 2.33 (s, 3H), 3.43 (d, J=3.6 Hz, 1H), 3.79 (s, 3H), 5.56 (s, 1H), 5.72 (d, J=3.6 Hz, 1H), 6.93 (d, J=8.4 Hz, 1H), 7.04 (d, J=8.4 Hz, 1H).

Step 6: Preparation of Intermediate methyl 2-(3-benzyloxy-2-bromo-6-methylphenyl)-2-hydroxyacetate (1f)

To a solution of methyl 2-(2-bromo-3-hydroxy-6-methyl-phenyl)-2-hydroxyacetate (1e) (2.58 g, 9.38 mmol) in acetone (50 mL) were successively added cesium carbonate (3.67 g, 11.25 mmol) benzyl bromide (1.23 mL, 10.32 mmol) and sodium iodide (281 mg, 1.88 mmol). The mixture was refluxed for 45 minutes then concentrated in vacuo. Water (50 mL) was added to the residue. The aqueous layer was extracted with ethyl acetate (2×50 mL). The combined organic layers were washed with a 2M sodium hydroxide solution (30 mL), brine (30 mL), dried over sodium sulfate and concentrated in vacuo. The residue was purified by flash chromatography on silica gel (cyclohexane/ethyl acetate: 80/20) to provide methyl 2-(3-benzyloxy-2-bromo-6-methylphenyl)-2-hydroxyacetate (1f) (2.38 g, 6.51 mmol, 69%) as a white solid.

$^1$H NMR (300 MHz, CDCl$_3$) δ 2.34 (s, 3H), 3.49 (d, J=4.4 Hz, 1H), 3.78 (s, 3H), 5.13 (s, 2H), 5.86 (d, J=4.4 Hz, 1H), 6.84 (d, J=8.4 Hz, 1H), 7.06 (d, J=8.4 Hz, 1H), 7.30-7.34 (m, 1H), 7.37-7.41 (m, 2H), 7.47 (d, J=7.4 Hz, 2H).

MS m/z ([M+H−H$_2$O]$^+$) 347/349.

Step 7: Preparation of Intermediate methyl 2-[3-benzyloxy-2-(3,4-dihydro-2H-1-benzopyran-6-yl)-6-methylphenyl]-2-hydroxyacetate (1g)

To a degassed mixture of methyl 2-(3-benzyloxy-2-bromo-6-methylphenyl)-2-hydroxyacetate (1f) (383 mg, 1.05 mmol), sodium carbonate (333 mg, 3.15 mmol), 6-(4,4,5,5-tetramethyl-1,3,2-dioxaborolan-2-yl)chroman (327 mg, 1.26 mmol) in dioxane (4 mL) and water (0.8 mL) was added palladium tetrakis(triphenylphosphine) (121 mg, 0.10 mmol). The mixture was heated at 120° C. overnight. Water (10 mL) was added. The aqueous layer was extracted with ethyl acetate (2×10 mL). The combined organic layers were washed with brine (10 mL), dried over sodium sulfate and concentrated in vacuo. The residue was purified by flash chromatography on silica gel (cyclohexane/ethyl acetate: 80/20) to provide methyl 2-[3-benzyloxy-2-(3,4-dihydro-2H-1-benzopyran-6-yl)-6-methylphenyl]-2-hydroxyacetate (1g) (347 mg, 0.83 mmol, 79%) as a yellow foam.

$^1$H NMR (300 MHz, CDCl$_3$) δ 2.01-2.08 (m, 2H), 2.26 and 2.28 (s, 3H), 2.78-2.82 (m, 2H), 3.09 and 3.11 (d, J=2.8 Hz, 1H), 3.70 and 3.72 (s, 3H), 4.21-4.26 (m, 2H), 4.97 (s, 2H), 5.26 (d, J=2.8 Hz, 1H), 6.81-6.89 (m, 2H), 6.98-7.16 (m, 5H), 7.22-7.30 (m, 3H). MS m/z ([M+H−H$_2$O]$^+$) 401.

Step 8: Preparation of Intermediate methyl 2-(tert-butoxy)-2-[3-benzyloxy-2-(3,4-dihydro-2H-1-benzopyran-6-yl)-6-methylphenyl]acetate (1h)

To a solution of methyl 2-[3-benzyloxy-2-(3,4-dihydro-2H-1-benzopyran-6-yl)-6-methylphenyl]-2-hydroxyacetate (1g) (347 mg, 0.83 mmol) in tert-butyl acetate (7 mL) at 0° C. was added perchloric acid (0.45 mL). The mixture was stirred at 0° C. for 90 minutes hours before being poured into a saturated aqueous solution of sodium hydrogenocarbonate (20 mL). The layers were separated and the aqueous layer was extracted with ethyl acetate (2×20 mL). The organic layers were washed with brine, dried over sodium sulfate and concentrated in vacuo. The residue was purified by flash chromatography on silica gel (cyclohexane/ethyl acetate 80/20) to provide the intermediate methyl 2-(tert-butoxy)-2-[3-benzyloxy-2-(3,4-dihydro-2H-1-benzopyran-6-yl)-6-methylphenyl]acetate (1h) (263 mg, 0.55 mmol, 66%).

$^1$H NMR (300 MHz, CDCl$_3$) δ 0.96 (s, 9H), 2.00-2.09 (m, 2H), 2.35 and 2.36 (s, 3H), 2.72-2.82 (m, 2H), 3.70 and 3.71 (s, 3H), 4.22-4.26 (m, 2H), 4.88-5.01 (m, 2H), 5.16 and 5.18 (s, 1H), 6.81-6.87 (m, 2H), 6.99-7.29 (m, 8H).

MS m/z ([M+Na]$^+$) 497.

Step 9: Preparation of Intermediate methyl 2-(tert-butoxy)-2-[2-(3,4-dihydro-2H-1-benzopyran-6-yl)-3-hydroxy-6-methylphenyl]acetate (1i)

A suspension of methyl 2-(tert-butoxy)-2-[3-benzyloxy-2-(3,4-dihydro-2H-1-benzopyran-6-yl)-6-methylphenyl]acetate (1h) (263 mg, 0.55 mmol) and palladium on carbon (30 mg) in ethyl acetate (5 mL) was stirred at room temperature under hydrogen atmosphere for 36 hours. The mixture was filtered over Millipore and concentrated in vacuo. The residue was purified by flash chromatography on silica gel (cyclohexane/ethyl acetate: 80/20) to provide methyl 2-(tert-butoxy)-2-[2-(3,4-dihydro-2H-1-benzopyran-6-yl)-3-hydroxy-6-methylphenyl]acetate (1i) (120 mg, 0.31 mmol, 56%).

$^1$H NMR (300 MHz, CDCl$_3$) δ 0.97 and 0.98 (s, 9H), 2.01-2.09 (m, 2H), 2.34 and 2.35 (s, 3H), 2.71-2.86 (m, 2H), 3.67 and 3.68 (s, 3H), 4.24-4.27 (m, 2H), 4.63 and 4.67 (s, 1H), 4.99 and 5.00 (s, 1H), 6.82-7.05 (m, 4H), 7.12-7.19 (m, 1H).

MS m/z ([M+Na]$^+$) 407.
MS m/z ([M−H]$^-$) 383.

Step 10: Preparation of Intermediate methyl 2-(tert-butoxy)-2-[2-(3,4-dihydro-2H-1-benzopyran-6-yl)-6-methyl-3-trifluoromethanesulfonyloxy-phenyl]acetate (1j)

A solution of methyl 2-(tert-butoxy)-2-[2-(3,4-dihydro-2H-1-benzopyran-6-yl)-3-hydroxy-6-methylphenyl]acetate (1i) (145 mg, 0.038 mmol) in anhydrous dichloromethane (5 mL) under nitrogen atmosphere at −78° C. were successively added triethylamine (158 μL, 1.136 mmol), and trifluoromethanesulfonic anhydride (79 μL, 0.47 mol). The mixture was stirred at this temperature for 1 hour before adding water (5 mL). Layers were separated. The aqueous layer was extracted with dichloromethane (5 mL). The combined organic layers were washed with a saturated solution of sodium hydrogenaocarbonate (5 mL), dried over sodium chloride and concentrated in vacuo to provide methyl 2-(tert-butoxy)-2-[2-(3,4-dihydro-2H-1-benzopyran-6-yl)-6-methyl-3-trifluoromethanesulfonyloxy-phenyl]acetate (1j) (193 mg, 0.37 mmol, 99%) as a colorless oil.

$^1$H NMR (300 MHz, CDCl$_3$) δ 0.95 and 0.96 (s, 9H), 2.00-2.09 (m, 2H), 2.43 and 2.45 (s, 3H), 2.68-2.87 (m, 2H), 3.70 and 3.71 (s, 3H), 4.22-4.26 (m, 2H), 5.11 and 5.13 (s, 1H), 6.82-6.87 (m, 1H), 6.94-7.11 (m, 2H), 7.15-7.21 (m, 2H).

MS m/z ([M−H]$^−$) 515.

Step 11: Preparation of Intermediate methyl 2-(tert-butoxy)-2-[3-cyclopropyl-2-(3,4-dihydro-2H-1-benzopyran-6-yl)-6-methylphenyl]acetate (1k)

A degassed solution of methyl 2-(tert-butoxy)-2-[2-(3,4-dihydro-2H-1-benzopyran-6-yl)-6-methyl-3-trifluoromethanesulfonyloxy-phenyl]acetate (1j) (50 mg, 0.096 mmol), cyclopropylboronic acid (42 mg, 0.48 mmol), sodium bromide (11 mg, 0.11 mmol), potassium phosphate tribasic monohydrate (74 mg, 0.32 mmol) and palladium tetrakis (triphenylphosphine) (11 mg, 0.001 mmol) in toluene (1 mL) was heated in microwaves at 120° C. for 4 hours. Water (5 mL) was added. The aqueous layer was extracted with ethyl acetate (2×5 mL). The combined organic layers were washed with a saturated solution of sodium hydrogenocarbonate (5 mL), brine (5 mL), dried over sodium sulfate and concentrated in vacuo. The residue was purified by preparative TLC (cyclohexane/ethyl acetate: 90/10) to provide methyl 2-(tert-butoxy)-2-[3-cyclopropyl-2-(3,4-dihydro-2H-1-benzopyran-6-yl)-6-methylphenyl]acetate (1k) (35 mg, 0.085 mmol, 87%).

$^1$H NMR (300 MHz, CDCl$_3$) δ 0.52-0.74 (m, 4H), 0.98 (s, 9H), 1.41-1.52 (m, 1H), 1.99-2.10 (m, 2H), 2.39 (s, 3H), 2.67-2.87 (m, 2H), 3.65 and 3.67 (s, 3H), 4.22-4.26 (m, 2H), 5.08 and 5.10 (s, 1H), 6.72-6.85 (m, 2H), 6.94-7.10 (m, 3H).

MS m/z ([M+Na]$^+$) 431.

Step 12: Preparation of 2-(tert-butoxy)-2-[3-cyclopropyl-2-(3,4-dihydro-2H-1-benzopyran-6-yl)-6-methylphenyl]acetic acid (Example 1)

A mixture of methyl 2-(tert-butoxy)-2-[3-cyclopropyl-2-(3,4-dihydro-2H-1-benzopyran-6-yl)-6-methylphenyl]acetate (1k) (279 mg, 0.68 mmol) and lithium hydroxide (131 mg, 5.46 mmol) in dioxane (4 mL) and water (2 mL) was heated at 110° C. for 24 hours. The mixture was concentrated in vacuo. Water (5 mL) was added to the residue and this mixture was extracted this diethyl ether (2×10 mL). The aqueous layer was acidified with 1M hydrochloric acid until pH 3 and extracted with diethyl ether (2×10 mL). The organic layer was dried over sodium sulfate and concentrated in vacuo to provide 2-(tert-butoxy)-2-[3-cyclopropyl-2-(3,4-dihydro-2H-1-benzopyran-6-yl)-6-methylphenyl]acetic acid (Example 1) (247 mg, 0.63 mmol, 91%) as a white solid.

$^1$H NMR (300 MHz, CDCl$_3$) δ 0.53-0.77 (m, 4H), 1.00 (s, 9H), 1.48-1.55 (m, 1H), 2.00-2.08 (m, 2H), 2.35 (s, 3H), 2.70-2.87 (m, 2H), 4.21-4.25 (m, 2H), 5.22 (s, 1H), 6.75-6.86 (m, 2H), 6.96-7.05 (m, 2H), 7.23 (bs, 1H).

MS m/z ([M−H]$^−$) 393.

Example 2

Synthesis of 2-(tert-butoxy)-2-[3-cyclopropyl-2-(3,4-dihydro-2H-1-benzopyran-6-yl)-6-(trifluoromethyl)phenyl]acetic acid

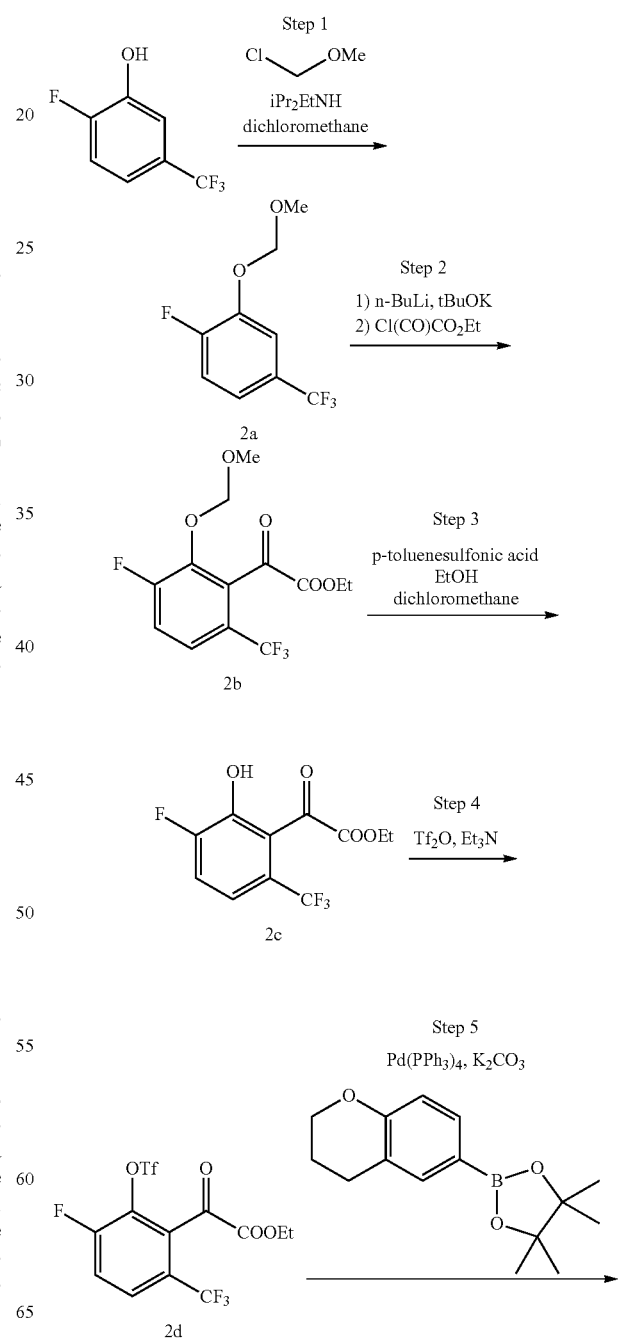

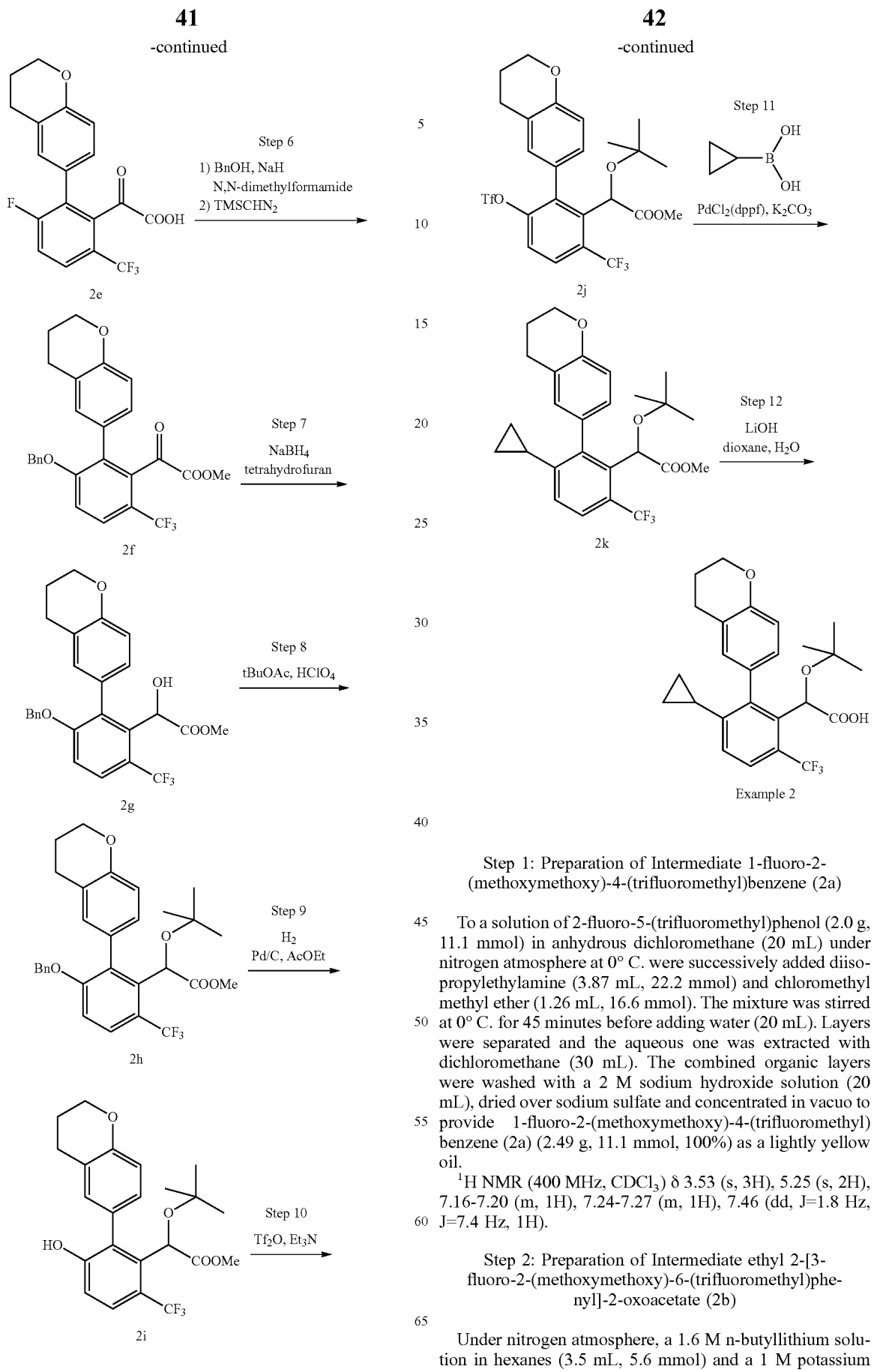

Step 1: Preparation of Intermediate 1-fluoro-2-(methoxymethoxy)-4-(trifluoromethyl)benzene (2a)

To a solution of 2-fluoro-5-(trifluoromethyl)phenol (2.0 g, 11.1 mmol) in anhydrous dichloromethane (20 mL) under nitrogen atmosphere at 0° C. were successively added diisopropylethylamine (3.87 mL, 22.2 mmol) and chloromethyl methyl ether (1.26 mL, 16.6 mmol). The mixture was stirred at 0° C. for 45 minutes before adding water (20 mL). Layers were separated and the aqueous one was extracted with dichloromethane (30 mL). The combined organic layers were washed with a 2 M sodium hydroxide solution (20 mL), dried over sodium sulfate and concentrated in vacuo to provide 1-fluoro-2-(methoxymethoxy)-4-(trifluoromethyl)benzene (2a) (2.49 g, 11.1 mmol, 100%) as a lightly yellow oil.

$^1$H NMR (400 MHz, CDCl$_3$) δ 3.53 (s, 3H), 5.25 (s, 2H), 7.16-7.20 (m, 1H), 7.24-7.27 (m, 1H), 7.46 (dd, J=1.8 Hz, J=7.4 Hz, 1H).

Step 2: Preparation of Intermediate ethyl 2-[3-fluoro-2-(methoxymethoxy)-6-(trifluoromethyl)phenyl]-2-oxoacetate (2b)

Under nitrogen atmosphere, a 1.6 M n-butyllithium solution in hexanes (3.5 mL, 5.6 mmol) and a 1 M potassium tert-butoxide solution in (5.6 mL, 5.6 mmol) were added to anhydrous (30 mL) at −78° C. The mixture was stirred for 15 minutes before adding dropwise a solution of 1-fluoro-2-(methoxymethoxy)-4-(trifluoromethyl)benzene (2a) (1.0 g, 4.46 mmol) in (10 mL). The mixture was stirred at −78° C. for 2 hours and was added via cannulation to a solution of ethyl oxalyl chloride (1.4 mL, 9.0 mmol) in (20 mL) at −78° C. The mixture was stirred at −78° C. for 45 minutes and water (50 mL) was added. Layers were separated and the aqueous layer was extracted with ethyl acetate (2×30 mL). The combined organic layers were washed with a saturated solution of sodium hydrogenocarbonate (30 mL), brine (30 mL), dried over sodium sulfate and concentrated in vacuo. The residue was purified by flash chromatography on silica gel (cyclohexane/ethyl acetate 90/10) to provide ethyl 2-[3-fluoro-2-(methoxymethoxy)-6-(trifluoromethyl)phenyl]-2-oxoacetate (840 mg, 2.59 mmol, 58%) (2b) as a yellow oil.

$^1$H NMR (300 MHz, CDCl$_3$) δ 1.36 (t, J=7.2 Hz, 3H), 3.45 (s, 3H), 4.38 (q, J=7.2 Hz, 2H), 5.16 (s, 2H), 7.28-7.34 (m, 1H), 7.43 (dd, J=4.4 Hz, J=8.8 Hz, 1H).

Step 3: Preparation of Intermediate ethyl 2-[3-fluoro-2-hydroxy-6-(trifluoromethyl)phenyl]-2-oxoacetate (2c)

To a solution of ethyl 2-[3-fluoro-2-(methoxymethoxy)-6-(trifluoromethyl)phenyl]-2-oxoacetate (2b) (500 mg, 1.54 mmol) and p-toluenesulfonic acid (59 mg, 0.31 mmol) in dichloromethane (7.5 mL) and ethanol (1.5 mL) was heated at 50° C. overnight. The mixture was concentrated in vacuo. The residue was purified by flash chromatography on silica gel (cyclohexane/ethyl acetate 60/40) to provide ethyl 2-[3-fluoro-2-hydroxy-6-(trifluoromethyl)phenyl]-2-oxoacetate (2c) (394 mg, 1.40 mmol, 91%) as a yellow oil.

$^1$H NMR (300 MHz, CDCl$_3$) δ 1.38 (t, J=7.2 Hz, 3H), 4.38 (q, J=7.2 Hz, 2H), 6.91 (d, J=2.7 Hz), 7.26-7.35 (m, 2H).

Step 4: Preparation of Intermediate ethyl 2-{3-fluoro-2-[(trifluoromethane)sulfonyloxy]-6-(trifluoromethyl)phenyl}-2-oxoacetate (2d)

To a solution of ethyl 2-[3-fluoro-2-hydroxy-6-(trifluoromethyl)phenyl]-2-oxoacetate (394 mg, 1.41 mmol) (2c) in anhydrous dichloromethane (5 mL) under nitrogen atmosphere at −78° C. were successively added triethylamine (0.24 mL 1.69 mmol) and triflic anhydride (0.26 mL, 1.55 mmol). The mixture was stirred at −78° C. for 45 minutes before adding water (10 mL). Layers were separated. The aqueous layer was extracted with dichloromethane (10 mL). The combined organic layers were washed with a saturated solution of sodium hydrogenocarbonate (10 mL), dried over sodium sulfate and concentrated in vacuo to ethyl 2-{3-fluoro-2-[(trifluoromethane)sulfonyloxy]-6-(trifluoromethyl)phenyl}-2-oxoacetate (2d) (548 mg, 1.32 mmol, 94%) as a yellow oil which was used without further purification.

$^1$H NMR (300 MHz, CDCl$_3$) δ 1.37 (t, J=7.2 Hz, 3H), 4.42 (q, J=7.2 Hz, 2H), 7.55 (t, J=8.7 Hz), 7.78 (dd, J=4.5 Hz, J=8.7 Hz, 1H).

Step 5: Preparation of Intermediate 2-[2-(3,4-dihydro-2H-1-benzopyran-6-yl)-3-fluoro-6-(trifluoromethyl)phenyl]-2-oxoacetic acid (2e)

A degassed solution of ethyl 2-{3-fluoro-2-[(trifluoromethane)sulfonyloxy]-6-(trifluoromethyl)phenyl}-2-oxoacetate (2d) (8.0 g, 19.41 mmol), potassium carbonate (10.73 g, 77.63 mmol), 6-(4,4,5,5-tetramethyl-1,3,2-dioxaborolan-2-yl)chroman (6.56 g, 25.23 mmol) and palladium tetrakis(triphenylphosphine) (2.24 g, 1.94 mmol) in dioxane (167 mL) and water (33.5 mL) was heated at 85° C. for 20 hours. Water (30 mL) was added and the reaction mixture was heated at 85° C. for 1h more. Water (170 mL) was added and dioxane was evaporated in vacuo. Diethyl ether (2×80 mL) was added and the layers were separated. The organic layer was washed with a saturated solution of sodium hydrogenocarbonate (170 mL). The combined aqueous layers were acidified with 2N hydrochloric acid until pH 2 then extracted with diethyl ether (2×170 mL). The organic layer was dried over sodium sulfate and concentrated in vacuo to provide 2-[2-(3,4-dihydro-2H-1-benzopyran-6-yl)-3-fluoro-6-(trifluoromethyl)phenyl]-2-oxoacetic acid (2e) (6.09g, 16.54 mmol, 85%) as a orange oil which was used without further purification.

$^1$H NMR (300 MHz, CDCl$_3$) δ 1.97-2.04 (m, 2H), 2.77 (t, J=6.5 Hz, 2H), 4.21 (t, J=5.2 Hz, 2H), 6.81 (s, 1H), 6.92 (m, 2H), 7.39 (t, J=8.6 Hz, 1H), 7.73 (dd, J=8.6, 4.8 Hz, 1H).

Step 6: Preparation of Intermediate methyl 2-[3-(benzyloxy)-2-(3,4-dihydro-2H-1-benzopyran-6-yl)-6-(trifluoromethyl)phenyl]-2-oxoacetate (2f)

To a suspension of sodium hydride 60% in oil (340 mg, 14.2 mmol) in anhydrous N,N-dimethylformamide (14 mL) at 0° C. under nitrogen atmosphere, was dropwise added anhydrous benzyl alcohol (1.47 mL, 14.2 mmol). The mixture was stirred at room temperature for 30 minutes before adding dropwise a solution of 2-[2-(3,4-dihydro-2H-1-benzopyran-6-yl)-3-fluoro-6-(trifluoromethyl)phenyl]-2-oxoacetic acid (2e) (1.306 g, 3.55 mmol) in anhydrous N,N-dimethylformamide (13 mL) at 0° C. The dark red mature was stirred at 60° C. for 3 hours. The dark green solution was cooled at 0° C. and water (80 mL) was added cautiously. The resulting basic solution was extracted with diethyl ether (2×70 mL). The aqueous phase was acidified with 1 M hydrochloric acid until pH 2, then extracted with AcOEt (3×70 mL). The combined organic layers were washed with brine (50 mL), dried over sodium sulfate and concentrated in vacuo. The residue was dissolved in toluene and concentrated. The residue was dissolved in cyclohexane (41.0 mL) and methanol (20.5 mL) at 0° C. and a 2 M solution of trimethylsilyldiazomethane in diethyl ether (4.4 mL, 8.87 mmol) was added. The mixture was stirred at room temperature for 30 minutes before adding acetic acid (0.5 mL). The mixture was concentrated in vacuo. The residue was dissolved in ethyl acetate (120 mL), washed with a saturated solution of sodium hydrogenocarbonate (120 mL), brine (120 mL), dried over sodium sulfate, concentrated in vacuo an then co-evaporated with toluene to provide methyl 2-[3-(benzyloxy)-2-(3,4-dihydro-2H-1-benzopyran-6-yl)-6-(trifluoro methyl)phenyl]-2-oxo acetate (2f) (1.31g, 2.78 mmol, 78%) as a orange oil that was used without further purification.

$^1$H NMR (300 MHz, CDCl$_3$) δ 1.97-2.05 (m, 2H), 2.75 (t, J=6.4 Hz, 2H), 3.55 (s, 3H), 4.19-4.22 (m, 2H), 5.15 (s, 2H), 6.80 (d, J=8.4 Hz, 1H), 6.85 (d, J=2.1 Hz, 1H), 6.99 (dd, J=2.1 Hz, J=8.4 Hz, 1H), 7.11 (d, J=8.7 Hz, 1H), 7.23-7.36 (m, 5H), 7.65 (d, J=8.7 Hz, 1H).

Step 7: Preparation of Intermediate methyl 2-[3-(benzyloxy)-2-(3,4-dihydro-2H-1-benzopyran-6-yl)-6-(trifluoromethyl)phenyl]-2-hydroxyacetate (2g)

To a solution of methyl 2-[3-(benzyloxy)-2-(3,4-dihydro-2H-1-benzopyran-6-yl)-6-(trifluoromethyl)phenyl]-2-oxoacetate (2f) (1.32 g, 2.81 mmol) in e (44 mL) at 0° C. was added portion-wise sodium borohydride (159 mg, 4.21 mmol). The mixture was stirred at 0° C. for 90 minutes. Acetic acid (0.5 mL) was added, followed by water (60 mL). The resulting solution was extracted with ethyl acetate (3×50 mL). The organic layer was washed with brine (30 mL) and dried over sodium sulfate. The residue was purified by flash chromatography on silica gel (cyclohexane/ethyl acetate 80/20) to provide methyl 2-[3-(benzyloxy)-2-(3,4-dihydro-2H-1-benzopyran-6-yl)-6-(trifluoromethyl)phenyl]-2-hydroxyacetate (2g) (1.04 g, 2.20 mmol, 78%).

$^1$H NMR (300 MHz, CDCl$_3$) δ 2.01-2.09 (m, 2H), 2.75-2.82 (m, 2H), 3.57 and 3.60 (2 s, 3H), 4.24 (t, J=5.1 Hz, 2H), 5.07 (s, 2H), 5.38 (bs, 1H), 6.79-6.85 (m, 2H), 6.97-7.14 (m, 4H), 7.24-7.31 (m, 3H), 7.65 (d, J=8.7 Hz, 1H).

Step 8: Preparation of Intermediate methyl 2-[3-(benzyloxy)-2-(3,4-dihydro-2H-1-benzopyran-6-yl)-6-(trifluoromethyl)phenyl]-2-(tert-butoxy)acetate (2h)

Under nitrogen, methyl 2-[3-(benzyloxy)-2-(3,4-dihydro-2H-1-benzopyran-6-yl)-6-(trifluoromethyl)phenyl]-2-hydroxyacetate (2g) (5.36 g, 11.35 mmol) was dissolved in tea-butyl acetate (142 mL), cooled at 0° C. and 70% perchloric acid (2.94 mL, 34.04 mmol) was added. The reaction mixture was stirred at room temperature for 2 hours. Then the reaction mixture was poured into a saturated solution of sodium hydrogenocarbonate. The mixture was extracted with ethyl acetate. The resulting organic layer was washed with brine, dried over sodium sulfate and concentrated in vacuo. The crude mixture was purified by DCVC (Dry Column Vacuum Chromatography, using 250 mL Silicagel, cyclohexane/ethyl acetate 100/0 to 60/40) to provide methyl 2-[3-(benzyloxy)-2-(3,4-dihydro-2H-1-benzopyran-6-yl)-6-(trifluoromethyl)phenyl]-2-(tert-butoxy)acetate (2h) (3.58 g, 6.77 mmol, 58%) as a yellow oil.

$^1$H NMR (300 MHz, CDCl$_3$) δ 0.99 and 1.36 and 1.37 (s, 9H), 2.00-2.09 (m, 2H), 2.70-2.85 (m, 2H), 3.59 and 3.61 and 3.69 and 3.70 (s, 3H), 4.22-4.27 (m, 2H), 5.00-5.41 (m, 3H), 6.81-7.32 (m, 9H), 7.63-7.70 (m, 1H).

Step 9: Preparation of Intermediate methyl 2-(tert-butoxy)-2-[2-(3,4-dihydro-2H-1-benzopyran-6-yl)-3-hydroxy-6-(trifluoromethyl)phenyl]acetate (2i)

A solution of methyl 2-[3-(benzyloxy)-2-(3,4-dihydro-2H-1-benzopyran-6-yl)-6-(trifluoromethyl)phenyl]-2-(tert-butoxy)acetate (2h) (3.48g, 6.57 mmol) in ethyl acetate (130 mL) was passed through the H-Cube (0.8 mL/min, full H$_2$ mode, 40° C.). The resulting solution was concentrated in vacuo to provide methyl 2-(tert-butoxy)-2-[2-(3,4-dihydro-2H-1-benzopyran-6-yl)-3-hydroxy-6-(trifluoromethyl)phenyl]acetate (2i) (2.62 g, 5.97 mmol, 91%) as a white solid.

$^1$H NMR (300 MHz, CDCl$_3$) δ 1.00 and 1.01 (s, 9H), 2.05 (m, 2H), 2.78 (m, 2H), 3.66 (s, 3H), 4.25 (m, 2H), 5.04 and 5.05 (s, 1H), 5.10 and 5.13 (s, 1H), 6.89-6.93 (m, 2H), 6.99 (d, J=10.0 Hz, 1H), 7.08-7.11 (m, 1H), 7.62 (d, J=8.7 Hz, 1H).

MS m/z ([M−H]$^-$) 437.

Step 10: Preparation of Intermediate methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (2j)

To a solution of methyl 2-(tert-butoxy)-2-[2-(3,4-dihydro-2H-1-benzopyran-6-yl)-3-hydroxy-6-(trifluoromethyl)phenyl]acetate (2i) (1.00 g, 2.28 mmol) in anhydrous dichloromethane (16 mL) under nitrogen atmosphere at −78° C. were successively added triethylamine (0.95 mL, 6.84 mmol) and triflic anhydride (0.48 mL, 2.85 mmol). The colorless solution was stirred at −78° C. for 45 minutes before adding water (30 mL). The layers were separated. The aqueous layer was extracted with dichloromethane (30 mL). The combined organic layers were washed with a saturated solution of sodium hydrogenocarbonate (30 mL), dried over sodium sulfate and concentrated in vacuo to provide methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (2j) (1.30 g, 2.28 mmol, 100%) as a orange oil.

$^1$H NMR (300 MHz, CDCl$_3$) δ 0.98 and 0.99 (s, 9H), 1.98-2.10 (m, 2H), 2.65-2.85 (m, 2H), 3.70 (s, 3H), 4.20-4.28 (m, 2H), 5.12 (s, 1H), 6.80-7.05 (m, 3H), 7.42 (d, J=8.7 Hz, 1H), 7.80 (d, J=8.7 Hz, 1H).

Step 11: Preparation of Intermediate methyl 2-(tert-butoxy)-2-[3-cyclopropyl-2-(3,4-dihydro-2H-1-benzopyran-6-yl)-6-(trifluoromethyl)phenyl]acetate (2k)

A degassed solution of methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (2j) (50 mg, 0.088 mmol), potassium carbonate (36 mg, 0.263 mmol), cyclopropylboronic acid (38 mg, 0.438 mmol) and [1,1'-Bis(diphenylphosphino)ferrocene]dichloropalladium(II), complex with dichloromethane (7 mg, 0.009 mmol) in dimethoxyethane (1 mL) and water (0.1 mL) was heated under microwaves at 120° C. for 3 hours. Water (5 mL) was added. The aqueous layer was extracted with ethyl acetate (2×5 mL). The combined organic layers were washed with a saturated solution of sodium hydrogenocarbonate (5 mL), brine (5 mL), dried over sodium sulfate and concentrated in vacuo. The residue was purified by preparative TLC (dichloromethane/ethyl acetate: 90/10) followed by a second one (dichloromethane/cyclohexane: 90/10) to provide methyl 2-(tert-butoxy)-2-[3-cyclopropyl-2-(3,4-dihydro-2H-1-benzopyran-6-yl)-6-(trifluoromethyl)phenyl]acetate (2k) (20 mg, 0.043 mmol, 49%).

$^1$H NMR (400 MHz, CDCl$_3$) δ 0.61-0.86 (m, 4H), 1.00 (s, 9H), 1.46-1.56 (m, 1H), 1.98-2.11 (m, 2H), 2.69-2.87 (m, 2H), 3.65 and 3.67 (s, 3H), 4.21-4.26 (m, 2H), 5.07 and 5.08 (s, 1H), 6.81 and 6.83 (d, J=8.4 Hz, 1H), 6.86-7.04 (m, 3H), 7.59 (d, J=8.3 Hz, 1H).

MS m/z ([M+Na]$^+$) 485.

Step 12: Preparation of 2-(tert-butoxy)-2-[3-cyclopropyl-2-(3,4-dihydro-2H-1-benzopyran-6-yl)-6-(trifluoromethyl)phenyl]acetic acid (Example 2)

Using the procedure described in example 1, step 12, methyl 2-(tert-butoxy)-2-[3-cyclopropyl-2-(3,4-dihydro-2H-1-benzopyran-6-yl)-6-(trifluoromethyl)phenyl]acetate (2k) (20 mg, 0.043 mmol) is converted into 2-(tert-butoxy)-2-[3-cyclopropyl-2-(3,4-dihydro-2H-1-benzopyran-6-yl)-6-(trifluoromethyl)phenyl]acetic acid (Example 2) (10 mg, 0.022 mmol, 52%).

$^1$H NMR (400 MHz, CDCl$_3$) δ 0.59-0.90 (m, 4H), 1.02 (s, 9H), 1.48-1.57 (m, 1H), 2.00-2.107 (m, 2H), 2.73-2.89 (m, 2H), 4.20-4.26 (m, 2H), 5.20 (bs, 1H), 6.80-7.00 (m, 3H), 7.30 (bs, 1H), 7.60 (d, J=8.3 Hz, 1H).

MS m/z ([M−H]$^-$) 447.

Example 3

Synthesis of 2-(tert-butoxy)-2-[3-cyclopropyl-2-(2,3-dihydropyrano[4,3,2-de]quinolin-7-yl)-6-methylphenyl]acetic acid

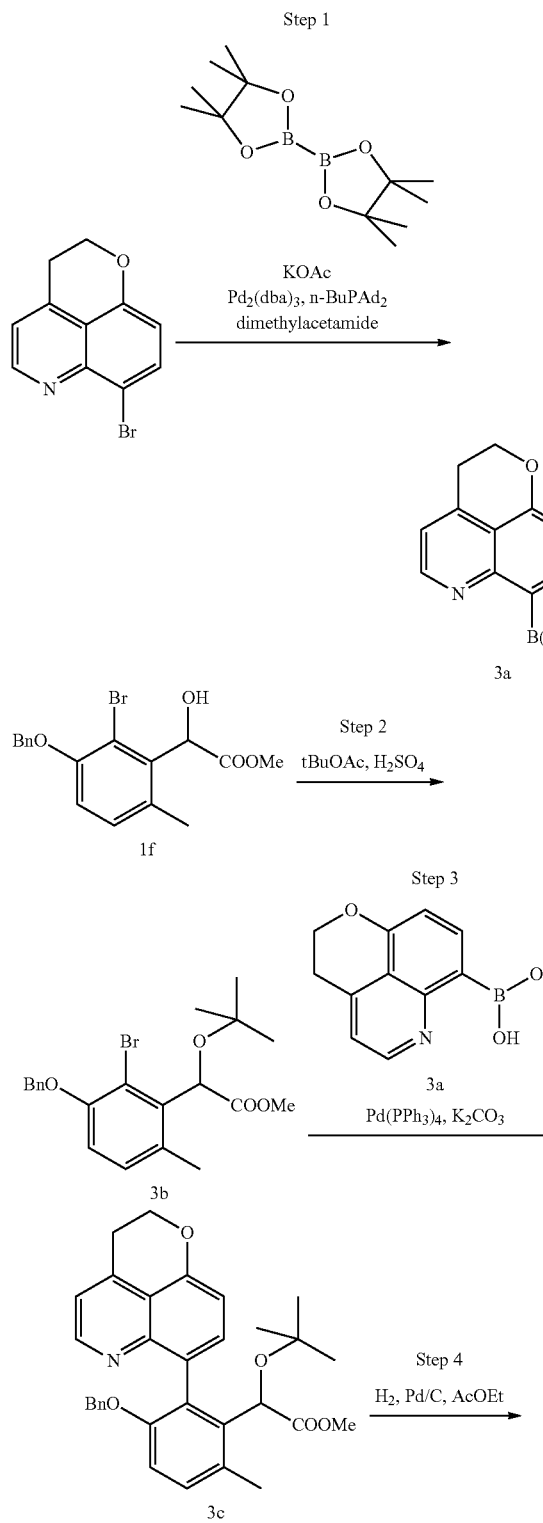

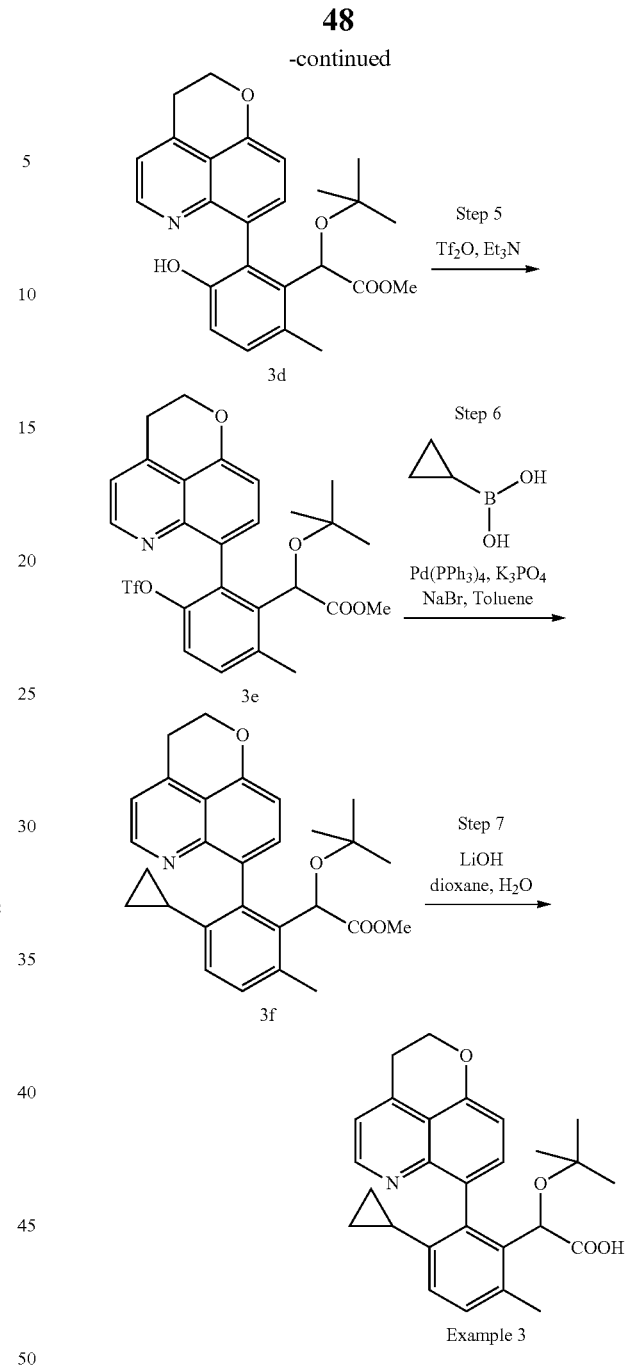

Step 1: Preparation of Intermediate (2,3-dihydropyrano[4,3,2-de]quinolin-7-yl)-boronic acid (3a)

A vial containing the 7-bromo-2,3-dihydro-1-oxa-6-azaphenalene (600 mg, 2.40 mmol, prepared according to WO2009/062289), tris(dibenzylidene acetone)dipalladium (0) (22 mg, 0.024 mmol), di(1-adamantyl)-n-butylphosphine (25.8 mg, 0.072 mmol), bis[pinacolato]diboron (731 mg, 2.88 mmol) and potassium acetate (706 mg, 7.20 mmol) was purged with argon for 10 minutes and then degassed anhydrous dimethylacetamide (2 mL) was added. The resulting mixture was stirred at 90° C. for 4 hours. The mixture was cooled to room temperature and water was added slowly (40 mL). The precipitate was filtered, washed with water (20 mL) and toluene (10 mL), dried in vacuo and triturated in diethyl ether. The powder was dissolved in acetonitrile and the solution was then filtered on Millipore and the filtrate concentrated in vacuo to provide (2,3-dihydropyrano[4,3,2-de]quinolin-7-yl)-boronic acid (3a) (301 mg, 1.39 mmol, 58%).

$^1$H NMR (400 MHz, DMSO-d$_6$+D$_2$O) δ 3.27 (t, 2H, J=5.8 Hz), 4.44 (t, 2H, J=5.8 Hz), 7.03 (d, J=7.8 Hz, 1H), 7.35 (d, J=4.5 Hz, 1H), 8.16 (d, J=7.8 Hz, 1H), 8.83 (d, J=4.5 Hz, 1H).

Step 2: Preparation of Intermediate methyl 2-(3-benzyloxy-2-bromo-6-methylphenyl)-2-(tert-butoxy)-acetate (3b)

To a suspension of methyl 2-(3-benzyloxy-2-bromo-6-methylphenyl)-2-hydroxyacetate (1f) (500 mg, 1.37 mmol) in tert-butyl acetate (14 mL) at 0° C. was added sulfuric acid (0.292 mL, 5.48 mmol). The mixture was stirred at room temperature for 8 hours. The mixture was diluted with ethyl acetate (50 mL), washed with a saturated solution of sodium hydrogenocarbonate (50 mL), dried over sodium sulfate and concentrated in vacuo. The residue was purified by flash chromatography on silica gel (cyclohexane/ethyl acetate: 90/10) to provide methyl 2-(3-benzyloxy-2-bromo-6-methylphenyl)-2-(tert-butoxy)-acetate (3b) (469 mg, 1.11 mmol, 81%) as a white solid.

$^1$H NMR (300 MHz, CDCl$_3$) δ 1.23 (s, 9H), 2.36 (s, 3H), 3.68 (s, 3H), 5.12 (s, 2H), 5.96 (s, 1H), 6.80 (d, J=8.4 Hz, 1H), 7.01 (d, J=8.4 Hz, 1H), 7.29-7.42 (m, 3H), 7.48-7.51 (m, 2H).

Step 3: Preparation of Intermediate methyl 2-[3-benzyloxy-2-(2,3-dihydropyrano[4,3,2-de]quinolin-7-yl)-6-methylphenyl]-2-(tert-butoxy)acetate (3c)

To a degassed mixture of methyl 2-(3-benzyloxy-2-bromo-6-methylphenyl)-2-(tert-butoxy)-acetate (3b) (200 mg, 0.47 mmol), potassium carbonate (177 mg, 1.28 mmol) and (2,3-dihydropyrano[4,3,2-de]quinolin-7-yl)-boronic acid (133 mg, 0.62 mmol) in dimethoxyethane (1.6 mL) and water (0.4 mL) was added palladium tetrakis(triphenylphosphine) (55 mg, 0.05 mmol). The mixture was heated under microwaves at 120° C. for 90 minutes. Water (5 mL) was added. The aqueous layer was extracted with ethyl acetate (2×5 mL). The combined organic layers were washed with brine (10 mL), dried over sodium sulfate and concentrated in vacuo. The residue was purified by flash chromatography on silica gel (cyclohexane/ethyl acetate: 70/30 up to 50/50) to provide both isomers (ratio: 1/2) of methyl 2-[3-benzyloxy-2-(2,3-dihydropyrano[4,3,2-de]quinolin-7-yl)-6-methylphenyl]-2-(tert-butoxy) (3c) (216 mg, 0.42 mmol, 89%).

Major Isomer:

$^1$H NMR (400 MHz, CDCl$_3$) δ 0.98 (s, 9H), 2.53 (s, 3H), 3.22-3.36 (m, 2H), 3.42 (s, 3H), 4.45-4.57 (m, 2H), 4.83 (d, J=12.4 Hz, 1H), 4.90 (d, J=12.4 Hz, 1H), 5.00 (s, 1H), 6.79-6.82 (m, 2H), 6.90 (d, J=8.3 Hz, 1H), 7.02-7.12 (m, 5H), 7.16 (d, J=8.4 Hz, 1H), 7.44 (d, J=7.8 Hz, 1H), 8.74 (d, J=4.3 Hz, 1H).

MS m/z ([M+H]$^+$) 512.

Minor Isomer:

$^1$H NMR (400 MHz, CDCl$_3$) δ 0.93 (s, 9H), 2.43 (s, 3H), 3.20-3.35 (m, 2H), 3.70 (s, 3H), 4.44-4.55 (m, 2H), 4.88 (s, 2H), 5.15 (s, 1H), 6.71 (d, J=7.4 Hz, 2H), 6.89 (d, J=8.3 Hz, 1H), 7.02-7.10 (m, 5H), 7.15 (d, J=8.3 Hz, 1H), 7.69 (dd, J=7.8 Hz, J=0.9 Hz, 1H), 8.73 (dd, J=4.3 Hz, J=0.8 Hz, 1H).

MS m/z ([M+H]$^+$) 512.

Step 4: Preparation of Intermediate methyl 2-(tert-butoxy)-2-[2-(2,3-dihydropyrano[4,3,2-de]quinolin-7-yl)-3-hydroxy-6-methylphenyl]acetate (3d)

A mixture of methyl 2-[3-benzyloxy-2-(2,3-dihydropyrano[4,3,2-de]quinolin-7-yl)-6-methylphenyl]-2-(tert-butoxy)acetate (3c) (143 mg, 0.279 mmol) and palladium on carbon (15 mg) in ethyl acetate was stirred at room temperature under a 4 bar hydrogen pressure for 30 hours. The mixture was filtered over Millipore and concentrated in vacuo. The residue was purified by preparative TLC (cyclohexane/ethyl acetate: 20/80) to provide methyl 2-(tert-butoxy)-2-[2-(2,3-dihydropyrano[4,3,2-de]quinolin-7-yl)-3-hydroxy-6-methylphenyl]acetate (3d) (29 mg, 0.069 mmol, 24%).

$^1$H NMR (400 MHz, CDCl$_3$) δ 0.86 (s, 9H), 2.48 (s, 3H), 3.22-3.38 (m, 2H), 3.47 (s, 3H), 4.46-4.56 (m, 2H), 4.94 (s, 1H), 6.91 (d, J=8.2 Hz, 1H), 7.04 (d, J=7.9 Hz, 1H), 7.11-7.13 (m, 2H), 7.44 (d, J=7.9 Hz, 1H), 8.78 (d, J=4.3 Hz, 1H).

MS m/z ([M+H]$^+$) 422.
MS m/z ([M−H]$^-$) 420.

Step 5: Preparation of Intermediate methyl 2-(tert-butoxy)-2-[2-(2,3-dihydropyrano[4,3,2-de]quinolin-7-yl)-6-methyl-3-trifluoromethanesulfonyloxy-phenyl]acetate (3e)

Using the procedure described in example 1, step 10, the intermediate methyl 2-(tert-butoxy)-2-[2-(2,3-dihydropyrano[4,3,2-de]quinolin-7-yl)-3-hydroxy-6-methylphenyl] acetate (3d) (29 mg, 0.069 mmol) is converted into methyl 2-(tert-butoxy)-2-[2-(2,3-dihydropyrano[4,3,2-de]quinolin-7-yl)-6-methyl-3-trifluoromethanesulfonyloxy-phenyl]acetate (3e) (24 mg, 0.043 mmol, 63%).

$^1$H NMR (400 MHz, CDCl$_3$) δ 0.96 (s, 9H), 2.62 (s, 3H), 3.22-3.35 (m, 2H), 3.38 (s, 3H), 4.46-4.57 (m, 2H), 5.02 (s, 1H), 7.05 (d, J=7.9 Hz, 1H), 7.09 (d, J=4.3 Hz, 1H), 7.23 (d, J=8.5 Hz, 1H), 7.29 (d, J=8.5 Hz, 1H), 7.47 (d, J=7.9 Hz, 1H), 8.73 (d, J=4.3 Hz, 1H). MS m/z ([M+H]$^+$) 554.

Step 6: Preparation of Intermediate methyl 2-(tert-butoxy)-2-[3-cyclopropyl-2-(2,3-dihydropyrano[4,3,2-de]quinolin-7-yl)-6-methylphenyl]acetate (3f)

Using the procedure described in example 1, step 11, the intermediate methyl 2-(tert-butoxy)-2-[2-(2,3-dihydropyrano[4,3,2-de]quinolin-7-yl)-6-methyl-3-trifluoromethanesulfonyloxy-phenyl]acetate (3e) (24 mg, 0.043 mmol) is converted, after purification by preparative TLC (cyclohexane/ethyl acetate: 50/50) into methyl 2-(tert-butoxy)-2-[3-cyclopropyl-2-(2,3-dihydropyrano[4,3,2-de]quinolin-7-yl)-6-methylphenyl]acetate (3f) (6 mg, 0.013 mmol, 30%).

$^1$H NMR (300 MHz, CDCl$_3$) δ 0.26-0.36 (m, 3H), 0.59-0.66 (m, 1H), 0.72 (s, 9H), 1.13-1.23 (m, 1H), 2.46 (s, 3H), 3.29 (t, J=5.8 Hz, 2H), 3.64 (s, 3H), 4.52 (t, J=5.8 Hz, 2H), 4.97 (s, 1H), 6.89 (d, J=7.9 Hz, 1H), 7.04-7.08 (m, 2H), 7.12 (d, J=7.9 Hz, 1H), 7.62 (d, J=7.9 Hz, 1H), 8.75 (d, J=4.3 Hz, 1H).

MS m/z ([M+H]$^+$) 446.

Step 7: Preparation of 2-(tert-butoxy)-2-[3-cyclopropyl-2-(2,3-dihydropyrano[4,3,2-de]quinolin-7-yl)-6-methylphenyl]acetic acid (Example 3)

Using the procedure described in example 1, step 12, the intermediate methyl 2-(tert-butoxy)-2-[3-cyclopropyl-2-(2, 3-dihydropyrano[4,3,2-de]quinolin-7-yl)-6-methylphenyl]acetate (3f) (6 mg, 0.013 mmol) is converted into 2-(tert-butoxy)-2-[3-cyclopropyl-2-(2,3-dihydropyrano[4,3,2-de]quinolin-7-yl)-6-methylphenyl]acetic acid (Example 3) (4 mg, 0.009 mmol, 66%) as a white solid.

$^1$H NMR (300 MHz, CDCl$_3$) δ 0.18-0.30 (m, 2H), 0.34-0.42 (m, 1H), 0.62-0.68 (m, 1H), 0.81 (s, 9H), 1.16-1.25 (m, 1H), 2.40 (s, 3H), 3.29 (t, J=5.8 Hz, 2H), 4.51 (t, J=5.8 Hz, 2H), 5.16 (s, 1H), 6.93 (d, J=7.9 Hz, 1H), 7.07-7.13 (m, 3H), 7.81 (d, J=7.5 Hz, 1H), 8.74 (d, J=4.3 Hz, 1H).

MS m/z ([M+H]$^+$) 432.
MS m/z ([M−H]$^−$) 430.

Example 4

Synthesis of 2-(tert-butoxy)-2-[2-(3,4-dihydro-2H-1-benzopyran-6-yl)-3-isopropenyl-6-methylphenyl]acetic acid

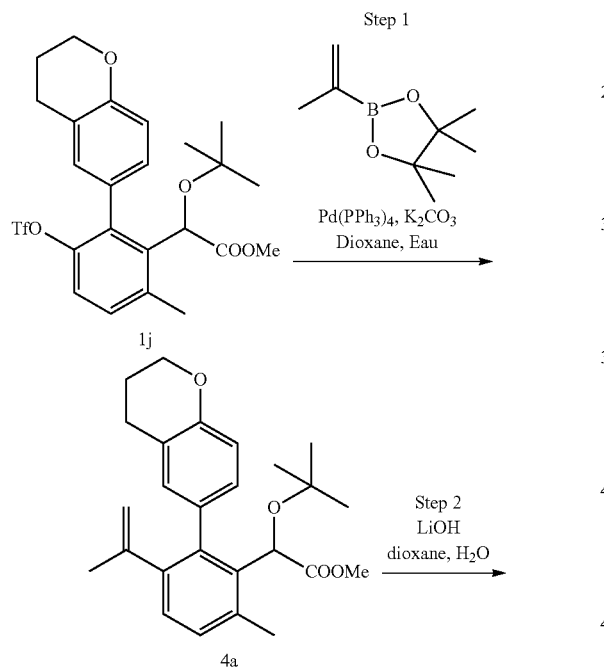

Step 1: Preparation of Intermediate methyl 2-(tert-butoxy)-2-[2-(3,4-dihydro-2H-1-benzopyran-6-yl)-3-isopropenyl-6-methylphenyl]acetate (4a)

A degassed solution of methyl 2-(tert-butoxy)-2-[2-(3,4-dihydro-2H-1-benzopyran-6-yl)-6-methyl-3-trifluorometh-anesulfonyloxy-phenyl]acetate (1j) (100 mg, 0.193 mmol), isopropenylboronic acid pinacol ester (65 mg, 0.386 mmol), potassium carbonate (72 mg, 0.52 mmol) and palladium tetrakis(triphenylphosphine) (22 mg, 0.019 mmol) in dioxane (1 mL) and water (0.25 mL) was heated in microwaves at 110° C. for 2 hours. Water (5 mL) was added. The aqueous layer was extracted with ethyl acetate (2×5 mL). The combined organic layers were washed with brine (5 mL), dried over sodium sulfate and concentrated in vacuo. The residue was purified by preparative TLC (cyclohexane/ethyl acetate: 90/10) to provide methyl 2-(tert-butoxy)-2-[2-(3,4-dihydro-2H-1-benzopyran-6-yl)-3-isopropenyl-6-methylphenyl]acetate (4a) (53 mg, 0.130 mmol, 67%).

$^1$H NMR (300 MHz, CDCl$_3$) δ 0.93 (s, 9H), 1.52 and 1.56 (s, 3H), 1.99-2.08 (m, 2H), 2.41 and 2.42 (s, 3H), 2.63-2.82 (m, 2H), 3.70 and 3.72 (s, 3H), 4.20-4.25 (m, 2H), 4.76-4.80 (m, 1H), 4.88-4.91 (m, 1H), 5.18 and 5.19 (s, 1H), 6.78 and 6.78 (d, J=8.3 Hz, 1H), 6.83-6.92 (m, 1H), 7.05-7.14 (m, 3H).

MS m/z ([M+Na]$^+$) 431.

Step 2: Preparation 2-(tert-butoxy)-2-[2-(3,4-dihydro-2H-1-benzopyran-6-yl)-3-isopropenyl-6-methylphenyl]acetic acid (Example 4)

Using the procedure described in example 1, step 12, the intermediate methyl 2-(tert-butoxy)-2-[2-(3,4-dihydro-2H-1-benzopyran-6-yl)-3-isopropenyl-6-methylphenyl]acetate (4a) (22 mg, 0.054 mmol) is converted into 2-(tert-butoxy)-2-[2-(3,4-dihydro-2H-1-benzopyran-6-yl)-3-isopropenyl-6-methyl phenyl]acetic acid (Example 4) (17 mg, 0.043 mmol, 81%) as a white solid.

$^1$H NMR (400 MHz, CDCl$_3$) δ 0.95 (s, 9H), 1.49 (s, 3H), 1.99-2.06 (m, 2H), 2.38 (s, 3H), 2.65-2.81 (m, 2H), 4.20-4.24 (m, 2H), 4.79-4.83 (m, 1H), 4.90-4.93 (m, 1H), 5.33 and 5.34 (s, 1H), 6.73 and 6.80 (d, J=8.3 Hz, 1H), 6.85-6.93 (m, 1H), 7.06-7.13 (m, 2H), 7.29 (bs, 1H).

MS m/z ([M−H]$^−$) 393.

Example 5

Synthesis of 2-(tert-butoxy)-2-[2-(3,4-dihydro-2H-1-benzopyran-6-yl)-3-isopropyl-6-methylphenyl]acetic acid

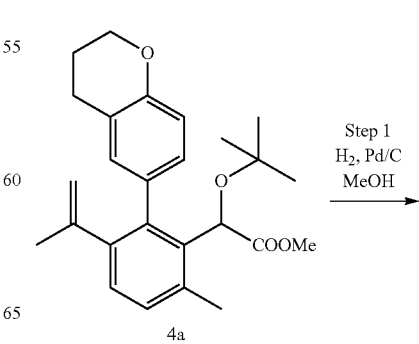

53
-continued

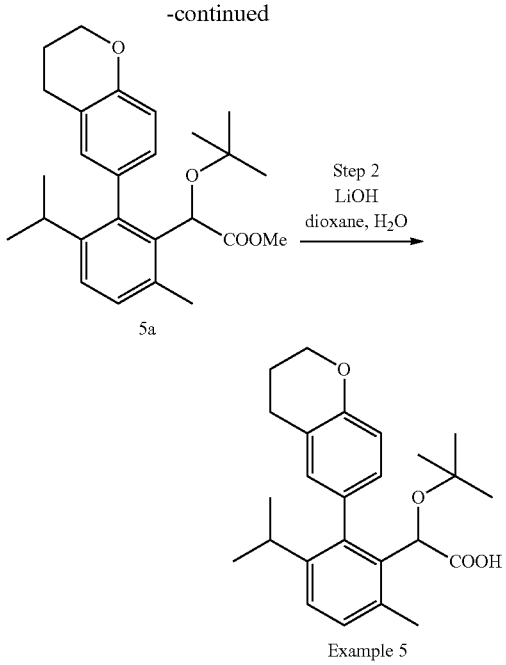

Step 1: Preparation of Intermediate methyl 2-(tert-butoxy)-2-[2-(3,4-dihydro-2H-1-benzopyran-6-yl)-3-isopropyl-6-methylphenyl]acetate (5a)

A mixture of methyl 2-(tert-butoxy)-2-[2-(3,4-dihydro-2H-1-benzopyran-6-yl)-3-isopropenyl-6-methylphenyl]acetate (4a) (53 mg, 0.129 mmol) and 10% palladium on carbon (17 mg) in methanol (5 mL) was stirred under hydrogen atmosphere overnight. The mixture was filtered on Millipore and the filtrate was concentrated in vacuo to provide methyl 2-(tert-butoxy)-2-[2-(3,4-dihydro-2H-1-benzopyran-6-yl)-3-isopropyl-6-methylphenyl]acetate (5a) (46 mg, 0.112 mmol, 86%) as a colorless oil.

$^1$H NMR (300 MHz, CDCl$_3$) δ 0.99-1.02 (m, 12H), 1.11 (d, J=6.9 Hz, 3H), 1.99-2.10 (m, 2H), 2.41 (s, 3H), 2.58-2.87 (m, 3H), 3.63 and 3.66 (s, 3H), 4.22-4.26 (m, 2H), 4.97 and 5.00 (s, 1H), 6.77-7.04 (m, 3H), 7.12 (d, J=8.0 Hz, 1H), 7.20 (d, J=8.0 Hz, 1H).

MS m/z ([M+Na]$^+$) 433.

Step 2: Preparation 2-(tert-butoxy)-2-[2-(3,4-dihydro-2H-1-benzopyran-6-yl)-3-isopropyl-6-methylphenyl]acetic acid (Example 5)

Using the procedure described in example 1, step 12, the intermediate methyl 2-(tert-butoxy)-2-[2-(3,4-dihydro-2H-1-benzopyran-6-yl)-3-isopropyl-6-methyl phenyl]acetate (5a) (46 mg, 0.112 mmol) is converted into 2-(tert-butoxy)-2-[2-(3,4-dihydro-2H-1-benzopyran-6-yl)-3-isopropyl-6-methylphenyl]acetic acid (Example 1) (44 mg, 0.112 mmol, 100%) as a white solid.

$^1$H NMR (300 MHz, CDCl$_3$) δ 0.95-1.02 (m, 12H), 1.14 (d, J=6.8 Hz, 3H), 1.99-2.08 (m, 2H), 2.35 and 2.36 (s, 3H), 2.63-2.84 (m, 3H), 4.23 (t, J=5.1 Hz, 2H), 5.12 (s, 1H), 6.78-6.91 (m, 2H), 7.11 (d, J=8.0 Hz, 1H), 7.17-7.23 (m, 2H).

MS m/z ([M–H]$^-$) 395.

54

Example 6

Synthesis of 2-(tert-butoxy)-2-[3-(cyclopentyl)-2-(3,4-dihydro-2H-1-benzopyran-6-yl)-6-(trifluoromethyl)phenyl]acetic acid

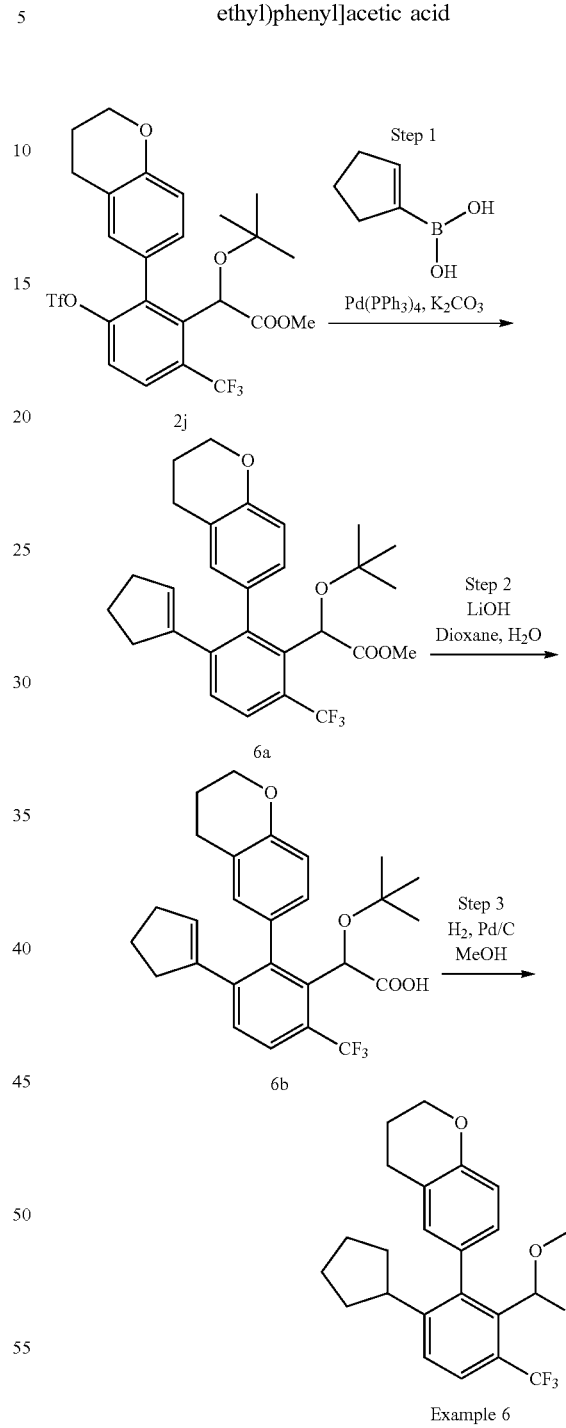

Step 1: Preparation of Intermediate methyl 2-(tert-butoxy)-2-[3-(cyclopent-1-en-1-yl)-2-(3,4-dihydro-2H-1-benzopyran-6-yl)-6-(trifluoromethyl)phenyl]acetate (6a)

A degassed solution of intermediate methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (2j) (120 mg, 0.210 mmol), potassium carbonate (116 mg, 0.841 mmol), 1-cyclopentenyl boronic acid (28 mg, 0.252 mmol) and palladium tetrakis(triphenylphosphine) (24 mg, 0.021 mmol) in dioxane (1.8 mL) and water (0.4 mL) was heated at 85° C. overnight. Water (2 mL) was added and dioxane was evaporated in vacuo. The aqueous residue was extracted with ethyl acetate (3×4 mL). The combined organics were washed with a saturated solution of sodium hydrogenocarbonate (4 mL), dried over sodium sulfate and concentrated in vacuo. The residue was purified on preparative TLC (cyclohexane/ethyl acetate: 9/1) to provide expected methyl 2-(tert-butoxy)-2-[3-(cyclopent-1-en-1-yl)-2-(3,4-dihydro-2H-1-benzopyran-6-yl)-6-(trifluoromethyl)phenyl]acetate (6a) (69 mg, 0.141 mmol, 67%) as a colourless oil.

$^1$H NMR (300 MHz, CDCl$_3$) δ 0.95 (s, 9H), 1.61-1.92 (m, 3H), 1.95-2.13 (m, 3H), 2.18-2.33 (m, 2H), 2.64-2.84 (m, 2H), 3.69 (s, 3H), 4.23 (t, J=5.2 Hz, 2H), 5.14 and 5.16 (s, 1H), 5.48-5.57 (m, 1H), 6.71-6.85 (m, 2H), 7.00-7.10 (m, 1H), 7.34 (d, J=8.2 Hz, 1H), 7.61 (d, J=8.2 Hz, 1H).

Step 2: Preparation of Intermediate 2-(tert-butoxy)-2-[3-(cyclopent-1-en-1-yl)-2-(3,4-dihydro-2H-1-benzopyran-6-yl)-6-(trifluoromethyl)phenyl]acetic acid (6b)

Using the procedure described in example 1, step 12, the intermediate methyl 2-(tert-butoxy)-2-[3-(cyclopent-1-en-1-yl)-2-(3,4-dihydro-2H-1-benzopyran-6-yl)-6-(trifluoromethyl)phenyl]acetate (6a) (69 mg, 0.141 mmol) is converted into 2-(tert-butoxy)-2-[3-(cyclopent-1-en-1-yl)-2-(3,4-dihydro-2H-1-benzopyran-6-yl)-6-(trifluoromethyl)phenyl]acetic acid (6b) (40 mg, 0.084 mmol, 59%) as a white solid.

$^1$H NMR (300 MHz, CDCl$_3$) δ 0.96 (s, 9H), 1.45-1.90 (m, 4H), 1.92-2.12 (m, 2H), 2.12-2.36 (m, 2H), 2.60-2.91 (m, 2H), 4.12-4.32 (t, J=4.6 Hz, 2H), 5.28 and 5.32 (s, 1H), 5.54 (s, 1H), 6.67-6.87 (m, 2H), 7.30-7.50 (m, 2H), 7.61 (d, J=8.2 Hz, 1H), 9.59 (bs, 1H).

MS m/z ([M−H]$^−$) 473.

Step 3: Preparation of 2-(tert-butoxy)-2-[3-(cyclopentyl)-2-(3,4-dihydro-2H-1-benzopyran-6-yl)-6-(trifluoromethyl)phenyl]acetic acid (Example 6)

A mixture of 2-(tert-butoxy)-2-[3-(cyclopent-1-en-1-yl)-2-(3,4-dihydro-2H-1-benzopyran-6-yl)-6-(trifluoromethyl)phenyl]acetic acid (6b) (15 mg, 0.031 mmol) and palladium on carbon (5 mg) in methanol (5 mL) was stirred under hydrogen atmosphere overnight. The mixture was filtered over Millipore and the filtrate was concentrated in vacuo to provide 2-(tert-butoxy)-2-[3-(cyclopentyl)-2-(3,4-dihydro-2H-1-benzopyran-6-yl)-6-(trifluoromethyl)phenyl]acetic acid (Example 6) (15 mg, 0.031 mmol, 100%) as a white solid.

$^1$H NMR (300 MHz, CD$_3$OD) δ 0.96 and 0.97 (s, 9H), 1.42-2.08 (m, 10H), 2.69-2.87 (m, 3H), 4.20-4.23 (m, 2H), 5.02 (s, 1H), 5.54 (s, 1H), 6.75-6.92 (m, 2H), 7.03-7.07 (m, 1H), 7.49 (d, J=8.4 Hz, 1H), 7.67 (d, J=8.4 Hz, 1H).

MS m/z ([M−H]$^−$) 475.

Example 7

Synthesis of 2-[4-(1H-1,3-benzodiazol-2-yl)-2-(3,4-dihydro-2H-1-benzopyran-6-yl)-3-methoxy-6-(trifluoromethyl)phenyl]-2-(tert-butoxy)acetic acid

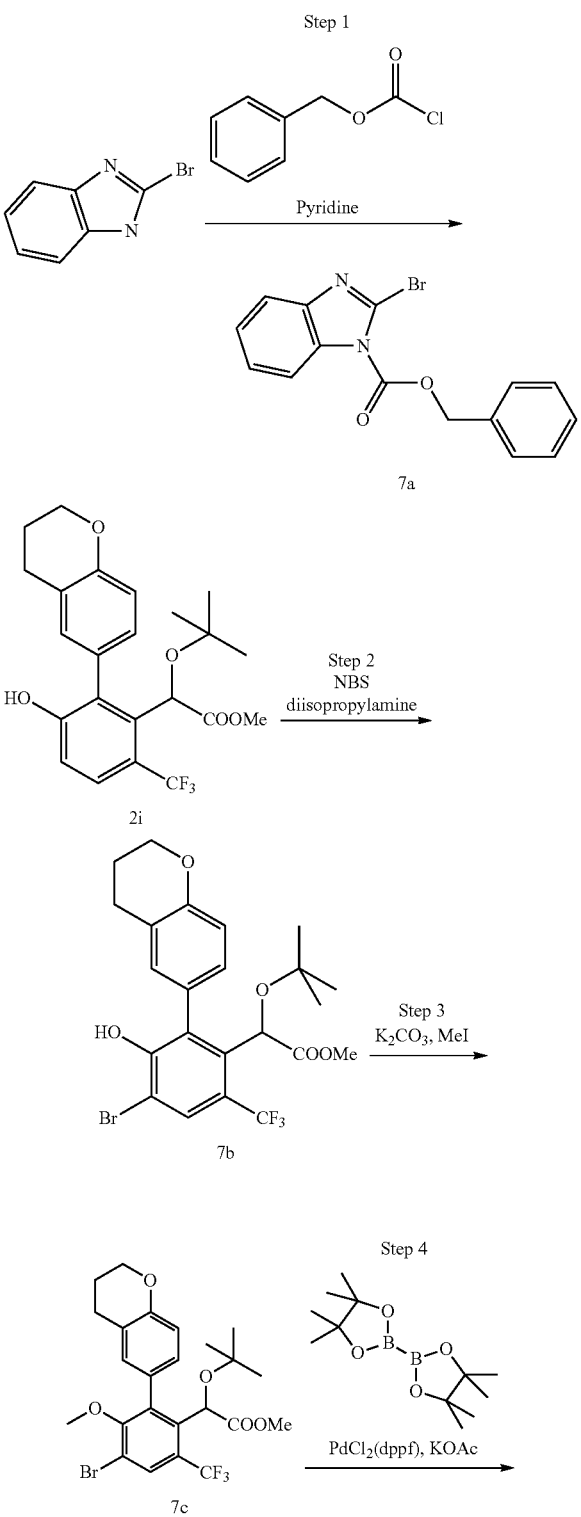

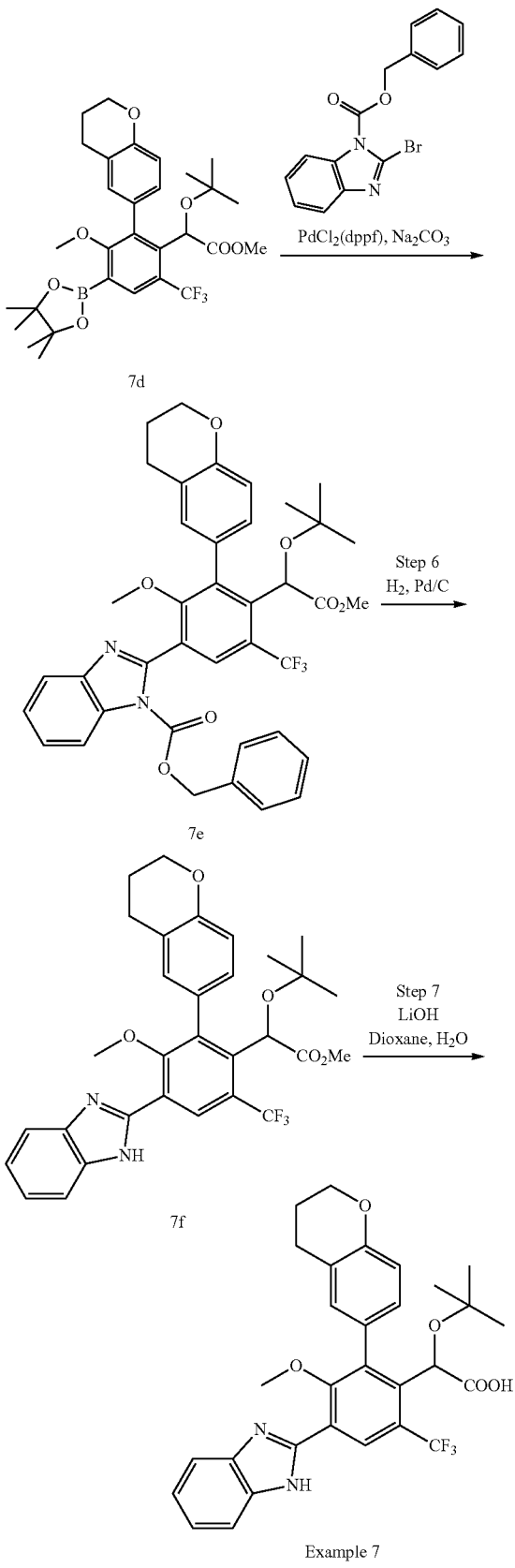

Step 1: Preparation of Intermediate benzyl 2-bromo-1H-1,3-benzodiazole-1-carboxylate (7a)

Under nitrogen atmosphere, benzyl chloroformate (0.174 mL, 1.218 mmol) was added to a solution of 2-bromo-1H-1,3-benzodiazole (200 mg, 1.015 mmol) and pyridine (0.123 mL, 1.523 mmol) in anhydrous dichloromethane (4 mL) at 0° C. The reaction mixture was stirred at room temperature for 3 hours, then cooled to 0° C. Water (5 mL) was added, and once at room temperature, the aqueous layer was extracted with dichloromethane (2×7 mL). The organic layer was dried over sodium sulfate and concentrated in vacuo. The residue was purified by preparative TLC (cyclohexane/ethyl acetate: 80/20) to provide benzyl 2-bromo-1H-1,3-benzodiazole-1-carboxylate (7a) (250 mg, 0.755 mmol, 74%).

$^1$H NMR (400 MHz, CDCl$_3$) δ 5.54 (s, 2H), 7.30-7.37 (m, 2H), 7.39-7.48 (m, 3H), 7.50-7.55 (m, 2H), 7.64-7.71 (m, 1H), 7.85-7.92 (m, 1H).

Step 2: Preparation of Intermediate methyl 2-[4-bromo-2-(3,4-dihydro-2H-1-benzopyran-6-yl)-3-hydroxy-6-(trifluoromethyl)phenyl]-2-(tert-butoxy) acetate (7b)

N-bromosuccinimide (20 mg, 0.114 mmol) was slowly added to a solution of methyl 2-(tert-butoxy)-2-[2-(3,4-dihydro-2H-1-benzopyran-6-yl)-3-hydroxy-6-(trifluoromethyl)phenyl]acetate (2i) (50 mg, 0.114 mmol) and diisopropylamine (3 μL, 0.023 mmol) in dichloromethane (1 mL). The reaction mixture was stirred at room temperature for 45 minutes and concentrated in vacuo. The crude was purified by preparative TLC (dichloromethane/ethyl acetate: 90/10) to provide methyl 2-[4-bromo-2-(3,4-dihydro-2H-1-benzopyran-6-yl)-3-hydroxy-6-(trifluoromethyl)phenyl]-2-(tert-butoxy)acetate (7b) (55 mg, 0.106 mmol, 93%).

$^1$H NMR (400 MHz, CDCl$_3$) δ 0.99 and 1.00 (s, 9H), 1.99-2.10 (m, 2H), 2.69-2.88 (m, 2H), 3.66 (s, 3H), 4.22-4.27 (m, 2H), 4.99 and 5.00 (s, 1H), 5.60 (bs, 1H), 6.87-6.97 (m, 2H), 7.02-7.09 (m, 1H), 7.85 (s, 1H).

MS m/z ([M+H]$^+$) 517/519.

Step 3: Preparation of Intermediate methyl 2-[4-bromo-2-(3,4-dihydro-2H-1-benzopyran-6-yl)-3-methoxy-6-(trifluoromethyl)phenyl]-2-(tert-butoxy) acetate (7c)

To a solution of methyl 2-[4-bromo-2-(3,4-dihydro-2H-1-benzopyran-6-yl)-3-hydroxy-6-(trifluoromethyl)phenyl]-2-(tert-butoxy)acetate (7b) (55 mg, 0.106 mmol) in acetone (2 mL), were added potassium carbonate (44 mg, 0.319 mmol) and iodomethane (11 μL, 0.212 mmol). The mixture was refluxed for 3h 30 then concentrated in vacuo. The residue was dissolved in water (5 mL) and extracted with ethyl acetate (2×5 mL). The organic layer was washed with a 2M solution of sodium hydroxide (5 mL), dried over sodium sulfate and concentrated in vacuo to provide methyl 2-[4-bromo-2-(3,4-dihydro-2H-1-benzopyran-6-yl)-3-methoxy-6-(trifluoromethyl)phenyl]-2-(tert-butoxy)acetate (7c) (52 mg, 0.097 mmol, 92%).

$^1$H NMR (400 MHz, CDCl$_3$) δ 0.94 and 0.95 (s, 9H), 1.98-2.10 (m, 2H), 2.67-2.89 (m, 2H), 3.42 and 3.45 (s, 3H), 3.70 (s, 3H), 4.22-4.28 (m, 2H), 5.02 and 5.03 (s, 1H), 6.81 and 6.85 (d, J=8.3 Hz, 1H), 6.94-7.08 (m, 2H), 7.91 (s, 1H).

MS m/z ([M+Na]$^+$) 555/557.

Step 4: Preparation of Intermediate methyl 2-(tert-butoxy)-2-[2-(3,4-dihydro-2H-1-benzopyran-6-yl)-3-methoxy-4-(tetramethyl-1,3,2-dioxaborolan-2-yl)-6-(trifluoromethyl)phenyl]acetate (7d)

A flame-dried vial containing the methyl 2-[4-bromo-2-(3,4-dihydro-2H-1-benzopyran-6-yl)-3-methoxy-6-(trifluoromethyl)phenyl]-2-(tert-butoxy)acetate (7c) (190 mg, 0.358 mmol), [1,1'-bis(diphenylphosphino)ferrocene]dichloropalladium(II), complex with dichloromethane (58.40 mg, 0.072 mmol), bis[pinacolato]diboron (182 mg, 0.715 mmol) and potassium acetate (106 mg, 1.073 mmol) was purged with argon for 10 minutes and then degassed anhydrous dioxane (1.5 mL) was added. The resulting mixture was stirred at 80° C. for 40 hours. The mixture was cooled to roam temperature and diluted in ethyl acetate (5 mL) and washed with water (2×5 mL) and brine (5 mL), dried over sodium sulfate, filtered and concentrated in vacuo. The residue was purified by preparative TLC (cyclohexane/ethyl acetate: 80/20) to provide methyl 2-(tert-butoxy)-2-[2-(3,4-dihydro-2H-1-benzopyran-6-yl)-3-methoxy-4-(tetramethyl-1,3,2-dioxaborolan-2-yl)-6-(trifluoromethyl)phenyl]acetate (7d) (170 mg, 0.294 mmol, 82%).

$^1$H NMR (400 MHz, CDCl$_3$) δ 0.93 and 0.95 (s, 9H), 1.36 and 1.37 (s, 12H), 1.99-2.08 (m, 2H), 2.65-2.87 (m, 2H), 3.41 and 3.45 (s, 3H), 3.69 (s, 3H), 4.20-4.27 (m, 2H), 5.07 and 5.08 (s, 1H), 6.78 and 6.80 (d, J=8.3 Hz, 1H), 6.87-7.07 (m, 2H), 8.05 and 8.06 (s, 1H).

Step 5-6: Preparation of Intermediate methyl 2-[4-(1H-1,3-benzodiazol-2-yl)-2-(3,4-dihydro-2H-1-benzopyran-6-yl)-3-methoxy-6-(trifluoromethyl)phenyl]-2-(tert-butoxy)acetate (7e)

To a solution of methyl 2-(tert-butoxy)-2-[2-(3,4-dihydro-2H-1-benzopyran-6-yl)-3-methoxy-4-(tetramethyl-1,3,2-dioxaborolan-2-yl)-6-(trifluoromethyl)phenyl]acetate (7d) (60 mg, 0.104 mmol) in dioxane (1.5 mL) was added benzyl 2-bromo-1H-1,3-benzodiazole-1-carboxylate (7a) (69 mg, 0.207 mmol) and saturated aqueous solution of sodium carbonate (1 mL). This mixture was stirred at room temperature for 20 minutes while passing a stream of argon. [1,1'-Bis(diphenylphosphino)ferrocene]dichloropalladium (II), complex with dichloromethane (8 mg, 0.010 mmol) was added and the resulting mixture was stirred at 80° C. for 16 hours. The reaction mixture was cooled to room temperature and diluted with ethyl acetate (5 mL). The organic layer was washed with water (2×5 mL) and brine (5 mL), dried over sodium sulfate and concentrated in vacuo. The residue was purified by preparative TLC (cyclohexane/ethyl acetate: 60/40). The resulting mixture of products was dissolved in ethyl acetate (2 mL). Palladium on carbon (7 mg) was added and the reaction mixture was stirred under hydrogen atmosphere for 16 hours. The mixture was filtered over Millipore and the filtrate concentrated in vacuo. The crude was purified by preparative TLC (dichloromethane/ethyl acetate: 95/5) to provide methyl 2-[4-(1H-1,3-benzodiazol-2-yl)-2-(3,4-dihydro-2H-1-benzopyran-6-yl)-3-methoxy-6-(trifluoromethyl)phenyl]-2-(tert-butoxy)acetate (7e) (11 mg, 0.019 mmol, 19% over two steps).

$^1$H NMR (300 MHz, CDCl$_3$) δ 0.98 (s, 9H), 2.04-2.14 (m, 2H), 2.77-2.90 (m, 2H), 3.44 (m, 3H), 3.74 and 3.75 (s, 3H), 4.26-4.32 (m, 2H), 5.13-5.16 (m, 1H), 6.86-6.94 (m, 1H), 7.00-7.10 (m, 1H), 7.16-7.26 (m, 1H), 7.26-7.37 (m, 3H), 7.42-7.52 (m, 1H), 7.85-7.92 (m, 1H).

Step 7: Preparation of 2-[4-(1H-1,3-benzodiazol-2-yl)-2-(3,4-dihydro-2H-1-benzopyran-6-yl)-3-methoxy-6-(trifluoromethyl)phenyl]-2-(tert-butoxy) acetic acid (Example 7)

Using the procedure described in example 1, step 12, methyl 2-[4-(1H-1,3-benzodiazol-2-yl)-2-(3,4-dihydro-2H-1-benzopyran-6-yl)-3-methoxy-6-(trifluoromethyl)phenyl]-2-(tert-butoxy)acetate (7e) (11 mg, 0.019 mmol) is converted to 2-[4-(1H-1,3-benzodiazol-2-yl)-2-(3,4-dihydro-2H-1-benzopyran-6-yl)-3-methoxy-6-(trifluoromethyl)phenyl]-2-(tert-butoxy)acetic acid (Example 7) (7 mg, 0.013 mmol, 65%).

$^1$H NMR (400 MHz, CDCl$_3$) δ 0.98 (s, 9H), 1.97-2.15 (m, 2H), 2.76-2.93 (m, 2H), 3.43 and 3.44 (s, 3H), 4.23-4.30 (m, 2H), 5.24 (bs, 1H), 6.91 and 6.93 (d, J=8.3 Hz, 1H), 7.01-7.10 (m, 1H), 7.29-7.32 (m, 2H), 7.44-7.90 (m, 3H), 8.87 and 8.88 (s, 1H).

MS m/z ([M+H]$^+$) 555.

Example 8

Synthesis of 2-(tert-butoxy)-2-[2-(3,4-dihydro-2H-1-benzopyran-6-yl)-3-(prop-1-en-2-yl)-6-(trifluoromethyl)phenyl]acetic acid

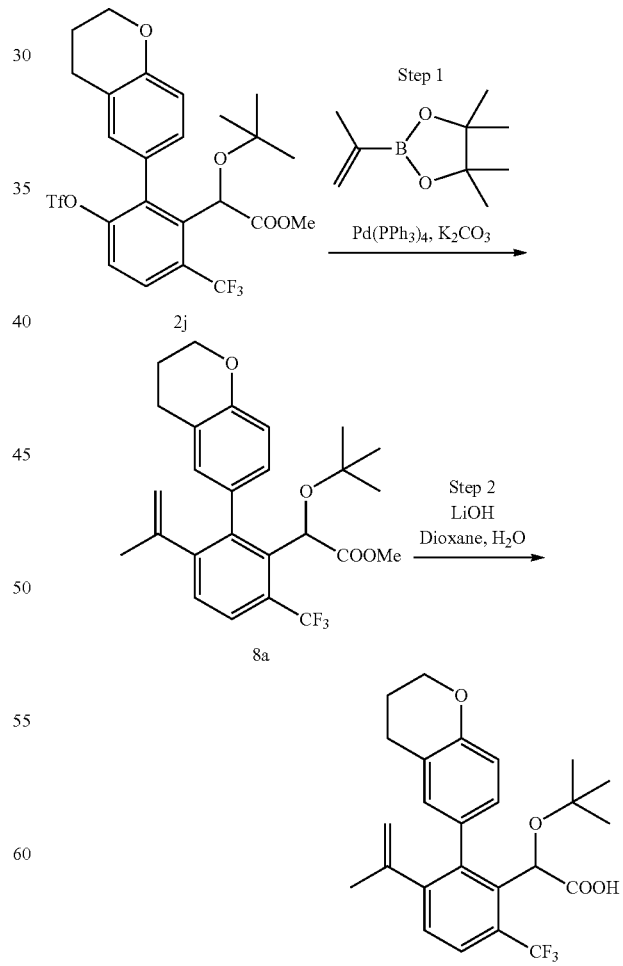

Example 8

Step 1: Preparation of Intermediate methyl 2-(tert-butoxy)-2-[2-(3,4-dihydro-2H-1-benzopyran-6-yl)-3-(prop-1-en-2-yl)-6-(trifluoromethyl)phenyl]acetate (8a)

Using the procedure described in example 6, step 1, the intermediate methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (2j) (110 mg, 0.193 mmol) is converted by reaction with isopropenylboronic acid pinacol ester (81 mg, 0.482 mmol), after purification by preparative TLC (cyclohexane/ethyl acetate: 80/20) into methyl 2-(tert-butoxy)-2-[2-(3,4-dihydro-2H-1-benzopyran-6-yl)-3-(prop-1-en-2-yl)-6-(trifluoromethyl)phenyl]acetate (8a) (88 mg, 0.190 mmol, 99%).

$^1$H NMR (400 MHz, CDCl$_3$) δ 0.95 and 0.96 (s, 9H), 1.54 (s, 3H), 2.00-2.07 (m, 2H), 2.67-2.81 (m, 2H), 3.69 and 3.70 (s, 3H), 4.20-4.25 (m, 2H), 4.81-4.86 (m, 1H), 4.95-5.00 (m, 1H), 5.12 and 5.13 (s, 1H), 6.75 and 6.76 (d, J=8.4 Hz, 1H), 6.78-6.88 (m, 1H), 7.01-7.08 (m, 1H), 7.30 (d, J=8.1 Hz, 1H), 7.64 (d, J=8.1 Hz, 1H).

MS m/z ([M+Na]$^+$) 485.

Step 2: Preparation of 2-(tert-butoxy)-2-[2-(3,4-dihydro-2H-1-benzopyran-6-yl)-3-(prop-1-en-2-yl)-6-(trifluoromethyl)phenyl]acetic acid (Example 8)

Using the procedure described in example 1, step 12, the intermediate methyl 2-(tert-butoxy)-2-[2-(3,4-dihydro-2H-1-benzopyran-6-yl)-3-(prop-1-en-2-yl)-6-(trifluoromethyl)phenyl]acetate (8a) (88 mg, 0.190 mmol) is converted into 2-(tert-butoxy)-2-[2-(3,4-dihydro-2H-1-benzopyran-6-yl)-3-(prop-1-en-2-yl)-6-(trifluoromethyl)phenyl]acetic acid (Example 8) (82 mg, 0.183 mmol, 96%).

$^1$H NMR (400 MHz, CDCl$_3$) δ 0.97 (s, 9H), 1.53 (s, 3H), 1.97-2.08 (m, 2H), 2.65-2.87 (m, 2H), 4.17-4.28 (m, 2H), 4.82-4.89 (m, 1H), 4.97-5.01 (m, 1H), 5.27 and 5.29 (s, 1H), 6.73-6.87 (m, 2H), 7.32-7.45 (m, 2H), 7.65 (d, J=8.1 Hz, 1H).

MS m/z ([M−H]$^−$) 447.

Example 9

Synthesis of 2-(tert-butoxy)-2-[2-(3,4-dihydro-2H-1-benzopyran-6-yl)-3-ethenyl-6-(trifluoromethyl)phenyl]acetic acid

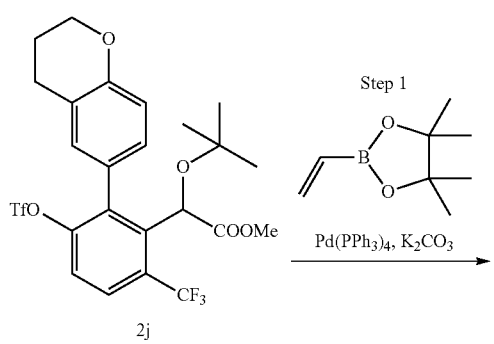

Step 1: Preparation of Intermediate methyl 2-(tert-butoxy)-2-[2-(3,4-dihydro-2H-1-benzopyran-6-yl)-3-ethenyl-6-(trifluoromethyl)phenyl]acetate (9a)

Using the procedure described in example 6, step 1, the intermediate methyl 2-(tert-butoxy)-2-[2-(3,4-dihydro-2H-1-benzopyran-6-yl)-3-[(trifluoromethane)sulfonyloxy]-6-(trifluoromethyl)phenyl]acetate (2j) (100 mg, 0.175 mmol) is converted by reaction with vinyl boronic acid pinacol ester (67 mg, 0.438 mmol), after purification by preparative TLC (cyclohexane/ethyl acetate: 80/20) into methyl 2-(tert-butoxy)-2-[2-(3,4-dihydro-2H-1-benzopyran-6-yl)-3-ethenyl-6-(trifluoromethyl)phenyl]acetate (9a) (62 mg, 0.138 mmol, 79%).

$^1$H NMR (400 MHz, CDCl$_3$) δ 0.98 (s, 9H), 1.98-2.10 (m, 2H), 2.68-2.86 (m, 2H), 3.66 and 3.67 (s, 3H), 4.20-4.30 (m, 2H), 5.08 and 5.09 (s, 1H), 5.15-5.20 (m, 1H), 5.67 (d, J=17.4 Hz, 1H), 6.33 and 6.34 (dd, J=17.4 Hz, J=11.0 Hz, 1H), 6.77-6.85 (m, 2H), 6.94-7.00 (m, 1H), 7.65 (d, J=8.3 Hz, 1H), 7.68 (d, J=8.3 Hz, 1H).

MS m/z ([M+Na]$^+$) 471.

Step 2: Preparation of 2-(tert-butoxy)-2-[2-(3,4-dihydro-2H-1-benzopyran-6-yl)-3-ethenyl-6-(trifluoromethyl)phenyl]acetic acid (Example 9)

Using the procedure described in example 1, step 12, the intermediate methyl 2-(tert-butoxy)-2-[2-(3,4-dihydro-2H-1-benzopyran-6-yl)-3-ethenyl-6-(trifluoro methyl)phenyl]acetate (9a) (62 mg, 0.138 mmol) is converted to 2-(tert-butoxy)-2-[2-(3,4-dihydro-2H-1-benzopyran-6-yl)-3-ethenyl-6-(trifluoromethyl)phenyl]acetic acid (Example 9) (56 mg, 0.129 mmol, 93%).

$^1$H NMR (400 MHz, CDCl$_3$) δ 1.00 (s, 9H), 2.00-2.08 (m, 2H), 2.70-2.87 (m, 2H), 4.22-4.26 (m, 2H), 5.15-5.25 (m, 2H), 5.68 (d, J=17.5 Hz, 1H), 6.32 and 6.34 (dd, J=17.5 Hz, J=11.0 Hz, 1H), 6.79-6.89 (m, 2H), 7.29 (bs, 1H), 7.69 (s, 2H).

MS m/z ([M−H]$^−$) 433.

Example 10

Synthesis of 2-(tert-butoxy)-2-[2-(3,4-dihydro-2H-1-benzopyran-6-yl)-3-(propan-2-yl)-6-(trifluoromethyl)phenyl]acetic acid

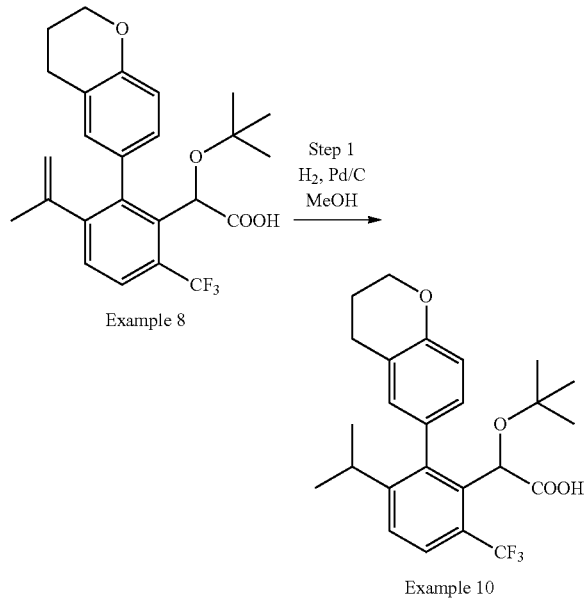

Step 1: Preparation of 2-(tert-butoxy)-2-[2-(3,4-dihydro-2H-1-benzopyran-6-yl)-3-(propan-2-yl)-6-(trifluoromethyl)phenyl]acetic acid (Example 10)

Using the procedure described in example 6, step 3, the 2-(tert-butoxy)-2-[2-(3,4-dihydro-2H-1-benzopyran-6-yl)-3-(prop-1-en-2-yl)-6-(trifluoromethyl)phenyl]acetic acid (Example 8) (62 mg, 0.138 mmol) is converted into 2-(tert-butoxy)-2-[2-(3,4-dihydro-2H-1-benzopyran-6-yl)-3-(propan-2-yl)-6-(trifluoro methyl)phenyl]acetic acid (Example 10) (50 mg, 0.111 mmol, 80%).

$^1$H NMR (300 MHz, CDCl$_3$) δ 0.96-1.20 (m, 15H), 2.00-2.09 (m, 2H), 2.65-2.89 (m, 3H), 4.17-4.28 (m, 2H), 5.12 (s, 1H), 6.78-6.92 (m, 2H), 7.20-7.32 (m, 1H), 7.43 (d, J=8.4 Hz, 1H), 7.68 (d, J=8.4 Hz, 1H).

MS m/z ([M–H]$^-$) 449.

Example 11

Synthesis of 2-(tert-butoxy)-2-[2-(3,4-dihydro-2H-1-benzopyran-6-yl)-3-ethyl-6-(trifluoromethyl)phenyl]acetic acid

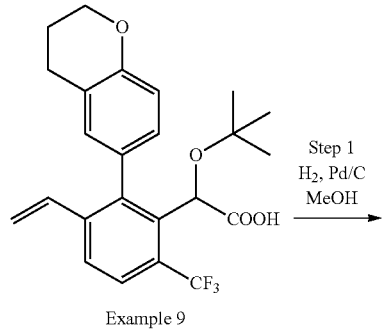

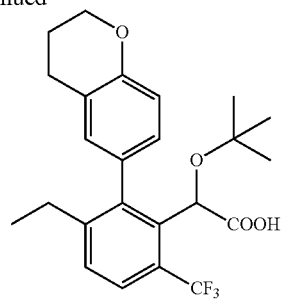

Step 1: Preparation of 2-(tert-butoxy)-2-[2-(3,4-dihydro-2H-1-benzopyran-6-yl)-3-ethyl-6-(trifluoromethyl)phenyl]acetic acid (Example 11)

Using the procedure described in example 6, step 3, the intermediate 2-(tert-butoxy)-2-[2-(3,4-dihydro-2H-1-benzopyran-6-yl)-3-ethenyl-6-(trifluoromethyl)phenyl]acetic acid (Example 9) (36 mg, 0.083 mmol) is converted into 2-(tert-butoxy)-2-[2-(3,4-dihydro-2H-1-benzopyran-6-yl)-3-ethyl-6-(trifluoromethyl)phenyl]acetic acid (Example 11) (29 mg, 0.066 mmol, 80%).

$^1$H NMR (300 MHz, CDCl$_3$) δ 1.00-1.10 (m, 12H), 2.00-2.08 (m, 2H), 2.32-2.41 (m, 2H), 2.68-2.93 (m, 2H), 4.20-4.27 (m, 2H), 5.15 (s, 1H), 6.79-6.91 (m, 2H), 7.24 (m, 1H), 7.37 (d, J=8.1 Hz, 1H), 7.65 (d, J=8.1 Hz, 1H).

MS m/z ([M–H]$^-$) 435.

Example 12

Synthesis of 2-(tert-butoxy)-2-(6-cyclopropyl-4'-methoxy-3-methyl-biphenyl-2-yl)acetic acid

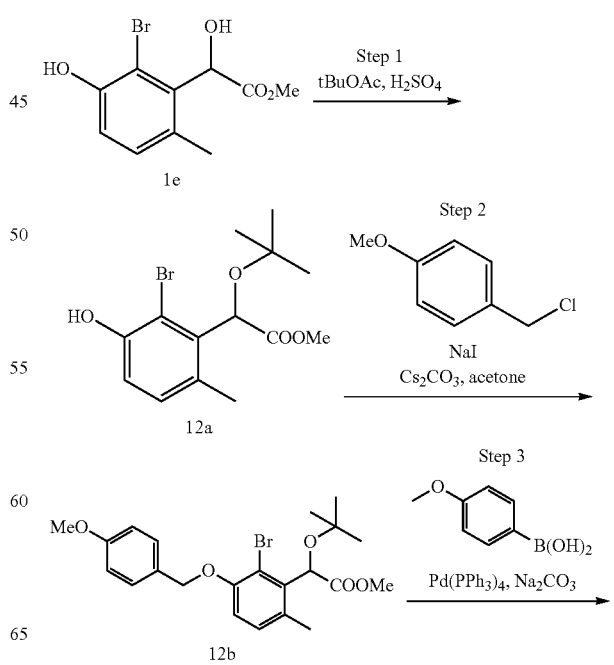

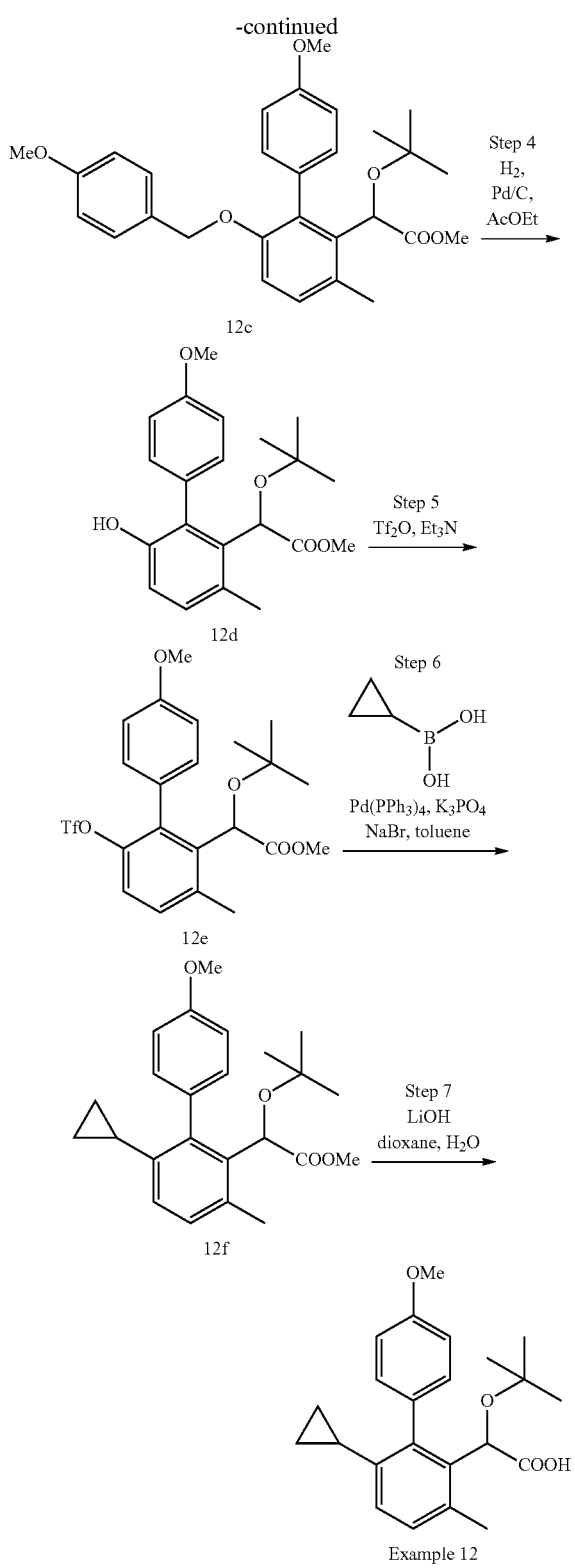

Example 12

Step 1: Preparation of Intermediate methyl 2-(2-bromo-3-hydroxy-6-methylphenyl)-2-(tert-butoxy)acetate (12a)

To a solution of methyl 2-(2-bromo-3-hydroxy-6-methyl-phenyl)-2-hydroxy-acetate (1e) (406 mg, 1.48 mmol) in tert-butyl acetate (15 mL) at 0° C. was added sulfuric add (0.315 mL, 5.90 mmol). The mixture was stirred at room temperature for 4 hours. The mixture was diluted with ethyl acetate (20 mL) and washed with a saturated solution of sodium hydrogenocarbonate. The organic layer was dried over sodium sulfate and concentrated in vacuo. The residue was purified by flash chromatography on silica gel (cyclohexane/ethyl acetate 80/20) to provide methyl 2-(2-bromo-3-hydroxy-6-methyl phenyl)-2-(tert-butoxy)acetate (12a) (195 mg, 0.59 mmol, 40%) as a light yellow solid.

$^1$H NMR (300 MHz, CDCl$_3$) δ 1.21 (s, 9H), 2.36 (s, 3H), 3.68 (s, 3H), 5.54 (s, 1H), 5.70 (s, 1H), 6.88 (d, J=8.2 Hz, 1H), 7.00 (d, J=8.2 Hz, 1H).

MS m/z ([M−H]$^−$) 329/331.

Step 2: Preparation of Intermediate methyl 2-[2-bromo-3-(4-methoxy-benzyloxy)-6-methylphenyl]-2-(tert-butoxy)-acetate (12b)

Using the procedure described in example 1, step 6, the intermediate methyl 2-(2-bromo-3-hydroxy-6-methyl phenyl)-2-(tert-butoxy)acetate (12a) (1.83 g, 5.52 mmol) is converted by reaction with 4-methoxybenzyl chloride (0.82 mL, 6.08 mmol), after purification by flash chromatography on silica gel (cyclohexane/ethyl acetate 90/10) into methyl 2-[2-bromo-3-(4-methoxy-benzyloxy)-6-methylphenyl]-2-(tert-butoxy)-acetate (12b) (2.34 g, 5.18 mmol, 93%) as a white solid.

$^1$H NMR (300 MHz, CDCl$_3$) δ 1.22 (s, 9H), 2.36 (s, 3H), 3.68 (s, 3H), 3.82 (s, 3H), 5.04 (s, 2H), 5.95 (s, 1H), 6.80 (d, J=8.4 Hz, 1H), 6.82 (d, J=8.7 Hz, 2H), 7.01 (d, J=8.4 Hz, 1H), 7.41 (d, J=8.7 Hz, 2H).

MS m/z ([M+Na]$^+$) 473/475.

Step 3: Preparation of Intermediate methyl 2-(tert-butoxy)-2-[4'-methoxy-6-(4-methoxy-benzyloxy)-3-methyl-biphenyl-2-yl]acetate (12c)

Using the procedure described in example 1, step 7, the intermediate methyl 2-[2-bromo-3-(4-methoxy-benzyloxy)-6-methylphenyl]-2-(tert-butoxy)-acetate (12b) (50 mg, 0.11 mmol) is converted by reaction with 4-methoxyphenylboronic acid (25 mg, 0.17 mmol), after purification by preparative TLC (cyclohexane/ethyl acetate 80/20), into methyl 2-(tert-butoxy)-2-[4'-methoxy-6-(4-methoxy-benzyloxy)-3-methyl-biphenyl-2-yl]acetate (12c) (36 mg, 0.075 mmol, 68%).

$^1$H NMR (300 MHz, CDCl$_3$) δ 0.94 (s, 9H), 2.35 (s, 3H), 3.71 (s, 3H), 3.77 (s, 3H), 3.87 (s, 3H), 4.82 (d, J=11.9 Hz, 1H), 4.89 (d, J=11.9 Hz, 1H), 5.14 (s, 1H), 6.76-6.82 (m, 2H), 6.86 (d, J=8.3 Hz, 1H), 6.91-6.99 (m, 2H), 7.02-7.08 (m, 3H), 7.22-7.27 (m, 1H), 7.31-7.36 (m, 1H).

MS m/z ([M+Na]$^+$) 501.

Step 4: Preparation of Intermediate methyl 2-(tert-butoxy)-2-(6-hydroxy-4'-methoxy-3-methyl-biphenyl-2-yl)acetate (12d)

A mixture of methyl 2-(tert-butoxy)-2-[4'-methoxy-6-(4-methoxy-benzyloxy)-3-methyl-biphenyl-2-yl]acetate (12c) (82 mg, 0.171 mmol) and palladium on carbon (18 mg) in ethyl acetate (5 mL) was stirred at room temperature under a 5 bar hydrogen pressure for 18 hours. The mixture was filtered over Millipore and concentrated in vacuo. The residue was purified by preparative TLC (cyclohexane/ethyl acetate 80/20) to provide methyl 2-(tert-butoxy)-2-[6-hydroxy-4'-methoxy-3-methyl-biphenyl-2-yl]acetate (12d) (56 mg, 0.156 mmol, 92%).

$^1$H NMR (300 MHz, CDCl$_3$) δ 0.96 (s, 9H), 2.35 (s, 3H), 3.69 (s, 3H), 3.88 (s, 3H), 4.61 (s, 1H), 4.98 (s, 1H), 6.84 (d, J=8.2 Hz, 1H), 6.99-7.09 (m, 3H), 7.22-7.26 (m, 1H), 7.41 (dd, J=2.0 Hz, J=8.4 Hz, 1H).

MS m/z ([M+Na]$^+$) 381.

MS m/z ([M−H]$^−$) 357.

Step 5: Preparation of Intermediate methyl 2-(tert-butoxy)-2-(4'-methoxy-3-methyl-6-trifluoromethanesulfonyloxy-biphenyl-2-yl]acetate (12e)

Using the procedure described in example 1, step 10, the intermediate methyl 2-(tert-butoxy)-2-(6-hydroxy-4'-methoxy-3-methyl-biphenyl-2-yl)acetate (12d) (56 mg, 0.156 mmol) is converted into intermediate methyl 2-(tert-butoxy)-2-(4'-methoxy-3-methyl-6-trifluoromethanesulfonyloxy-biphenyl-2-yl]acetate (12e) (63 mg, 0.128 mmol, 82%).

$^1$H NMR (300 MHz, CDCl$_3$) δ 0.95 (s, 9H), 2.44 (s, 3H), 3.72 (s, 3H), 3.87 (s, 3H), 5.10 (s, 1H), 6.95-7.01 (m, 2H), 7.16-7.23 (m, 3H), 7.31-7.36 (m, 1H).

MS m/z ([M−H]$^−$) 489.

Step 6: Preparation of Intermediate methyl 2-(tert-butoxy)-2-(6-cyclopropyl-4'-methoxy-3-methyl-biphenyl-2-yl]acetate (12f)

Using the procedure described in example 1, step 11, the intermediate methyl 2-(tert-butoxy)-2-(4'-methoxy-3-methyl-6-trifluoromethanesulfonyloxy-biphenyl-2-yl]acetate (12e) (63 mg, 0.128 mmol) is converted, after purification by preparative TLC (cyclohexane/ethyl acetate 85/15) into methyl 2-(tert-butoxy)-2-(6-cyclopropyl-4'-methoxy-3-methyl-biphenyl-2-yl]acetate (12f) (10 mg, 0.026 mmol, 20%).

$^1$H NMR (300 MHz, CDCl$_3$) δ 0.52-0.74 (m, 4H), 0.97 (s, 9H), 1.37-1.48 (m, 1H), 2.40 (s, 3H), 3.68 (s, 3H), 3.87 (s, 3H), 5.08 (s, 1H), 6.78 (d, J=7.9 Hz, 1H), 6.92-7.00 (m, 2H), 7.06 (d, J=7.9 Hz, 1H), 7.20-7.25 (m, 1H), 7.29-7.34 (m, 1H).

MS m/z ([M+Na]$^+$) 405.

Step 7: Preparation of 2-(tert-butoxy)-2-(6-cyclopropyl-4'-methoxy-3-methyl-biphenyl-2-yl]acetic acid (Example 12)

Using the procedure described in example 1, step 12, the intermediate methyl 2-(tert-butoxy)-2-(6-cyclopropyl-4'-methoxy-3-methyl-biphenyl-2-yl]acetate (12e) (10 mg, 0.026 mmol) is converted into 2-(tert-butoxy)-2-(6-cyclopropyl-4'-methoxy-3-methyl-biphenyl-2-yl]acetic acid (Example 12) (9 mg, 0.024 mmol, 90%) as a colorless oil.

$^1$H NMR (400 MHz, CDCl$_3$) δ 0.50-0.62 (m, 3H), 0.70-0.76 (m, 1H), 1.00 (s, 9H), 1.44-1.52 (m, 1H), 2.36 (s, 3H), 3.86 (s, 3H), 5.21 (s, 1H), 6.80 (d, J=7.9 Hz, 1H), 6.93-7.00 (m, 2H), 7.05 (d, J=7.9 Hz, 1H), 7.22-7.27 (m, 1H), 7.46-7.52 (m, 1H).

MS m/z ([M−H]$^−$) 367.

Example 13

Synthesis of (S)-2-(tert-butoxy)-2-[3-cyclopropyl-2-(3,4-dihydro-2H-1-benzopyran-6-yl)-6-methylphenyl]acetic acid

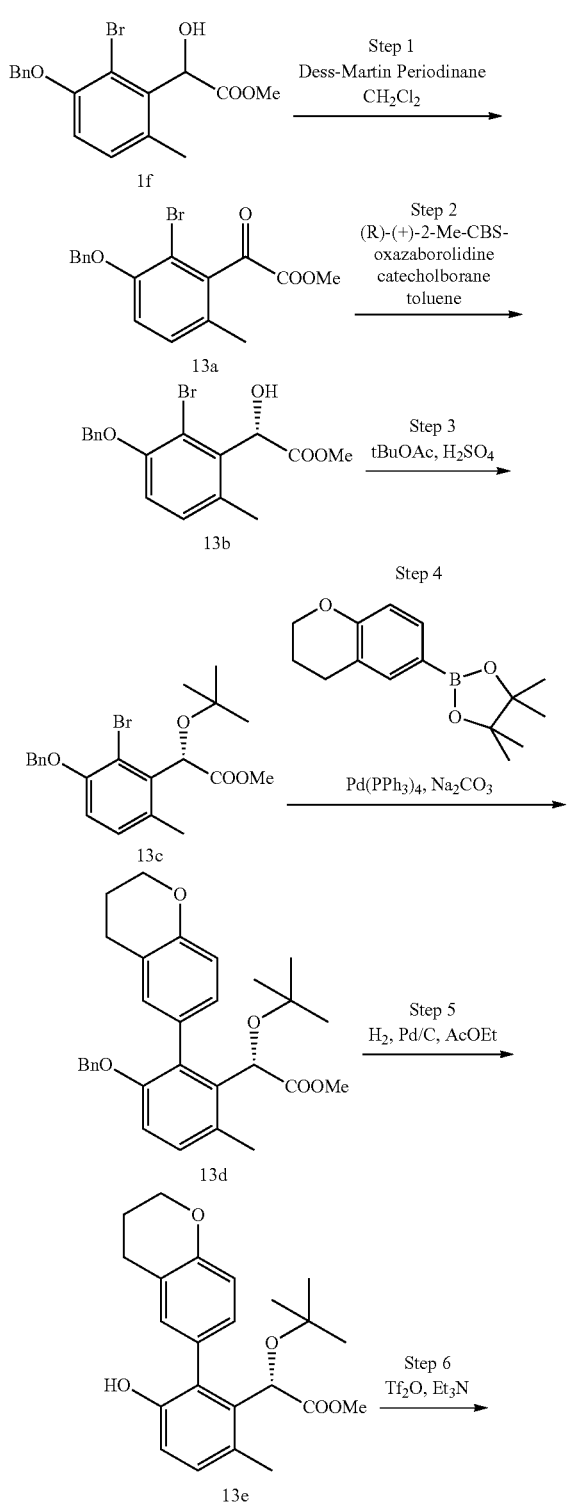

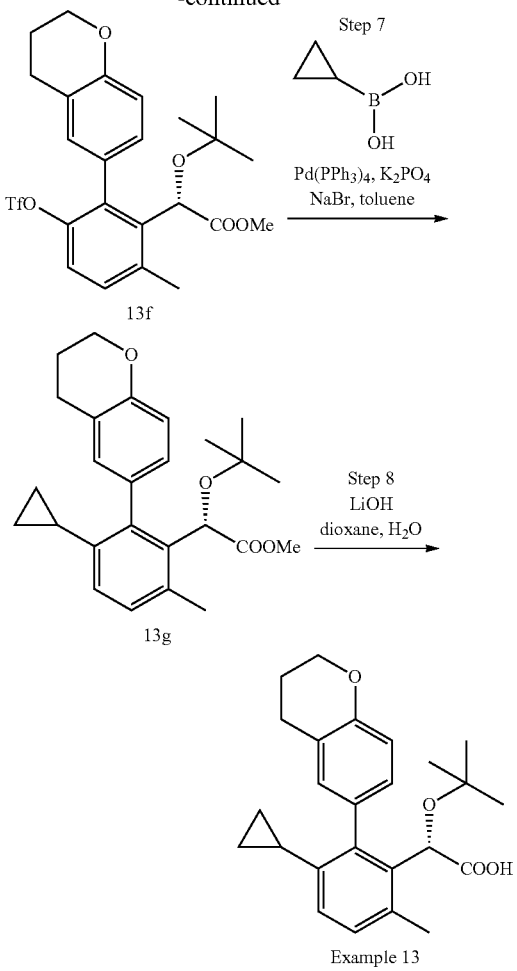

Step 1: Preparation of Intermediate methyl (3-benzyloxy-2-bromo-6-methyl-phenyl)-oxo-acetate (13a)

In a round bottom flask, under argon atmosphere, at room temperature, Dess-Martin periodinane (3.47 g, 7.95 mmol) was added in three portions at a solution of methyl (3-benzyloxy-2-bromo-6-methyl-phenyl)-hydroxy-acetate (1f) (2.42 g, 6.63 mmol) in dichloromethane (29 mL). After 1h 15 at room temperature, the mixture was quenched with saturated sodium bicarbonate solution and extracted with dichloromethane. The organic layer was washed twice with a saturated solution of sodium thiosulfate, brine, dried over sodium sulfate and concentrated in vacuo, to provide methyl (3-benzyloxy-2-bromo-6-methyl-phenyl)-oxo-acetate (13a) (2.40 g, 6.61 mmol, 99%), as an oil which crystallized in a light yellow solid.

$^1$H NMR (300 MHz, CDCl$_3$) δ 2.22 (s, 3H), 3.92 (s, 3H), 5.15 (s, 2H), 6.94 (d, J=8.4 Hz, 1H), 7.13 (d, J=8.4 Hz, 1H), 7.27-7.47 (m, 5H).

Step 2: Preparation of Intermediate methyl (S)-(3-benzyloxy-2-bromo-6-methyl-phenyl)-hydroxy-acetate (13b)

In a round bottom flask, under argon atmosphere, methyl (3-benzyloxy-2-bromo-6-methyl-phenyl)-oxo-acetate (13a) (100 mg, 0.28 mmol) and (R)-(+)-2-Methyl-CBS-oxazaborolidine (61 mg, 0.22 mmol) were dissolved in toluene (1 mL). The mixture was cooled to -20° C. and catecholborane (38.8 μL, 0.36 mmol) in toluene (415 μL) was slowly added. The mixture was stirred until the reaction was completed. After 80 minutes, the mixture was quenched with methanol, then saturated sodium bicarbonate solution was added. It was stirred for 30 minutes and extracted twice with ethyl acetate. The combined organic layers were washed with saturated sodium bicarbonate solution five or six times (until the aqueous layer was no longer colored), then once with a 1N hydrochloric acid aqueous solution, saturated brine, dried over sodium sulfate and concentrated in vacuo. The residue was purified by preparative TLC (cyclohexane/ethyl acetate 80/20) to provide methyl (S)-(3-benzyloxy-2-bromo-6-methyl-phenyl)-hydroxy-acetate (13b) (66 mg, 0.8 mmol, 65%) with an enantiomeric excess of 94.8% (Chiralcel® IA column, Daicel Chemical Industries, mobile phase heptane/2-PrOH 7/3, flow rate 1 mL/min, detection by photo-diode-array detector at 220 nm, retention time of 8.41 minutes).

$^1$H NMR (300 MHz, CDCl$_3$) δ 2.34 (s, 3H), 3.49 (d, J=4.4 Hz, 1H), 3.78 (s, 3H), 5.13 (s, 2H), 5.86 (d, J=4.4 Hz, 1H), 6.84 (d, J=8.4 Hz, 1H), 7.06 (d, J=8.4 Hz, 1H), 7.30-7.34 (m, 1H), 7.37-7.41 (m, 2H), 7.47 (d, J=7.4 Hz, 2H).

Step 3: Preparation of Intermediate methyl (S)-2-(3-benzyloxy-2-bromo-6-methylphenyl)-2-(tert-butoxy)-acetate (13c)

Using the procedure described in example 12, step 1, the intermediate methyl (S)-(3-benzyloxy-2-bromo-6-methyl-phenyl)-hydroxy-acetate (13b) (500 mg, 1.37 mmol) is converted into intermediate methyl (S)-2-(3-benzyloxy-2-bromo-6-methylphenyl)-2-(tert-butoxy)-acetate (13c) (469 mg, 1.11 mmol, 81%) as a white solid.

$^1$H NMR (300 MHz, CDCl$_3$) δ 1.23 (s, 9H), 2.36 (s, 3H), 3.68 (s, 3H), 5.12 (s, 2H), 5.96 (s, 1H), 6.80 (d, J=8.4 Hz, 1H), 7.01 (d, J=8.4 Hz, 1H), 7.29-7.42 (m, 3H), 7.48-7.51 (m, 2H).

Step 4: Preparation of Intermediate methyl (S)-2-(tert-butoxy)-2-[3-benzyloxy-2-(3,4-dihydro-2H-1-benzopyran-6-yl)-6-methylphenyl]acetate (13d)

In a sealed round bottom flask, to a degassed solution of methyl (S)-2-(3-benzyloxy-2-bromo-6-methylphenyl)-2-(tert-butoxy)-acetate (13c) (330 mg, 0.783 mmol) and chroman-6-boronic acid, pinacol ester (224 mg, 0.862 mmol) in dioxane (4 mL) was added a solution of sodium carbonate (249 mg, 2.35 mmol) in water (0.8 mL) followed by palladium tetrakis(triphenylphosphine) (91 mg, 0.078 mmol). The mixture was heated at 120° C. for 16 hours. The mixture was cooled at room temperature. Water (10 mL) was added. The aqueous layer was extracted with ethyl acetate (3×10 mL). The organic layer was washed with brine (20 mL), dried over sodium sulfate and concentrated in vacuo. The residue was purified by flash chromatography on silica gel (cyclohexane/ethyl acetate 90/10) to provide methyl (S)-2-(tert-butoxy)-2-[3-benzyloxy-2-(3,4-dihydro-2H-1-benzopyran-6-yl)-6-methyl phenyl]acetate (13d) (816 mg, 1.71 mmol, 100%) as a white solid.

$^1$H NMR (300 MHz, CDCl$_3$) δ 0.96 (s, 9H), 2.00-2.09 (m, 2H), 2.35 and 2.36 (s, 3H), 2.72-2.82 (m, 2H), 3.70 and 3.71

(s, 3H), 4.22-4.26 (m, 2H), 4.88-5.01 (m, 2H), 5.16 and 5.18 (s, 1H), 6.81-6.87 (m, 2H), 6.99-7.29 (m, 8H).

Step 5: Preparation of Intermediate methyl (S)-2-(tert-butoxy)-2-[2-(3,4-dihydro-2H-1-benzopyran-6-yl)-3-hydroxy-6-methylphenyl]acetate (13e)

Using the procedure described in example 12, step 4, the intermediate methyl (S)-2-(tert-butoxy)-2-[3-benzyloxy-2-(3,4-dihydro-2H-1-benzopyran-6-yl)-6-methylphenyl]acetate (13d) (816 mg, 1.72 mmol) is converted into intermediate methyl (S)-2-(tert-butoxy)-2-[2-(3,4-dihydro-2H-1-benzopyran-6-yl)-3-hydroxy-6-methylphenyl]acetate (13e) (586 mg, 1.52 mmol, 89%).

$^1$H NMR (300 MHz, CDCl$_3$) δ 0.97 and 0.98 (s, 9H), 2.01-2.09 (m, 2H), 2.34 and 2.35 (s, 3H), 2.71-2.86 (m, 2H), 3.67 and 3.68 (s, 3H), 4.24-4.27 (m, 2H), 4.63 and 4.67 (s, 1H), 4.99 and 5.00 (s, 1H), 6.82-7.05 (m, 4H), 7.12-7.19 (m, 1H).

Step 6: Preparation of Intermediate methyl (S)-2-(tert-butoxy)-2-[2-(3,4-dihydro-2H-1-benzopyran-6-yl)-6-methyl-3-trifluoromethanesulfonyloxy-phenyl]acetate (13f)

To a solution of methyl (S)-2-(tert-butoxy)-2-[2-(3,4-dihydro-2H-1-benzopyran-6-yl)-3-hydroxy-6-methylphenyl]acetate (13e) (580 mg, 1.51 mmol) in anhydrous dichloromethane (15 mL) under nitrogen atmosphere at −78° C. were successively added triethylamine (0.631 mL, 4.53 mmol), and trifluoromethanesulfonic anhydride (0.32 mL, 1.89 mmol). The mixture was stirred at this temperature for 30 minutes before adding water (10 mL). Layers were separated. The aqueous layer was extracted with dichloromethane (10 mL). The combined organic layers were washed with a saturated solution of sodium hydrogenaocarbonate (10 mL), dried over sodium chloride and concentrated in vacuo to provide the intermediate methyl (S)-2-(tert-butoxy)-2-[2-(3,4-dihydro-2H-1-benzopyran-6-yl)-6-methyl-3-trifluoromethanesulfonyloxy-phenyl]acetate (13f) (721 mg, 1.40 mmol, 92%) as a brown oil which was used without further purification.

$^1$H NMR (300 MHz, CDCl$_3$) δ 0.95 and 0.96 (s, 9H), 2.00-2.09 (m, 2H), 2.43 and 2.45 (s, 3H), 2.68-2.87 (m, 2H), 3.70 and 3.71 (s, 3H), 4.22-4.26 (m, 2H), 5.11 and 5.13 (s, 1H), 6.82-6.87 (m, 1H), 6.94-7.11 (m, 2H), 7.15-7.21 (m, 2H).

Step 7: Preparation of Intermediate methyl (S)-2-(tert-butoxy)-2-[3-cyclopropyl-2-(3,4-dihydro-2H-1-benzopyran-6-yl)-6-methylphenyl]acetate (13g)

Using the procedure described in example 1, step 11, the intermediate methyl (S)-2-(tert-butoxy)-2-[2-(3,4-dihydro-2H-1-benzopyran-6-yl)-6-methyl-3-trifluoromethanesulfonyloxy-phenyl]acetate (13f) (360 mg, 0.697 mmol) is converted into intermediate methyl (S)-2-(tert-butoxy)-2-[3-cyclopropyl-2-(3,4-dihydro-2H-1-benzopyran-6-yl)-6-methylphenyl]acetate (13g) (199 mg, 0.487 mmol, 69%) as a lightly yellow oil.

$^1$H NMR (300 MHz, CDCl$_3$) δ 0.52-0.74 (m, 4H), 0.98 (s, 9H), 1.41-1.52 (m, 1H), 1.99-2.10 (m, 2H), 2.39 (s, 3H), 2.67-2.87 (m, 2H), 3.65 and 3.67 (s, 3H), 4.22-4.26 (m, 2H), 5.08 and 5.10 (s, 1H), 6.72-6.85 (m, 2H), 6.94-7.10 (m, 3H).

Step 8: Preparation of (S)-2-(tert-butoxy)-2-[3-cyclopropyl-2-(3,4-dihydro-2H-1-benzopyran-6-yl)-6-methylphenyl]acetic acid (Example 13)

Using the procedure described in example 1, step 12, the methyl (S)-2-(tert-butoxy)-2-[3-cyclopropyl-2-(3,4-dihydro-2H-1-benzopyran-6-yl)-6-methylphenyl]acetate (13g) (378 mg, 0.925 mmol) is converted into (S)-2-(tert-butoxy)-2-[3-cyclopropyl-2-(3,4-dihydro-2H-1-benzopyran-6-yl)-6-methylphenyl]acetic acid (Example 13) (313 mg, 0.793 mmol, 85%).

$^1$H NMR (300 MHz, CDCl$_3$) δ 0.50-0.73 (m, 4H), 0.88 and 0.89 (s, 9H), 1.35-1.44 (m, 1H), 1.86-2.01 (m, 2H), 2.30 (s, 3H), 2.61-2.83 (m, 2H), 4.13-4.20 (m, 2H), 4.91 and 4.95 (s, 1H), 6.69-6.73 (m, 1H), 6.78 and 6.81 (d, J=8.3 Hz, 1H), 6.89-7.06 (m, 2H), 12.37 (s, 1H).

MS m/z ([M−H]$^−$) 393.

Example 14

Synthesis of 2-(tert-butoxy)-2-(6-cyclopropyl-3,4'-dimethyl-biphenyl-2-yl)-acetic acid

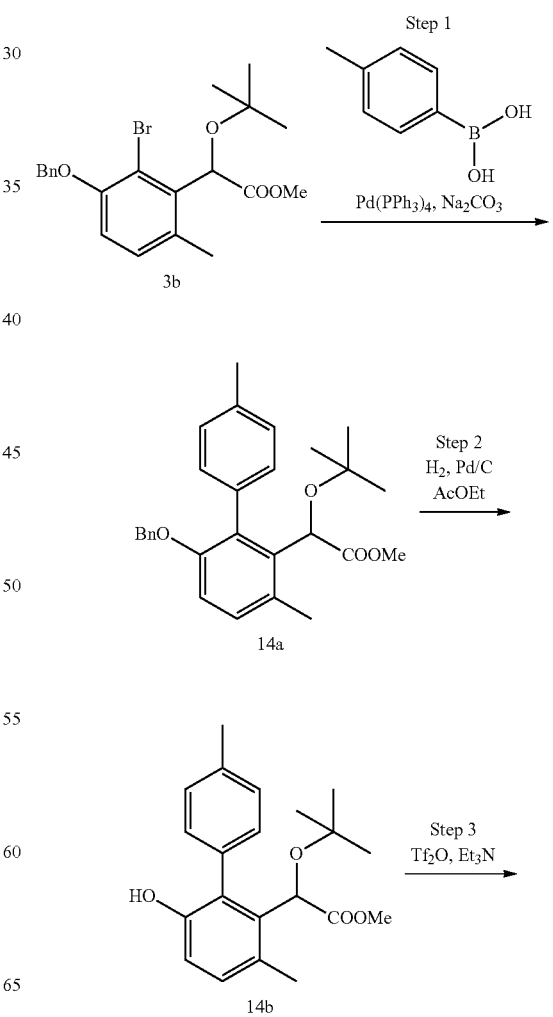

-continued

Step 4

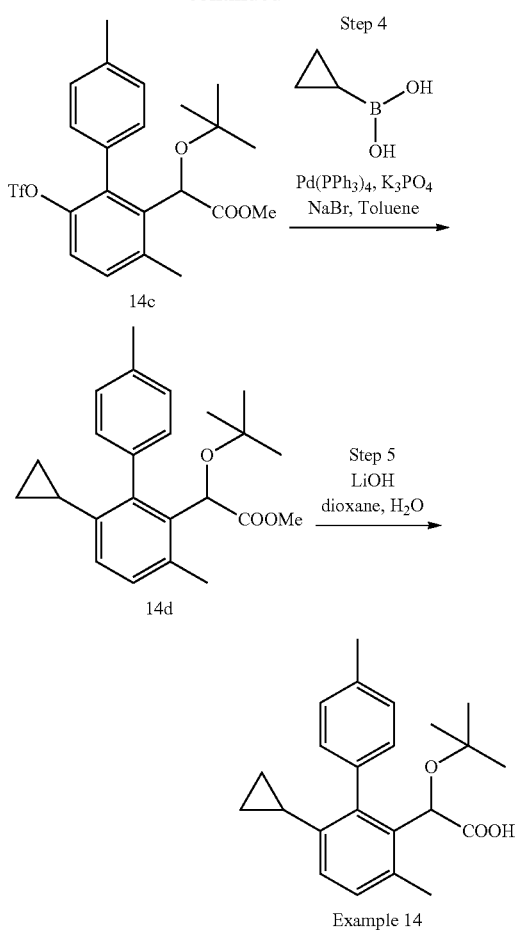

Example 14

Step 1: Preparation of Intermediate methyl 2-(6-benzyloxy-3,4'-dimethyl-biphenyl-2-yl)-2-(tert-butoxy)acetate (14a)

Using the procedure described in example 1, step 7, the intermediate methyl 2-(3-benzyloxy-2-bromo-6-methylphenyl)-2-(tert-butoxy)-acetate (3b) (100 mg, 0.24 mmol) is converted by reaction with 4-methylphenylboronic acid (39 mg, 0.28 mmol), after purification by preparative TLC (cyclohexane/ethyl acetate 80/20), into methyl 2-(6-benzyloxy-3,4'-dimethyl-biphenyl-2-yl)-2-(tert-butoxy)acetate (14a) (52 mg, 0.12 mmol, 51%).

$^1$H NMR (400 MHz, CDCl$_3$) δ 0.95 (s, 9H), 2.37 (s, 3H), 2.43 (s, 3H), 3.71 (s, 3H), 4.91 (d, J=12.5 Hz, 1H), 4.97 (d, J=12.5 Hz, 1H), 5.13 (s, 1H), 6.85 (d, J=8.3 Hz, 1H), 7.06 (d, J=8.3 Hz, 1H), 7.09-7.14 (m, 2H), 7.19-7.32 (m, 7H).

MS m/z ([M+Na]$^+$) 455.

Step 2: Preparation of Intermediate methyl 2-(tert-butoxy)-2-(6-hydroxy-3,4'-dimethyl-biphenyl-2-yl)-acetate (14b)

Using the procedure described in example 12, step 4, the intermediate methyl 2-(6-benzyloxy-3,4'-dimethyl-biphenyl-2-yl)-2-(tert-butoxy)acetate (14a) (99 mg, 0.23 mmol) is converted into intermediate methyl 2-(tert-butoxy)-2-(6-hydroxy-3,4'-dimethyl-biphenyl-2-yl)-acetate (14b) (78 mg, 0.23 mmol, 100%) which was used without further purification.

$^1$H NMR (300 MHz, CDCl$_3$) δ 0.95 (s, 9H), 2.35 (s, 3H), 2.44 (s, 3H), 3.69 (s, 3H), 4.59 (s, 1H), 4.97 (s, 1H), 6.85 (d, J=8.2 Hz, 1H), 7.05 (d, J=8.2 Hz, 1H), 7.18-7.24 (m, 1H), 7.27-7.39 (m, 3H).

MS m/z ([M+Na]$^+$) 365.

Step 3: Preparation of Intermediate methyl 2-(tert-butoxy)-2-(3,4'-dimethyl-6-trifluoromethanesulfonyloxy-biphenyl-2-yl)-acetate (14c)

Using the procedure described in example 1, step 10, the intermediate methyl 2-(tert-butoxy)-2-(6-hydroxy-3,4'-dimethyl-biphenyl-2-yl)-acetate (14b) (78 mg, 0.23 mmol) is converted, after purification by preparative TLC (cyclohexane/ethyl acetate 80/20), into methyl 2-(tert-butoxy)-2-(3,4'-dimethyl-6-trifluoromethanesulfonyloxy-biphenyl-2-yl)-acetate (14c) (91 mg, 0.19 mmol, 84%).

$^1$H NMR (400 MHz, CDCl$_3$) δ 0.93 (s, 9H), 2.43 (s, 3H), 2.46 (s, 3H), 3.72 (s, 3H), 5.08 (s, 1H), 7.16-7.30 (m, 6H).

MS m/z ([M−H]$^-$) 473.

Step 4: Preparation of Intermediate methyl 2-(tert-butoxy)-2-(6-cyclopropyl-3,4'-dimethyl-biphenyl-2-yl)-acetate (14d)

Using the procedure described in example 1, step 11, the intermediate methyl 2-(tert-butoxy)-2-(3,4'-dimethyl-6-trifluoromethanesulfonyloxy-biphenyl-2-yl)-acetate (14c) (91 mg, 0.19 mmol) is converted, after purification by preparative TLC (cyclohexane/ethyl acetate 90/10), into methyl 2-(tert-butoxy)-2-(6-cyclopropyl-3,4'-dimethyl-biphenyl-2-yl)-acetate (14d) (54 mg, 0.15 mmol, 77%).

$^1$H NMR (300 MHz, CDCl$_3$) δ 0.51-0.64 (m, 3H), 0.64-0.74 (m, 1H), 0.96 (s, 9H), 1.37-1.45 (m, 1H), 2.40 (s, 3H), 2.42 (s, 3H), 3.67 (s, 3H), 5.05 (s, 1H), 6.77 (d, J=7.9 Hz, 1H), 7.05 (d, J=7.9 Hz, 1H), 7.17-7.30 (m, 4H).

MS m/z ([M+Na]$^+$) 389.

Step 5: Preparation of 2-(tert-butoxy)-2-(6-cyclopropyl-3,4'-dimethyl-biphenyl-2-yl)-acetic acid (Example 14)

Using the procedure described in example 1, step 12, the intermediate methyl 2-(tert-butoxy)-2-(6-cyclopropyl-3,4'-dimethyl-biphenyl-2-yl)-acetate (14d) (54 mg, 0.15 mmol) is converted into 2-(tert-butoxy)-2-(6-cyclopropyl-3,4'-dimethyl-biphenyl-2-yl)-acetic acid (Example 14) (35 mg, 0.10 mmol, 67%).

$^1$H NMR (300 MHz, CDCl$_3$) δ 0.49-0.64 (m, 3H), 0.66-0.77 (m, 1H), 0.99 (s, 9H), 1.41-1.53 (m, 1H), 2.36 (s, 3H), 2.41 (s, 3H), 5.18 (s, 1H), 6.80 (d, J=7.9 Hz, 1H), 7.05 (d, J=7.9 Hz, 1H), 7.17-7.28 (m, 3H), 7.42-7.47 (m, 1H).

MS m/z ([M+Na]$^+$) 375.

MS m/z ([M−H]$^-$) 351.

Example 15

Synthesis of 2-(tert-butoxy)-2-(6-cyclopropyl-4'-fluoro-3-methyl-biphenyl-2-yl)-acetic acid

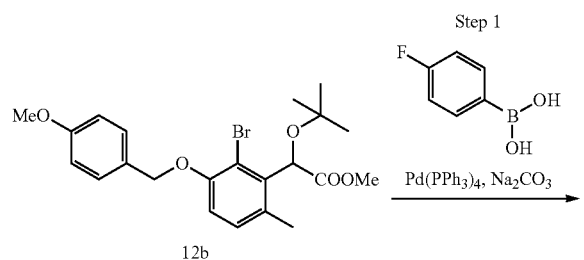

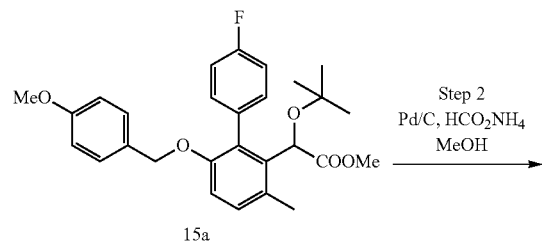

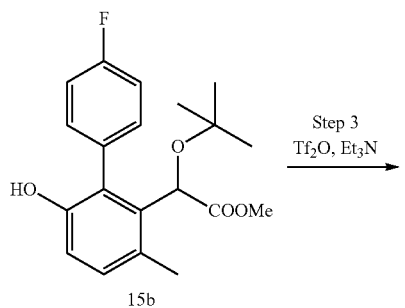

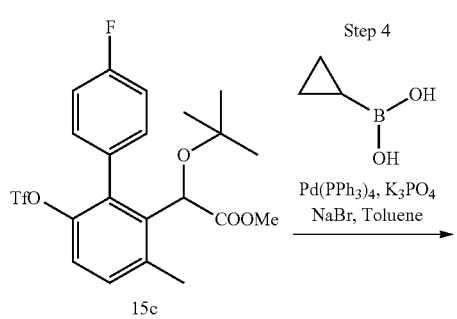

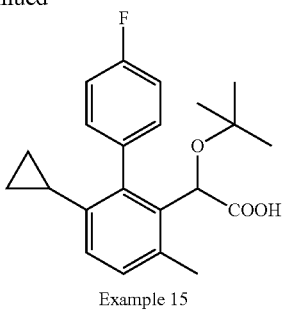

Example 15

Step 1: Preparation of Intermediate methyl 2-[4'-fluoro-6-(4-methoxy-benzyloxy)-3-methyl-biphenyl-2-yl]-2-(tert-butoxy)acetate (15a)

Using the procedure described in example 1, step 7, the intermediate methyl 2-[2-bromo-3-(4-methoxy-benzyloxy)-6-methyl-phenyl]-2-(tert-butoxy)-acetate (12b) (150 mg, 0.33 mmol) is converted by reaction with 4-fluorophenyl-boronic acid (56 mg, 0.40 mmol), after purification by preparative TLC (cyclohexane/ethyl acetate: 80/20) into methyl 2-[4'-fluoro-6-(4-methoxy-benzyloxy)-3-methyl-biphenyl-2-yl]-2-(tert-butoxy)acetate (15a) (139 mg, 0.30 mmol, 90%).

$^1$H NMR (300 MHz, CDCl$_3$) δ 0.94 (s, 9H), 2.36 (s, 3H), 3.71 (s, 3H), 3.78 (s, 3H), 4.82 (d, J=11.8 Hz, 1H), 4.90 (d, J=11.8 Hz, 1H), 5.04 (s, 1H), 6.76-6.82 (m, 2H), 6.88 (d, J=8.4 Hz, 1H), 6.99-7.16 (m, 5H), 7.24-7.31 (m, 1H), 7.34-7.41 (m, 1H).

MS m/z ([M+Na]$^+$) 489.

Step 2: Preparation of Intermediate methyl 2-(tert-butoxy)-2-(4'-fluoro-6-hydroxy-3-methyl-biphenyl-2-y)-acetate (15b)

Palladium on activated charcoal (10% Pd by weight, 13.9 mg) was added to a solution of methyl 2-[4'-fluoro-6-(4-methoxy-benzyloxy)-3-methyl-biphenyl-2-yl]-2-(tert-butoxy)acetate (15a) (139 mg, 0.30 mmol) and ammonium formate (470 mg, 7.45 mmol) in methanol (3 mL). The mixture was refluxed for 120 minutes, cooled to room temperature, filtered through a pad of Celite® and rinsed with methanol and ethyl acetate. The filtrate was concentrated in vacuo. The residue was dissolved in ethyl acetate (5 mL) and successively washed with water (5 mL) and brine (5 mL). The organic layer was dried over sodium sulfate, concentrated in vacuo to provide methyl 2-(tert-butoxy)-2-(4'-fluoro-6-hydroxy-3-methyl-biphenyl-2-y)-acetate (15b) (103 mg, 0.30 mmol, 100%), which was used without further purification.

$^1$H NMR (400 MHz, CDCl$_3$) δ 0.96 (s, 9H), 2.36 (s, 3H), 3.69 (s, 3H), 4.49 (bs, 1H), 4.91 (s, 1H), 6.85 (d, J=8.3 Hz, 1H), 7.07 (d, J=8.3 Hz, 1H), 7.16-7.26 (m, 2H), 7.28-7.33 (m, 1H), 7.45-7.51 (m, 1H).

MS m/z ([M+Na]$^+$) 369.
MS m/z ([M−H]$^-$) 345.

Step 3: Preparation of Intermediate methyl 2-(tert-butoxy)-2-(4'-fluoro-3-methyl-6-trifluoromethane-sulfonyloxy-biphenyl-2-y)-acetate (15c)

Using the procedure described in example 1, step 10, the intermediate methyl 2-(tert-butoxy)-2-(4'-fluoro-6-hydroxy- 3-methyl-biphenyl-2-y)-acetate (15b) (103 mg, 0.30 mmol) is converted, after purification by preparative TLC (cyclohexane/ethyl acetate 80/20), to methyl 2-(tert-butoxy)-2-(4'-fluoro-3-methyl-6-trifluoromethanesulfonyloxy-biphenyl-2-y)-acetate (15c) (114 mg, 0.24 mmol, 80%).

$^1$H NMR (400 MHz, CDCl$_3$) δ 0.95 (s, 9H), 2.46 (s, 3H), 3.72 (s, 3H), 5.05 (s, 1H), 7.11-7.30 (m, 5H), 7.39-7.45 (m, 1H).

MS m/z ([M−H]$^−$) 477.

Step 4: Preparation of Intermediate methyl 2-(tert-butoxy)-2-(6-cyclopropyl-4'-fluoro-3-methyl-biphenyl-2-yl)-acetate (15d)

Using the procedure described in example 1, step 11, the intermediate methyl 2-(tert-butoxy)-2-(4'-fluoro-3-methyl-6-trifluoromethanesulfonyloxy-biphenyl-2-y)-acetate (15c) (114 mg, 0.24 mmol) is converted, after purification by preparative TLC (cyclohexane/ethyl acetate 90/10), into methyl 2-(tert-butoxy)-2-(6-cyclopropyl-4'-fluoro-3-methyl-biphenyl-2-yl)-acetate (15d) (66 mg, 0.19 mmol, 75%).

$^1$H NMR (300 MHz, CDCl$_3$) δ 0.50-0.74 (m, 4H), 0.97 (s, 9H), 1.30-1.42 (m, 1H), 2.40 (s, 3H), 3.67 (s, 3H), 4.99 (s, 1H), 6.80 (d, J=7.9 Hz, 1H), 7.04-7.18 (m, 3H), 7.23-7.30 (m, 1H), 7.34-7.42 (m, 1H).

MS m/z ([M+Na]$^+$) 393.

Step 5: Preparation of 2-(tert-butoxy)-2-(6-cyclopropyl-4'-fluoro-3-methyl-biphenyl-2-yl)-acetic acid (Example 15)

Using the procedure described in example 1, step 12, the intermediate methyl 2-(tert-butoxy)-2-(6-cyclopropyl-4'-fluoro-3-methyl-biphenyl-2-yl)-acetate (15d) (66 mg, 0.18 mmol) is converted to 2-(tert-butoxy)-2-(6-cyclopropyl-4'-fluoro-3-methyl-biphenyl-2-yl)-acetic acid (Example 15) (51 mg, 0.14 mmol, 80%).

$^1$H NMR (300 MHz, CDCl$_3$) δ 0.48-0.64 (m, 3H), 0.68-0.77 (m, 1H), 1.00 (s, 9H), 1.36-1.48 (m, 1H), 2.37 (s, 3H), 5.11 (s, 1H), 6.84 (d, J=7.9 Hz, 1H), 7.04-7.20 (m, 3H), 7.24-7.35 (m, 1H), 7.50-7.61 (m, 1H).

MS m/z ([M+Na]$^+$) 379.
MS m/z ([M−H]$^−$) 355.

Example 16

Synthesis of 2-(tert-butoxy)-2-[3-cyclopropyl-6-methyl-2-(5-methyl-chroman-6-yl)-phenyl]acetic acid

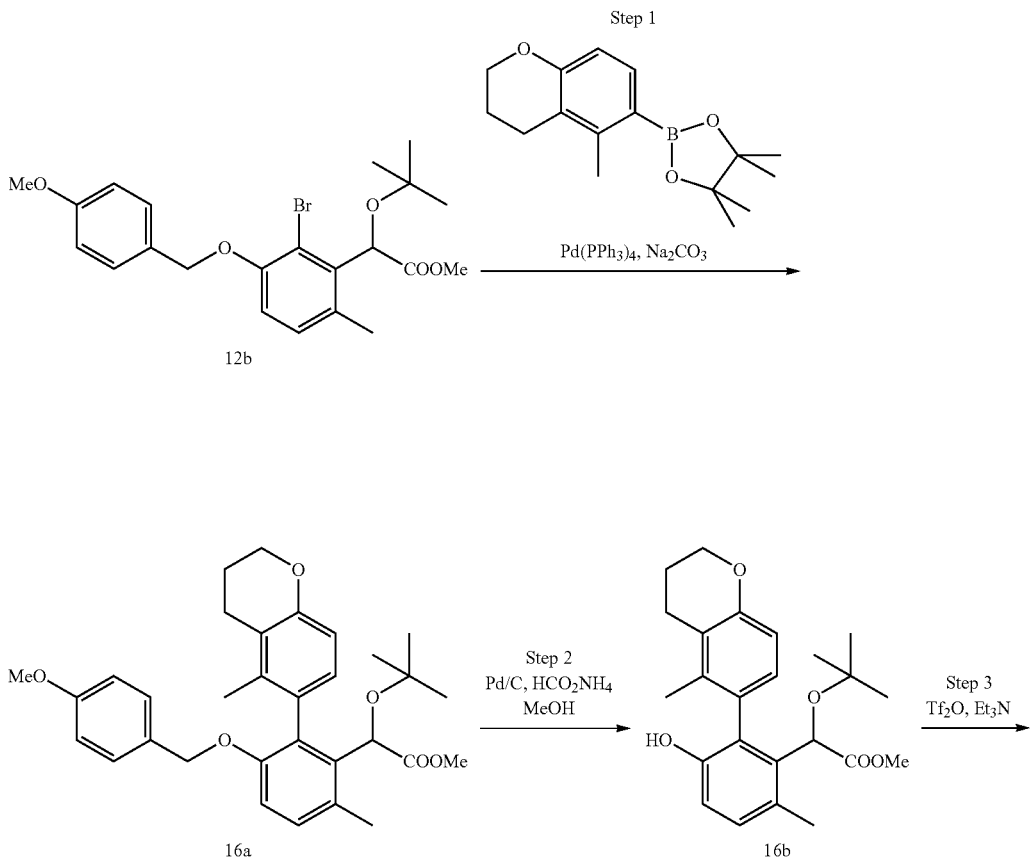

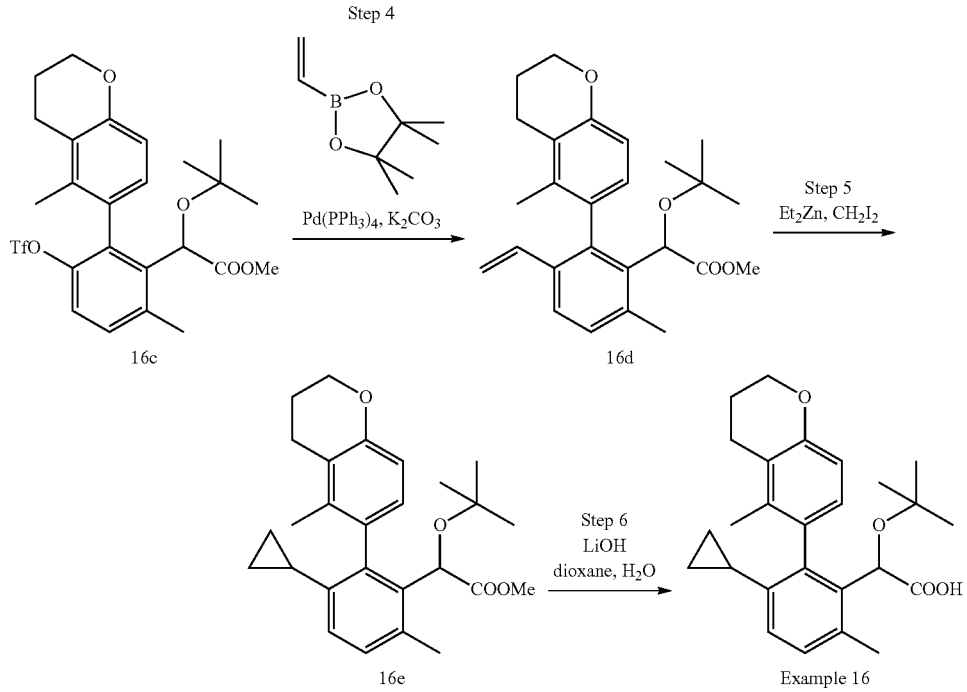

Step 1: Preparation of Intermediate methyl 2-[3-(4-methoxy-benzyloxy)-6-methyl-2-(5-methyl-chroman-6-yl)-phenyl]-2-(tert-butoxy)-acetate (16a)

Using the procedure described in example 1, step 7, the intermediate methyl 2-[2-bromo-3-(4-methoxy-benzyloxy)-6-methyl-phenyl]-2-(tert-butoxy)-acetate (12b) (150 mg, 0.33 mmol) is converted by reaction with 4,4,5,5-tetramethyl-2-(5-methyl-3,4-dihydro-2H-1-benzopyran-6-yl)-1,3,2-dioxaborolane (109 mg, 0.40 mmol), after purification by preparative TLC (cyclohexane/ethyl acetate 80/20) into methyl 2-[3-(4-methoxy-benzyloxy)-6-methyl-2-(5-methyl-chroman-6-yl)-phenyl]-2-(tert-butoxy)-acetate (16a) (129 mg, 0.25 mmol, 75%).

$^1$H NMR (400 MHz, CDCl$_3$) δ 1.11 (s, 9H), 1.85 (s, 3H), 2.06-2.16 (m, 2H), 2.45 (s, 3H), 2.65-2.73 (m, 2H), 3.56 (s, 3H), 3.77 (s, 3H), 4.18-4.24 (m, 2H), 4.81-4.88 (m, 2H), 5.08 (s, 1H), 6.71 (d, J=8.3 Hz, 1H), 6.76 (d, J=8.6 Hz, 2H), 6.81 (d, J=8.3 Hz, 1H), 6.87 (d, J=8.3 Hz, 1H), 6.96 (d, J=8.6 Hz, 2H), 7.06 (d, J=8.3 Hz, 1H).

MS m/z ([M+Na]$^+$) 541.

Step 2: Preparation of Intermediate methyl 2-(tert-butoxy)-2-[3-hydroxy-6-methyl-2-(5-methyl-chroman-6-yl)-phenyl]acetate (16b)

Using the procedure described in example 15, step 2, the intermediate methyl 2-[3-(4-methoxy-benzyloxy)-6-methyl-2-(5-methyl-chroman-6-yl)-phenyl]-2-(tert-butoxy)-acetate (16a) (129 mg, 0.25 mmol) is converted, after purification by preparative TLC (dichloromethane/ethyl acetate 70/30) into methyl 2-(tert-butoxy)-2-[3-hydroxy-6-methyl-2-(5-methyl-chroman-6-yl)-phenyl]acetate (16b) (91 mg, 0.23 mmol, 92%).

$^1$H NMR (400 MHz, CDCl$_3$) δ 1.09 (s, 9H), 1.91 (s, 3H), 2.06-2.17 (m, 2H), 2.43 (s, 3H), 2.67-2.75 (m, 2H), 3.58 (s, 3H), 4.18-4.24 (m, 2H), 4.40 (s, 1H), 4.93 (s, 1H), 6.77 (d, J=8.3 Hz, 1H), 6.83 (d, J=8.3 Hz, 1H), 6.93 (d, J=8.3 Hz, 1H), 7.06 (d, J=8.3 Hz, 1H).

MS m/z ([M+Na]$^+$) 421.
MS m/z ([M−H]$^−$) 397.

Step 3: Preparation of Intermediate methyl 2-(tert-butoxy)-2-[6-methyl-2-(5-methyl-chroman-6-yl)-3-trifluoromethanesulfonyloxy-phenyl]acetate (16c)

Using the procedure described in example 1, step 10, the intermediate methyl 2-(tert-butoxy)-2-[3-hydroxy-6-methyl-2-(5-methyl-chroman-6-yl)-phenyl]acetate (16b) (91 mg, 0.23 mmol) is converted, after purification by preparative TLC (cyclohexane/ethyl acetate 85/15), into methyl 2-(tert-butoxy)-2-[6-methyl-2-(5-methyl-chroman-6-yl)-3-trifluoro methanesulfonyloxy-phenyl]acetate (16c) (106 mg, 0.20 mmol, 87%).

$^1$H NMR (400 MHz, CDCl$_3$) δ 1.09 (s, 9H), 1.84 (s, 3H), 2.06-2.13 (m, 2H), 2.53 (s, 3H), 2.65-2.71 (m, 2H), 3.58 (s, 3H), 4.16-4.22 (m, 2H), 5.08 (s, 1H), 6.72 (d, J=8.4 Hz, 1H), 6.88 (d, J=8.4 Hz, 1H), 7.16 (d, J=8.5 Hz, 1H), 7.21 (d, J=8.5 Hz, 1H).

MS m/z ([M−H]$^−$) 529.

Step 4: Preparation of Intermediate methyl 2-(tert-butoxy)-2-[6-methyl-2-(5-methyl-chroman-6-yl)-3-vinyl-phenyl]acetate (16d)

A degassed solution of methyl 2-(tert-butoxy)-2-[6-methyl-2-(5-methyl-chroman-6-yl)-3-trifluoromethanesulfonyloxy-phenyl]acetate (16c) (106 mg, 0.20 mmol), potassium carbonate (75 mg, 0.54 mmol), vinylboronic acid pinacol ester (62 mg, 0.40 mmol) and palladium tetrakis (triphenylphosphine) (23 mg, 0.020 mmol) in dioxane (1 mL) and water (0.25 mL) was heated under microwaves at 120° C. for 5 hours. Water (2 mL) was added and the mixture was extracted with AcOEt (3×4 mL). The organic layer was washed with brine (6 mL), dried over sodium sulfate and concentrated in vacuo. The residue was purified by preparative TLC (cyclohexane/AcOEt 85/15) to provide methyl 2-(tert-butoxy)-2-[6-methyl-2-(5-methyl-chroman-6-yl)-3-vinyl-phenyl]acetate (16d) (30 mg, 0.073 mmol, 37%).

$^1$H NMR (400 MHz, CDCl$_3$) δ 1.09 (s, 9H), 1.77 (s, 3H), 2.06-2.15 (m, 2H), 2.51 (s, 3H), 2.65-2.72 (m, 2H), 3.56 (s, 3H), 4.17-4.23 (m, 2H), 4.95 (dd, J=1.3 Hz, J=11.0 Hz, 1H), 5.04 (s, 1H), 5.52 (dd, J=1.3 Hz, J=17.5 Hz, 1H), 6.14 (dd, J=11.0 Hz, J=17.5 Hz, 1H), 6.70 (d, J=8.3 Hz, 1H), 6.83 (d, J=8.3 Hz, 1H), 7.14 (d, J=8.0 Hz, 1H), 7.47 (d, J=8.0 Hz, 1H). MS m/z ([M+Na]$^+$) 431.

Step 5: Preparation of Intermediate methyl 2-(tert-butoxy)-2-[3-cyclopropyl-6-methyl-2-(5-methyl-chroman-6-yl)-phenyl]acetate (16e)

Under nitrogen atmosphere, a solution of methyl 2-(tert-butoxy)-2-[6-methyl-2-(5-methyl-chroman-6-yl)-3-vinyl-phenyl]acetate (16d) (30 mg, 0.073 mmol) in anhydrous 1,2-dichloroethane (2 mL) was cooled to 0° C. Diiodomethane (59 μL, 0.734 mmol) and a diethylzinc solution 15 wt. % in toluene (334 μL, 0.367 mmol) were added, and the reaction mixture was stirred at room temperature for 40 hours. The mixture was quenched with a saturated solution of ammonium chloride (5 mL) and extracted with ethyl acetate (2×5 mL). The organic layer was washed with brine (6 mL), dried over sodium sulfate and concentrated in vacuo. The residue was purified by preparative TLC (cyclohexane/AcOEt 95/5) to provide methyl 2-(tert-butoxy)-2-[3-cyclopropyl-6-methyl-2-(5-methyl-chroman-6-yl)-phenyl]acetate (16e) (6.7 mg, 0.016 mmol, 22%).

$^1$H NMR (400 MHz, CDCl$_3$) δ 0.48-0.69 (m, 4H), 1.08 (s, 9H), 1.23-1.33 (m, 1H), 1.86 (s, 3H), 2.05-2.16 (m, 2H), 2.47 (s, 3H), 2.63-2.76 (m, 2H), 3.57 (s, 3H), 4.16-4.24 (m, 2H), 5.03 (s, 1H), 6.68-6.72 (m, 2H), 6.89 (d, J=8.3 Hz, 1H), 7.06 (d, J=8.0 Hz, 1H).

MS m/z ([M+Na]$^+$) 445.

Step 6: Preparation of 2-(tert-butoxy)-2-[3-cyclopropyl-6-methyl-2-(5-methyl-chroman-6-yl)-phenyl] acetic acid (Example 16)

Using the procedure described in example 1, step 12, the intermediate methyl 2-(tert-butoxy)-2-[3-cyclopropyl-6-methyl-2-(5-methyl-chroman-6-yl)-phenyl]acetate (16e) (6.7 mg, 0.016 mmol) is converted into 2-(tert-butoxy)-2-[3-cyclopropyl-6-methyl-2-(5-methyl-chroman-6-yl)-phenyl]acetic acid (6 mg, 0.015 mmol, 93%).

$^1$H NMR (400 MHz, CDCl$_3$) δ 0.48-0.59 (m, 2H), 0.59-0.70 (m, 2H), 1.11 (s, 9H), 1.27-1.36 (m, 1H), 1.94 (s, 3H), 2.04-2.12 (m, 2H), 2.38 (s, 3H), 2.62-2.72 (m, 2H), 4.15-4.20 (m, 2H), 5.11 (s, 1H), 6.69 (d, J=8.3 Hz, 1H), 6.73 (d, J=7.9 Hz, 1H), 6.88-6.94 (m, 1H), 7.05 (d, J=7.9 Hz, 1H).
MS m/z ([M+Na]$^+$) 431.
MS m/z ([M–H]$^-$) 407.

Example 17

Synthesis of (trans-3-bicyclopropyl-2-yl-2-chroman-6-yl-6-methyl-phenyl)-tert-butoxy-acetic acid

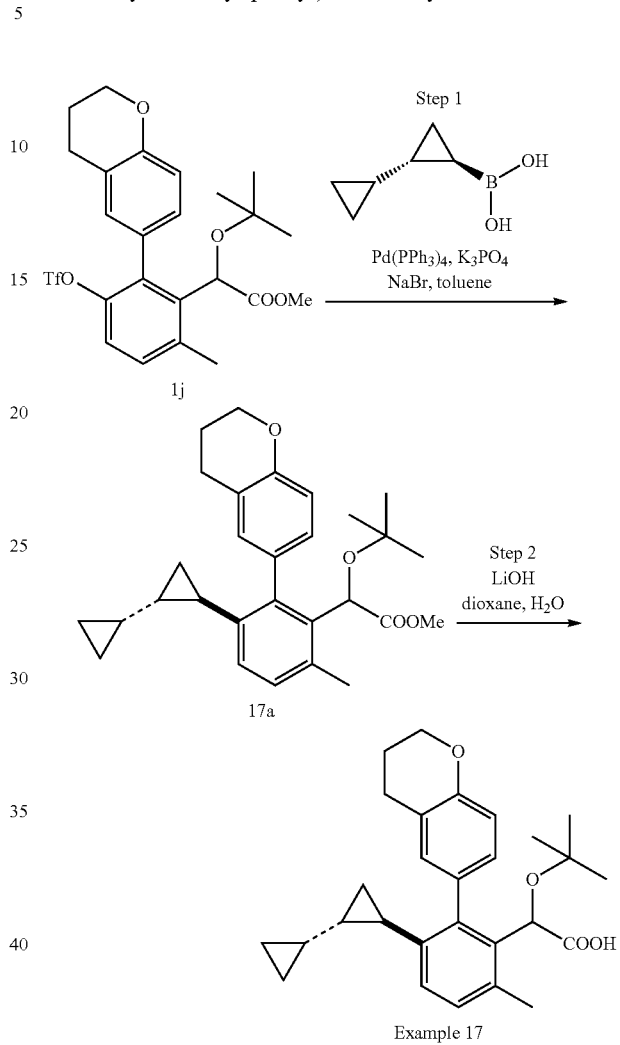

Example 17

Step 1: Preparation of Intermediate tert-butoxy-[2-chroman-6-yl-6-methyl-3-(trans-2-cyclopropyl-cyclopropyl)-phenyl]-acetic acid methyl ester (17a)

Using the procedure described in example 1, step 11, the intermediate methyl 2-(tert-butoxy)-2-[2-(3,4-dihydro-2H-1-benzopyran-6-yl)-6-methyl-3-trifluoromethanesulfonyloxy-phenyl]acetate (1j) (100 mg, 0.19 mmol) is converted by reaction with trans-2-cyclopropyl-cyclopropylboronic acid (138 mg, 1.10 mmol), after purification by preparative TLC (cyclohexane/ethyl acetate 90/10), into the intermediate tert-butoxy-[2-chroman-6-yl-6-methyl-3-(trans-2-cyclopropyl-cyclopropyl)-phenyl]-acetic acid methyl ester (17a) (9 mg, 0.035 mmol, 10%) contaminated with 20% of trans-2-cyclopropyl-cycloproprylboronic acid.

$^1$H NMR (400 MHz, CDCl$_3$) δ −0.18−−0.12 (m, 1H), −0.01-0.43 (m, 3H), 0.45-0.95 (m, 4H), 1.01-1.08 (m, 9H), 1.27-1.38 (m, 1H), 2.04-2.13 (m, 2H), 2.42 and 2.43 (s, 3H), 2.72-2.89 (m, 2H), 3.69 and 3.71 (s, 3H), 4.26-4.30 (m, 2H), 5.11-5.14 (m, 1H), 6.71-7.15 (m, 5H).

MS m/z ([M+Na]$^+$) 471.

83

Step 2: Preparation of 3-(trans-bicyclopropyl-2-yl)-2-chroman-6-yl-6-methyl-phen yl-tert-butoxy-acetic acid (Example 17)

Using the procedure described in example 1, step 12, the tert-butoxy-[2-chroman-6-yl-6-methyl-3-(trans-2-cyclopropyl-cyclopropyl)-phenyl]-acetic acid methyl ester (17a) (9 mg, 0.020 mmol, purity of 80%) is converted into 3-(trans-bicyclopropyl-2-yl)-2-chroman-6-yl-6-methyl-phenyl-tert-butoxy-acetic acid (Example 17) (9.2 mg, 0.021 mmol, 100%, purity of 70%) as a white solid.

$^1$H NMR (400 MHz, CDCl$_3$) δ −0.24-−0.20 (m, 1H), −0.01-0.53 (m, 3H), 0.67-0.91 (m, 2H), 1.01 (m, 9H), 1.15-1.43 (m, 2H), 1.56 (bs, 1H), 2.00-2.10 (m, 2H); 2.34 (s, 3H), 2.73-2.87 (m, 2H), 4.22-4.25 (m, 2H), 5.22-5.25 (m, 1H), 6.70-7.03 (m, 4H), 7.19-7.23 (m, 1H), 9.82 (bs, 1H).

MS m/z ([M+Na]$^+$) 457.

MS m/z ([M−H]$^−$) 433.

Example 18

Synthesis of 2-(tert-butoxy)-2-[3-cyclopropyl-2-(4,4-dimethyl-cyclohex-1-enyl)-6-methyl-phenyl]acetic acid

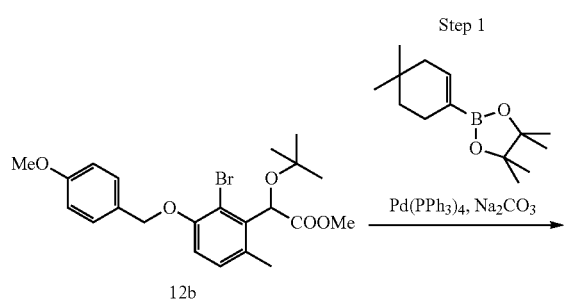

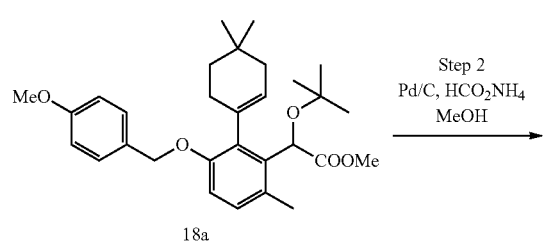

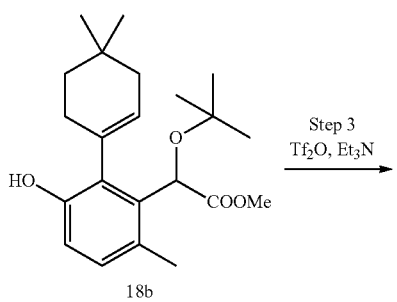

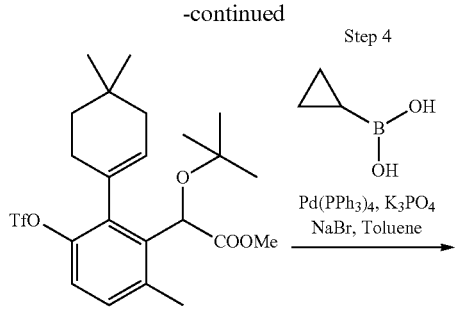

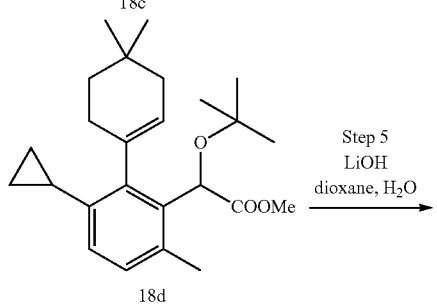

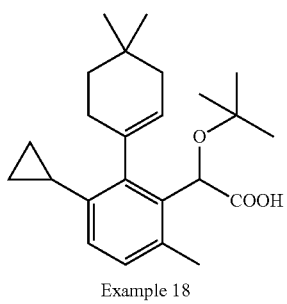 [SMILES: Cc1ccc(C2CC2)c(C2=CCC(C)(C)CC2)c1C(OC(C)(C)C)C(=O)O]

Example 18

Step 1: Preparation of Intermediate methyl 2-[2-(4,4-dimethyl-cyclohex-1-enyl)-3-(4-methoxy-benzyloxy)-6-methyl-phenyl]-2-(tert-butoxy)acetate (18a)

Using the procedure described in example 1, step 7, the intermediate methyl 2-[2-bromo-3-(4-methoxy-benzyloxy)-6-methyl-phenyl]-2-(tert-butoxy)-acetate (12b) (150 mg, 0.33 mmol) is converted by reaction with 4,4-(dimethylcyclohexene-1-yl)boronic acid pinacol ester (94 mg, 0.40 mmol), after purification by preparative TLC (cyclohexane/ethyl acetate 90/10) into methyl 2-[2-(4,4-dimethyl-cyclohex-1-enyl)-3-(4-methoxy-benzyloxy)-6-methyl-phenyl]-2-(tert-butoxy)acetate (18a) (144 mg, 0.30 mmol, 90%).

$^1$H NMR (400 MHz, CDCl$_3$) δ 0.84 and 0.90 (s, 3H), 0.99 and 1.01 (s, 3H), 1.18 and 1.20 (s, 9H), 1.38-1.49 (m, 2H), 1.84-2.07 and 2.58-2.70 (m, 3H), 2.24-2.32 (m, 1H), 2.36 and 2.40 (s, 3H), 3.63 and 3.65 (s, 3H), 3.81 (s, 3H), 4.86-4.97 (m, 2H), 5.40 and 5.63 (bs, 1H), 5.49 and 5.57 (s, 1H), 6.78 (d, J=8.3 Hz, 1H), 6.84-6.90 (m, 2H), 6.97 (d, J=8.3 Hz, 1H), 7.28-7.34 (m, 2H).

Step 2: Preparation of Intermediate methyl 2-(tert-butoxy)-2-[2-(4,4-dimethyl-cyclohex-1-enyl)-3-hydroxy-6-methyl-phenyl]acetate (18b)

Using the procedure described in example 15, step 2, the intermediate methyl 2-[2-(4,4-dimethyl-cyclohex-1-enyl)-3-(4-methoxy-benzyloxy)-6-methyl-phenyl]-2-(tert-butoxy)acetate (18a) (144 mg, 0.30 mmol) is converted into methyl 2-(tert-butoxy)-2-[2-(4,4-dimethyl-cyclohex-1-enyl)-3-hydroxy-6-methyl-phenyl]acetate (18b) (103 mg, 0.29 mmol, 95%) which was used without further purification.

$^1$H NMR (400 MHz, CDCl$_3$) δ 1.04 (s, 3H), 1.07 (s, 3H), 1.18 and 1.21 (s, 9H), 1.46-1.61 (m, 2H), 1.94-2.30 (m, 3H), 2.34 and 2.41 (s, 3H), 2.44-2.55 (m, 1H), 3.63 and 3.66 (s, 3H), 4.94 and 5.10 (s, 1H), 5.20 and 5.27 (s, 1H), 5.63-5.81 (m, 1H), 6.74-7.10 (m, 3H).

MS m/z ([M+Na]$^+$) 383.
MS m/z ([M−H]$^−$) 359.

Step 3: Preparation of Intermediate methyl 2-(tert-butoxy)-2-[2-(4,4-dimethyl-cyclohex-1-enyl)-6-methyl-3-trifluoromethanesulfonyloxy-phenyl]acetate (18c)

Using the procedure described in example 1, step 10, the intermediate methyl 2-(tert-butoxy)-2-[2-(4,4-dimethyl-cyclohex-1-enyl)-3-hydroxy-6-methyl-phenyl]acetate (18b) (103 mg, 0.29 mmol) is converted, after purification by preparative TLC (cyclohexane/ethyl acetate 85/15), into methyl 2-(tert-butoxy)-2-[2-(4,4-dimethyl-cyclohex-1-enyl)-6-methyl-3-trifluoromethanesulfonyloxy-phenyl]acetate (18c) (134 mg, 0.27 mmol, 95%).

$^1$H NMR (400 MHz, CDCl$_3$) δ 1.02-1.07 (m, 6H), 1.18 and 1.19 (s, 9H), 1.44-1.66 (m, 2H), 1.86-2.19 (m, 3H), 2.30-2.42 (m, 1H), 2.46 and 2.48 (s, 3H), 3.66 (s, 3H), 5.41 and 5.42 (s, 1H), 5.53-5.76 (m, 1H), 7.07 (d, J=8.5 Hz, 1H), 7.10 (d, J=8.5 Hz, 1H).

Step 4: Preparation of Intermediate methyl 2-(tert-butoxy)-2-[3-cyclopropyl-2-(4,4-dimethyl-cyclohex-1-enyl)-6-methyl-phenyl]acetate (18d)

Using the procedure described in example 1, step 11, the intermediate methyl 2-(tert-butoxy)-2-[2-(4,4-dimethyl-cyclohex-1-enyl)-6-methyl-3-trifluoromethanesulfonyloxy-phenyl]acetate (18c) (80 mg, 0.162 mmol) is converted, after purification by preparative TLC (cyclohexane/ethyl acetate 80/20) into methyl 2-(tert-butoxy)-2-[3-cyclopropyl-2-(4,4-dimethyl-cyclohex-1-enyl)-6-methyl-phenyl]acetate (18d) (32 mg, 0.083 mmol, 51%).

$^1$H NMR (300 MHz, CDCl$_3$) δ 0.50-0.75 (m, 2H), 0.77-0.91 (m, 2H), 1.03 (s, 3H), 1.07 (s, 3H), 1.19 and 1.21 (s, 9H), 1.48-1.57 (m, 2H), 1.85-2.05 (m, 3H), 2.15-2.30 (m, 1H), 2.36-2.55 (m, 4H), 3.63 and 3.64 (s, 3H), 5.41-5.62 (m, 2H), 6.68 and 6.70 (d, J=7.9 Hz, 1H), 6.95 (d, J=7.9 Hz, 1H).

MS m/z ([M+Na]$^+$) 407.

Step 5: Preparation of 2-(tert-butoxy)-2-[3-cyclopropyl-2-(4,4-dimethyl-cyclohex-1-enyl)-6-methyl-phenyl]acetic acid (Example 18)

Using the procedure described in example 1, step 12, the intermediate methyl 2-(tert-butoxy)-2-[3-cyclopropyl-2-(4,4-dimethyl-cyclohex-1-enyl)-6-methyl-phenyl]acetate (18d) (32 mg, 0.083 mmol) is converted into 2-(tert-butoxy)-2-[3-cyclopropyl-2-(4,4-dimethyl-cyclohex-1-enyl)-6-methyl-phenyl]acetic acid (18d) (22 mg, 0.059 mmol, 71%).

$^1$H NMR (300 MHz, CDCl$_3$) δ 0.50-0.75 (m, 2H), 0.78-0.94 (m, 2H), 0.98-1.08 (m, 6H), 1.19-1.26 (m, 9H), 1.46-1.56 (m, 2H), 1.81-2.10 (m, 3H), 2.10-2.64 (m, 5H), 5.28-5.98 (m, 2H), 6.68-6.77 (m, 1H), 6.91-7.00 (m, 1H).

MS m/z ([M+Na]$^+$) 393.
MS m/z ([M−H]$^−$) 369.

Example 19

Synthesis of 2-(2-chroman-6-yl-3-cyclopropyl-6-methyl-phenyl)-2-ethoxy-acetic acid

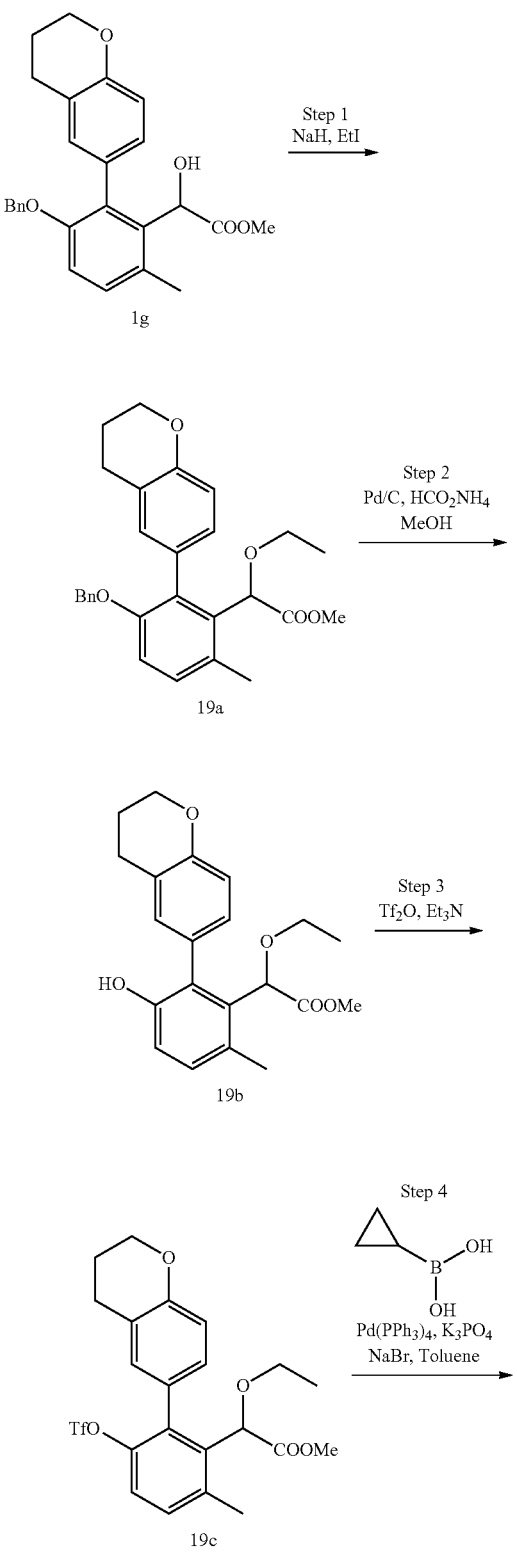

-continued

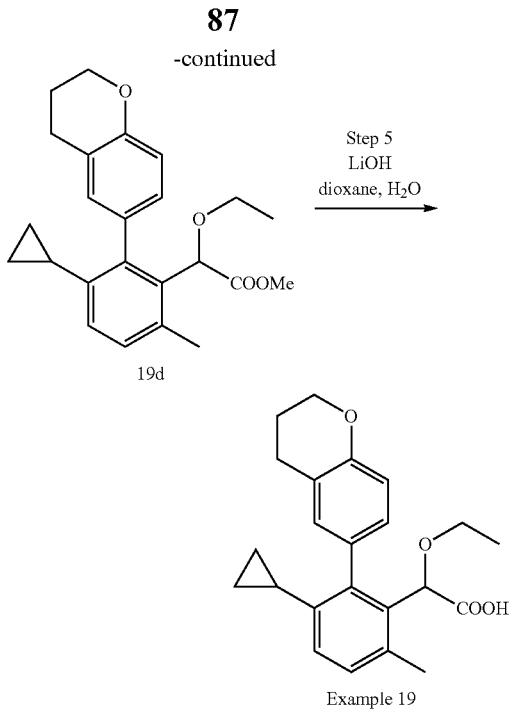

Example 19

Step 1: Preparation of Intermediate methyl 2-(3-benzyloxy-2-chroman-6-yl-6-methyl-phenyl)-2-ethoxy acetate (19a)

Under nitrogen atmosphere, a solution of methyl 2-[3-benzyloxy-2-(3,4-dihydro-2H-1-benzopyran-6-yl)-6-methylphenyl]-2-hydroxyacetate (1g) (100 mg, 0.24 mmol) in anhydrous N,N-dimethylformamide (5 mL) was cooled to 0° C. Sodium hydride 60% in oil (9.5 mg, 0.24 mmol) was added portionwise. After 15 minutes stirring, iodoethane (58 µL, 0.72 mmol) was added and the mixture was stirred at room temperature for 5 hours. The mixture was quenched at 0° C. with water (5 mL) and extracted with ethyl acetate (2×5 mL). The organic layer was washed with brine (10 mL), then dried over sodium sulfate and concentrated in vacuo. The residue was purified by preparative TLC (cyclohexane/ethyl acetate 90/10) to provide methyl 2-(3-benzyloxy-2-chroman-6-yl-6-methyl-phenyl)-2-ethoxy acetate (19a) (106 mg, 0.24 mmol, 100%).

$^1$H NMR (400 MHz, CDCl$_3$) δ 1.08-1.13 (m, 3H), 2.01-2.09 (m, 2H), 2.30 (s, 3H), 2.71-2.86 (m, 2H), 3.23-3.33 (m, 1H), 3.35-3.51 (m, 1H), 3.69 and 3.70 (s, 3H), 4.21-4.26 (m, 2H), 4.93-4.99 (m, 2H), 5.01 and 5.02 (s, 1H), 6.83 and 6.84 (d, J=8.2 Hz, 1H), 6.86 and 6.88 (d, J=2.0 Hz, 1H), 6.92-7.09 (m, 3H), 7.13-7.18 (m, 2H), 7.20-7.30 (m, 3H).

MS m/z ([M+Na]$^+$) 469.

Step 2: Preparation of Intermediate methyl 2-(2-chroman-6-yl-3-hydroxy-6-methyl-phenyl)-2-ethoxy acetate (19b)

Using the procedure described in example 15, step 2, the intermediate methyl 2-(3-benzyloxy-2-chroman-6-yl-6-methyl-phenyl)-2-ethoxy acetate (19a) (106 mg, 0.24 mmol) is converted into methyl 2-(2-chroman-6-yl-3-hydroxy-6-methyl-phenyl)-2-ethoxy acetate (19b) (82 mg, 0.23 mmol, 97%) which was used without further purification.

$^1$H NMR (400 MHz, CDCl$_3$) δ 1.08-1.14 (m, 3H), 2.01-2.10 (m, 2H), 2.29 (s, 3H), 2.73-2.87 (m, 2H), 3.23-3.33 (m, 1H), 3.35-3.49 (m, 1H), 3.68 and 3.69 (s, 3H), 4.22-4.27 (m, 2H), 4.66 and 4.68 (s, 1H), 4.86 and 4.87 (s, 1H), 6.84-6.99 (m, 3H), 7.03-7.10 (m, 2H).

MS m/z ([M+Na]$^+$) 379.

Step 3: Preparation of Intermediate methyl 2-(2-chroman-6-yl-6-methyl-3-trifluoro methanesulfonyloxy-phenyl)-2-ethoxy-acetate (19c)

Using the procedure described in example 1, step 10, the intermediate methyl 2-(2-chroman-6-yl-3-hydroxy-6-methyl-phenyl)-2-ethoxy acetate (19b) (82 mg, 0.23 mmol) is converted into methyl 2-(2-chroman-6-yl-6-methyl-3-trifluoromethanesulfonyloxy-phenyl)-2-ethoxy-acetate (19c) (104 mg, 0.21 mmol, 93%) which was used without further purification.

$^1$H NMR (300 MHz, CDCl$_3$) δ 1.11 and 1.12 (t, J=7.0 Hz, 3H), 1.99-2.09 (m, 2H), 2.39 and 2.40 (s, 3H), 2.68-2.90 (m, 2H), 3.20-3.32 (m, 1H), 3.39-3.51 (m, 1H), 3.69 and 3.70 (s, 3H), 4.20-4.27 (m, 2H), 4.96 and 4.97 (s, 1H), 6.81-6.87 (m, 1H), 6.89-6.04 (m, 2H), 7.21 (s, 2H).

MS m/z ([M−H]$^-$) 487.

Step 4: Preparation of Intermediate methyl 2-(2-chroman-6-yl-3-cyclopropyl-6-methyl-phenyl)-2-ethoxy-acetate (19d)

Using the procedure described in example 1, step 11, the intermediate methyl 2-(2-chroman-6-yl-6-methyl-3-trifluoromethanesulfonyloxy-phenyl)-2-ethoxy-acetate (19c) (104 mg, 0.21 mmol) is converted, after purification by preparative TLC (cyclohexane/ethyl acetate 80/20), into methyl 2-(2-chroman-6-yl-3-cyclopropyl-6-methyl-phenyl)-2-ethoxy-acetate (19d) (40 mg, 0.105 mmol, 49%).

$^1$H NMR (300 MHz, CDCl$_3$) δ 0.49-0.74 (m, 4H), 1.09 and 1.11 (t, J=7.0 Hz, 3H), 1.42-1.53 (m, 1H), 1.99-2.11 (m, 2H), 2.32 (s, 3H), 2.70-2.88 (m, 2H), 3.19-3.33 (m, 1H), 3.33-3.51 (m, 1H), 3.67 and 3.69 (s, 3H), 4.20-4.27 (m, 2H), 4.93 and 4.96 (s, 1H), 6.74-6.85 (m, 2H), 6.88-7.09 (m, 3H).

MS m/z ([M+Na]$^+$) 403.

Step 5: Preparation of 2-(2-chroman-6-yl-3-cyclopropyl-6-methyl-phenyl)-2-ethoxy-acetic acid (Example 19)

Using the procedure described in example 1, step 12, the intermediate methyl 2-(2-chroman-6-yl-3-cyclopropyl-6-methyl-phenyl)-2-ethoxy-acetate (19d) (40 mg, 0.105 mmol) is converted to 2-(2-chroman-6-yl-3-cyclopropyl-6-methyl-phenyl)-2-ethoxy-acetic acid (Example 19) (30 mg, 0.082 mmol, 78%).

$^1$H NMR (300 MHz, CDCl$_3$) δ 0.51-0.76 (m, 4H), 1.10 and 1.11 (t, J=7.0 Hz, 3H), 1.44-1.54 (m, 1H), 1.99-2.09 (m, 2H), 2.31 and 2.32 (s, 3H), 2.72-2.87 (m, 2H), 3.20-3.42 (m, 2H), 4.20-4.26 (m, 2H), 5.04 and 5.06 (s, 1H), 6.77-6.84 (m, 2H), 6.87-6.94 (m, 1H), 7.01-7.09 (m, 2H).

MS m/z ([M+Na]$^+$) 389.

MS m/z ([M−H]$^-$) 365.

Example 20

Synthesis of 2-(tert-butoxy)-2-(4'-chloro-6-cyclopropyl-3-methyl-biphenyl-2-yl)acetic acid

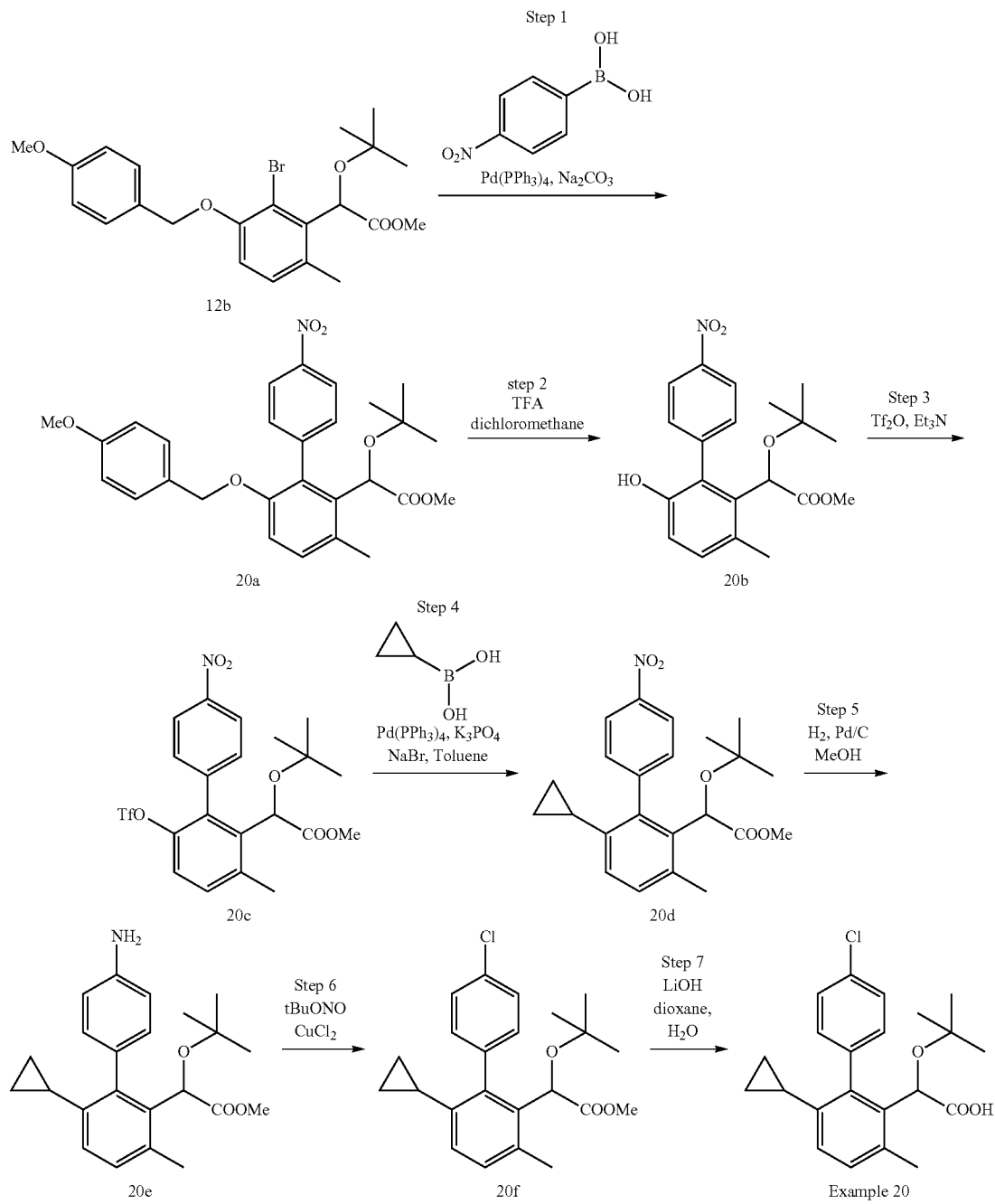

Step 1: Preparation of Intermediate methyl 2-(tert-butoxy)-2-[6-(4-methoxy-benzyloxy)-3-methyl-4'-nitro-biphenyl-2-yl]acetate (20a)

Using the procedure described in example 1, step 7, the intermediate methyl 2-[2-bromo-3-(4-methoxy-benzyloxy)-6-methyl-phenyl]-2-(tert-butoxy)-acetate (12b) (500 mg, 1.11 mmol) is converted by reaction with 4-nitrophenylboronic acid (222 mg, 1.33 mmol), after purification by flash chromatography on silica gel (cyclohexane/ethyl acetate 100/0 to 95/05), into methyl 2-(tert-butoxy)-2-[6-(4-methoxy-benzyloxy)-3-methyl-4'-nitro-biphenyl-2-yl]acetate (20a) (497 mg, 1.01 mmol, 91%).

$^1$H NMR (300 MHz, CDCl$_3$) δ 0.94 (s, 9H), 2.38 (s, 3H), 3.71 (s, 3H), 3.77 (s, 3H), 4.84 (d, J=11.8 Hz, 1H), 4.88 (s, 1H), 4.91 (d, J=11.8 Hz, 1H), 6.76-6.82 (m, 2H), 6.91 (d, J=8.4 Hz, 1H), 6.97-7.03 (m, 2H), 7.15 (d, J=8.4 Hz, 1H), 7.45 (dd, J=1.7 Hz, J=8.4 Hz, 1H), 7.60 (dd, J=1.7 Hz, J=8.4 Hz, 1H), 8.23 (dd, J=2.4 Hz, J=8.4 Hz, 1H), 8.28 (dd, J=2.4 Hz, J=8.4 Hz, 1H).

MS m/z ([M+Na]$^+$) 516.

Step 2: Preparation of Intermediate methyl 2-(tert-butoxy)-2-(6-hydroxy-3-methyl-4'-nitro-biphenyl-2-yl)acetate (20b)

Trifluoroacetic acid (0.98 mL, 12.79 mmol) was added to a solution of methyl 2-(tert-butoxy)-2-[6-(4-methoxy-benzyloxy)-3-methyl-4'-nitro-biphenyl-2-yl]acetate (20a) (485 mg, 0.98 mmol) in dichloromethane (19.6 mL). The reaction was stirred at room temperature for 5 minutes and immediately quenched with a saturated solution of sodium bicarbonate (25 mL). The mixture was extracted with dichloromethane (2×20 mL), dried over sodium sulfate and concentrated in vacuo. The residue was purified by preparative TLC (cyclohexane/ethyl acetate 60/40) to provide methyl 2-(tert-butoxy)-2-(6-hydroxy-3-methyl-4'-nitro-biphenyl-2-yl) acetate (20b) (319 mg, 0.59 mmol, 87%).

MS m/z ([M+Na]$^+$) 396.
MS m/z ([M−H]$^−$) 472.

Step 3: Preparation of Intermediate methyl 2-(tert-butoxy)-2-(3-methyl-4'-nitro-6-trifluoromethanesulfonyloxy-biphenyl-2-yl)acetate (20c)

Using the procedure described in example 1, step 10, the intermediate methyl 2-(tert-butoxy)-2-(6-hydroxy-3-methyl-4'-nitro-biphenyl-2-yl) acetate (20b) (360 mg, 0.96 mmol) is converted, to methyl 2-(tert-butoxy)-2-(3-methyl-4'-nitro-6-trifluoromethanesulfonyloxy-biphenyl-2-yl) acetate (20c) (487 mg, 0.96 mmol, 100%) which was used without further purification.

$^1$H NMR (300 MHz, CDCl$_3$) δ 0.96 (s, 9H), 2.49 (s, 3H), 3.72 (s, 3H), 4.88 (s, 1H), 7.24 (d, J=7.3 Hz, 1H), 7.32 (d, J=7.3 Hz, 1H), 7.44-7.50 (m, 1H), 7.62-7.68 (m, 1H), 8.30-8.37 (m, 2H).

MS m/z ([M−H]$^−$) 504.

Step 4: Preparation of Intermediate methyl 2-(tert-butoxy)-2-(6-cyclopropyl-3-methyl-4'-nitro-biphenyl-2-yl)acetate (20d)

Using the procedure described in example 1, step 11, the intermediate methyl 2-(tert-butoxy)-2-(3-methyl-4'-nitro-6-trifluoromethanesulfonyloxy-biphenyl-2-yl)acetate (20c) (387 mg, 0.77 mmol) is converted, after purification by preparative TLC (cyclohexane/ethyl acetat80/20), into methyl 2-(tert-butoxy)-2-(6-cyclopropyl-3-methyl-4'-nitro-biphenyl-2-yl)acetate (20d) (209 mg, 0.53 mmol, 69%).

$^1$H NMR (400 MHz, CDCl$_3$) δ 0.51-0.63 (m, 3H), 0.63-0.72 (m, 1H), 0.98 (s, 9H), 1.22-1.30 (m, 1H), 2.43 (s, 3H), 3.67 (s, 3H), 4.85 (s, 1H), 6.86 (d, J=8.0 Hz, 1H), 7.13 (d, J=8.0 Hz, 1H), 7.47 (dd, J=1.6 Hz, J=8.0 Hz, 1H), 7.62 (dd, J=1.6 Hz, J=8.2 Hz, 1H), 8.26-8.34 (m, 2H).

Step 5: Preparation of Intermediate methyl 2-(4'-amino-6-cyclopropyl-3-methyl-biphenyl-2-yl)-2-(tert-butoxy)acetate (20e)

A solution of methyl 2-(tert-butoxy)-2-(6-cyclopropyl-3-methyl-4'-nitro-biphenyl-2-yl) acetate (20d) (209 mg, 0.53 mmol) and palladium on carbon (21 mg) in methanol (8 mL) was stirred at room temperature under hydrogen atmosphere for 1 hour. The mixture was filtered over Millipore and concentrated in vacuo to provide methyl 2-(4'-amino-6-cyclopropyl-3-methyl-biphenyl-2-yl)-2-(tert-butoxy)acetate (20e) (190 mg, 0.52 mmol, 98%) which was used without further purification.

$^1$H NMR (400 MHz, CDCl$_3$) δ 0.50-0.65 (m, 3H), 0.66-0.74 (m, 1H), 0.98 (s, 9H), 1.43-1.51 (m, 1H), 2.39 (s, 3H), 3.67 (s, 3H), 5.14 (s, 1H), 6.74-6.84 (m, 3H), 7.04 (d, J=7.9 Hz, 1H), 7.11 (dd, J=1.9 Hz, J=7.9 Hz, 1H), 7.20 (dd, J=1.9 Hz, J=7.9 Hz, 1H).

MS m/z ([M+Na]$^+$) 390.

Step 6: Preparation of Intermediate methyl 2-(tert-butoxy)-2-(4'-chloro-6-cyclopropyl-3-methyl-biphenyl-2-yl) acetate (20f)

Under nitrogen atmosphere, tert-butyl nitrite (23 μL, 0.20 mmol) was added to a suspension of copper (II) chloride (26 mg, 0.19 mmol) in anhydrous acetonitrile (1 mL), previously cooled to 0° C. A solution of methyl 2-(4-amino-6-cyclopropyl-3-methyl-biphenyl-2-yl)-2-(tert-butoxy)acetate (20e) (50 mg, 0.14 mmol) in anhydrous acetonitrile (1 mL) was added dropwise. The reaction mixture was stirred at room temperature overnight and concentrated in vacuo. The residue was purified by preparative TLC (cyclohexane/ethyl acetate 85/15) to provide methyl 2-(tert-butoxy)-2-(4'-chloro-6-cyclopropyl-3-methyl-biphenyl-2-yl) acetate (20f) (24 mg, 0.06 mmol, 46%).

$^1$H NMR (400 MHz, CDCl$_3$) δ 0.52-0.65 (m, 3H), 0.65-0.73 (m, 1H), 0.98 and 0.99 (s, 9H), 1.31-1.40 (m, 1H), 2.41 (s, 3H), 3.67 and 3.68 (s, 3H), 4.96 and 4.97 (s, 1H), 6.78-6.84 (m, 1H), 7.06-7.12 (m, 1H), 7.22-7.28 (m, 1H), 7.33-7.46 (m, 3H).

MS m/z ([M+Na]$^+$) 409.

Step 7: Preparation of 2-(tert-butoxy)-2-(4'-chloro-6-cyclopropyl-3-methyl-biphenyl-2-yl) acetic acid (Example 20)

Using the procedure described in example 1, step 12, the intermediate methyl 2-(tert-butoxy)-2-(4'-chloro-6-cyclopropyl-3-methyl-biphenyl-2-yl) acetate (20f) (24 mg, 0.062 mmol) is converted to 2-(tert-butoxy)-2-(4'-chloro-6-cyclopropyl-3-methyl-biphenyl-2-yl) acetic acid (Example 20) (23 mg, 0.062 mmol, 99%).

$^1$H NMR (400 MHz, CDCl$_3$) δ 0.48-0.64 (m, 3H), 0.68-0.76 (m, 1H), 1.01 (s, 9H), 1.36-1.45 (m, 1H), 2.37 (s, 3H), 5.08 (s, 1H), 6.84 (d, J=7.9 Hz, 1H), 7.08 (d, J=7.9 Hz, 1H), 7.22-7.29 (m, 1H), 7.35-7.45 (m, 2H), 7.50-7.58 (m, 1H).

MS m/z ([M+Na]$^+$) 395.
MS m/z ([M−H]$^−$) 371.

Example 21

Synthesis of tert-butoxy-[3-cyclopropyl-2-(8-fluoro-5-methyl-chroman-6-yl)-6-methyl-phenyl]-acetic acid

Step 2: Preparation of Intermediate tert-butoxy-[2-(8-fluoro-5-methyl-chroman-6-yl)-3-hydroxy-6-methyl-phenyl]-acetic acid methyl ester (21 b)

Using the procedure described in example 15, step 2, the intermediate 3-benzyloxy-2-(8-fluoro-5-methyl-chroman-6-

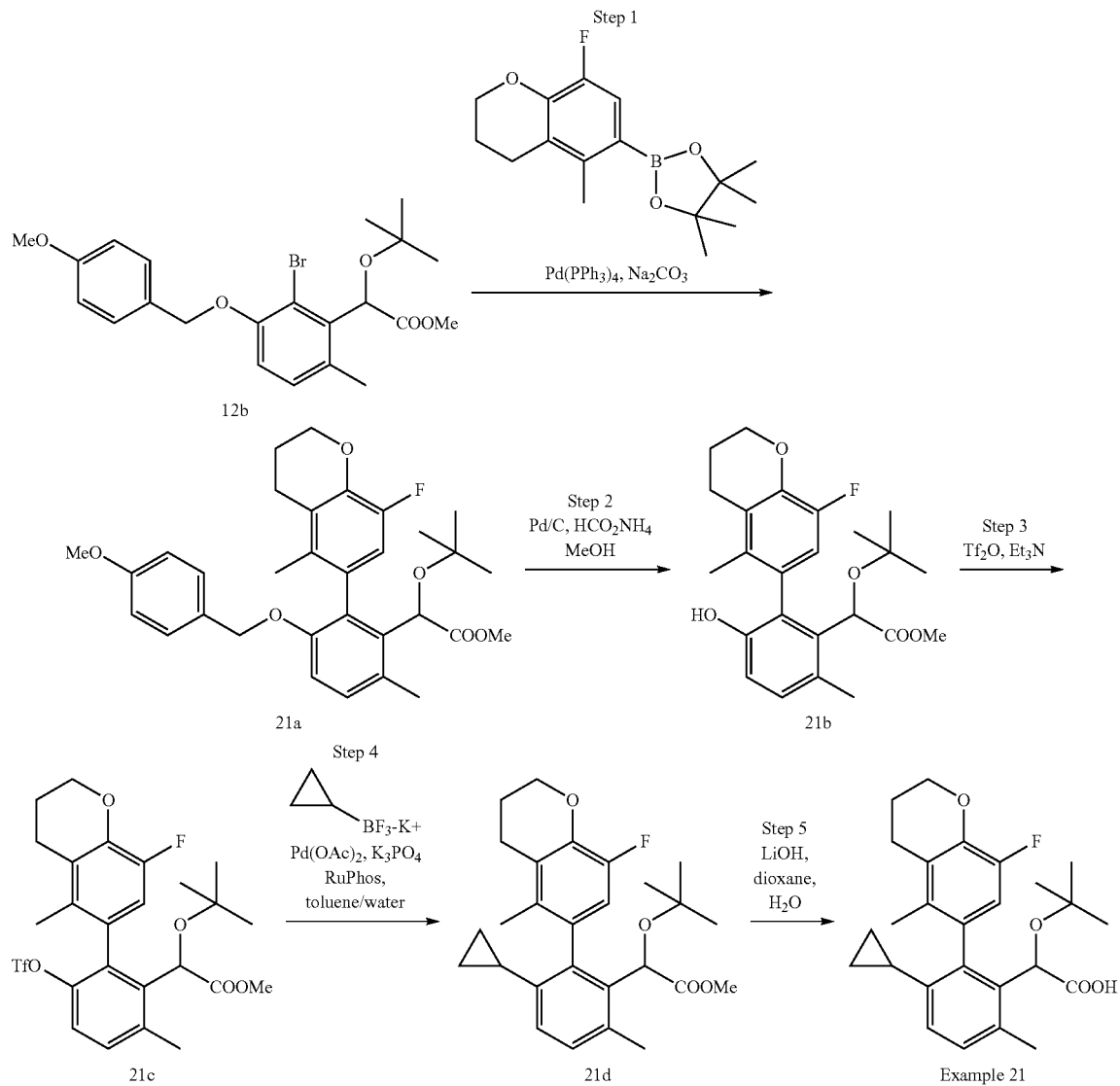

Step 1: Preparation of Intermediate[3-benzyloxy-2-(8-fluoro-5-methyl-chroman-6-yl)-6-methyl-phenyl]-tert-butoxy-acetic acid methyl ester (21a)

Using the procedure described in example 1, step 7, the intermediate methyl 2-(3-benzyloxy-2-bromo-6-methylphenyl)-2-(tert-butoxy)-acetate (12b) (500 mg, 1.19 mmol), in reaction with 2-(8-fluoro-3,4-dihydro-2H-1-benzopyran-6-yl)-4,4,5,5-tetramethyl-1,3,2-dioxaborolane (416 mg, 1.42 mmol), is converted, after purification by preparative TLC (cyclohexane/ethyl acetate 80/20), into [3-benzyloxy-2-(8-fluoro-5-methyl-chroman-6-yl)-6-methyl-phenyl]-tert-butoxy-acetic acid methyl ester (21a) (526 mg, 1.04 mmol, 87%).

MS m/z ([M+Na]$^+$) 529.

yl)-6-methyl-phenyl]-tert-butoxy-acetic acid methyl ester (21a) (520 mg, 1.03 mmol) is converted, after purification by preparative TLC (cyclohexane/ethyl acetate 70/30) into tert-butoxy-[2-(8-fluoro-5-methyl-chroman-6-yl)-3-hydroxy-6-methyl-phenyl]-acetic acid methyl ester (21 b) (320 mg, 0.77 mmol, 75%).

$^1$H NMR (300 MHz, CDCl$_3$) δ 1.10 (s, 9H), 1.88 (s, 3H), 2.08-2.20 (m, 2H), 2.43 (s, 3H), 2.68-2.77 (m, 2H), 3.58 (s, 3H), 4.25-4.32 (m, 2H), 4.38 (s, 1H), 4.92 (s, 1H), 6.77 (d, J=11.2 Hz, 1H), 6.83 (d, J=8.3 Hz, 1H), 7.07 (d, J=8.3 Hz, 1H).

Step 3: Preparation of Intermediate tert-butoxy-[2-(8-fluoro-5-methyl-chroman-6-yl)-6-methyl-3-trifluoromethanesulfonyloxy-phenyl]-acetic acid methyl ester (21c)

Using the procedure described in example 1, step 10, the intermediate tert-butoxy-[2-(8-fluoro-5-methyl-chroman-6-yl)-3-hydroxy-6-methyl-phenyl]-acetic acid methyl ester (21 b) (320 mg, 0.77 mmol) is converted into tert-butoxy-[2-(8-fluoro-5-methyl-chroman-6-yl)-6-methyl-3-trifluoromethanesulfonyloxy-phenyl]-acetic acid methyl ester (21c) (420 mg, 0.77 mmol, 99%), which was used without further purification.

$^1$H NMR (400 MHz, CDCl$_3$) δ 1.11 (s, 9H), 1.81 (s, 3H), 2.09-2.17 (m, 2H), 2.53 (s, 3H), 2.66-2.73 (m, 2H), 3.59 (s, 3H), 4.24-4.31 (m, 2H), 5.04 (s, 1H), 6.74 (d, J=11.2 Hz, 1H), 7.17 (d, J=8.5 Hz, 1H), 7.23 (d, J=8.5 Hz, 1H).
MS m/z ([M−H]$^-$) 547.

Step 4: Preparation of Intermediate tert-butoxy-[3-cyclopropyl-2-(8-fluoro-5-methyl-chroman-6-yl)-6-methyl-phenyl]-acetic acid methyl ester (21d)

A solution of tert-butoxy-[2-(8-fluoro-5-methyl-chroman-6-yl)-6-methyl-3-trifluoromethane sulfonyloxy-phenyl]-acetic acid methyl ester (21c) (420 mg, 0.77 mmol), potassium cyclopropyltrifluoroborate (147 mg, 0.99 mmol), potassium phosphate tribasic monohydrate (581 mg, 2.53 mmol), and 2-dicyclohexylphosphino-2',6'-diisopropoxybiphenyl (RuPhos) (143 mg, 0.31 mmol) in a mixture of toluene (2.3 mL) and water (0.75 mL) was bubbled with nitrogen for 5 minutes. Palladium (II) acetate (17 mg, 0.08 mmol) was added and the reaction mixture was heated at 100° C. for 4 hours. Water (5 mL) was added. The aqueous layer was extracted with ethyl acetate (2×5 mL). The combined organic layers were washed with brine (5 mL), dried over sodium sulfate and concentrated in vacuo. The residue was purified by preparative TLC (cyclohexane/ethyl acetate 80/20) to provide tert-butoxy-[3-cyclopropyl-2-(8-fluoro-5-methyl-chroman-6-yl)-6-methyl-phenyl]-acetic acid methyl ester (21d) (293 mg, 0.66 mmol, 87%).

$^1$H NMR (300 MHz, CDCl$_3$) δ 0.46-0.71 (m, 4H), 1.10 (s, 9H), 1.19-1.32 (m, 1H), 1.82 (s, 3H), 2.08-2.19 (m, 2H), 2.46 (s, 3H), 2.66-2.76 (m, 2H), 3.57 (s, 3H), 4.24-4.31 (m, 2H), 4.99 (s, 1H), 6.68-6.78 (m, 2H), 7.07 (d, J=7.9 Hz, 1H).
MS m/z ([M+Na]$^+$) 463.

Step 5: Preparation of tert-butoxy-[3-cyclopropyl-2-(8-fluoro-5-methyl-chroman-6-yl)-6-methyl-phenyl]-acetic acid (Example 21)

Using the procedure described in example 1, step 12, the intermediate tert-butoxy-[3-cyclopropyl-2-(8-fluoro-5-methyl-chroman-6-yl)-6-methyl-phenyl]-acetic acid methyl ester (21d) (33 mg, 0.07 mmol) is converted to tert-butoxy-[3-cyclopropyl-2-(8-fluoro-5-methyl-chroman-6-yl)-6-methyl-phenyl]-acetic acid (Example 21) (28 mg, 0.06 mmol, 88%).

$^1$H NMR (300 MHz, CDCl$_3$) δ 0.50-0.59 (m, 2H), 0.59-0.71 (m, 2H), 1.13 (s, 9H), 1.23-1.36 (m, 1H), 1.90 (s, 3H), 2.06-2.17 (m, 2H), 2.39 (s, 3H), 2.63-2.76 (m, 2H), 4.22-4.30 (m, 2H), 5.08 (s, 1H), 6.70-6.80 (m, 2H), 7.07 (d, J=7.9 Hz, 1H).
MS m/z ([M+Na]$^+$) 449.
MS m/z ([M−H]$^-$) 425.

Example 22

Synthesis of tert-Butoxy-(2-chroman-6-yl-3-cyclopropyl methyl-6-methyl-phenyl)-acetic acid

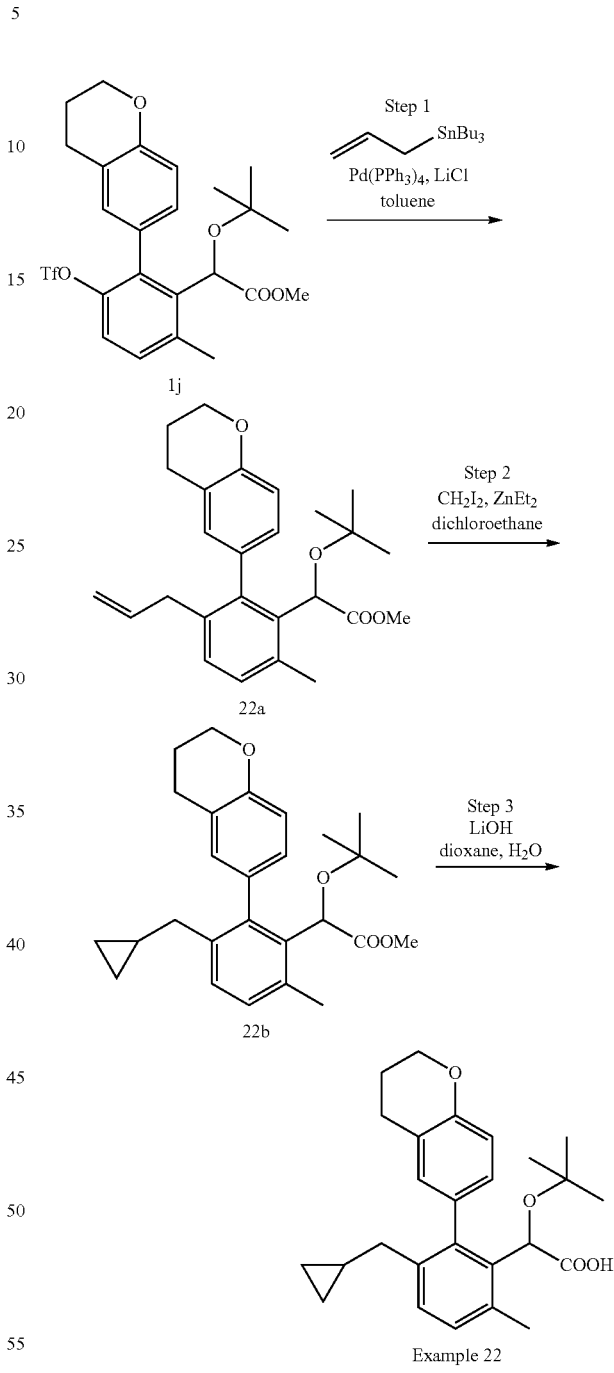

Example 22

Step 1: Preparation of Intermediate (3-allyl-2-chroman-6-yl-6-methyl-phenyl)-tert-butoxy-acetic acid methyl ester (22a)

A degassed solution of methyl 2-(tert-butoxy)-2-[2-(3,4-dihydro-2H-1-benzopyran-6-yl)-6-methyl-3-trifluoromethanesulfonyloxy-phenyl]acetate (1j) (200 mg, 0.387 mmol), allyl tributylstannane (141 mg, 0.426 mmol), lithium chloride (49 mg, 1.16 mmol) and palladium tetrakis(triphenylphosphine) (45 mg, 0.039 mmol) in toluene (2.5 mL) was heated at 110° C. for 18 hours. Aqueous ammonia 10% (30 mL) was added. The aqueous layer was extracted with ethyl acetate (3×10 mL). The combined organic layers were washed with brine (5 mL), dried over sodium sulfate and concentrated in vacuo. The residue was purified by preparative TLC (cyclohexane/ethyl acetate 80/20) to provide (3-allyl-2-chroman-6-yl-6-methyl-phenyl)-tert-butoxy-acetic acid methyl ester (22a) (80 mg, 0.147 mmol, 38%).

$^1$H NMR (400 MHz, CDCl$_3$) δ 0.99 (s, 9H), 2.00-2.10 (m, 2H), 2.42 (s, 3H), 2.67-2.85 (m, 2H), 2.99-3.19 (m, 2H), 3.65 and 3.67 (s, 3H), 4.23-4.25 (m, 2H), 4.84 (d, J=17.0 Hz, 1H), 4.94 (d, J=10.0 Hz, 1H), 5.05 and 5.07 (s, 1H), 5.75-5.85 (m, 1H), 6.78-7.12 (m, 5H)

MS m/z ([M+Na]$^+$) 431.

Step 2: Preparation of Intermediate tert-butoxy-(2-chroman-6-yl-3-cyclopropylmethyl-6-methyl-phenyl)-acetic acid methyl ester (22b)

To a solution of (3-allyl-2-chroman-6-yl-6-methyl-phenyl)-tert-butoxy-acetic acid methyl ester (22a) (80 mg, 0.147 mmol) and diiodomethane (118 μL, 1.47 mmol) in 1,2-dichloroethane (1 mL) under argon was added slowly a 1M solution of diethyl zinc in heptane (734 μL, 0.734 mmol). The reaction was stirred overnight to room temperature. The mixture was concentrated in vacuo. A saturated solution of ammonium chloride (10 mL) was added to the residue and extracted with ethyl acetate (3×5 mL). The combined organic layers were washed with water (10 mL), dried over sodium sulfate and concentrated in vacuo. The residue was diluted in a mixture of acetone/acetonitrile (0.5/0.5 mL) To this solution was added 4-methylmorpholine oxide (22 mg, 0.191 mmol) and a solution of osmium tetraoxide 4% wt in water (45 μl, 0.007 mmol) and the reaction was stirred overnight. The mixture was concentrated in vacuo and the residue was purified by preparative TLC (cyclohexane/ethyl acetate 90/10) to provide tert-butoxy-(2-chroman-6-yl-3-cyclopropyl methyl-6-methyl-phenyl)-acetic acid methyl ester (22b) (11 mg, 0.026 mmol, 17%)

$^1$H NMR (400 MHz, CDCl$_3$) δ −0.05-0.07 (m, 2H), 0.36-0.47 (m, 2H), 0.75-0.83 (m, 1H), 0.99 (s, 9H), 1.98-2.09 (m, 2H), 2.12-2.25 (m, 2H), 2.38-2.42 (2s, 3H), 2.65-2.81 (m, 2H), 3.64 and 3.66 (s, 3H), 4.21-4.27 (m, 2H), 5.00 and 5.03 (s, 1H), 6.77-7.11 (m, 4H), 7.30-7.33 (m, 1H).

MS m/z ([M+Na]$^+$) 445.

Step 3: Preparation of tert-Butoxy-(2-chroman-6-yl-3-cyclopropylmethyl-6-methyl-phenyl)-acetic acid (Example 22)

Using the procedure described in example 1, step 12, the intermediate tert-Butoxy-(2-chroman-6-yl-3-cyclopropylmethyl-6-methyl-phenyl)-acetic acid methyl ester (22b) (11 mg, 0.026 mmol) is converted into tert-butoxy-(2-chroman-6-yl-3-cyclopropylmethyl-6-methyl-phenyl)-acetic acid (Example 22) (6.5 mg, 0.016 mmol, 61%) as a white solid.

$^1$H NMR (400 MHz, CD$_3$OD) δ −0.12-−0.06 (m, 1H), −0.02-0.04 (m, 1H), 0.31-0.41 (m, 2H), 0.68-0.80 (m, 1H), 0.94 (s, 9H), 1.93-2.07 (m, 2H), 2.10-2.33 (m, 2H), 2.41 (s, 3H), 2.69-2.87 (m, 2H), 4.16-4.23 (m, 2H), 4.96 and 4.99 (s, 1H), 6.68-6.76 (m, 1H), 6.85-6.89 (m, 1H), 6.97-7.03 (m, 1H), 7.19-7.35 (m, 2H).

MS m/z ([M+Na]$^+$) 431.
MS m/z ([M−H]$^−$) 407.

Example 23

Synthesis of 2-[3-cyclopropyl-2-(3,4-dihydro-2H-1-benzopyran-6-yl)-6-methylphenyl]-2-cyclopropoxy-acetic acid

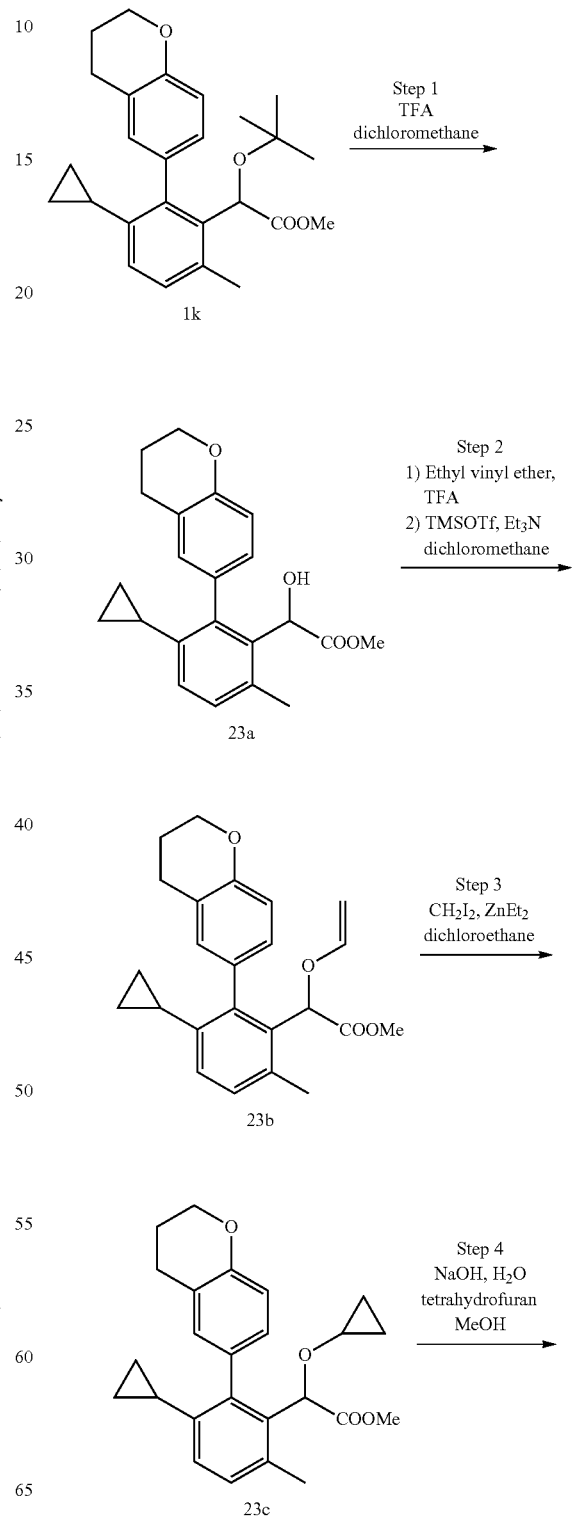

-continued

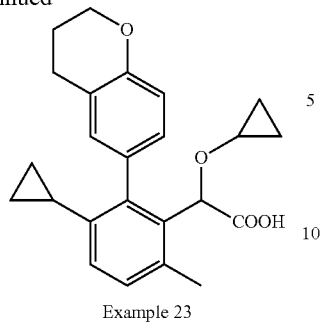

Example 23

Step 1: Preparation of Intermediate methyl 2-[3-cyclopropyl-2-(3,4-dihydro-2H-1-benzopyran-6-yl)-6-methylphenyl]-2-hydroxyacetate (23a)

To a solution of methyl 2-(tert-butoxy)-2-[3-cyclopropyl-2-(3,4-dihydro-2H-1-benzopyran-6-yl)-6-methylphenyl]acetate 1k (957 mg, 2.34 mmol) in anhydrous dichloromethane (21 mL) at 0° C. under nitrogen atmosphere was dropwise aided trifluoroacetic acid (1.05 mL). The mixture was stirred 2 hours at 0° C. then neutralized with a saturated solution of sodium hydrogenocarbonate. The organic layer was separated, washed with brine, dried over sodium sulfate and concentrated in vacuo to provide methyl 2-[3-cyclopropyl-2-(3,4-dihydro-2H-1-benzopyran-6-yl)-6-methylphenyl]-2-hydroxyacetate (23a) (825 mg, 2.34 mmol, 100%) as a slight yellow amorphous solid.

$^1$H NMR (400 MHz, CDCl$_3$) δ 0.51-0.71 (m, 4H), 1.43-1.51 (m, 1H), 2.01-2.08 (m, 2H), 2.29 et 2.30 (s, 3H), 2.77-2.83 (m, 2H), 3.01 and 3.06 (d, J=2.96 Hz, 1H), 3.70 and 3.71 (s, 3H), 4.21-4.26 (m, 2H), 5.20 and 5.22 (d, J=2.96 Hz, 1H), 6.78-6.83 (m, 2H), 6.94-7.01 (m, 2H), 7.06-7.09 (m, 1H).

MS m/z ([M+Na]$^+$) 375.

Step 2: Preparation of Intermediate methyl 2-[3-cyclopropyl-2-(3,4-dihydro-2H-1-benzopyran-6-yl)-6-methylphenyl]-2-vinyloxyacetate (23b)

To a stirred solution of methyl 2-[3-cyclopropyl-2-(3,4-dihydro-2H-1-benzopyran-6-yl)-6-methylphenyl]-2-hydroxyacetate (23a) (665 mg, 1.887 mmol) in ethyl vinyl ether (3.6 mL) at room temperature was added TFA (1 drop). The stirring was continued for 4 days before the reacting mixture was concentrated in vacuo. The residue was purified by flash chromatography on silica gel (cyclohexane/ethyl acetate from 90/10 to 80/20) to furnish the intermediate acetal (720 mg, 1.696 mmol, 90%) and starting material (64 mg, 0.181 mmol, 9%). The intermediate acetal was directly dissolved in anhydrous dichloromethane (2.4 mL), cooled down to 0° C. and triethylamine (355 L, 2.54 mmol) and trimethylsilyl trifluoromethanesulfonate (400 L, 2.20 mmol) were added dropwise. The mixture was stirred at room temperature 2 hours before the reaction was quenched with a 1M sodium hydroxide solution. The organic layer was separated, washed with brine, dried over sodium sulfate and concentrated under reduced pressure. The crude material was purified by chromatography on silica gel (cyclohexane/ethyl acetate 80/20) to give methyl 2-[3-cyclopropyl-2-(3,4-dihydro-2H-1-benzopyran-6-yl)-6-methylphenyl]-2-vinyloxyacetate (23b) (580 mg, 1.53 mmol, 81%) as a colorless oil.

$^1$H NMR (400 MHz, CDCl$_3$) δ 0.52-0.74 (m, 4H), 1.46-1.55 (m, 1H), 2.01-2.09 (m, 2H), 2.32 et 2.33 (s, 3H), 2.76-2.83 (m, 2H), 3.69 and 3.71 (s, 3H), 3.97-4.00 (m, 1H), 4.21-4.29 (m, 3H), 5.32 and 5.34 (s, 1H), 6.07-6.17 (m, 1H), 6.79-7.05 (m, 4H), 7.07-7.09 (m, 1H)

MS m/z ([M+H]$^+$) 401.

Step 3: Preparation of Intermediate methyl 2-[3-cyclopropyl-2-(3,4-dihydro-2H-1-benzopyran-6-yl)-6-methylphenyl]-2-cyclopropoxyacetate (23c)

To a stirred solution of methyl 2-[3-cyclopropyl-2-(3,4-dihydro-2H-1-benzopyran-6-yl)-6-methylphenyl]-2-vinyloxyacetate (23b) (580 mg, 1.53 mmol) in 1,2-dichloroethane (30 mL) at 0° C. was added diethyl zinc (15% in toluene, 27.9 mL, 30.65 mmol) and then diiodomethane (4.94 mL, 61.30 mmol) dropwisely. The stirring was continued for 16 hours at room temperature before the reaction was quenched with a saturated ammonium chloride aqueous solution and extracted twice with ethyl acetate. The organic layer was washed with brine, dried over sodium sulfate and concentrated under reduced pressure. The crude material was purified by chromatography on silica gel (cyclohexane/ethyl acetate 90/10) to give methyl 2-[3-cyclopropyl-2-(3,4-dihydro-2H-1-benzopyran-6-yl)-6-methylphenyl]-2-cyclopropoxyacetate (23c) (447 mg, 1.14 mmol, 74%) as a colourless oil.

$^1$H NMR (300 MHz, CDCl$_3$) δ 0.21-0.74 (m, 8H), 1.43-1.53 (m, 1H), 2.01-2.10 (m, 2H), 2.32 (s, 3H), 2.77-2.83 (m, 2H), 3.26-3.41 (m, 1H), 3.67 and 3.70 (s, 3H), 4.22-4.26 (m, 2H), 5.03 and 5.08 (s, 1H), 6.76-7.07 (m, 5H).

MS m/z ([M+Na]$^+$) 415.

Step 4: Preparation of 2-[3-cyclopropyl-2-(3,4-dihydro-2H-1-benzopyran-6-yl)-6-methylphenyl]-2-cyclopropoxyacetic acid (Example 23)

A mixture of methyl 2-[3-cyclopropyl-2-(3,4-dihydro-2H-1-benzopyran-6-yl)-6-methylphenyl]-2-cyclopropoxyacetate (23c) (252 mg, 0.642 mmol) and sodium hydroxide 2M in water (642 L, 1.284 mmol) in a 1/1 mixture of e/methanol (6.4 mL) was heated at 70° C. for 16 hours. The mixture was concentrated in vacuo. Water (4 mL) was added to the residue and the aqueous layer was acidified with a 1M hydrochloric acid until pH 3 and extracted with ethyl acetate (2×15 mL). The combined organic layers were washed with brine, dried over sodium sulfate and concentrated in vacuo to provide 2-[3-cyclopropyl-2-(3,4-dihydro-2H-1-benzopyran-6-yl)-6-methylphenyl]-2-cyclopropoxyacetic acid (Example 23) (220.9 mg, 0.584 mmol, 91%) as a white amorphous solid without further purification.

$^1$H NMR (400 MHz, CDCl$_3$) δ 0.23-0.75 (m, 8H), 1.45-1.53 (m, 1H), 2.00-2.10 (m, 2H), 2.32 and 2.34 (s, 3H), 2.71-2.86 (m, 2H), 3.18-3.30 (m, 1H), 4.21-4.25 (m, 2H), 5.12 and 5.14 (s, 1H), 6.78-6.84 (m, 2H), 6.91-6.97 (m, 1H), 7.00-7.08 (m, 2H).

MS m/z ([M+Na]$^+$) 401.
MS m/z ([M−H]$^−$) 377.

Example 24

Synthesis of (S)-2-[3-cyclopropyl-2-(3,4-dihydro-2H-1-benzopyran-6-yl)-6-methylphenyl]-2-cyclopropoxyacetic acid

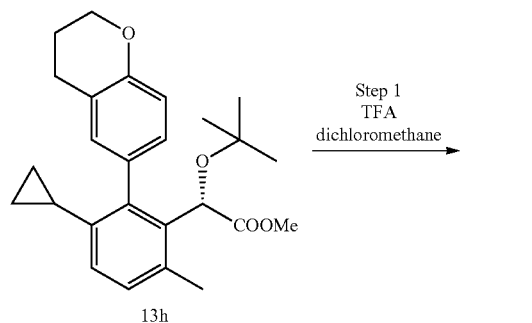

13h

Step 1
TFA
dichloromethane

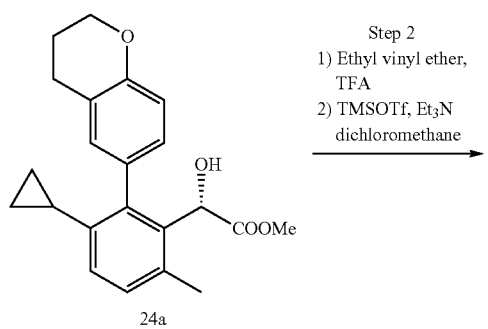

24a

Step 2
1) Ethyl vinyl ether, TFA
2) TMSOTf, Et₃N
dichloromethane

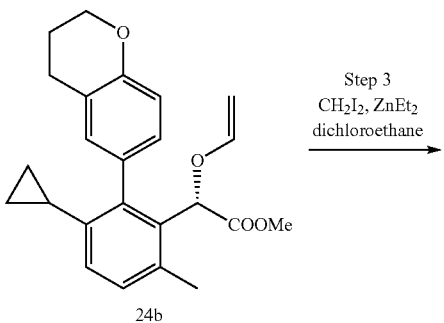

24b

Step 3
CH₂I₂, ZnEt₂
dichloroethane

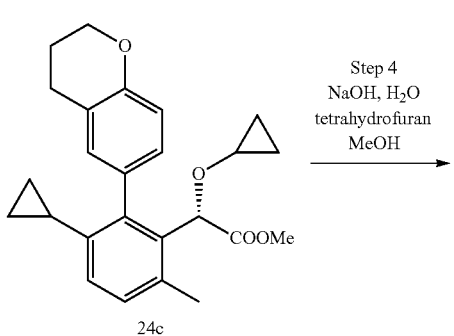

24c

Step 4
NaOH, H₂O
tetrahydrofuran
MeOH

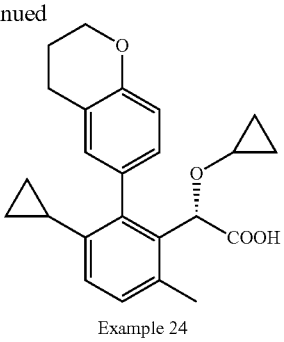

Example 24

Step 1: Preparation of Intermediate (S)-methyl 2-[3-cyclopropyl-2-(3,4-dihydro-2H-1-benzopyran-6-yl)-6-methylphenyl]-2-hydroxyacetate (24a)

Using the procedure described in example 23, step 1, the methyl (S)-2-(tert-butoxy)-2-[3-cyclopropyl-2-(3,4-dihydro-2H-1-benzopyran-6-yl)-6-methylphenyl]acetate (13h) (1.074 g, 2.629 mmol) is converted into (S)-methyl 2-[3-cyclopropyl-2-(3,4-dihydro-2H-1-benzopyran-6-yl)-6-methylphenyl]-2-hydroxyacetate (24a) (861 mg, 2.443 mmol, 93%).

¹H NMR (400 MHz, CDCl₃) δ 0.51-0.71 (m, 4H), 1.43-1.51 (m, 1H), 2.01-2.08 (m, 2H), 2.29 et 2.30 (s, 3H), 2.77-2.83 (m, 2H), 3.01 and 3.06 (d, J=2.96 Hz, 1H), 3.70 and 3.71 (s, 3H), 4.21-4.26 (m, 2H), 5.20 and 5.22 (d, J=2.96 Hz, 1H), 6.78-6.83 (m, 2H), 6.94-7.01 (m, 2H), 7.06-7.09 (m, 1H).

MS m/z ([M+Na]⁺) 375.

Step 2: Preparation of Intermediate (S)-methyl 2-[3-cyclopropyl-2-(3,4-dihydro-2H-1-benzopyran-6-yl)-6-methylphenyl]-2-vinyloxyacetate (24b)

Using the procedure described in example 23, step 2, the (S)-methyl 2-[3-cyclopropyl-2-(3,4-dihydro-2H-1-benzopyran-6-yl)-6-methylphenyl]-2-hydroxyacetate (24a) (861 mg, 2.443 mmol) is converted into (S)-methyl 2-[3-cyclopropyl-2-(3,4-dihydro-2H-1-benzopyran-6-yl)-6-methylphenyl]-2-vinyloxyacetate (24b) (225 mg, 0.594 mmol, 65%).

¹H NMR (400 MHz, CDCl₃) δ 0.52-0.74 (m, 4H), 1.46-1.55 (m, 1H), 2.01-2.09 (m, 2H), 2.32 et 2.33 (s, 3H), 2.76-2.83 (m, 2H), 3.69 and 3.71 (s, 3H), 3.97-4.00 (m, 1H), 4.21-4.29 (m, 3H), 5.32 and 5.34 (s, 1H), 6.07-6.17 (m, 1H), 6.79-7.05 (m, 4H), 7.07-7.09 (m, 1H)

MS m/z ([M+H]⁺) 401.

Step 3: Preparation of Intermediate (S)-methyl 2-[3-cyclopropyl-2-(3,4-dihydro-2H-1-benzopyran-6-yl)-6-methylphenyl]-2-cyclopropoxyacetate (24c)

Using the procedure described in example 23, step 3, the (S)-methyl 2-[3-cyclopropyl-2-(3,4-dihydro-2H-1-benzopyran-6-yl)-6-methylphenyl]-2-vinyloxyacetate (24b) (370 mg, 0.978 mmol) is converted into (S)-methyl 2-[3-cyclopropyl-2-(3,4-dihydro-2H-1-benzopyran-6-yl)-6-methylphenyl]-2-cyclopropoxyacetate (24c) (316 mg, 0.805 mmol, 82%).

¹H NMR (300 MHz, CDCl₃) δ 0.21-0.74 (m, 8H), 1.43-1.53 (m, 1H), 2.01-2.10 (m, 2H), 2.32 (s, 3H), 2.77-2.83 (m,

2H), 3.26-3.41 (m, 1H), 3.67 and 3.70 (s, 3H), 4.22-4.26 (m, 2H), 5.03 and 5.08 (s, 1H), 6.76-7.07 (m, 5H).
MS m/z ([M+Na]$^+$) 415.

Step 4: Preparation of (S) 2-[3-cyclopropyl-2-(3,4-dihydro-2H-1-benzopyran-6-yl)-6-methylphenyl]-2-cyclopropoxyacetic acid (Example 24)

Using the procedure described in example 23, step 4, the (S)-methyl 2-[3-cyclopropyl-2-(3,4-dihydro-2H-1-benzopyran-6-yl)-6-methylphenyl]-2-cyclopropoxyacetate (24c) (309 mg, 0.787 mmol) is converted into (S) 2-[3-cyclopropyl-2-(3,4-dihydro-2H-1-benzopyran-6-yl)-6-methylphenyl]-2-cyclopropoxyacetic acid (Example 24) (279 mg, 0.737 mmol, 94%).

$^1$H NMR (400 MHz, CDCl$_3$) δ 0.23-0.75 (m, 8H), 1.45-1.53 (m, 1H), 2.00-2.10 (m, 2H), 2.32 and 2.34 (s, 3H), 2.71-2.86 (m, 2H), 3.18-3.30 (m, 1H), 4.21-4.25 (m, 2H), 5.12 and 5.14 (s, 1H), 6.78-6.84 (m, 2H), 6.91-6.97 (m, 1H), 7.00-7.08 (m, 2H).
MS m/z ([M+Na]$^+$) 401.
MS m/z ([M−H]$^-$) 377.

Example 25

Synthesis of tert-butoxy-[2-chroman-6-yl-6-methyl-3-(1-methyl-cyclopropyl)-phenyl]-acetic acid

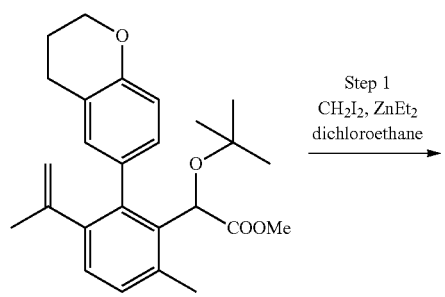

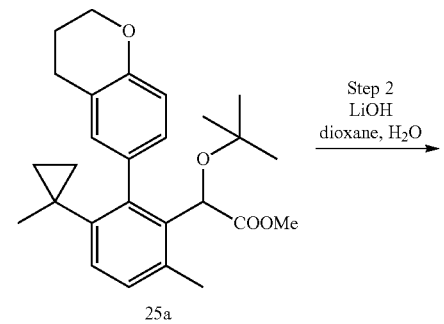

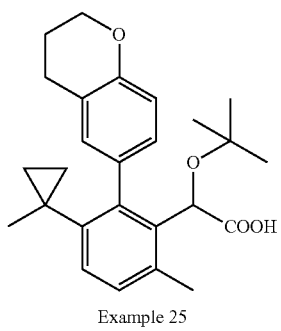

Step 1: Preparation of Intermediate tert-butoxy-[2-chroman-6-yl-6-methyl-3-(1-methyl-cyclopropyl)-phenyl]-acetic acid methyl ester (25a)

Using the procedure described in example 22, step 2, the methyl 2-(tert-butoxy)-2-[2-(3,4-dihydro-2H-1-benzopyran-6-yl)-3-isopropenyl-6-methylphenyl]acetate (4a) (42 mg, 0.103 mmol) is converted into tert-butoxy-[2-chroman-6-yl-6-methyl-3-(1-methyl-cyclopropyl)-phenyl]-acetic acid methyl ester (25a) (15 mg, 0.035 mmol, 34%).

$^1$H NMR (400 MHz, CDCl$_3$) δ 0.24-0.28 (m, 1H), 0.38-0.42 (m, 1H), 0.54-0.65 (m, 2H), 0.99 (s, 9H), 1.07 and 1.08 (s, 3H), 1.99-2.13 (m, 2H), 2.40 and 2.41 (s, 3H), 2.67-2.86 (m, 2H), 3.63 and 3.66 (s, 3H), 4.21-4.28 (m, 2H), 5.00 and 5.02 (s, 1H), 6.80 (dd, J=8.2 Hz, J=6.9 Hz, 1H), 6.93-7.07 (m, 3H), 7.27 and 7.28 (s, 1H).
MS m/z ([M+Na]$^+$) 445.

Step 2: Preparation of tert-butoxy-[2-chroman-6-yl-6-methyl-3-(1-methyl-cyclopropyl)-phenyl]-acetic acid (Example 25)

Using the procedure described in example 1, step 12, the intermediate tert-butoxy-[2-chroman-6-yl-6-methyl-3-(1-methyl-cyclopropyl)-phenyl]-acetic acid methyl ester (25a) (15 mg, 0.035 mmol) is converted into tert-butoxy-[2-chroman-6-yl-6-methyl-3-(1-methyl-cyclopropyl)-phenyl]-acetic acid (Example 25) (11.5 mg, 0.028 mmol, 81%) as a white solid.

$^1$H NMR (400 MHz, CDCl$_3$) δ 0.21-0.25 (m, 1H), 0.42-046 (m, 1H), 0.51-0.63 (m, 2H), 0.98 (s, 9H), 1.07 and 1.08 (s, 3H), 1.97-2.12 (m, 2H), 2.33 (s, 3H), 2.71-2.89 (m, 2H), 4.22-4.29 (m, 2H), 5.12 and 5.14 (s, 1H), 6.80 (d, J=8.3 Hz, 1H), 6.92-7.09 (m, 2H), 7.18-7.30 (m, 2H).
MS m/z ([M+Na]$^+$) 431.
MS m/z ([M−H]$^-$) 407.

Example 26

Synthesis of tert-Butoxy-[2-chroman-6-yl-6-methyl-3-(cis-2-methyl-cyclopropyl)-phenyl]-acetic acid

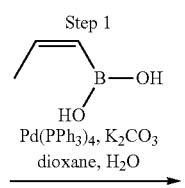

-continued

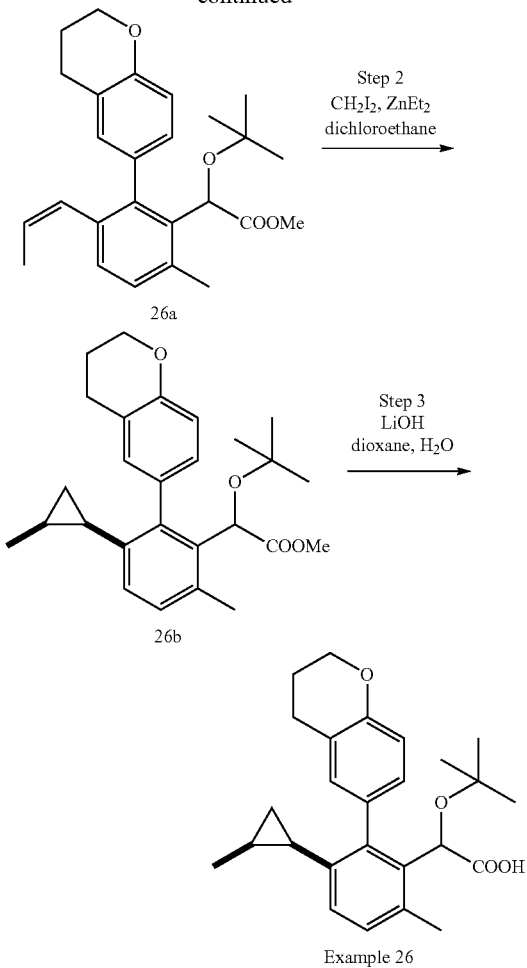

Example 26

Step 1: Preparation of Intermediate tert-butoxy-[2-chroman-6-yl-6-methyl-3-((Z)-propenyl)-phenyl]-acetic acid methyl ester (26a)

A degassed solution of methyl 2-(tert-butoxy)-2-[2-(3,4-dihydro-2H-1-benzopyran-6-yl)-6-methyl-3-trifluoromethanesulfonyloxy-phenyl]acetate (1j) (100 mg, 0.19 mmol), cis-1-propen-1-ylboronic acid (50 mg, 0.582 mmol), potassium carbonate (80 mg, 0.580 mmol) and palladium tetrakis (triphenylphosphine) (22 mg, 0.02 mmol) in a mixture of 1,4-dioxane and water (1.6/0.4 mL) was heated in microwaves at 110° C. for 2 hours. Water (5 mL) was added. The aqueous layer was extracted with ethyl acetate (2×5 mL). The combined organic layers were washed with brine (5 mL), dried over sodium sulfate and concentrated in vacuo. The residue was purified by preparative TLC (cyclohexane/ethyl acetate 90/10) to provide tert-butoxy-[2-chroman-6-yl-6-methyl-3-((Z)-propenyl)-phenyl]-acetic acid methyl ester (26a) (70 mg, 0.17 mmol, 88%).

$^1$H NMR (300 MHz, CDCl$_3$) δ 0.96 (s, 9H), 1.77-1.82 (m, 3H), 1.98-2.09 (m, 2H), 2.43 (s, 3H), 2.60-2.82 (m, 2H), 3.67 and 3.70 (s, 3H), 4.22-4.25 (m, 2H), 5.11 and 5.13 (s, 1H), 5.46-5.57 (m, 1H), 5.90-5.96 (m, 1H), 6.74-6.85 (m, 2H), 7.00-7.08 (m, 2H), 7.19-7.22 (m, 1H).

MS m/z ([M+Na]$^+$) 431.

Step 2: Preparation of Intermediate tert-butoxy-[2-chroman-6-yl-6-methyl-3-(cis-2-methyl-cyclopropyl)-phenyl]-acetic acid methyl ester (26b)

Using the procedure described in example 22, step 2, the tert-butoxy-[2-chroman-6-yl-6-methyl-3-((Z)-propenyl)-phenyl]-acetic acid methyl ester (26a) (70 mg, 0.171 mmol) is converted into tert-butoxy-[2-chroman-6-yl-6-methyl-3-(cis-2-methyl-cyclopropyl)-phenyl]-acetic acid methyl ester (26b) (20 mg, 0.042 mmol, 20%).

$^1$H NMR (400 MHz, CDCl$_3$) δ 0.58-0.64 (m, 1H), 0.73-0.77 (m, 1H), 0.80-0.82 (m, 2H), 0.97-1.00 (m, 9H), 1.09-1.25 (m, 1H), 1.46-1.55 (m, 1H), 2.00-2.10 (m, 2H), 2.40 and 2.42 (s, 3H), 2.68-2.87 (m, 2H), 3.67 and 3.69 (s, 3H), 4.20-4.30 (m, 2H), 5.07-5.13 (m, 1H), 6.74-7.06 (m, 4H), 6.79-7.11 (m, 5H).

MS m/z ([M+Na]$^+$) 445.

Step 3: Preparation of tert-Butoxy-[2-chroman-6-yl-6-methyl-3-(cis-2-methyl-cyclopropyl)-phenyl]-acetic acid (Example 26)

Using the procedure described in example 1, step 12, the intermediate tert-Butoxy-[2-chroman-6-yl-6-methyl-3-(cis-2-methyl-cyclopropyl)-phenyl]-acetic acid methyl ester (26b) (20 mg, 0.042 mmol) is converted to tert-butoxy-[2-chroman-6-yl-6-methyl-3-(cis-2-methyl-cyclopropyl)-phenyl]-acetic acid (Example 26) (5.3 mg, 0.013 mmol, 27%) as a white solid.

$^1$H NMR (400 MHz, CDCl$_3$) δ 0.57-0.62 (m, 1H), 0.80-0.83 (m, 3H), 0.99-1.02 (m, 9H), 1.10-1.34 (m, 1H), 1.47-1.55 (m, 2H), 1.98-2.10 (m, 2H), 2.35 and 2.36 (s, 3H), 2.70-2.88 (m, 2H), 4.19-4.27 (m, 2H), 5.20-5.26 (m, 1H), 6.74-7.06 (m, 4H), 7.15-7.22 (m, 1H), 9.79 (bs, 1H).

MS m/z ([M+Na]$^+$) 431.
MS m/z ([M–H]$^-$) 407.

Example 27

Synthesis of (2-chroman-6-yl-3-cyclopropyl-6-trifluoromethyl-phenyl)-cyclopropoxy-acetic acid

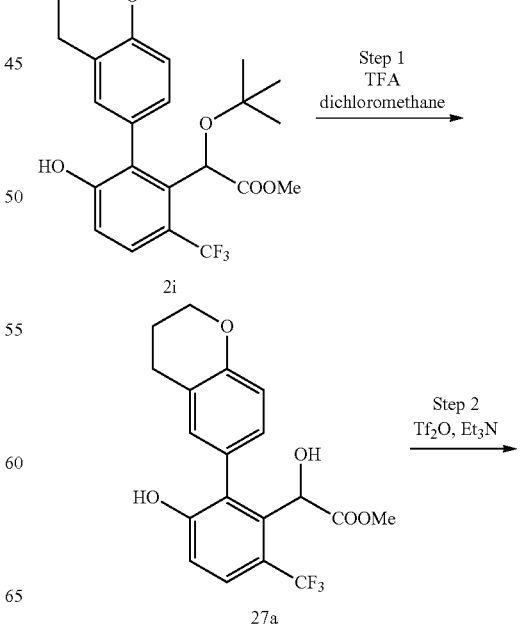

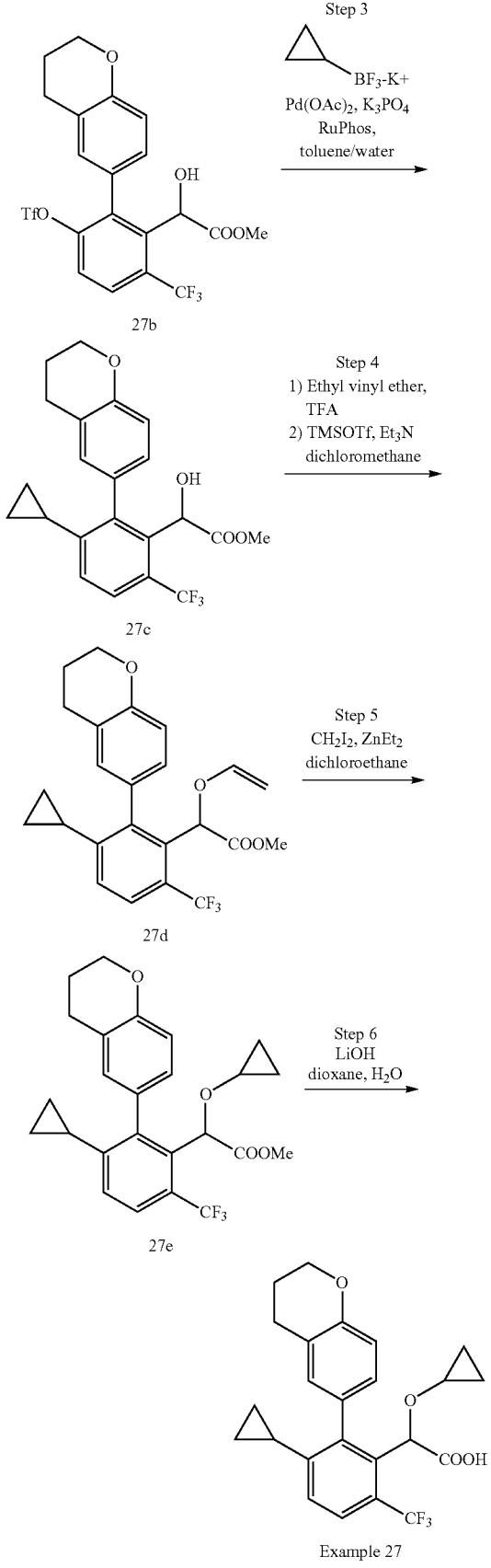

Example 27

Step 1: Preparation of Intermediate methyl (2-chroman-6-yl-3-hydroxy-6-trifluoromethyl-phenyl)-hydroxy-acetate (27a)

Using the procedure described in example 23, step 1, methyl 2-(tert-butoxy)-2-[2-(3,4-dihydro-2H-1-benzopyran-6-yl)-3-hydroxy-6-(trifluoromethyl)phenyl]acetate (2i) (300 mg, 0.68 mmol) is converted to methyl (2-chroman-6-yl-3-hydroxy-6-trifluoromethyl-phenyl)-hydroxy-acetate (27a) (260 mg, 0.68 mmol, 99%) which was used without further purification.

$^1$H NMR (300 MHz, CDCl$_3$) δ 1.96-2.12 (m, 2H), 2.70-2.90 (m, 2H), 3.12 (bs, 1H), 3.58 and 3.60 (s, 3H), 4.21-4.30 (m, 2H), 5.12 (s, 1H), 5.33 and 5.35 (s, 1H), 6.77-6.83 (m, 1H), 6.84-6.94 (m, 1H), 7.05 (d, J=8.7 Hz, 1H), 7.08-7.14 (m, 1H), 7.65 (d, J=8.7 Hz, 1H)

MS m/z ([M−H]$^-$) 381.

Step 2: Preparation of Intermediate methyl (2-chroman-6-yl-3-trifluoromethane sulfonyloxy-6-trifluoromethyl-phenyl)-hydroxy-acetate (27b)

Using the procedure described in example 1, step 10, the intermediate methyl (2-chroman-6-yl-3-hydroxy-6-trifluoromethyl-phenyl)-hydroxy-acetate (27a) (260 mg, 0.68 mmol), is converted into methyl (2-chroman-6-yl-3-trifluoromethanesulfonyloxy-6-trifluoromethyl-phenyl)-hydroxy-acetate (27b) (350 mg, 0.68 mmol, 100%) which was used without further purification.

$^1$H NMR (300 MHz, CDCl$_3$) δ 1.97-2.09 (m, 2H), 2.68-2.86 (m, 2H), 3.19 (bs, 1H), 3.59 and 3.61 (s, 3H), 4.20-4.28 (m, 2H), 5.40 (s, 1H), 6.73-6.86 (m, 2H), 7.02-7.09 (m, 1H), 7.47 (d, J=8.8 Hz, 1H), 7.83 (d, J=8.8 Hz, 1H).

MS m/z ([M−H]$^-$) 513.

Step 3: Preparation of Intermediate methyl (2-chroman-6-yl-3-cyclopropyl-6-trifluoro methyl-phenyl)-hydroxy-acetate (27c)

Using the procedure described in example 21, step 4, the intermediate methyl (2-chroman-6-yl-3-trifluoromethanesulfonyloxy-6-trifluoromethyl-phenyl)-hydroxy-acetate (27b) (350 mg, 0.68 mmol), is converted, after purification by preparative TLC (cyclohexane/ethyl acetate 70/30), into methyl (2-chroman-6-yl-3-cyclopropyl-6-trifluoromethyl-phenyl)-hydroxy-acetate (27c) (85 mg, 0.21 mmol, 31%).

$^1$H NMR (400 MHz, CDCl$_3$) δ 0.57-0.72 (m, 2H), 0.72-0.85 (m, 2H), 1.41-1.51 (m, 1H), 1.98-2.11 (m, 2H), 2.71-2.86 (m, 2H), 3.07 and 3.09 (d, J=4.3 Hz, 1H), 3.58 and 3.61 (s, 3H), 4.20-4.27 (m, 2H), 5.38 (d, J=4.3 Hz, 1H), 6.74-6.85 (m, 2H), 6.93 (d, J=8.3 Hz, 1H), 7.01-7.06 (m, 1H), 7.62 (d, J=8.3 Hz, 1H).

Step 4: Preparation of Intermediate methyl (2-chroman-6-yl-3-cyclopropyl-6-trifluoro methyl-phenyl)-vinyloxy-acetate (27d)

Using the procedure described in example 23, step 2, the intermediate methyl (2-chroman-6-yl-3-cyclopropyl-6-trifluoromethyl-phenyl)-hydroxy-acetate (27c) (85 mg, 0.21 mmol) is converted, after purification by preparative TLC (cyclohexane/ethyl acetate 80/20) into methyl (2-chroman-6-yl-3-cyclopropyl-6-trifluoromethyl-phenyl)-vinyloxy-acetate (27d) (65 mg, 0.15 mmol, 72%).

$^1$H NMR (300 MHz, CDCl$_3$) δ 0.58-0.89 (m, 4H), 1.45-1.57 (m, 1H), 1.99-2.10 (m, 2H), 2.74-2.85 (m, 2H), 3.59 and 3.61 (s, 3H), 4.03 and 4.04 (dd, J=2.0 Hz, J=6.4 Hz, 1H), 4.19-4.26 (m, 2H), 4.31 and 4.33 (dd, J=2.0 Hz, J=14.0 Hz, 1H), 5.47 (s, 1H), 6.16 and 6.20 (dd, J=6.4 Hz, J=14.0 Hz, 1H), 6.76-6.86 (m, 2H), 6.95 (d, J=8.4 Hz, 1H), 7.02-7.08 (m, 1H), 7.63 (d, J=8.4 Hz, 1H).

MS m/z ([M+Na]+) 455.

Step 5: Preparation of Intermediate methyl (2-chroman-6-yl-3-cyclopropyl-6-trifluoromethyl-phenyl)-cyclopropoxy-acetate (27e)

Using the procedure described in example 23, step 3, the intermediate methyl (2-chroman-6-yl-3-cyclopropyl-6-trifluoromethyl-phenyl)-vinyloxy-acetate (27d) (65 mg, 0.15 mmol) is converted, after purification by preparative TLC (cyclohexane/ethyl acetate 80/20) into methyl (2-chroman-6-yl-3-cyclopropyl-6-trifluoromethyl-phenyl)-cyclopropoxy-acetate (27e) (47 mg, 0.11 mmol, 70%).

$^1$H NMR (300 MHz, CDCl$_3$) δ 0.29-0.38 (m, 2H), 0.47-0.58 (m, 2H), 0.62-0.73 (m, 2H), 0.75-0.86 (m, 2H), 1.45-1.55 (m, 1H), 2.00-2.11 (m, 2H), 2.71-2.84 (m, 2H), 3.29-3.38 (m, 1H), 3.61 and 3.62 (s, 3H), 4.20-4.27 (m, 2H), 5.19 and 5.20 (s, 1H), 6.77-7.01 (m, 4H), 7.61 (d, J=8.4 Hz, 1H).

MS m/z ([M+Na]+) 469.

Step 6: Preparation of (2-chroman-6-yl-3-cyclopropyl-6-trifluoromethyl-phenyl)-cyclopropoxy-acetic acid (Example 27)

Using the procedure described in example 1, step 12, the intermediate methyl (2-chroman-6-yl-3-cyclopropyl-6-trifluoromethyl-phenyl)-cyclopropoxy-acetate (27e) (47 mg, 0.11 mmol) is converted to (2-chroman-6-yl-3-cyclopropyl-6-trifluoromethyl-phenyl)-cyclopropoxy-acetic acid (Example 27) (32 mg, 0.07 mmol, 70%).

$^1$H NMR (400 MHz, CDCl$_3$) δ 0.31-0.55 (m, 4H), 0.62-0.72 (m, 2H), 0.75-0.87 (m, 2H), 1.47-1.56 (m, 1H), 1.99-2.09 (m, 2H), 2.72-2.84 (m, 2H), 3.21-3.30 (m, 1H), 4.20-4.26 (m, 2H), 5.22 and 5.25 (s, 1H), 6.79-6.91 (m, 2H), 6.95 (d, J=8.4 Hz, 1H), 7.01-7.07 (m, 1H), 7.63 (d, J=8.4 Hz, 1H).

MS m/z ([M+Na]+) 455.

Example 28

Synthesis of (2-chroman-6-yl-3-cyclopropyl-6-methyl-phenyl)-propoxy-acetic acid

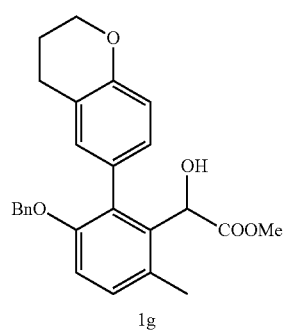

1g

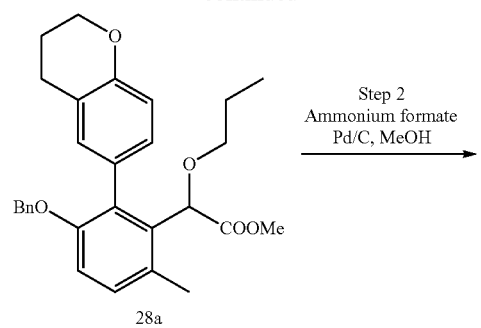

28a

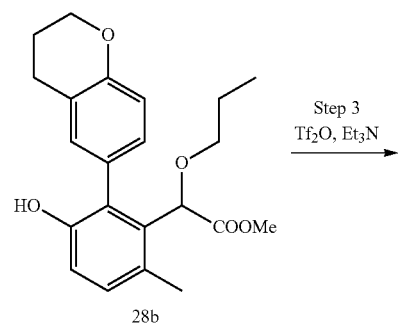

28b

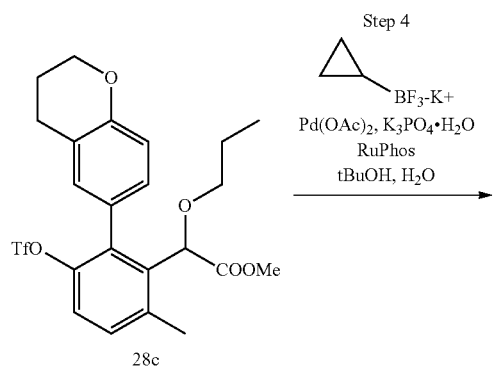

28c

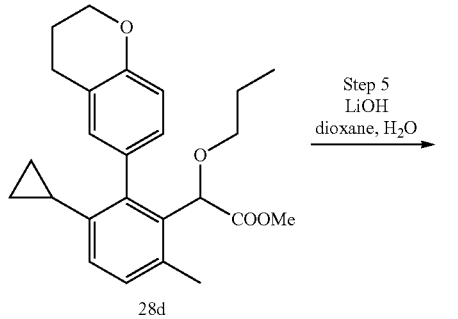

28d

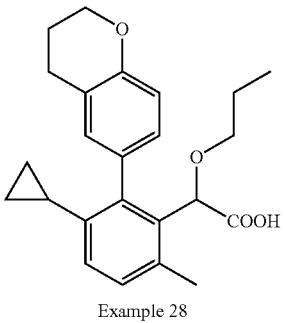 [SMILES: CCCOC(C(=O)O)c1c(C)ccc(C2CC2)c1-c1ccc2c(c1)CCCO2]

Example 28

Step 1: Preparation of Intermediate (3-benzyloxy-2-chroman-6-yl-6-methyl-phenyl)-propoxy-acetic acid methyl ester (28a)

To a solution of methyl 2-[3-benzyloxy-2-(3,4-dihydro-2H-1-benzopyran-6-yl)-6-methylphenyl]-2-hydroxyacetate (1g) (128 mg, 0.306 mmol) in anhydrous N,N-dimethylformamide (3 mL) under nitrogen atmosphere at 0° C. were successively added, lithium bis(trimethylsilyl)amide 1 M in e (351 µL, 0.351 mmol) and 2-iodopropane (228 µL, 1.71 mmol). The reaction was stirred at room temperature for 3 hours before adding water (10 mL). Layers were separated and the aqueous one was extracted with ethyl acetate (2×10 mL). The combined organic layers was dried over sodium sulfate and concentrated in vacuo. The residue was purified by flash chromatography on silica gel (cyclohexane/ethyl acetate 90/10) to provide (3-benzyloxy-2-chroman-6-yl-6-methyl-phenyl)-propoxy-acetic acid methyl ester (28a) (102 mg, 0.221 mmol, 72%) as a colorless oil.

MS m/z ([M+Na]$^+$) 483.

Step 2: Preparation of Intermediate (2-chroman-6-yl-3-hydroxy-6-methyl-phenyl)-propoxy-acetic acid methyl ester (28b)

To a solution of (3-benzyloxy-2-chroman-6-yl-6-methyl-phenyl)-propoxy-acetic acid methyl ester (28a) (102 mg, 0.221 mmol) and ammonium formate (349 mg, 5.53 mmol), in anhydrous methanol (1 mL) degassed with argon, was added palladium on carbon 10% (12 mg, 0.011 mmol). The reaction was refluxed for 16 hours then cooled to room temperature and was filtered over Millipore. Water (5 mL) was added. The aqueous layer was extracted with ethyl acetate (2×5 mL). The combined organic layers were washed with brine (10 mL), dried over sodium sulfate and concentrated in vacuo to provide 2-chroman-6-yl-3-hydroxy-6-methyl-phenyl)-propoxy-acetic acid methyl ester (28b) (36 mg, 0.097 mmol, 44%) as a white solid.

$^1$H NMR (300 MHz, CDCl$_3$) δ 0.84 (t, 3H, J=7.4 Hz), 1.47-1.51 (m, 2H), 2.02-2.11 (m, 2H), 2.29 (s, 3H), 2.77-2.83 (m, 2H), 3.12-3.19 (m, 1H), 3.28-3.39 (m, 1H), 3.67 and 3.68 (s, 3H), 4.23-4.27 (m, 2H), 4.65 and 4.66 (s, 1H), 4.83 and 4.84 (s, 1H), 6.86-6.95 (m, 3H), 7.05-7.07 (m, 2H).

MS m/z ([M+Na]$^+$) 393.

Step 3: Preparation of Intermediate (2-chroman-6-yl-6-methyl-3-trifluoromethane sulfonyloxy-phenyl)-propoxy-acetic acid methyl ester (28c)

Using the procedure described in example 1, step 10, the intermediate 2-chroman-6-yl-3-hydroxy-6-methyl-phenyl)-propoxy-acetic acid methyl ester (28b) (36 mg, 0.097 mmol) is converted into the intermediate (2-chroman-6-yl-6-methyl-3-trifluoromethanesulfonyloxy-phenyl)-propoxy-acetic acid methyl ester (28c) (51 mg, 0.097 mmol, 100%) as a brown oil.

$^1$H NMR (300 MHz, CDCl$_3$) δ 0.84 (dt, 3H, J=7.4 Hz, J=1.4 Hz), 1.44-1.53 (m, 2H), 2.00-2.07 (m, 2H), 2.38 and 2.39 (s, 3H), 2.68-2.88 (m, 2H), 3.09-3.17 (m, 1H), 3.33-3.42 (m, 1H), 3.68 and 3.69 (s, 3H), 4.21-4.24 (m, 2H), 4.93 and 4.94 (s, 1H), 6.82-6.84 (m, 1H), 6.90-7.03 (m, 2H), 7.20 (s, 2H).

MS m/z ([M+Na]$^+$) 525.

Step 4: Preparation of Intermediate (2-chroman-6-yl-3-cyclopropyl-6-methyl-phenyl)-propoxy-acetic acid methyl ester (28d)

A degassed solution of (2-Chroman-6-yl-6-methyl-3-trifluoromethanesulfonyloxy-phenyl)-propoxy-acetic acid methyl ester (28c) (51 mg, 0.097 mmol), potassium phosphate tribasic monohydrate (144 mg, 0.626 mmol), potassium cyclopropyltrifluoroborate (20 mg, 0.132 mmol), palladium acetate (0.6 mg, 0.025 mmol) and 2-dicyclohexylphosphino-2',6'-diisopropoxybiphenyl (RuPhos) (2.3 mg, 0.050 mmol) in tert-butanol (0.1 mL) and water (0.1 mL) was heated at 105° C. overnight. Water (5 mL) was added. The aqueous layer was extracted with ethyl acetate (2×5 mL). The combined organic layers were washed with brine (10 mL), dried over sodium sulfate and concentrated in vacuo. The residue was purified by preparative TLC (cyclohexane/ethyl acetate 90/10) to provide (2-chroman-6-yl-3-cyclopropyl-6-methyl-phenyl)-propoxy-acetic acid methyl ester (28d) (18 mg, 0.045 mmol, 47%).

$^1$H NMR (300 MHz, CDCl$_3$) δ 0.51-0.72 (m, 4H), 0.81-0.87 (m, 3H), 1.43-1.56 (m, 3H), 2.02-2.09 (m, 2H), 3.32 (s, 3H), 2.70-2.88 (m, 2H), 3.09-3.18 (m, 1H), 3.27-3.42 (m, 1H), 3.66 and 3.68 (s, 3H), 4.22-4.25 (m, 2H), 4.91 and 4.93 (s, 1H), 6.77 (dd, 1H, J=7.9 Hz, J=1.4 Hz), 6.82 (dd, 1H, J=8.3 Hz, J=3.4 Hz), 6.89-7.03 (m, 2H), 7.06 (d, 1H, J=8.0 Hz).

MS m/z ([M+Na]$^+$) 417.

Step 5: Preparation of (2-chroman-6-yl-3-cyclopropyl-6-methyl-phenyl)-propoxy-acetic acid (Example 28)

Using the procedure described in example 1, step 12, the intermediate (2-chroman-6-yl-3-cyclopropyl-6-methyl-phenyl)-propoxy-acetic acid methyl ester (28d) (18 mg, 0.045 mmol) is converted into (2-chroman-6-yl-3-cyclopropyl-6-methyl-phenyl)-propoxy-acetic acid (6.3 mg, 0.016 mmol, 36%) (Example 28) as a white solid.

$^1$H NMR (300 MHz, CDCl$_3$) δ 0.55-076 (m, 4H), 0.81-0.87 (m, 3H), 1.43-1.54 (m, 3H), 2.00-2.09 (m, 2H), 3.32 and 3.33 (s, 3H), 2.68-2.88 (m, 2H), 3.13-3.30 (m, 2H), 4.22-4.25 (m, 2H), 5.02 and 5.03 (s, 1H), 6.77-6.84 (m, 2H), 6.88-6.93 (m, 1H), 7.02-7.09 (m, 2H).

MS m/z ([M+Na]$^+$) 403.

MS m/z ([M−H]$^−$) 379.

Example 29

Synthesis of (2-chroman-6-yl-3-cyclopropyl-6-methyl-phenyl)-cyclopropyl methoxy-acetic acid

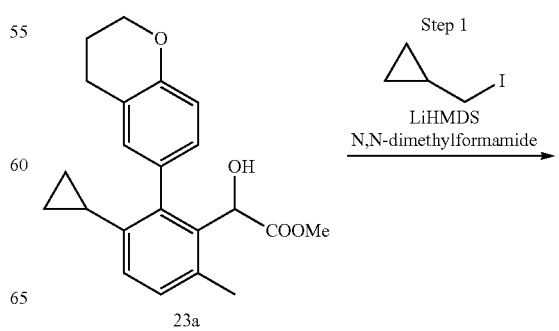

-continued

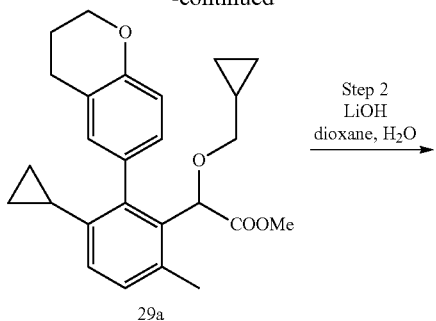

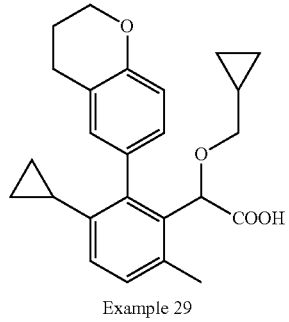

Example 29

Step 1: Preparation of Intermediate (2-chroman-6-yl-3-cyclopropyl-6-methyl-phenyl)-cyclopropyl-methoxy-acetic acid methyl ester (29a)

Using the procedure described in example 28, step 1, the intermediate (2-chroman-6-yl-3-cyclopropyl-6-methyl-phenyl)-hydroxy-acetic acid methyl ester (23a) (50 mg, 0.142 mmol) is converted, by reaction with iodomethylcyclopropane (145 mg, 0.795 mmol), after purification by preparative TLC (cyclohexane/ethyl acetate 90/10), into (2-chroman-6-yl-3-cyclopropyl-6-methyl-phenyl)-cyclopropylmethoxy-acetic acid methyl ester (29a) (7 mg, 0.017 mmol, 12%) as white solid.

$^1$H NMR (300 MHz, CDCl$_3$) δ 0.04-0.10 (m, 2H), 0.35-0.45 (m, 2H), 0.50-0.74 (m, 4H), 0.87-1.00 (m, 1H), 1.43-1.53 (m, 1H), 1.99-2.09 (m, 2H), 2.34 (s, 3H), 2.68-2.88 (m, 2H), 2.94-3.03 (m, 1H), 3.23-3.35 (m, 1H), 3.66 and 3.69 (s, 3H), 4.21-4.25 (m, 2H), 4.99 and 5.00 (s, 1H), 6.75-6.84 (m, 2H), 6.89-7.07 (m, 3H).

MS m/z ([M+Na]$^+$) 429.

Step 2: Preparation of (2-chroman-6-yl-3-cyclopropyl-6-methyl-phenyl)-cyclopropyl methoxy-acetic acid (Example 29)

Using the procedure described in example 1, step 12, the intermediate (2-chroman-6-yl-3-cyclopropyl-6-methyl-phenyl)-cyclopropylmethoxy-acetic acid methyl ester (29a) (7 mg, 0.017 mmol) is converted into (2-chroman-6-yl-3-cyclopropyl-6-methyl-phenyl)-cyclopropylmethoxy-acetic acid (Example 29) (3.8 mg, 0.010 mmol, 56%) as a white solid.

$^1$H NMR (400 MHz, CD$_3$OD) δ −0.10-0.04 (m, 2H), 0.34 (bs, 2H), 0.48-0.72 (m, 4H), 1.43-1.51 (m, 1H), 1.94-2.07 (m, 2H), 2.36 (bs, 3H), 2.71-2.86 (m, 3H), 3.20-3.40 (m, 2H), 4.17-4.20 (m, 2H), 4.74-4.94 (m, 2H), 6.72-6.76 (m, 2H), 6.87 (d, 1H, J=7.5 Hz), 7.01 (d, 1H, J=7.8 Hz), 7.13 (bs, 1H).

MS m/z ([M+Na]$^+$) 415.
MS m/z ([M−H]$^−$) 391.

Example 30

Synthesis of (2-chroman-6-yl-3-cyclopropyl-6-methyl-phenyl)-(2,2,2-trifluoro-ethoxy)-acetic acid

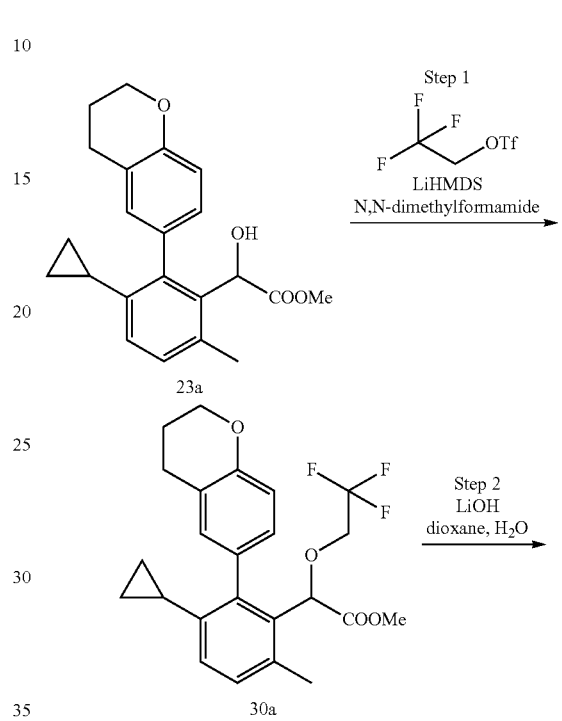

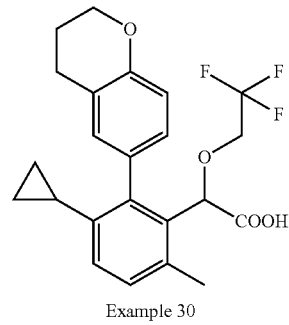

Example 30

Step 1: Preparation of Intermediate (2-chroman-6-yl-3-cyclopropyl-6-methyl-phenyl)-(2,2,2-trifluoro-ethoxy)-acetic acid methyl ester (30a)

Using the procedure described in example 28, step 1, the intermediate (2-chroman-6-yl-3-cyclopropyl-6-methyl-phenyl)-hydroxy-acetic acid methyl ester (23a) (50 mg, 0.142 mmol) is converted by reaction with 2,2,2-trifluoroethyl trifluoromethanesulfonate (115 μL, 0.755 mmol), after purification by preparative TLC (cyclohexane/ethyl acetate 90/10) into (2-chroman-6-yl-3-cyclopropyl-6-methyl-phenyl)-(2,2,2-trifluoro-ethoxy)-acetic acid methyl ester (30a) (30 mg, 0.069 mmol, 48%) as a colorless oil.

$^1$H NMR (300 MHz, CDCl$_3$) δ 0.50-062 (m, 2H), 0.64-0.74 (m, 2H), 1.42-1.54 (m, 1H), 2.00-2.08 (m, 2H), 2.26 and 2.28 (s, 3H), 2.60-2.85 (m, 2H), 3.49-3.61 (m, 1H), 3.67 and 3.68 (s, 3H), 3.83-4.15 (m, 1H), 4.21-4.24 (m, 2H), 5.02

(s, 1H), 6.78-6.83 (m, 2H), 6.89-6.99 (m, 2H), 7.07 (d, 1H, J=7.9 Hz).

MS m/z ([M+Na]$^+$) 457.

Step 2: Preparation of (2-chroman-6-yl-3-cyclopropyl-6-methyl-phenyl)-(2,2,2-trifluoro-ethoxy)-acetic acid (Example 30)

Using the procedure described in example 1, step 12, the intermediate (2-chroman-6-yl-3-cyclopropyl-6-methyl-phenyl)-(2,2,2-trifluoro-ethoxy)-acetic acid methyl ester (30a) (30 mg, 0.069 mmol) is converted into (2-chroman-6-yl-3-cyclopropyl-6-methyl-phenyl)-(2,2,2-trifluoro-ethoxy)-acetic acid (Example 30) (15 mg, 0.035 mmol, 51%) as a white solid after purification on TLC preparative (dichloromethane/methanol 95/5).

$^1$H NMR (400 MHz, CD$_3$OD) δ 0.48-0.74 (m, 4H), 1.44-1.52 (m, 1H), 1.92-2.06 (m, 2H), 2.35 (s, 3H), 2.74-2.86 (m, 2H), 3.40-3.59 (m, 1H), 3.82-4.02 (m, 1H), 4.15-4.23 (m, 2H), 4.75-5.00 (m, 1H), 6.70-6.80 (m, 2H), 6.89 (d, 1H, J=8.0 Hz), 7.04 (d, 1H, J=7.8 Hz), 7.10 (bs, 1H).

MS m/z ([M+Na]$^+$) 443.

MS m/z ([M−H]$^-$) 419.

Example 31

Synthesis of 2-chroman-6-yl-6-methyl-3-propyl-phenyl)-isopropoxy-acetic acid

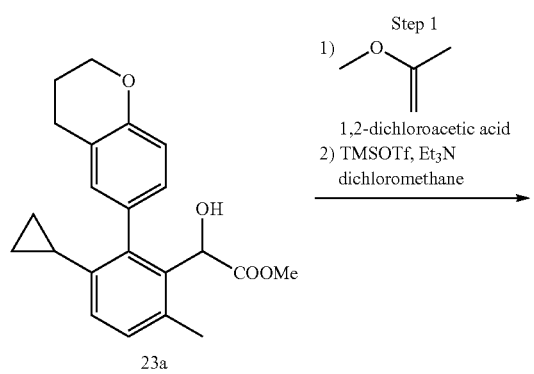

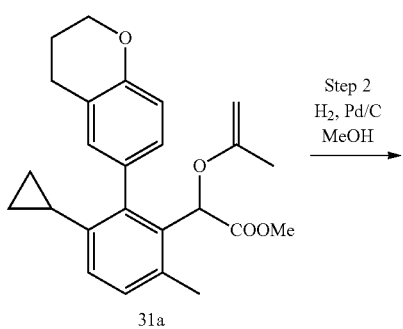

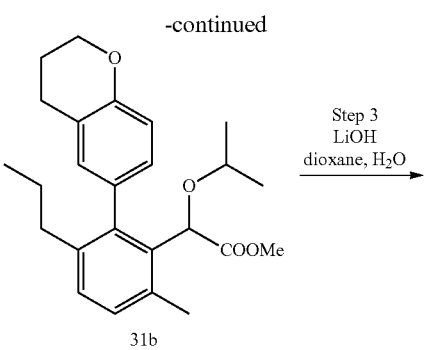

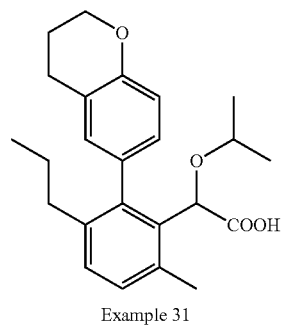

Example 31

Step 1: Preparation of Intermediate (2-chroman-6-yl-3-cyclopropyl-6-methyl-phenyl)-isopropenyloxy-acetic acid methyl ester (31a)

To a stirred solution of (2-chroman-6-yl-3-cyclopropyl-6-methyl-phenyl)-hydroxy-acetic acid methyl ester (23a) (149 mg, 0.423 mmol) in 2-methoxypropene (800 μL) at room temperature was added 1,2-dichloroacetic acid (1 drop). The stirring was continued for 4 days before the reacting mixture was concentrated by nitrogen flush. The residue was directly dissolved in anhydrous dichloromethane (1 mL), cooled down to 0° C. and triethylamine (88 μL, 0.634 mmol) and trimethylsilyl trifluoromethanesulfonate (100 μL, 0.550 mmol) were added dropwisely to −78° C. The mixture was stirred at room temperature 48 hours before the reaction was quenched with a 1M sodium hydroxide solution. The organic layer was separated, washed with brine, dried over sodium sulfate and concentrated under reduced pressure. The crude material was purified by chromatography on TLC preparative (cyclohexane/ethyl acetate 95/5) to give (2-chroman-6-yl-3-cyclopropyl-6-methyl-phenyl)-isopropenyloxy-acetic acid methyl ester (31a) (30 mg, 0.078 mmol, 18%) containing 21% of starting material (23a) as a colorless oil.

MS m/z ([M+Na]$^+$) 415.

Step 2: Preparation of Intermediate (2-chroman-6-yl-6-methyl-3-propyl-phenyl)-isopropoxy-acetic acid methyl ester (31b)

A mixture of (2-chroman-6-yl-3-cyclopropyl-6-methyl-phenyl)-isopropenyloxy-acetic acid methyl ester (31a) (30 mg, 0.053 mmol) and palladium on carbon 5% (17 mg, 0.008 mmol) in methanol was stirred at room temperature under one atmosphere hydrogen pressure for 16 hours. The mixture was filtered over Millipore and concentrated in vacuo. The residue was purified by preparative TLC (cyclohexane/ethyl acetate 90/10) to provide 2-chroman-6-yl-6- methyl-3-propyl-phenyl)-isopropoxy-acetic acid methyl ester (31b) (17 mg, 0.042 mmol, 80%).

$^1$H NMR (400 MHz, CDCl$_3$) δ 0.79 (t, 3H, J=7.3 Hz), 0.93 (d, 3H, J=6.1 Hz), 1.05 (d, 3H, J=6.1 Hz), 1.36-1.46 (m, 2H), 1.96-2.12 (m, 2H), 2.20-2.30 (m, 2H), 2.36 (s, 3H), 2.68-2.85 (m, 2H), 3.48-3.59 (m, 1H), 3.65 (s, 3H), 4.19-4.28 (m, 2H), 4.94 (s, 1H), 6.76-6.84 (m, 2H), 6.90-6.95 (m, 1H), 7.08 (d, 1H, J=7.8 Hz), 7.12 (d, 1H, J=7.8 Hz). MS m/z ([M+Na]$^+$) 419.

Step 3: Preparation of 2-chroman-6-yl-6-methyl-3-propyl-phenyl)-isopropoxy-acetic acid (Example 31)

Using the procedure described in example 1, step 12, the intermediate 2-chroman-6-yl-6-methyl-3-propyl-phenyl)-isopropoxy-acetic acid methyl ester (31b) (17 mg, 0.042 mmol) is converted into 2-chroman-6-yl-6-methyl-3-propyl-phenyl)-isopropoxy-acetic acid (Example 31) (12 mg, 0.031 mmol, 74%) as a white solid after purification by preparative TLC (dichloromethane/methanol 95/5).

$^1$H NMR (400 MHz, CDCl$_3$) δ 0.78 (t, 3H, J=7.3 Hz), 0.90 (d, 3H, J=4.7 Hz), 1.05 (d, 3H, J=5.2 Hz), 1.37-1.46 (m, 2H), 1.98-2.10 (m, 2H), 2.16-2.40 (m, 5H), 2.67-2.86 (m, 2H), 3.42-3.56 (m, 1H), 4.18-4.27 (m, 2H), 5.00 and 5.03 (s, 1H), 6.77-6.84 (m, 2H), 6.90-7.15 (m, 3H).

MS m/z ([M+Na]$^+$) 405.

MS m/z ([M−H]$^−$) 381.

Example 32

Synthesis of cyclopropoxy-[3-cyclopropyl-6-methyl-2-(5-methyl-chroman-6-yl)-phenyl]-acetic acid

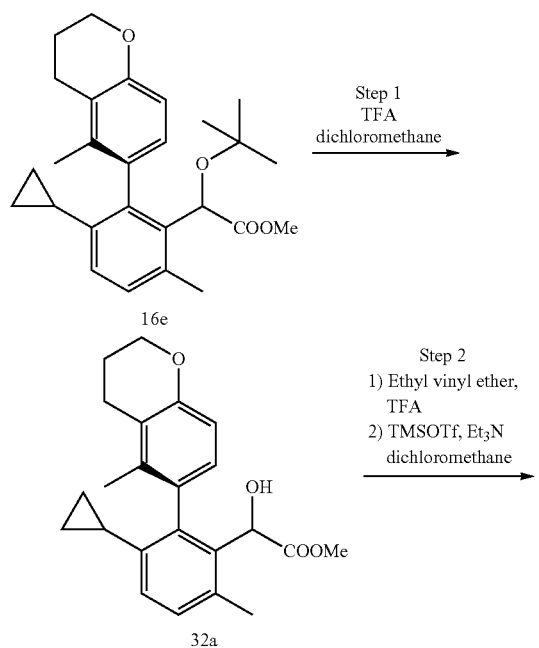

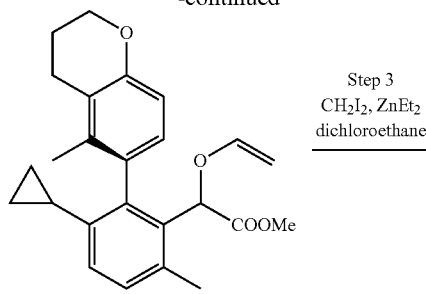

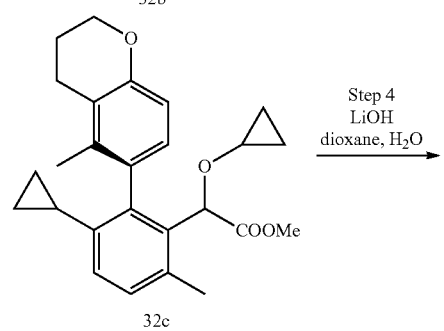

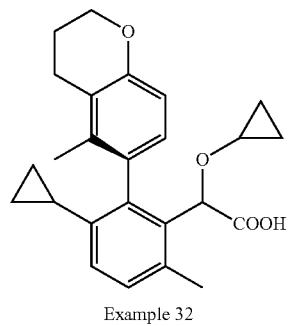

Example 32

Step 1: Preparation of Intermediate methyl[3-cyclopropyl-6-methyl-2-(5-methyl-chroman-6-yl)-phenyl]-hydroxy-acetate (32a)

Using the procedure described in example 23, step 1, methyl 2-(tert-butoxy)-2-[3-cyclopropyl-6-methyl-2-(5-methyl-chroman-6-yl)-phenyl]acetate (16e) (226 mg, 0.54 mmol) is converted to methyl[3-cyclopropyl-6-methyl-2-(5-methyl-chroman-6-yl)-phenyl]-hydroxy-acetate (32a) (191 mg, 0.52 mmol, 97%) which was used without further purification.

$^1$H NMR (300 MHz, CDCl$_3$) δ 0.48-0.75 (m, 4H), 1.28-1.40 (m, 1H), 1.91 (s, 3H), 2.03-2.14 (m, 2H), 2.28 (s, 3H), 2.69 (t, J=6.6 Hz, 2H), 2.93 (d, J=2.8 Hz, 1H), 3.69 (s, 3H), 4.15-4.21 (m, 2H), 5.06 (d, J=2.8 Hz, 1H), 6.70-6.78 (m, 2H), 6.88 (d, J=8.3 Hz, 1H), 7.08 (d, J=8.0 Hz, 1H).

Step 2: Preparation of Intermediate methyl[3-cyclopropyl-6-methyl-2-(5-methyl-chroman-6-yl)-phenyl]-vinyloxy-acetate (32b)

Using the procedure described in example 23, step 2, the intermediate methyl[3-cyclopropyl-6-methyl-2-(5-methyl-chroman-6-yl)-phenyl]-hydroxy-acetate (32a) (191 mg, 0.52 mmol) is converted, after purification by preparative TLC (cyclohexane/ethyl acetate 80/20) into methyl[3-cyclopropyl-6-methyl-2-(5-methyl-chroman-6-yl)-phenyl]-vinyloxy-acetate (32b) (35 mg, 0.089 mmol, 17%).
$^1$H NMR (300 MHz, CDCl$_3$) δ 0.52-0.74 (m, 4H), 1.29-1.40 (m, 1H), 1.92 (s, 3H), 2.06-2.13 (m, 2H), 2.32 (s, 3H), 2.70 (t, J=6.6 Hz, 2H), 3.67 (s, 3H), 3.99 (dd, J=1.9 Hz, J=6.4 Hz, 1H), 4.17-4.22 (m, 2H), 4.27 (dd, J=1.9 Hz, J=13.9 Hz, 1H), 5.17 (s, 1H), 6.12 (dd, J=6.4 Hz, J=13.9 Hz, 1H), 6.72 (d, J=8.3 Hz, 1H), 6.77 (d, J=8.0 Hz, 1H), 6.82 (d, J=8.3 Hz, 1H), 7.10 (d, J=8.0 Hz, 1H).
MS m/z ([M+Na]$^+$) 415.

Step 3: Preparation of Intermediate methyl cyclopropoxy-[3-cyclopropyl-6-methyl-2-(5-methyl-chroman-6-yl)-phenyl]-acetate (32c)

Using the procedure described in example 23, step 3, the intermediate methyl[3-cyclopropyl-6-methyl-2-(5-methyl-chroman-6-yl)-phenyl]-vinyloxy-acetate (32b) (35 mg, 0.089 mmol) is converted, after purification by preparative TLC (cyclohexane/ethyl acetate 80/20) into methyl cyclopropoxy-[3-cyclopropyl-6-methyl-2-(5-methyl-chroman-6-yl)-phenyl]-acetate (32c) (18 mg, 0.044 mmol, 49%).
$^1$H NMR (300 MHz, CDCl$_3$) δ 0.22-0.30 (m, 1H), 0.34-0.46 (m, 2H), 0.51-0.71 (m, 5H), 1.27-1.38 (m, 1H), 1.91 (s, 3H), 2.06-2.16 (m, 2H), 2.32 (s, 3H), 2.64-2.77 (m, 2H), 3.44-3.50 (m, 1H), 3.64 (s, 3H), 4.16-4.24 (m, 2H), 4.93 (s, 1H), 6.69-6.76 (m, 2H), 6.86 (d, J=8.3 Hz, 1H), 7.06 (d, J=8.0 Hz, 1H).
MS m/z ([M+Na]$^+$) 429.

Step 4: Preparation of cyclopropoxy-[3-cyclopropyl-6-methyl-2-(5-methyl-chroman-6-yl)-phenyl]-acetic acid (Example 32)

Using the procedure described in example 1, step 12, the intermediate methyl cyclopropoxy-[3-cyclopropyl-6-methyl-2-(5-methyl-chroman-6-yl)-phenyl]-acetate (32c) (18 mg, 0.044 mmol) is converted into cyclopropoxy-[3-cyclopropyl-6-methyl-2-(5-methyl-chroman-6-yl)-phenyl]-acetic acid (Example 32) (11 mg, 0.028 mmol, 63%).
$^1$H NMR (300 MHz, CDCl$_3$) δ 0.32-0.43 (m, 2H), 0.44-0.72 (m, 6H), 1.30-1.40 (m, 1H), 1.92 (s, 3H), 2.05-2.13 (m, 2H), 2.32 (s, 3H), 2.62-2.75 (m, 2H), 3.29-3.35 (m, 1H), 4.15-4.22 (m, 2H), 5.00 (s, 1H), 6.69 (d, J=8.3 Hz, 1H), 6.78 (d, J=8.0 Hz, 1H), 6.88 (d, J=8.3 Hz, 1H), 7.09 (d, J=8.0 Hz, 1H).
MS m/z ([M+Na]$^+$) 415.
MS m/z ([M−H]$^−$) 391.

Example 33

Synthesis of (2-chroman-6-yl-3-cyclopropyl-6-methyl-phenyl)-cyclobutoxy-acetic acid

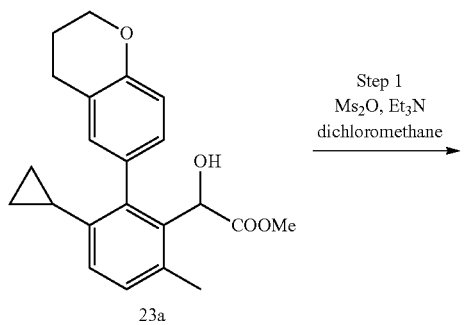

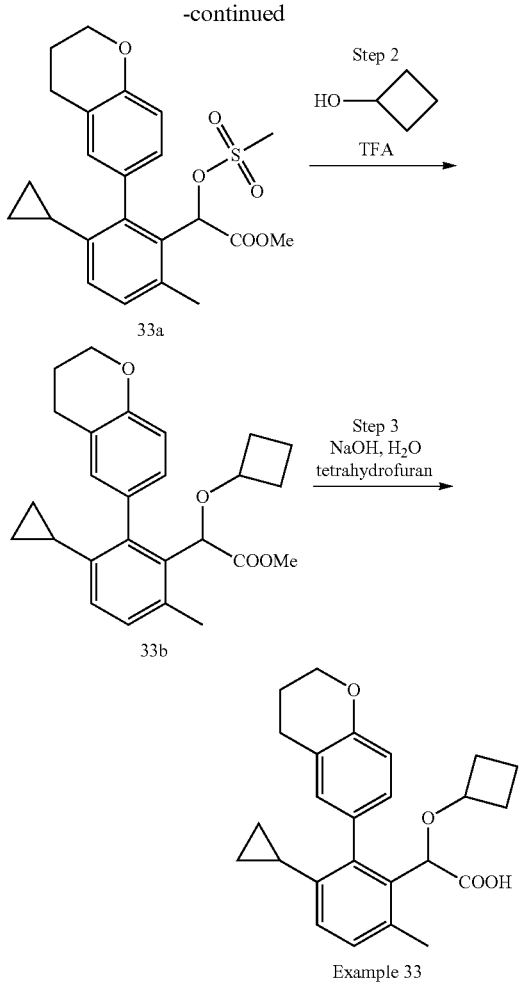

Step 1: Preparation of Intermediate (2-chroman-6-yl-3-cyclopropyl-6-methyl-phenyl)-methanesulfonyloxy-acetic acid methyl ester (33a)

To a solution of intermediate (2-chroman-6-yl-3-cyclopropyl-6-methyl-phenyl)-hydroxy-acetic acid methyl ester (23a) (219 mg, 0.624 mmol) in anhydrous dichloromethane (4 mL) at 0° C. under nitrogen atmosphere were successively added triethylamine (174 μL, 1.25 mmol), and methanesulfonic anhydride (119 mg, 1.25 mmol). The mixture was stirred at room temperature overnight before adding water (5 mL). Layers were separated. The aqueous layer was extracted with ethyl acetate (2×5 mL). The combined organic layers were washed with a saturated solution of sodium chloride (5 mL), dried over sodium sulfate and concentrated in vacuo to provide (2-chroman-6-yl-3-cyclopropyl-6-methyl-phenyl)-methanesulfonyloxy-acetic acid methyl ester (33a) (232 mg, 0.323 mmol, 51%) containing 40% of starting material (23a) as a colorless oil. This oil will be used for the next step without further purification.
MS m/z ([M+Na]$^+$) 453.

Step 2: Preparation of Intermediate (2-chroman-6-yl-3-cyclopropyl-6-methyl-phenyl)-cyclobutoxy-acetic acid methyl ester (33b)

To a solution of methyl (2-chroman-6-yl-3-cyclopropyl-6-methyl-phenyl)-methanesulfonyl oxy-acetic acid methyl ester (33a) (114 mg, 0.265 mmol) in cyclobutanol (0.5 mL) was added trifluoroacetic acid (23 μL, 0.291 mmol). The mixture was stirred at 90° C. for 2 hours and poured in solution of saturated sodium bicarbonate (10 mL). The aqueous layer was extracted with ethyl acetate (2×5 mL). The combined organic layers were washed with water (20 mL), dried over sodium sulfate and concentrated in vacuo. The residue was purified on preparative TLC (cyclohexane/dichloromethane 55/45) to provide (2-chroman-6-yl-3-cyclopropyl-6-methyl-phenyl)-cyclobutoxy-acetic acid methyl ester (33b) (14 mg, 0.034 mmol, 13%) as a white solid.

¹H NMR (400 MHz, CDCl₃) δ 0.51-0.75 (m, 4H), 1.24-1.38 (m, 1H), 1.44-1.61 (m, 2H), 1.71-1.94 (m, 3H), 1.96-2.05 (m, 3H), 2.32 and 2.33 (s, 3H), 2.72-2.86 (m, 2H), 3.66 and 3.69 (s, 3H), 3.77-3.90 (m, 1H), 4.19-4.28 (m, 2H), 4.89 and 4.94 (s, 1H), 6.77 (dd, 1H, J=7.9 Hz, J=2.1 Hz), 6.82 (d, 1H, J=8.4 Hz), 6.92-7.01 (m, 2H), 7.05 (d, 1H, J=7.9 Hz).

MS m/z ([M+Na]⁺) 429.

Step 3: Preparation of (2-chroman-6-yl-3-cyclopropyl-6-methyl-phenyl)-cyclobutoxy-acetic acid (Example 33)

A mixture of (2-chroman-6-yl-3-cyclopropyl-6-methyl-phenyl)-cyclobutoxy-acetic acid methyl ester (33b) (14 mg, 0.034 mmol) and sodium hydroxide 2M in water (0.5 mL, 1.00 mmol) in tetrahydrofuran (1 mL) was heated at 90° C. for 48 hours. Water (5 mL) was added to the residue and the aqueous layer was acidified with a 1M hydrochloric acid until pH 3 and extracted with ethyl acetate (2×5 mL). The combined organic layers were washed with brine, dried over sodium sulfate and concentrated in vacuo. The residue was purified on preparative TLC (dichloromethane/methanol 90/10) to provide (2-chroman-6-yl-3-cyclopropyl-6-methyl-phenyl)-cyclobutoxy-acetic acid (Example 33) (13 mg, 0.033 mmol, 99%) as a white solid.

¹H NMR (300 MHz, CD₃OD) δ 0.47-0.73 (m, 4H), 1.22-1.40 (m, 1H), 1.42-1.60 (m, 2H), 1.64-1.92 (m, 4H), 1.94-2.08 (m, 2H), 2.33 (bs, 3H), 2.70-2.92 (m, 2H), 3.68-3.90 (m, 1H), 4.14-4.22 (m, 2H), 4.89 (bs, 1H), 6.73-6.80 (m, 2H), 6.90-7.16 (m, 3H).

MS m/z ([M+Na]⁺) 415.
MS m/z ([M−H]⁻) 391.

Example 34

Synthesis of (2-chroman-6-yl-3-cyclopropyl-6-methyl-phenyl)-(2,2-difluoro-ethoxy)-acetic acid

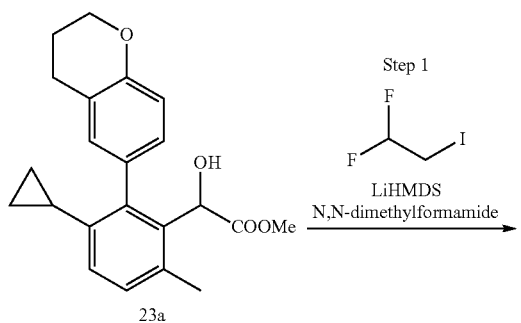

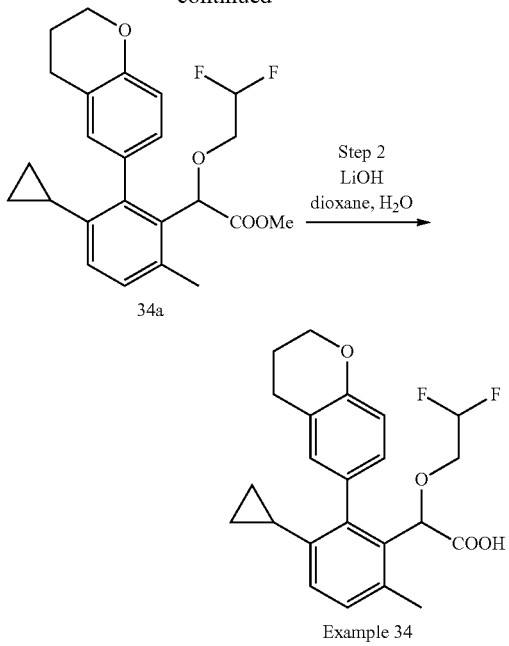

Example 34

Step 1: Preparation of Intermediate (2-chroman-6-yl-3-cyclopropyl-6-methyl-phenyl)-(2,2-difluoro-ethoxy)-acetic acid methyl ester (34a)

Using the procedure described in example 28, step 1, the intermediate (2-chroman-6-yl-3-cyclopropyl-6-methyl-phenyl)-hydroxy-acetic acid methyl ester (23a) (50 mg, 0.142 mmol) is converted, by reaction with 1,1-difluoro-2-iodoethane (153 mg, 0.795 mmol), after purification by preparative TLC (cyclohexane/ethyl acetate 80/20), into (2-chroman-6-yl-3-cyclopropyl-6-methyl-phenyl)-(2,2-difluoro-ethoxy)-acetic acid methyl ester (34a) (5 mg, 0.012 mmol, 8%) as yellow oil.

¹H NMR (300 MHz, CDCl₃) δ 0.51-0.76 (m, 4H), 1.42-1.53 (m, 1H), 2.02-2.09 (m, 2H), 2.29 and 2.30 (s, 3H), 2.74-2.86 (m, 2H), 3.33-3.48 (m, 1H), 3.59-3.82 (m, 4H), 4.19-4.30 (m, 2H), 4.96 and 4.99 (s, 1H), 5.58-6.00 (m, 1H), 6.78-6.85 (m, 2H), 6.91-7.01 (m, 2H), 7.07 (d, 1H, J=7.9 Hz).

MS m/z ([M+Na]⁺) 439

Step 2: Preparation of (2-chroman-6-yl-3-cyclopropyl-6-methyl-phenyl)-(2,2-difluoro-ethoxy)-acetic acid (Example 34)

Using the procedure described in example 1, step 12, the intermediate (2-chroman-6-yl-3-cyclopropyl-6-methyl-phenyl)-(2,2-difluoro-ethoxy)-acetic acid methyl ester (34a) (5 mg, 0.012 mmol) is converted into (2-chroman-6-yl-3-cyclopropyl-6-methyl-phenyl)-(2,2-difluoro-ethoxy)-acetic acid (Example 34) (2 mg, 0.005 mmol, 41%) as white solid.

¹H NMR (300 MHz, CDCl₃) δ 0.52-0.78 (m, 4H), 1.43-1.55 (m, 1H), 1.97-2.10 (m, 2H), 2.29-2.36 (m, 3H), 2.77-2.85 (m, 2H), 3.38-3.61 (m, 2H), 4.19-4.28 (m, 2H), 5.11 and 5.12 (s, 1H), 5.54-5.95 (m, 1H), 6.79-6.85 (m, 2H), 6.88-7.04 (m, 2H), 7.09 (d, 1H, J=8.0 Hz).

MS m/z ([M+Na]⁺) 425.
MS m/z ([M−H]⁻) 401.

Example 35

Synthesis of (2-chroman-6-yl-3-cyclopropyl-6-methyl-phenyl)-(2-fluoro-ethoxy)-acetic acid

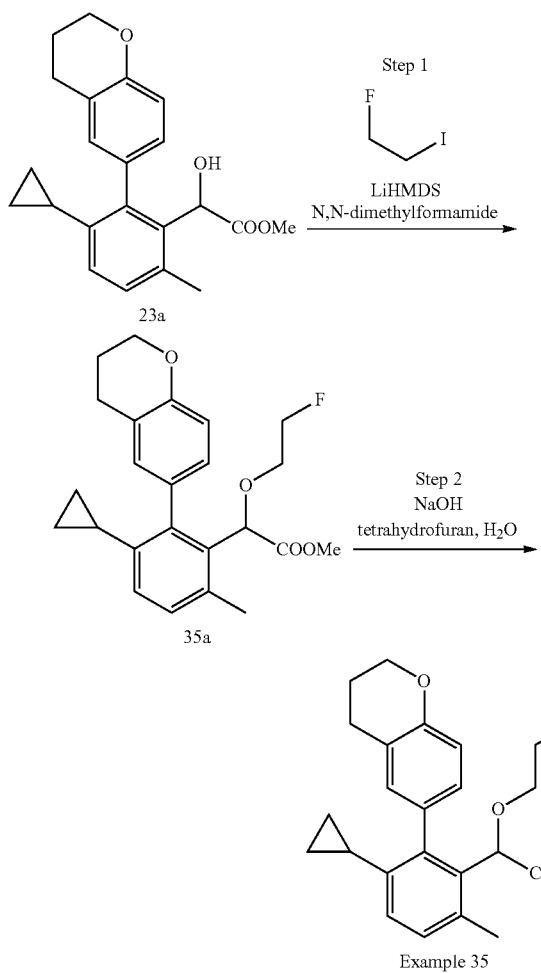

Step 1: Preparation of Intermediate (2-chroman-6-yl-3-cyclopropyl-6-methyl-phenyl)-(2-fluoro-ethoxy)-acetic acid methyl ester (35a)

Using the procedure described in example 28, step 1, the intermediate (2-chroman-6-yl-3-cyclopropyl-6-methyl-phenyl)-hydroxy-acetic acid methyl ester (23a) (50 mg, 0.142 mmol) is converted by reaction with 1-fluoro-2-iodoethane (138 mg, 0.795 mmol), after purification by preparative TLC (cyclohexane/ethyl acetate 80/20) into (2-chroman-6-yl-3-cyclopropyl-6-methyl-phenyl)-(2-fluoro-ethoxy)-acetic acid methyl ester (35a) (34 mg, 0.085 mmol, 60%) as yellow oil.

$^1$H NMR (300 MHz, CDCl$_3$) δ 0.51-0.73 (m, 4H), 1.44-1.54 (m, 1H), 2.00-2.10 (m, 2H), 2.32 (s, 3H), 2.72-2.86 (m, 2H), 3.37-3.84 (m, 5H), 4.20-4.26 (m, 2H), 4.31-4.62 (m, 2H), 4.96 and 5.00 (s, 1H), 6.77-6.84 (m, 2H), 6.88-7.05 (m, 2H), 7.07 (d, 1H, J=7.9 Hz).

MS m/z ([M+Na]$^+$) 421.

Step 2: Preparation of (2-chroman-6-yl-3-cyclopropyl-6-methyl-phenyl)-(2-fluoro-ethoxy)-acetic acid (Example 35)

Using the procedure described in example 33, step 3, the intermediate (2-chroman-6-yl-3-cyclopropyl-6-methyl-phenyl)-(2-fluoro-ethoxy)-acetic acid methyl ester (35a) (34 mg, 0.085 mmol) is converted into (2-chroman-6-yl-3-cyclopropyl-6-methyl-phenyl)-(2-fluoro-ethoxy)-acetic acid (Example 35) (20 mg, 0.052 mmol, 61%) as white solid.

$^1$H NMR (300 MHz, CDCl$_3$) δ 0.52-0.79 (m, 4H), 1.42-1.53 (m, 1H), 2.00-2.08 (m, 2H), 2.34 (s, 3H), 2.73-2.85 (m, 2H), 3.41-3.70 (m, 2H), 4.19-4.26 (m, 2H), 4.31-4.38 (m, 1H), 4.47-4.54 (m, 1H), 5.08 and 5.09 (s, 1H), 6.74-6.86 (m, 2H), 6.87-6.94 (m, 1H), 6.98-7.12 (m, 2H).

MS m/z ([M+Na]$^+$) 407.

MS m/z ([M−H]$^-$) 383.

Example 36

Synthesis of (2-chroman-6-yl-3-cyclopropyl-6-methyl-phenyl)-isopropoxy-acetic acid

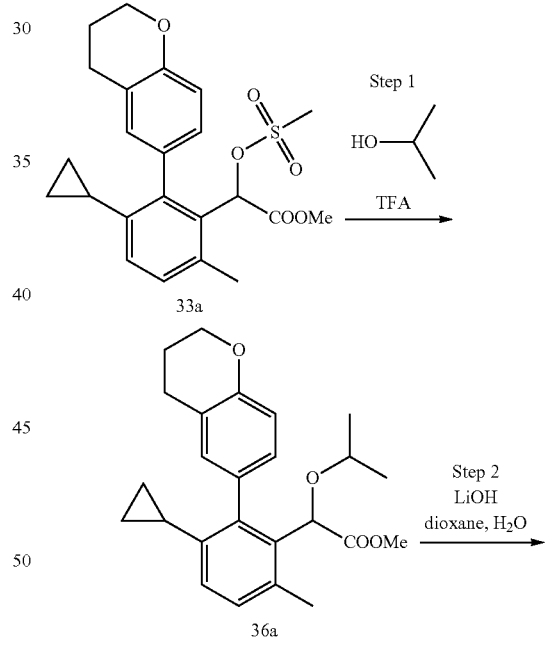

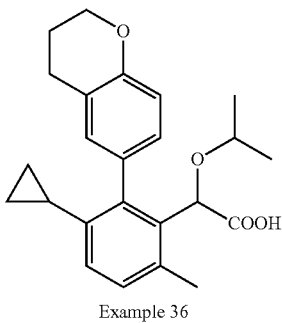

Step 1: Preparation of Intermediate (2-chroman-6-yl-3-cyclopropyl-6-methyl-phenyl)-isopropoxy-acetic acid methyl ester (36a)

Using the procedure described in example 33, step 2, the intermediate (2-chroman-6-yl-3-cyclopropyl-6-methyl-phenyl)-methanesulfonyloxy-acetic acid methyl ester (36a) (102 mg, 0.237 mmol) is converted by reaction with isopropanol (0.5 mL), after purification by preparative TLC (cyclohexane/dichloromethane 50/50) into (2-chroman-6-yl-3-cyclopropyl-6-methyl-phenyl)-isopropoxy-acetic acid methyl ester (36a) (20 mg, 0.051 mmol, 21%).

$^1$H NMR (300 MHz, CDCl$_3$) δ 0.49-0.75 (m, 4H), 0.95 (dd, 3H, J=6.1 Hz, J=2.8 Hz), 1.03 (dd, 3H, J=9.7 Hz, J=6.1 Hz), 1.42-1.53 (m, 1H), 1.98-2.13 (m, 2H), 2.35 (s, 3H), 2.67-2.88 (m, 2H), 3.43-3.59 (m, 1H), 3.66 and 3.68 (s, 3H), 4.21-4.27 (m, 2H), 5.01 and 5.05 (s, 1H), 6.76 (dd, J=7.9 Hz, 1H), 6.82 (t, J=8.5 Hz, 1H), 6.90-7.03 (m, 2H), 7.05 (d, J=8.0 Hz, 1H).

MS m/z ([M+Na]$^+$) 417.

Step 2: Preparation of (2-chroman-6-yl-3-cyclopropyl-6-methyl-phenyl)-isopropoxy-acetic acid (Example 36)

Using the procedure described in example 1, step 12, the (2-chroman-6-yl-3-cyclopropyl-6-methyl-phenyl)-isopropoxy-acetic acid methyl ester (36a) (20 mg, 0.051 mmol) is converted after purification by preparative TLC (dichloromethane/methanol 90/10) into (2-chroman-6-yl-3-cyclopropyl-6-methyl-phenyl)-isopropoxy-acetic acid (Example 36) (12 mg, 0.031 mmol, 61%) as a white solid.

$^1$H NMR (300 MHz, CD$_3$OD) δ 0.50-0.75 (m, 4H), 0.80-1.00 (m, 6H), 1.42-1.53 (m, 1H), 1.95-2.10 (m, 2H), 2.35 (bs, 3H), 2.70-2.88 (m, 2H), 3.40-3.70 (m, 1H), 4.13-4.25 (m, 2H), 5.00 (bs, 1H), 6.74-6.78 (m, 2H), 6.90-6.94 (m, 1H), 7.02-7.15 (m, 2H).

MS m/z ([M+Na]$^+$) 403.
MS m/z ([M−H]$^−$) 379.

Example 37

Synthesis of cyclopropoxy-[3-cyclopropyl-2-(8-fluoro-5-methyl-chroman-6-yl)-6-methyl-phenyl]-acetic acid

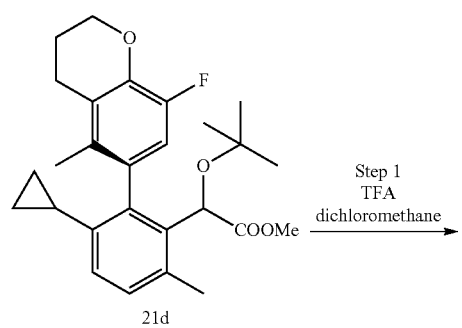

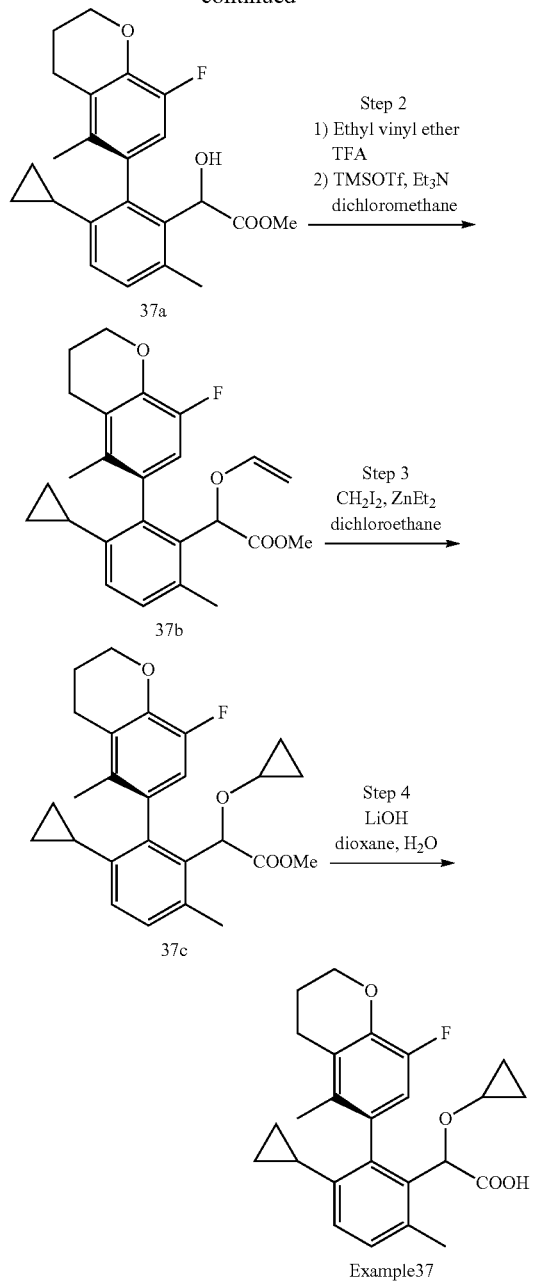

Example 37

Step 1: Preparation of Intermediate methyl[3-cyclopropyl-2-(8-fluoro-5-methyl-chroman-6-yl)-6-methyl-phenyl]-hydroxy-acetate (37a)

Using the procedure described in example 23, step 1, methyl tert-butoxy-[3-cyclopropyl-2-(8-fluoro-5-methyl-chroman-6-yl)-6-methyl-phenyl]-acetate (21d) (290 mg, 0.66 mmol) is converted into methyl[3-cyclopropyl-2-(8-fluoro-5-methyl-chroman-6-yl)-6-methyl-phenyl]-hydroxy-acetate (37a) (230 mg, 0.60 mmol, 90%) which was used without further purification.

$^1$H NMR (400 MHz, CDCl$_3$) δ 0.49-0.74 (m, 4H), 1.27-1.36 (m, 1H), 1.86 (s, 3H), 2.08-2.15 (m, 2H), 2.28 (s, 3H), 2.70 (t, J=6.6 Hz, 2H), 2.94 (d, J=2.8 Hz, 1H), 3.70 (s, 3H), 4.23-4.28 (m, 2H), 5.04 (d, J=2.8 Hz, 1H), 6.75 (d, J=11.3 Hz, 1H), 6.76 (d, J=8.0 Hz, 1H), 7.09 (d, J=8.0 Hz, 1H).

Step 2: Preparation of Intermediate methyl[3-cyclopropyl-2-(8-fluoro-5-methyl-chroman-6-yl)-6-methyl-phenyl]-vinyloxy-acetate (37b)

Using the procedure described in example 23, step 2, the intermediate methyl[3-cyclopropyl-2-(8-fluoro-5-methyl-chroman-6-yl)-6-methyl-phenyl]-hydroxy-acetate (37a) (100 mg, 0.26 mmol) is converted, after purification by preparative TLC (cyclohexane/ethyl acetate 70/30) into methyl[3-cyclopropyl-2-(8-fluoro-5-methyl-chroman-6-yl)-6-methyl-phenyl]-vinyloxy-acetate (37b) (51 mg, 0.12 mmol, 48%).

$^1$H NMR (400 MHz, CDCl$_3$) δ 0.50-0.75 (m, 4H), 1.29-1.38 (m, 1H), 1.88 (s, 3H), 2.08-2.18 (m, 2H), 2.32 (s, 3H), 2.66-2.77 (m, 2H), 3.68 (s, 3H), 4.04 (d, J=6.4 Hz, 1H), 4.22-4.30 (m, 3H), 5.14 (s, 1H), 6.14 (dd, J=6.4 Hz, J=13.9 Hz, 1H), 6.68 (d, J=11.3 Hz, 1H), 6.78 (d, J=8.0 Hz, 1H), 7.11 (d, J=8.0 Hz, 1H).

MS m/z ([M+Na]$^+$) 433.

Step 3: Preparation of Intermediate methyl cyclopropoxy-[3-cyclopropyl-2-(8-fluoro-5-methyl-chroman-6-yl)-6-methyl-phenyl]-acetate (37c)

Using the procedure described in example 23, step 3, the intermediate methyl[3-cyclopropyl-2-(8-fluoro-5-methyl-chroman-6-yl)-6-methyl-phenyl]-vinyloxy-acetate (37b) (50 mg, 0.12 mmol) is converted, after purification by preparative TLC (cyclohexane/ethyl acetate 80/20) to methyl cyclopropoxy-[3-cyclopropyl-2-(8-fluoro-5-methyl-chroman-6-yl)-6-methyl-phenyl]-acetate (37c) (44 mg, 0.10 mmol, 85%).

$^1$H NMR (400 MHz, CDCl$_3$) δ 0.29-0.35 (m, 1H), 0.38-0.50 (m, 2H), 0.50-0.73 (m, 5H), 1.27-1.36 (m, 1H), 1.87 (s, 3H), 2.08-2.19 (m, 2H), 2.32 (s, 3H), 2.65-2.78 (m, 2H), 3.41-3.48 (m, 1H), 3.64 (s, 3H), 4.24-4.31 (m, 2H), 4.90 (s, 1H), 6.70-6.77 (m, 2H), 7.08 (d, J=8.0 Hz, 1H).

MS m/z ([M+Na]$^+$) 447.

Step 6: Preparation of cyclopropoxy-[3-cyclopropyl-2-(8-fluoro-5-methyl-chroman-6-yl)-6-methyl-phenyl]-acetic acid (Example 37)

Using the procedure described in example 1, step 12, the intermediate methyl cyclopropoxy-[3-cyclopropyl-2-(8-fluoro-5-methyl-chroman-6-yl)-6-methyl-phenyl]-acetate (37c) (44 mg, 0.10 mmol) is converted into cyclopropoxy-[3-cyclopropyl-2-(8-fluoro-5-methyl-chroman-6-yl)-6-methyl-phenyl]-acetic acid (Example 37) (32 mg, 0.078 mmol, 75%).

$^1$H NMR (400 MHz, CDCl$_3$) δ 0.37-0.61 (m, 6H), 0.64-0.73 (m, 2H), 1.29-1.39 (m, 1H), 1.89 (s, 3H), 2.08-2.17 (m, 2H), 2.31 (s, 3H), 2.64-2.76 (m, 2H), 3.27-3.34 (m, 1H), 4.22-4.31 (m, 2H), 4.95 (s, 1H), 6.75 (d, J=11.4 Hz, 1H), 6.79 (d, J=8.0 Hz, 1H), 7.10 (d, J=8.0 Hz, 1H).

MS m/z ([M+Na]$^+$) 433.

MS m/z ([M−H]$^−$) 409.

Example 38

Synthesis of (S)-tert-butoxy-[3-cyclopropyl-6-methyl-2-(5-methyl-chroman-6-yl)-phenyl]-acetic acid

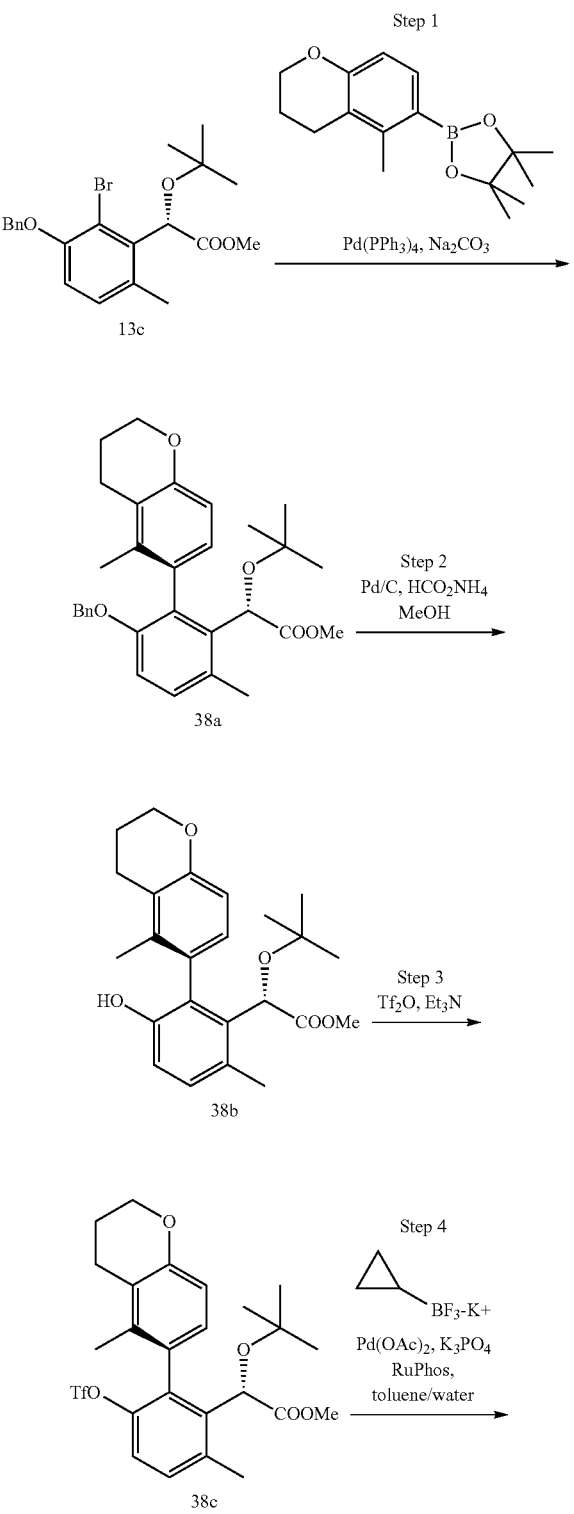

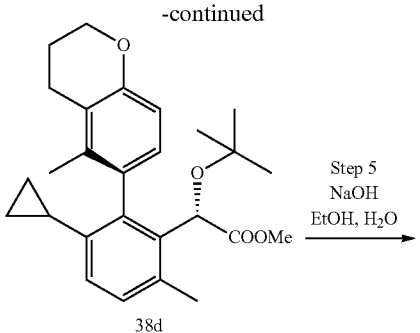

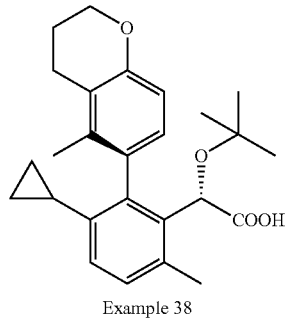

Example 38

Step 1: Preparation of Intermediate methyl (S)-[3-benzyloxy-6-methyl-2-(5-methyl-chroman-6-yl)-phenyl]-tert-butoxy-acetate (38a)

Using the procedure described in example 1, step 7, the intermediate methyl (S)-2-(3-benzyloxy-2-bromo-6-methyl-phenyl)-2-(tert-butoxy)-acetate (13c) (3.00 g, 7.12 mmol) is converted by reaction with 4,4,5,5-tetramethyl-2-(5-methyl-3,4-dihydro-2H-1-benzopyran-6-yl)-1,3,2-dioxaborolane (2.34 g, 8.54 mmol), after purification by flash chromatography on silica gel (cyclohexane/ethyl acetate from 100/0 to 95/5) into methyl (S)-[3-benzyloxy-6-methyl-2-(5-methyl-chroman-6-yl)-phenyl]-tert-butoxy-acetate (38a) (3.13 g, 6.98 mmol, 90%).

$^1$H NMR (400 MHz, CDCl$_3$) δ 1.12 (s, 9H), 1.87 (s, 3H), 2.06-2.18 (m, 2H), 2.46 (s, 3H), 2.65-2.74 (m, 2H), 3.57 (s, 3H), 4.18-4.25 (m, 2H), 4.88-4.97 (m, 2H), 5.10 (s, 1H), 6.72 (d, J=8.3 Hz, 1H), 6.81 (d, J=8.3 Hz, 1H), 6.89 (d, J=8.3 Hz, 1H), 7.01-7.09 (m, 3H), 7.18-7.25 (m, 3H).

MS m/z ([M+Na]$^+$) 511.

Step 2: Preparation of Intermediate methyl (S)-tert-butoxy-[3-hydroxy-6-methyl-2-(5-methyl-chroman-6-yl)-phenyl]-acetate (38b)

Using the procedure described in example 15, step 2, the intermediate methyl (S)-[3-benzyloxy-6-methyl-2-(5-methyl-chroman-6-yl)-phenyl]-tert-butoxy-acetate (38a) (3.13 g, 6.98 mmol) is converted, after purification by flash chromatography on silica gel (cyclohexane/ethyl acetate from 100/0 to 90/10) into methyl (S)-tert-butoxy-[3-hydroxy-6-methyl-2-(5-methyl-chroman-6-yl)-phenyl]-acetate (38b) (2.01 g, 5.04 mmol, 78%).

$^1$H NMR (400 MHz, CDCl$_3$) δ 1.09 (s, 9H), 1.91 (s, 3H), 2.06-2.17 (m, 2H), 2.43 (s, 3H), 2.67-2.75 (m, 2H), 3.58 (s, 3H), 4.18-4.24 (m, 2H), 4.40 (s, 1H), 4.93 (s, 1H), 6.77 (d, J=8.3 Hz, 1H), 6.83 (d, J=8.3 Hz, 1H), 6.93 (d, J=8.3 Hz, 1H), 7.06 (d, J=8.3 Hz, 1H).

MS m/z ([M-H]$^-$) 398.

Step 3: Preparation of Intermediate methyl (S)-tert-butoxy-[6-methyl-2-(5-methyl-chroman-6-yl)-3-trifluoromethanesulfonyloxy-phenyl]-acetate (38c)

Using the procedure described in example 1, step 10, the intermediate methyl (S)-tert-butoxy-[3-hydroxy-6-methyl-2-(5-methyl-chroman-6-yl)-phenyl]-acetate (38b) (2.01 g, 5.04 mmol) is converted into methyl (S)-tert-butoxy-[6-methyl-2-(5-methyl-chroman-6-yl)-3-trifluoromethanesulfonyloxy-phenyl]-acetate (38c) (2.68 g, 5.04 mmol, 100%), which was used without further purification.

MS m/z ([M-H]$^-$) 529.

Step 4: Preparation of Intermediate methyl (S)-tert-butoxy-[3-cyclopropyl-6-methyl-2-(5-methyl-chroman-6-yl)-phenyl]-acetate (38d)

Using the procedure described in example 21, step 4, the intermediate methyl (S)-tert-butoxy-[6-methyl-2-(5-methyl-chroman-6-yl)-3-trifluoromethanesulfonyloxy-phenyl]-acetate (38c) (2.68 g, 5.04 mmol), is converted, after purification by flash chromatography on silica gel (cyclohexane/ethyl acetate from 100/0 to 80/20) to methyl (S)-tert-butoxy-[3-cyclopropyl-6-methyl-2-(5-methyl-chroman-6-yl)-phenyl]-acetate (38d) (1.14 g, 2.69 mmol, 53%).

$^1$H NMR (400 MHz, CDCl$_3$) δ 0.48-0.69 (m, 4H), 1.08 (s, 9H), 1.23-1.33 (m, 1H), 1.86 (s, 3H), 2.05-2.16 (m, 2H), 2.47 (s, 3H), 2.63-2.76 (m, 2H), 3.57 (s, 3H), 4.16-4.24 (m, 2H), 5.03 (s, 1H), 6.70 (d, J=8.0 Hz, 2H), 6.89 (d, J=8.3 Hz, 1H), 7.06 (d, J=8.0 Hz, 1H).

MS m/z ([M+Na]$^+$) 445.

Step 5: Preparation of (S)-tert-butoxy-[3-cyclopropyl-6-methyl-2-(5-methyl-chroman-6-yl)-phenyl]-acetic acid (Example 38)

To a solution of methyl (S)-tert-butoxy-[3-cyclopropyl-6-methyl-2-(5-methyl-chroman-6-yl)-phenyl]-acetate (38d) (285 mg, 0.67 mmol) in ethanol (2.8 mL) was added a 2M sodium hydroxide solution (1.35 mL, 2.70 mmol). The mixture was heated at 70° C. for 16 hours. Ethanol was evaporated in vacuo. Water (5 mL) was added. The residual ethanol was removed in vacuo. The aqueous resulting solution was extracted with ethyl acetate (2×5 mL). The organic layer was washed with 1M hydrochloric acid (10 mL), dried over sodium sulfate and concentrated in vacuo to provide (S)-tert-butoxy-[3-cyclopropyl-6-methyl-2-(5-methyl-chroman-6-yl)-phenyl]-acetic acid (Example 38) (241 mg, 0.59 mmol, 87%).

$^1$H NMR (400 MHz, CDCl$_3$) δ 0.48-0.59 (m, 2H), 0.59-0.70 (m, 2H), 1.11 (s, 9H), 1.27-1.36 (m, 1H), 1.94 (s, 3H), 2.04-2.12 (m, 2H), 2.38 (s, 3H), 2.62-2.72 (m, 2H), 4.15-4.20 (m, 2H), 5.11 (s, 1H), 6.69 (d, J=8.3 Hz, 1H), 6.73 (d, J=8.0 Hz, 1H), 6.91 (d, J=8.3 Hz, 1H), 7.06 (d, J=7.9 Hz, 1H).

MS m/z ([M+Na]$^+$) 431.

MS m/z ([M-H]$^-$) 407.

Example 39

Synthesis of (2-chroman-6-yl-3-cyclopropyl-6-methyl-phenyl)-(1-methyl-cyclopropoxy)-acetic acid

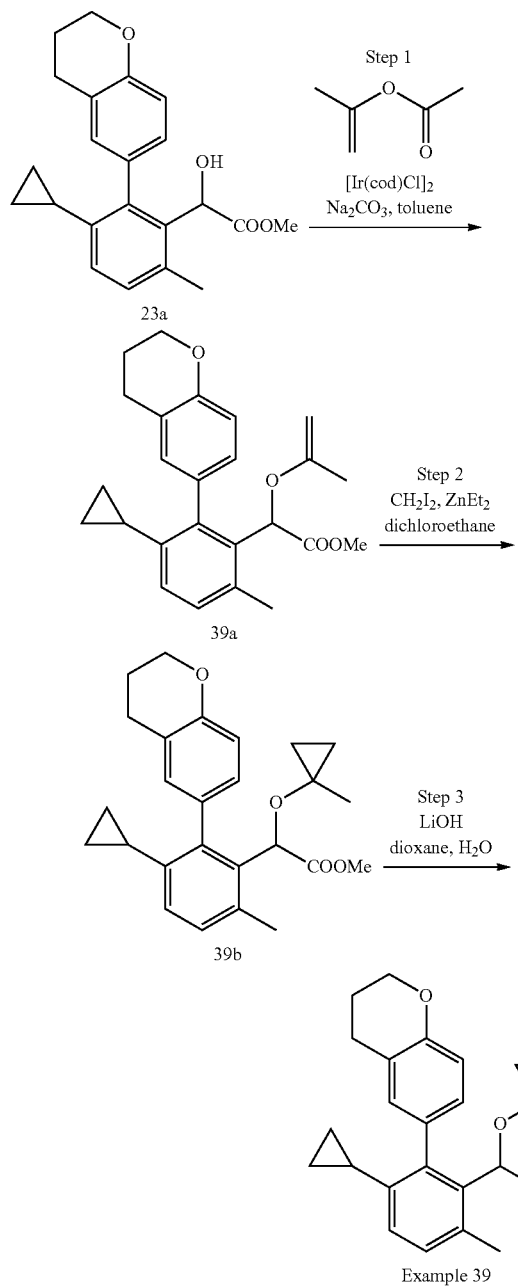

Step 1: Preparation of Intermediate (2-chroman-6-yl-3-cyclopropyl-6-methyl-phenyl)-isopropenyloxy-acetic acid methyl ester (39a)

To a degassed mixture of (2-chroman-6-yl-3-cyclopropyl-6-methyl-phenyl)-hydroxy-acetic acid methyl ester (23a) (86 mg, 0.244 mmol) and sodium carbonate (15.5 mg, 0.146 mmol) in toluene (0.5 mL) were added isopropenyl acetate (54 μL, 0.488 mmol) and bis(1,5-cyclooctadiene)diiridium (I) dichloride (16 mg, 0.024 mmol). The mixture was heated under microwaves at 120° C. for 42 hours. The mixture was concentrated in vacuo. The residue was purified by flash chromatography on silica gel (cyclohexane/ethyl acetate/triethylamine 95/5/0.5) to provide (2-chroman-6-yl-3-cyclopropyl-6-methyl-phenyl)-isopropenyloxy-acetic acid methyl ester (39a) (25 mg, 0.049 mmol, 20%) as a colorless oil containing 24% of starting material (23a). This oil will be used for the next step without further purification.

Desired product MS m/z ([M+Na]$^+$) 415.

Step 2: Preparation of Intermediate (2-chroman-6-yl-3-cyclopropyl-6-methyl-phenyl)-(1-methyl-cyclopropoxy)-acetic acid methyl ester (39b)

Using the procedure described in example 23, step 3, the intermediate (2-Chroman-6-yl-3-cyclopropyl-6-methyl-phenyl)-isopropenyloxy-acetic acid methyl ester (39a) (25 mg, 0.064 mmol) is converted, after purification by preparative TLC (cyclohexane/AcOEt 80/20), into (2-chroman-6-yl-3-cyclopropyl-6-methyl-phenyl)-(1-methyl-cyclopropoxy)-acetic acid methyl ester (39b) (10 mg, 0.024 mmol, 38%).

$^1$H NMR (400 MHz, CDCl$_3$) δ 0.13-0.30 (m, 4H), 0.47-0.79 (m, 6H), 1.09 and 1.10 (s, 3H), 1.48-1.58 (m, 1H), 2.02-2.15 (m, 2H), 2.31 (s, 3H), 2.74-2.92 (m, 2H), 3.70 and 3.73 (s, 3H), 4.23-4.34 (m, 2H), 5.22 and 5.25 (s, 1H), 6.80 (dd, J=7.9 Hz, J=2.7 Hz, 1H), 6.87 (t, J=8.1 Hz, 1H), 7.02-7.08 (m, 3H).

MS m/z ([M+Na]$^+$) 429.

Step 3: Preparation of (2-chroman-6-yl-3-cyclopropyl-6-methyl-phenyl)-(1-methyl-cyclopropoxy)-acetic acid (Example 39)

Using the procedure described in example 1, step 12, the (2-chroman-6-yl-3-cyclopropyl-6-methyl-phenyl)-(1-methyl-cyclopropoxy)-acetic acid methyl ester (39b) (10 mg, 0.024 mmol) is converted into (2-chroman-6-yl-3-cyclopropyl-6-methyl-phenyl)-(1-methyl-cyclopropoxy)-acetic acid (Example 39) (5 mg, 0.012 mmol, 50%) as a white solid.

$^1$H NMR (400 MHz, CDCl$_3$) δ 0.19-0.31 (m, 2H), 0.44-0.77 (m, 6H), 1.05 and 1.06 (s, 3H), 1.46-1.55 (m, 1H), 2.00-2.10 (m, 2H), 2.26 and 2.28 (s, 3H), 2.70-2.87 (m, 2H), 4.19-4.28 (m, 2H), 5.25 and 5.27 (s, 1H), 6.77-6.85 (m, 2H), 6.96-7.10 (m, 3H).

MS m/z ([M+Na]$^+$) 415.
MS m/z ([M−H]$^−$) 391.

Example 40

Synthesis of (S)-cyclopropoxy-[3-cyclopropyl-6-methyl-2-(5-methyl-chroman-6-yl)-phenyl]-acetic acid

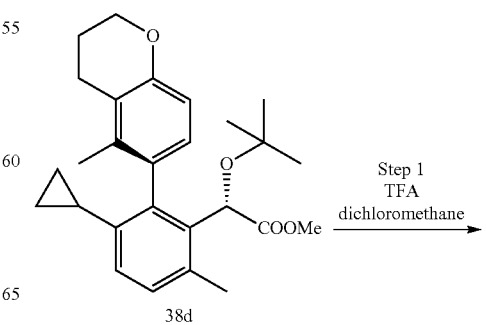

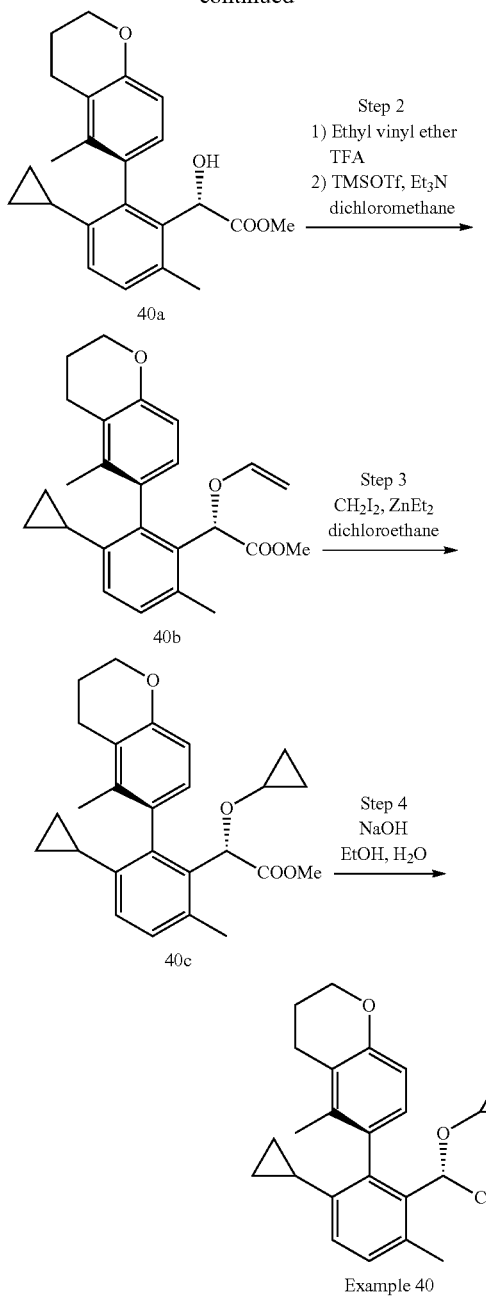

2.69 (t, J=6.6 Hz, 2H), 2.93 (bs, 1H), 3.69 (s, 3H), 4.15-4.21 (m, 2H), 5.06 (s, 1H), 6.70-6.77 (m, 2H), 6.88 (d, J=8.3 Hz, 1H), 7.08 (d, J=8.0 Hz, 1H).

Step 2: Preparation of methyl (S)-[3-cyclopropyl-6-methyl-2-(5-methyl-chroman-6-yl)-phenyl]-vinyloxy-acetate (40b)

Using the procedure described in example 23, step 2, the intermediate methyl (S)-[3-cyclopropyl-6-methyl-2-(5-methyl-chroman-6-yl)-phenyl]-hydroxy-acetate (40a) (737 mg, 2.01 mmol) is converted, after purification by preparative TLC (cyclohexane/ethyl acetate 80/20) into methyl (S)-[3-cyclopropyl-6-methyl-2-(5-methyl-chroman-6-yl)-phenyl]-vinyloxy-acetate (40b) (417 mg, 1.06 mmol, 53%).

$^1$H NMR (300 MHz, CDCl$_3$) δ 0.52-0.74 (m, 4H), 1.29-1.40 (m, 1H), 1.92 (s, 3H), 2.06-2.13 (m, 2H), 2.32 (s, 3H), 2.70 (t, J=6.6 Hz, 2H), 3.67 (s, 3H), 3.99 (dd, J=1.9 Hz, J=6.4 Hz, 1H), 4.17-4.22 (m, 2H), 4.27 (dd, J=1.9 Hz, J=13.9 Hz, 1H), 5.17 (s, 1H), 6.12 (dd, J=6.4 Hz, J=13.9 Hz, 1H), 6.72 (d, J=8.3 Hz, 1H), 6.77 (d, J=8.0 Hz, 1H), 6.82 (d, J=8.3 Hz, 1H), 7.10 (d, J=8.0 Hz, 1H).

MS m/z ([M+Na]$^+$) 415.

Step 3: Preparation of methyl (S)-cyclopropoxy-[3-cyclopropyl-6-methyl-2-(5-methyl-chroman-6-yl)-phenyl]-acetate (40c)

Using the procedure described in example 23, step 3, the intermediate methyl (S)-[3-cyclopropyl-6-methyl-2-(5-methyl-chroman-6-yl)-phenyl]-vinyloxy-acetate (40b) (417 mg, 1.06 mmol) is converted, after purification by preparative TLC (cyclohexane/ethyl acetate 80/20) into methyl (S)-cyclopropoxy-[3-cyclopropyl-6-methyl-2-(5-methyl-chroman-6-yl)-phenyl]-acetate (40c) (238 mg, 0.59 mmol, 55%).

$^1$H NMR (300 MHz, CDCl$_3$) δ 0.21-0.32 (m, 1H), 0.32-0.48 (m, 2H), 0.51-0.73 (m, 5H), 1.27-1.38 (m, 1H), 1.91 (s, 3H), 2.06-2.16 (m, 2H), 2.32 (s, 3H), 2.66-2.75 (m, 2H), 3.43-3.51 (m, 1H), 3.64 (s, 3H), 4.16-4.24 (m, 2H), 4.93 (s, 1H), 6.69-6.76 (m, 2H), 6.86 (d, J=8.3 Hz, 1H), 7.06 (d, J=8.0 Hz, 1H).

MS m/z ([M+Na]$^+$) 429.

Step 4: Preparation of (S)-cyclopropoxy-[3-cyclopropyl-6-methyl-2-(5-methyl-chroman-6-yl)-phenyl]-acetic acid (Example 40)

Using the procedure described in example 38, step 5, the intermediate methyl (S)-cyclopropoxy-[3-cyclopropyl-6-methyl-2-(5-methyl-chroman-6-yl)-phenyl]-acetate (40c) (238 mg, 0.59 mmol) is converted to (S)-cyclopropoxy-[3-cyclopropyl-6-methyl-2-(5-methyl-chroman-6-yl)-phenyl]-acetic acid (Example 40) (180 mg, 0.46 mmol, 78%).

$^1$H NMR (300 MHz, CDCl$_3$) δ 0.32-0.73 (m, 8H), 1.30-1.41 (m, 1H), 1.92 (s, 3H), 2.03-2.15 (m, 2H), 2.31 (s, 3H), 2.64-2.73 (m, 2H), 3.27-3.36 (m, 1H), 4.15-4.22 (m, 2H), 5.00 (s, 1H), 6.69 (d, J=8.3 Hz, 1H), 6.78 (d, J=8.0 Hz, 1H), 6.88 (d, J=8.3 Hz, 1H), 7.09 (d, J=8.0 Hz, 1H).

Step 1: Preparation of methyl (S)-[3-cyclopropyl-6-methyl-2-(5-methyl-chroman-6-yl)-phenyl]-hydroxy-acetate (40a)

Using the procedure described in example 23, step 1, methyl (S)-tert-butoxy-[3-cyclopropyl-6-methyl-2-(5-methyl-chroman-6-yl)-phenyl]-acetate (38d) (850 mg, 2.01 mmol) is converted into methyl (S)-[3-cyclopropyl-6-methyl-2-(5-methyl-chroman-6-yl)-phenyl]-hydroxy-acetate (40a) (737 mg, 2.01 mmol, 97%) which was used without further purification.

$^1$H NMR (300 MHz, CDCl$_3$) δ 0.48-0.75 (m, 4H), 1.28-1.40 (m, 1H), 1.91 (s, 3H), 2.03-2.14 (m, 2H), 2.28 (s, 3H),

MS m/z ([M+Na]⁺) 415.
MS m/z ([M–H]⁻) 391.

Example 41

Synthesis of (S)-tert-butoxy-[3-cyclopropyl-2-(8-fluoro-5-methyl-chroman-6-yl)-6-methyl-phenyl]-acetic acid

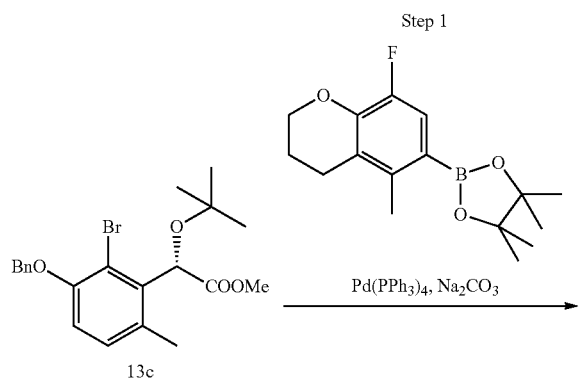

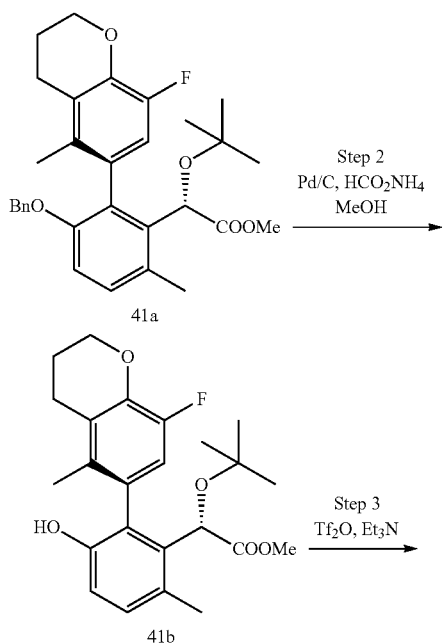

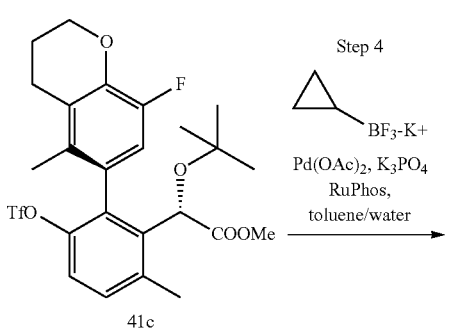

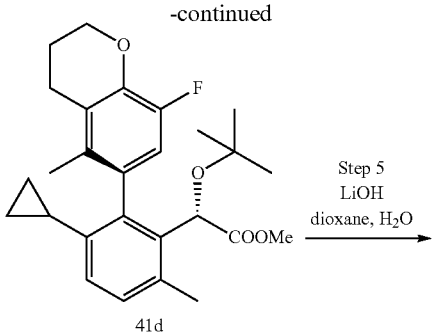

Step 1: Preparation of Intermediate (S)-[3-benzyloxy-2-(8-fluoro-5-methyl-chroman-6-yl)-6-methyl-phenyl]-tert-butoxy-acetic acid methyl ester (41a)

Using the procedure described in example 1, step 7, the intermediate (S)-methyl 2-(3-benzyloxy-2-bromo-6-methyl-phenyl)-2-(tert-butoxy)-acetate (13c) (3.32 g, 7.89 mmol), in reaction with 2-(8-fluoro-3,4-dihydro-2H-1-benzopyran-6-yl)-4,4,5,5-tetramethyl-1,3,2-dioxaborolane (2.76 g, 9.46 mmol), is converted, after purification by chromatography on silica gel (cyclohexane/ethyl acetate 80/20), into (S)-[3-benzyloxy-2-(8-fluoro-5-methyl-chroman-6-yl)-6-methyl-phenyl]-tert-butoxy-acetic acid methyl ester (41a) (1.45 g, 2.86 mmol, 36%).

¹H NMR (300 MHz, CDCl₃) δ 1.12 (s, 9H), 1.83 (s, 3H), 2.07-2.20 (m, 2H), 2.45 (s, 3H), 2.64-2.76 (m, 2H), 3.57 (s, 3H), 4.27-4.31 (m, 2H), 4.94 (m, 2H), 5.05 (s, 1H), 6.72 (d, J=11.7 Hz, 1H), 6.81 (d, J=8.4 Hz, 1H), 7.04-7.09 (m, 3H), 7.22-7.27 (m, 3H).

MS m/z ([M+Na]⁺) 529.

Step 2: Preparation of Intermediate (S)-tert-butoxy-[2-(8-fluoro-5-methyl-chroman-6-yl)-3-hydroxy-6-methyl-phenyl]-acetic acid methyl ester (41b)

Using the procedure described in example 15, step 2, the intermediate (S)-3-benzyloxy-2-(8-fluoro-5-methyl-chroman-6-yl)-6-methyl-phenyl]-tert-butoxy-acetic acid methyl ester (41a) (3.19 g, 6.29 mmol) is converted, after purification by chromatography on silica gel (cyclohexane/ethyl acetate 70/30) into (S)-tert-butoxy-[2-(8-fluoro-5-methyl-chroman-6-yl)-3-hydroxy-6-methyl-phenyl]-acetic acid methyl ester (41a) (2.61 g, 6.27 mmol, 100%).

¹H NMR (300 MHz, CDCl₃) δ 1.10 (s, 9H), 1.88 (s, 3H), 2.08-2.20 (m, 2H), 2.43 (s, 3H), 2.68-2.77 (m, 2H), 3.58 (s, 3H), 4.25-4.32 (m, 2H), 4.38 (s, 1H), 4.92 (s, 1H), 6.77 (d,

J=11.2 Hz, 1H), 6.83 (d, J=8.3 Hz, 1H), 7.07 (d, J=8.3 Hz, 1H).

MS m/z ([M–H]⁻) 415.

Step 3: Preparation of Intermediate (S)-tert-butoxy-[2-(8-fluoro-5-methyl-chroman-6-yl)-6-methyl-3-trifluoromethanesulfonyloxy-phenyl]-acetic acid methyl ester (41c)

Using the procedure described in example 1, step 10, the intermediate (S)-tert-butoxy-[2-(8-fluoro-5-methyl-chroman-6-yl)-3-hydroxy-6-methyl-phenyl]-acetic acid methyl ester (41b) (2.61 g, 6.27 mmol) is converted into (S)-tert-butoxy-[2-(8-fluoro-5-methyl-chroman-6-yl)-6-methyl-3-trifluoromethanesulfonyloxy-phenyl]-acetic acid methyl ester (41c) (3.26 g, 5.94 mmol, 95%), which was used without further purification.

$^1$H NMR (400 MHz, CDCl$_3$) δ 1.11 (s, 9H), 1.81 (s, 3H), 2.09-2.17 (m, 2H), 2.53 (s, 3H), 2.66-2.73 (m, 2H), 3.59 (s, 3H), 4.24-4.31 (m, 2H), 5.04 (s, 1H), 6.74 (d, J=11.2 Hz, 1H), 7.17 (d, J=8.5 Hz, 1H), 7.23 (d, J=8.5 Hz, 1H).

MS m/z ([M–H]⁻) 547.

Step 4: Preparation of Intermediate (S)-tert-butoxy-[3-cyclopropyl-2-(8-fluoro-5-methyl-chroman-6-yl)-6-methyl-phenyl]-acetic acid methyl ester (41d)

Using the procedure described in example 21, step 4, the intermediate (S)-tert-butoxy-[2-(8-fluoro-5-methyl-chroman-6-yl)-6-methyl-3-trifluoromethanesulfonyloxy-phenyl]-acetic acid methyl ester (41c) (3.26 g, 5.94 mmol) is converted, after purification by chromatography on silica gel (cyclohexane/ethyl acetate 95/5) into (S)-tert-butoxy-[3-cyclopropyl-2-(8-fluoro-5-methyl-chroman-6-yl)-6-methyl-phenyl]-acetic acid methyl ester (41d) (2.38 g, 5.41 mmol, 91%).

$^1$H NMR (300 MHz, CDCl$_3$) δ 0.46-0.58 (m, 2H), 0.58-0.71 (m, 2H), 1.10 (s, 9H), 1.19-1.32 (m, 1H), 1.82 (s, 3H), 2.08-2.19 (m, 2H), 2.46 (s, 3H), 2.66-2.76 (m, 2H), 3.57 (s, 3H), 4.24-4.31 (m, 2H), 4.99 (s, 1H), 6.71 (d, J=7.8 Hz, 1H), 6.74 (d, J=10.3 Hz, 1H), 7.07 (d, J=7.8 Hz, 1H).

MS m/z ([M+Na]⁺) 463.

Step 5: Preparation of (S)-tert-butoxy-[3-cyclopropyl-2-(8-fluoro-5-methyl-chroman-6-yl)-6-methyl-phenyl]-acetic acid (Example 41)

Using the procedure described in example 1, step 12, the intermediate (S)-tert-butoxy-[3-cyclopropyl-2-(8-fluoro-5-methyl-chroman-6-yl)-6-methyl-phenyl]-acetic acid methyl ester (41d) (315 mg, 0.72 mmol) is converted to (S)-tert-butoxy-[3-cyclopropyl-2-(8-fluoro-5-methyl-chroman-6-yl)-6-methyl-phenyl]-acetic acid (Example 41) (204 mg, 0.48 mmol, 67%).

$^1$H NMR (400 MHz, CDCl$_3$) δ 0.53-0.56 (m, 2H), 0.64-0.68 (m, 2H), 1.13 (s, 9H), 1.24-1.31 (m, 1H), 1.91 (s, 3H), 2.09-2.14 (m, 2H), 2.39 (s, 3H), 2.63-2.76 (m, 2H), 4.25-4.28 (m, 2H), 5.09 (s, 1H), 6.76 (d, J=8.0 Hz, 1H), 6.78 (d, J=10.4 Hz, 1H), 7.08 (d, J=8.0 Hz, 1H), 9.43-9.97 (bs, 1H).

MS m/z ([M+Na]⁺) 449.

MS m/z ([M–H]⁻) 425.

Example 42

Synthesis of tert-butoxy-(6-chroman-6-yl-7-cyclopropyl-quinolin-5-yl)-acetic acid

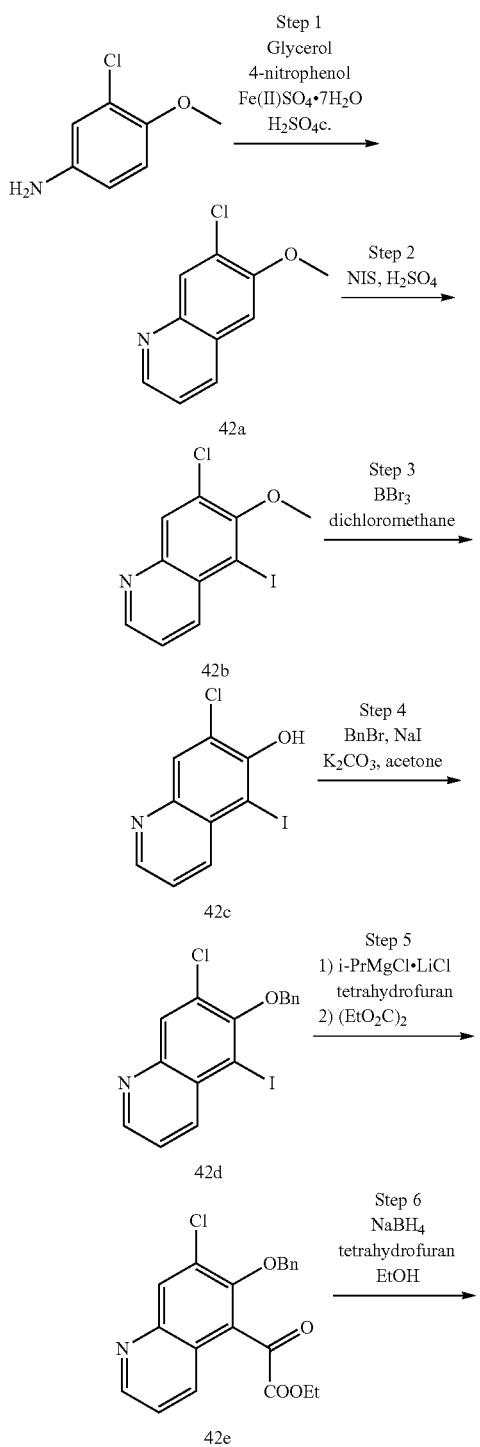

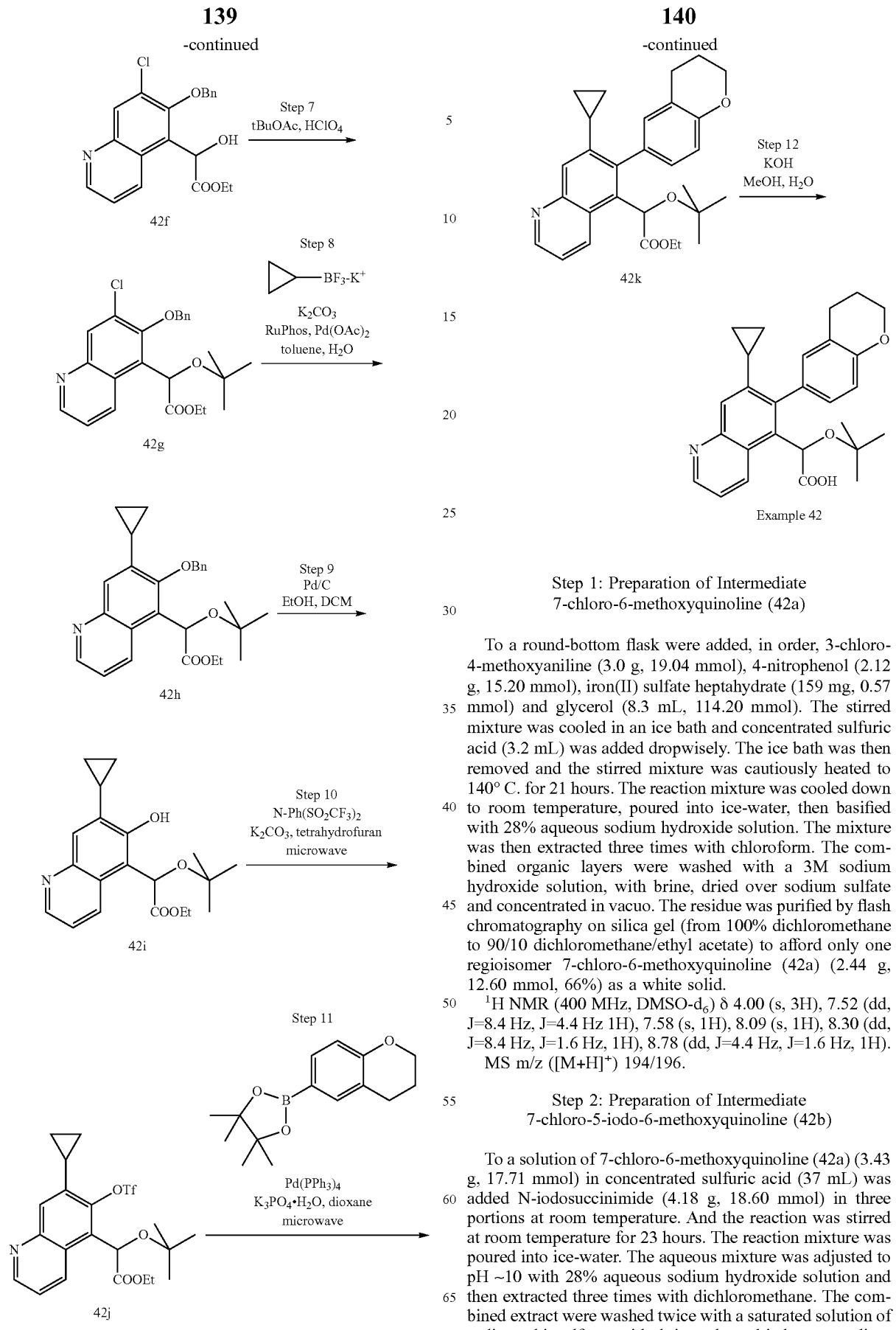

Step 1: Preparation of Intermediate 7-chloro-6-methoxyquinoline (42a)

To a round-bottom flask were added, in order, 3-chloro-4-methoxyaniline (3.0 g, 19.04 mmol), 4-nitrophenol (2.12 g, 15.20 mmol), iron(II) sulfate heptahydrate (159 mg, 0.57 mmol) and glycerol (8.3 mL, 114.20 mmol). The stirred mixture was cooled in an ice bath and concentrated sulfuric acid (3.2 mL) was added dropwisely. The ice bath was then removed and the stirred mixture was cautiously heated to 140° C. for 21 hours. The reaction mixture was cooled down to room temperature, poured into ice-water, then basified with 28% aqueous sodium hydroxide solution. The mixture was then extracted three times with chloroform. The combined organic layers were washed with a 3M sodium hydroxide solution, with brine, dried over sodium sulfate and concentrated in vacuo. The residue was purified by flash chromatography on silica gel (from 100% dichloromethane to 90/10 dichloromethane/ethyl acetate) to afford only one regioisomer 7-chloro-6-methoxyquinoline (42a) (2.44 g, 12.60 mmol, 66%) as a white solid.

$^1$H NMR (400 MHz, DMSO-$d_6$) δ 4.00 (s, 3H), 7.52 (dd, J=8.4 Hz, J=4.4 Hz 1H), 7.58 (s, 1H), 8.09 (s, 1H), 8.30 (dd, J=8.4 Hz, J=1.6 Hz, 1H), 8.78 (dd, J=4.4 Hz, J=1.6 Hz, 1H). MS m/z ([M+H]$^+$) 194/196.

Step 2: Preparation of Intermediate 7-chloro-5-iodo-6-methoxyquinoline (42b)

To a solution of 7-chloro-6-methoxyquinoline (42a) (3.43 g, 17.71 mmol) in concentrated sulfuric acid (37 mL) was added N-iodosuccinimide (4.18 g, 18.60 mmol) in three portions at room temperature. And the reaction was stirred at room temperature for 23 hours. The reaction mixture was poured into ice-water. The aqueous mixture was adjusted to pH ~10 with 28% aqueous sodium hydroxide solution and then extracted three times with dichloromethane. The combined extract were washed twice with a saturated solution of sodium thiosulfate, with brine, then dried over sodium sulfate and concentrated in vacuo to provide 7-chloro-5-iodo-6-methoxyquinoline (42b) (5.55 g, 17.36 mmol, 98%) as a grey solid without purification.

$^1$H NMR (400 MHz, DMSO-$d_6$) δ 3.91 (s, 3H), 7.67 (dd, J=8.6 Hz, J=4.2 Hz, 1H), 8.24 (s, 1H), 8.41 (d, J=8.6 Hz, 1H), 8.88 (dd, J=4.2 Hz, J=1.6 Hz, 1H).

MS m/z ([M+H]$^+$) 320/322.

Step 3: Preparation of Intermediate 7-chloro-5-iodo-quinolin-6-ol (42c)

To a solution of 7-chloro-5-iodo-6-methoxyquinoline (42b) (5.50 g, 17.21 mmol) in dichloromethane (165 mL) was slowly added boron tribromide (1M in dichloromethane, 86 mL, 86.06 mmol). The mixture was stirred for 3 days and cooled to −5° C. Methanol (45 mL) was slowly added and the mixture was stirred for 20 minutes at room temperature. The solvents were removed in vacuo. The resulting yellow solid was dissolved in methanol (60 mL) and treated with 1N sodium hydroxide solution (pH ~12). The mixture was stirred for 3 hours and acetic acid was added to adjust pH to 4-5. The mixture was filtered and washed twice with water. The grey solid was dried under reduced pressure to give 7-chloro-5-iodo-quinolin-6-ol (42c) (4.91 g, 16.07 mmol, 93%).

$^1$H NMR (400 MHz, DMSO-$d_6$) δ 7.58 (dd, J=8.6 Hz, J=4.4 Hz, 1H), 8.14 (s, 1H), 8.30-8.32 (m, 1H), 8.73 (dd, J=4.4/1.6 Hz, 1H), 10.63 (bs, 1H).

MS m/z ([M+H]$^+$) 306/308.

Step 4: Preparation of Intermediate 6-benzyloxy-7-chloro-5-iodoquinoline (42d)

To a solution of 7-chloro-5-iodo-quinolin-6-ol (42c) (4.91 g, 16.07 mmol) in acetone (45 mL) were successively added potassium carbonate (2.70 g, 19.28 mmol), benzyl bromide (2.1 mL, 17.68 mmol) and sodium iodide (482 mg, 3.21 mmol). The mixture was refluxed for 3 hours. The solvent was removed by evaporation in vacuo. The residue was dissolved in water and ethyl acetate. The aqueous layer was extracted with ethyl acetate twice. The organic layers were washed with brine, dried over sodium sulfate and concentrated in vacuo. The residue was purified by flash chromatography on silica gel (from 100% dichloromethane to 98/2 dichloromethane/ethyl acetate) to provide 6-benzyloxy-7-chloro-5-iodoquinoline (42d) (4.87 g, 12.31 mmol, 77%) as a white solid.

$^1$H NMR (400 MHz, DMSO-$d_6$) δ 5.10 (s, 2H), 7.42-7.49 (m, 3H), 7.65-7.70 (m, 3H), 8.30 (s, 1H), 8.44 (dd, J=0.7 Hz, J=8.6 Hz, 1H), 8.90 (dd, J=4.2 Hz, J=1.4 Hz, 1H).

MS m/z ([M+H]$^+$) 396/398.

Step 5: Preparation of Intermediate (6-benzyloxy-7-chloro-quinolin-5-yl)-oxo-acetic acid ethyl ester (42e)

In a round bottom flask, under argon atmosphere, at −30° C., isopropylmagnesium chloride lithium chloride complex solution (1.3M in tetrahydrofuran, 9.25 mL, 12.02 mmol) was slowly added over 20 minutes to a stirred solution of 6-benzyloxy-7-chloro-5-iodoquinoline (42d) (4.67 g, 11.44 mmol) in (21 mL). The reaction mixture was then stirred for 5 minutes with the temperature maintained at −30° C. The mixture was cooled to −50° C. and diethyl oxalate (1.70 mL, 12.58 mmol) was slowly added with a syringe. It was stirred at −40° C. for 1 hour and gently warmed to room temperature for 1 hour more. The mixture was cooled to 0° C., quenched with a saturated solution of ammonium chloride and extracted twice with ethyl acetate. The combined organic layers were washed with brine, dried over sodium sulphate and concentrated in vacuo. The residue was purified by flash chromatography on silica gel (from 100% dichloromethane to 96/4 dichloromethane/ethyl acetate) to provide (6-benzyloxy-7-chloro-quinolin-5-yl)-oxo-acetic acid ethyl ester (42e) (3.20 g, 8.65 mmol, 76%) as a white solid.

$^1$H NMR (400 MHz, CDCl$_3$) δ 1.15 (t, J=7.2 Hz, 3H), 4.10 (q, J=7.2 Hz, 2H), 5.14 (s, 2H), 7.36-7.42 (m, 3H), 7.47-7.52 (m, 3H), 8.42 (s, 1H), 8.55-8.57 (m, 1H), 8.93 (dd, J=4.2 Hz, J=1.6 Hz, 1H).

MS m/z ([M+H]$^+$) 370/372.

Step 6: Preparation of Intermediate (6-benzyloxy-7-chloro-quinolin-5-yl)-hydroxy-acetic acid ethyl ester (42f)

Under argon atmosphere, sodium borohydride (85 mg, 2.26 mmol) was added to a solution of (6-benzyloxy-7-chloro-quinolin-5-yl)-oxo-acetic acid ethyl ester (42e) (980 mg, 2.65 mmol) in (16.6 mL) and ethanol (4.2 mL) at −5° C. and the mixture was stirred for 40 minutes. Then the mixture was quenched with ethanol and water and extracted with ethyl acetate twice. The combined organic layers were washed with 1N hydrochloric acid aqueous solution, with brine, dried over sodium sulphate and concentrated in vacuo. The residue was purified by flash chromatography on silica gel (from 100% dichloromethane to 90/10 dichloromethane/ethyl acetate) to provide (6-benzyloxy-7-chloro-quinolin-5-yl)-hydroxy-acetic acid ethyl ester (42f) (973 mg, 2.62 mmol, 99%) as a white solid.

$^1$H NMR (400 MHz, CDCl$_3$) δ 1.09 (t, J=7.2 Hz, 3H), 3.35 (d, J=2.8 Hz, 1H), 4.11-4.22 (m, 2H), 5.14 (s, 2H), 5.98 (d, J=2.8 Hz, 1H), 7.39-7.44 (m, 4H), 7.55-7.57 (m, 2H), 8.26 (s, 1H), 8.40-8.42 (m, 1H), 8.88 (dd, J=1.6 Hz, J=4.2 Hz, 1H).

MS m/z ([M+H]$^+$) 372/374.

Step 7: Preparation of Intermediate (6-benzyloxy-7-chloro-quinolin-5-yl)-tert-butoxy-acetic acid ethyl ester (42g)

Under argon atmosphere, at room temperature, perchloric acid (3.8 mL, 62.80 mmol) was added in one quick portion to a solution of (6-benzyloxy-7-chloro-quinolin-5-yl)-hydroxy-acetic acid ethyl ester (1f) (2.78 g, 7.48 mmol) and the flask was sealed. The mixture was stirred at room temperature for 4 hours. The mixture was cooled at 0° C. and quenched with a saturated solution of sodium hydrogenocarbonate and extracted with ethyl acetate twice. The organic layer was washed with brine, dried over sodium sulfate and concentrated in vacuo. The residue was purified by flash chromatography on silica gel (from 95/5 to 80/20 dichloromethane/ethyl acetate) to provide (6-benzyloxy-7-chloro-quinolin-5-yl)-tert-butoxy-acetic acid ethyl ester (42g) (2.60 g, 6.08 mmol, 81%) as a white powder.

$^1$H NMR (400 MHz, CDCl$_3$) δ 1.12-1.15 (m, 12H), 4.05-4.21 (m, 2H), 5.11 (d, J=10.4 Hz, 1H), 5.39 (d, J=10.4 Hz, 1H), 6.09 (s, 1H), 7.36-7.48 (m, 4H), 7.60-7.62 (m, 2H), 8.18 (s, 1H), 8.83-8.87 (m, 2H).

MS m/z ([M+H]$^+$) 428/430.

Step 8: Preparation of Intermediate (6-benzyloxy-7-cyclopropyl-quinolin-5-yl)-tert-butoxy-acetic acid ethyl ester (42h)

To a degassed mixture of (6-benzyloxy-7-chloro-quinolin-5-yl)-tert-butoxy-acetic acid ethyl ester (42g) (2.90 g, 6.78 mmol), potassium carbonate (2.8 g, 20.30 mmol), potassium cyclopropyltrifluoroborate (1.6 g, 10.84 mmol) in toluene (25 mL) and water (2.4 mL), were added palladium (II) acetate (76 mg, 0.34 mmol) and 2-dicyclohexylphosphino-2',6'-diisopropoxybiphenyl ("RuPhos", 221 mg, 0.47 mmol). The mixture was heated at 90° C. for 21 hours and then water was added. The aqueous layer was extracted with ethyl acetate twice. The combined organic layers were washed with brine, dried over sodium sulfate and concentrated in vacuo. The residue was purified by flash chromatography on silica gel (cyclohexane/ethyl acetate 80/20) to provide (6-benzyloxy-7-cyclopropyl-quinolin-5-yl)-tert-butoxy-acetic acid ethyl ester (42h) (2.73 g, 6.30 mmol, 93%).

$^1$H NMR (400 MHz, CDCl$_3$) δ 0.81-0.88 (m, 1H), 1.02-1.16 (m, 6H), 1.18 (s, 9H), 2.33-2.40 (m, 1H), 4.03-4.23 (m, 2H), 5.21 (d, J=11.2 Hz, 1H), 5.30 (d, J=11.2 Hz, 1H), 6.15 (s, 1H), 7.29 (dd, J=4.2 Hz, J=8.6 Hz, 1H), 7.37-7.48 (m, 3H), 7.55-7.59 (m, 3H), 8.77 (dd, J=4.2 Hz, J=1.6 Hz, 1H), 8.80-8.83 (m, 1H).

MS m/z ([M+H]$^+$) 434.

Step 9: Preparation of Intermediate tert-butoxy-(7-cyclopropyl-6-hydroxy-quinolin-5-yl)-acetic acid ethyl ester (42i)

A suspension of (6-benzyloxy-7-cyclopropyl-quinolin-5-yl)-tert-butoxy-acetic acid ethyl ester (42h) (2.47 g, 5.70 mmol) and palladium on carbon (10%, 61 mg) in ethanol (38 mL) and dichloromethane (13 mL) was stirred at room temperature under hydrogen atmosphere for 3 hours. The mixture was filtered over Millipore and concentrated in vacuo. The residue was purified by flash chromatography on silica gel (dichloromethane/ethyl acetate 90/10) to provide tert-butoxy-(7-cyclopropyl-6-hydroxy-quinolin-5-yl)-acetic acid ethyl ester (42i) (1.96 g, 5.70 mmol, 100%).

$^1$H NMR (400 MHz, CDCl$_3$) δ 0.82-0.86 (m, 2H), 1.06-1.09 (m, 2H), 1.14 (t, J=7.2 Hz, 3H), 1.33 (s, 9H), 2.33-2.39 (m, 1H), 4.04-4.20 (m, 2H), 5.88 (s, 1H), 7.33 (dd, J=4.2 Hz, J=8.6 Hz, 1H), 7.52 (s, 1H), 8.31 (d, J=8.6 Hz, 1H), 8.70 (dd, J=4.2 Hz, J=1.6 Hz 1H), 9.18 (bs, 1H).

MS m/z ([M+H]$^+$) 344.

Step 10: Preparation of Intermediate tert-butoxy-(7-cyclopropyl-6-trifluoromethane sulfonyloxy-quinolin-5-yl)-acetic acid ethyl ester (42j)

Under argon atmosphere, tert-butoxy-(7-cyclopropyl-6-hydroxy-quinolin-5-yl)-acetic acid ethyl ester (42i) (1.96 g, 5.70 mmol), N-phenyl-bis(trifluoromethane-sulfonimide) (2.22 g, 6.23 mmol), potassium carbonate (2.0 g, 14.55 mmol) and (12 mL) were mixed in a microwave vial Biotage® (10-20 mL) with a magnetic stirrer. The reaction mixture was stirred and heated at 110° C. for 75 minutes in a Biotage® Initiator™ 2.5 Microwave Synthetizer. The mixture was diluted with a saturated solution of ammonium chloride and ethyl acetate. Layers were separated and the organic one was washed with brine, dried over sodium sulfate, filtered and concentrated in vacuo. The residue was purified by flash chromatography on silica gel (cyclohexane/ethyl acetate 80/20) to provide tert-butoxy-(7-cyclopropyl-6-trifluoromethanesulfonyloxy-quinolin-5-yl)-acetic acid ethyl ester (42j) (1.75 g, 3.68 mmol, 65%) as a white solid.

$^1$H NMR (400 MHz, CDCl$_3$) δ 0.86-0.98 (m, 2H), 1.04-1.20 (m, 5H), 1.21 (s, 9H), 2.20-2.25 (m, 1H), 3.98-4.06 (m, 1H), 4.14-4.22 (m, 1H), 5.88 (s, 1H), 7.37 (dd, J=8.6 Hz, J=4.2 Hz, 1H), 7.78 (s, 1H), 8.73-8.75 (m, 1H), 8.90 (dd, J=1.6 Hz, J=4.2 Hz, 1H).

MS m/z ([M+H]$^+$) 476.

Step 11: Preparation of Intermediate tert-butoxy-(6-chroman-6-yl-7-cyclopropyl-quinolin-5-yl)-acetic acid ethyl ester (42k)

Under argon atmosphere, tert-butoxy-(7-cyclopropyl-6-trifluoromethanesulfonyloxy-quinolin-5-yl)-acetic acid ethyl ester (42j) (758 mg, 1.59 mmol), chroman-6-boronic acid, pinacol ester (498 mg, 1.91 mmol), potassium phosphate tribasic monohydrate (732 mg, 3.18 mmol) and dioxane (6.8 mL) were added in a microwave vial Biotage® (10-20 mL) with a magnetic stirrer. The mixture was degassed under argon for 10 minutes and palladium tetrakis (triphenylphosphine) (111 mg, 0.10 mmol) was added. The vial was sealed and heated in a Biotage® Initiator™ 2.5 Microwave Synthetizer at 160° C. for 7 hours. The mixture was diluted with ethyl acetate, filtered over Celite® (several washings with ethyl acetate were made) and the filtrate was concentrated in vacuo. The residue was purified by flash chromatography on silica gel (cyclohexane/ethyl acetate 85/15) to provide tert-butoxy-(6-chroman-6-yl-7-cyclopropyl-quinolin-5-yl)-acetic acid ethyl ester (42k) (277 mg, 0.60 mmol, 38%), as a mixture of atropoisomers.

$^1$H NMR (400 MHz, CDCl$_3$) δ 0.77-0.87 (m, 4H), 1.04 (s, 9H), 1.10-1.18 (m, 3H), 1.56-1.61 (m, 1H), 2.07-2.11 (m, 2H), 2.81-2.87 (m, 2H), 3.95-4.19 (m, 2H), 4.26-4.30 (m, 2H), 5.35-5.39 (m, 1H), 6.86-7.07 (m, 2H), 7.14-7.18 (m, 1H), 7.31 (dd, J=8.62 Hz, J=4.2 Hz, 1H), 7.58 (d, J=2.3 Hz, 1H), 8.81 (dd, J=1.6 Hz, J=4.2 Hz, 1H), 9.01-9.04 (m, 1H).

MS m/z ([M+H]$^+$) 460.

Step 12: Preparation of tert-butoxy-(6-chroman-6-yl-7-cyclopropyl-quinolin-5-yl)-acetic acid (Example 42)

A mixture of tert-butoxy-(6-chroman-6-yl-7-cyclopropyl-quinolin-5-yl)-acetic acid ethyl ester (42k) (44 mg, 0.10 mmol) and potassium hydroxide (11 mg, 0.19 mmol) in methanol (0.9 mL) and water (1 mL) was heated at 70° C. for 16 hours. The mixture was concentrated in vacuo. Water and ethyl acetate were added to the residue and this mixture was acidified with 1M hydrochloric acid until pH 4-5. The aqueous layer was extracted twice. The organic layer was washed with brine and dried over sodium sulfate and concentrated in vacuo. The residue was purified by preparative TLC (dichloromethane/methanol 90/10) to provide tert-butoxy-(6-chroman-6-yl-7-cyclopropyl-quinolin-5-yl)-acetic acid (Example 42) (28 mg, 0.06 mmol, 68%) as a white solid, as a mixture of atropoisomers.

$^1$H NMR (400 MHz, CDCl$_3$) δ 0.75-0.89 (m, 4H), 1.00 (s, 9H), 1.62-1.64 (m, 1H), 2.05-2.09 (m, 2H), 2.79-2.86 (m, 2H), 4.22-4.30 (m, 2H), 5.51-5.53 (m, 1H), 6.87-7.11 (m, 3H), 7.31-7.35 (m, 1H), 7.61 (s, 1H), 8.56-8.82 (m, 2H).

MS m/z ([M+H]$^+$) 432.

MS m/z ([M−H]$^-$) 430.

Example 43

Synthesis of tert-butoxy-(2-chroman-6-yl-3-cyclobutyl-6-methyl-phenyl)-acetic acid

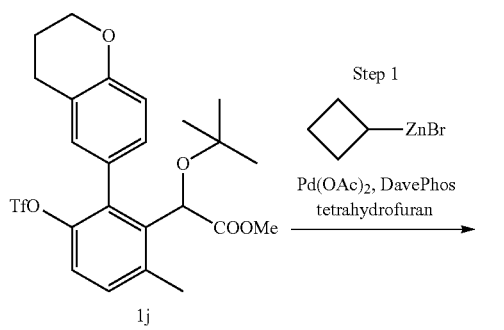

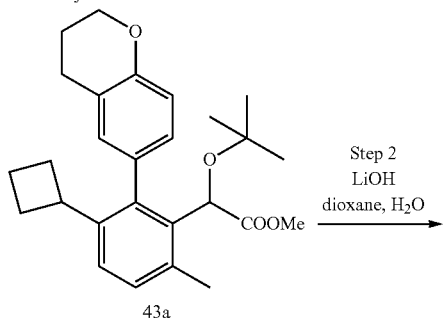

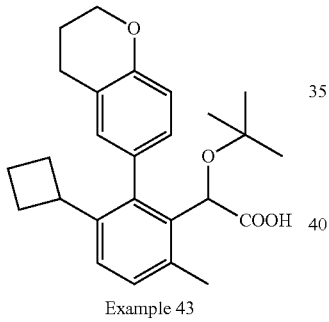

Example 43

Step 1: Preparation of Intermediate tert-butoxy-(2-chroman-6-yl-3-cyclobutyl-6-methyl-phenyl)-acetic acid methyl ester (43a)

To methyl 2-(tert-butoxy)-2-[2-(3,4-dihydro-2H-1-benzopyran-6-yl)-6-methyl-3-trifluoromethanesulfonyloxy-phenyl]acetate (1j) (220 mg, 0.426 mmol) and was added a solution of cyclobutyylzinc bromide 0.5 M in (3.40 mL, 1.70 mmol). The mixture was degassed by bubbling argon for 5 minutes. 2-Dicyclohexylphosphino-2'-(N,N-dimethylamino)biphenyl (DavePhos) (17 mg, 0.043 mmol) and palladium acetate (4.70 mg, 0.021 mmol) were successively added and the mixture was heated at 60° C. for 4 hours. The heating was stopped and when the temperature reached 30° C., a saturated aqueous solution of ammonium chloride (10 mL) was added. The aqueous layer was extracted with cyclohexane (3×5 mL). The combined organic layers were washed with brine (20 mL), dried over sodium sulfate, filtered and concentrated in vacuo. The residue was purified by preparative TLC (cyclohexane/ethyl acetate 90/10) to provide tert-butoxy-(2-chroman-6-yl-3-cyclobutyl-6-methyl-phenyl)-acetic acid methyl ester (43a) (143 mg, 0.338 mmol, 79%) as a yellow oil.

$^1$H NMR (300 MHz, CDCl$_3$) δ 0.97 (s, 9H), 1.60-1.79 (m, 3H), 1.88-2.12 (m, 5H), 2.41 (s, 3H), 2.62-2.87 (m, 2H), 3.19-3.30 (m, 1H), 3.64 and 3.66 (s, 3H), 4.21-4.29 (m, 2H), 5.03 and 5.05 (s, 1H), 6.77-6.87 (m, 2H), 6.95-7.02 (m, 1H), 7.12 (d, 1H J=7.9 Hz), 7.26 (d, 1H, J=7.9 Hz).

MS m/z ([M+Na]$^+$) 445.

Step 2: Preparation of tert-butoxy-(2-chroman-6-yl-3-cyclobutyl-6-methyl-phenyl)-acetic acid (Example 43)

Using the procedure described in example 1, step 12, the tert-butoxy-(2-chroman-6-yl-3-cyclobutyl-6-methyl-phenyl)-acetic acid methyl ester (43a) (143 mg, 0.338 mmol) is converted, after purification on silica gel (cyclohexane/ethyl acetate from 90/0 to 70/30) into tert-butoxy-(2-chroman-6-yl-3-cyclobutyl-6-methyl-phenyl)-acetic acid (Example 43) (131 mg, 0.320 mmol, 94%) as a white solid.

$^1$H NMR (300 MHz, CDCl$_3$) δ 0.99 (s, 9H), 1.57-1.92 (m, 4H), 2.00-2.11 (m, 4H), 2.36 (s, 3H), 2.67-2.86 (m, 2H), 3.21-3.39 (m, 1H), 4.19-4.30 (m, 2H), 5.18 (s, 1H), 6.78-6.87 (m, 2H), 7.11-7.19 (m, 2H), 7.26-7.28 (m, 1H), 9.10-10.60 (bs, 1H).

MS m/z ([M+Na]$^+$) 431.

MS m/z ([M−H]$^-$) 407.

Example 44

Synthesis of (S)-cyclopropoxy-[3-cyclopropyl-2-(8-fluoro-5-methyl-chroman-6-yl)-6-methyl-phenyl]-acetic acid

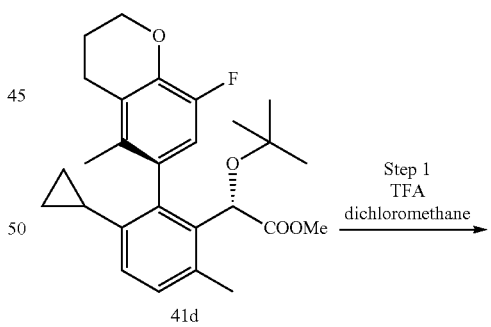

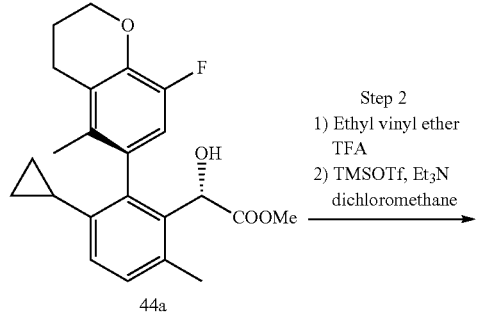

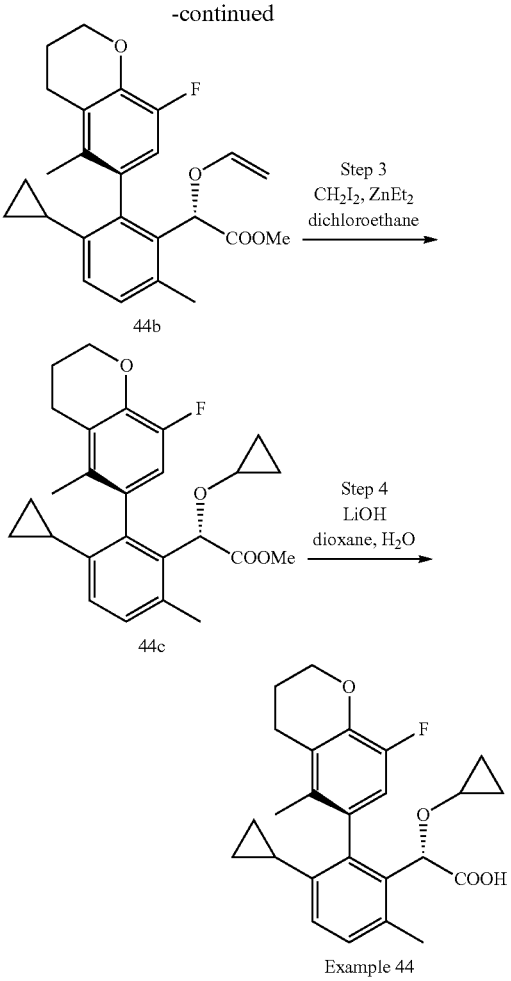

44b

44c

Example 44

Step 1: Preparation of Intermediate (S)-[3-cyclopropyl-2-(8-fluoro-5-methyl-chroman-6-yl)-6-methyl-phenyl]-hydroxy-acetic acid methyl ester (44a)

Using the procedure described in example 23, step 1, (S)-tert-butoxy-[3-cyclopropyl-2-(8-fluoro-5-methyl-chroman-6-yl)-6-methyl-phenyl]-acetic acid methyl ester (41d) (2.07 g, 4.69 mmol) is converted into (S)-[3-cyclopropyl-2-(8-fluoro-5-methyl-chroman-6-yl)-6-methyl-phenyl]-hydroxy-acetic acid methyl ester (44a) (1.68 g, 4.36 mmol, 93%) which was used without further purification.

$^1$H NMR (400 MHz, CDCl$_3$) δ 0.49-0.63 (m, 2H), 0.63-0.74 (m, 2H), 1.27-1.36 (m, 1H), 1.86 (s, 3H), 2.08-2.16 (m, 2H), 2.28 (s, 3H), 2.67-2.73 (m, 2H), 2.94 (d, J=2.8 Hz, 1H), 3.70 (s, 3H), 4.23-4.28 (m, 2H), 5.04 (d, J=2.8 Hz, 1H), 6.75 (d, J=11.3 Hz, 1H), 6.76 (d, J=8.0 Hz, 1H), 7.09 (d, J=8.0 Hz, 1H).

MS m/z ([M+Na]$^+$) 407.

Step 2: Preparation of Intermediate (S)-[3-cyclopropyl-2-(8-fluoro-5-methyl-chroman-6-yl)-6-methyl-phenyl]-vinyloxy-acetic acid methyl ester (44b)

To a stirred solution of (S)-[3-cyclopropyl-2-(8-fluoro-5-methyl-chroman-6-yl)-6-methyl-phenyl]-hydroxy-acetic acid methyl ester (44a) (1.54 g, 4.00 mmol) in a mixture of ethyl vinyl ether (8.0 mL) and dichloromethane (8.0 mL) at room temperature was added TFA (90 µL, 1.20 mmol). The stirring was continued for 7 hours before the reacting mixture was quenched by addition of triethylamine (220 µL, 1.60 mmol) and concentrated in vacuo. The intermediate acetal was directly dissolved in anhydrous dichloromethane (10 mL), cooled down to 0° C. before triethylamine (840 µL, 600 mmol) and trimethylsilyl trifluoromethanesulfonate (940 µL, 5.20 mmol) were added dropwisely. The mixture was stirred at room temperature 2 hours before the reaction was quenched with a 1M sodium hydroxide solution. The organic layer was separated, washed with brine, dried over sodium sulfate and concentrated under reduced pressure. The crude material was purified by chromatography on silica gel (cyclohexane/ethyl acetate 70/30) to give (S)-[3-cyclopropyl-2-(8-fluoro-5-methyl-chroman-6-yl)-6-methyl-phenyl]-vinyloxy-acetic acid methyl ester (44b) (1.31 g, 3.19 mmol, 80%) as a yellow solid.

$^1$H NMR (400 MHz, CDCl$_3$) δ 0.51-0.61 (m, 2H), 0.62-0.74 (m, 2H), 1.30-1.37 (m, 1H), 1.88 (s, 3H), 2.10-2.16 (m, 2H), 2.32 (s, 3H), 2.70-2.73 (m, 2H), 3.68 (s, 3H), 4.03 (dd, J=6.4 Hz, J=2.0 Hz, 1H), 4.24-4.28 (m, 3H), 5.14 (s, 1H), 6.14 (dd, J=13.6 Hz, J=6.4 Hz, 1H), 6.69 (d, J=11.6 Hz, 1H), 6.78 (d, J=8.0 Hz, 1H), 7.11 (d, J=8.0 Hz, 1H). MS m/z ([M+Na]$^+$) 433.

Step 3: Preparation of Intermediate (S)-cyclopropoxy-[3-cyclopropyl-2-(8-fluoro-5-methyl-chroman-6-yl)-6-methyl-phenyl]-acetic acid methyl ester (44c)

Using the procedure described in example 23, step 3, the intermediate (S)-[3-cyclopropyl-2-(8-fluoro-5-methyl-chroman-6-yl)-6-methyl-phenyl]-vinyloxy-acetic acid methyl ester (44b) (503 mg, 1.23 mmol) is converted, after purification by chromatography on silica gel (cyclohexane/ethyl acetate 80/20) into (S)-cyclopropoxy-[3-cyclopropyl-2-(8-fluoro-5-methyl-chroman-6-yl)-6-methyl-phenyl]-acetic acid methyl ester (44c) (520 mg, 1.23 mmol, 100%).

$^1$H NMR (400 MHz, CDCl$_3$) δ 0.29-0.36 (m, 1H), 0.38-0.49 (m, 2H), 0.51-0.62 (m, 3H), 0.63-0.72 (m, 2H), 1.28-1.35 (m, 1H), 1.87 (s, 3H), 2.10-2.17 (m, 2H), 2.32 (s, 3H), 2.70-2.74 (m, 2H), 3.42-3.47 (m, 1H), 3.64 (s, 3H), 4.26-4.29 (m, 2H), 4.90 (s, 1H), 6.73 (d, J=11.6 Hz, 1H), 6.75 (d, J=7.6 Hz, 1H), 7.07 (d, J=7.6 Hz, 1H).

MS m/z ([M+Na]$^+$) 447.

Step 4: Preparation of (S)-cyclopropoxy-[3-cyclopropyl-2-(8-fluoro-5-methyl-chroman-6-yl)-6-methyl-phenyl]-acetic acid (Example 44)

Using the procedure described in example 1, step 12, the intermediate (S)-cyclopropoxy-[3-cyclopropyl-2-(8-fluoro-5-methyl-chroman-6-yl)-6-methyl-phenyl]-acetic acid methyl ester (44c) (520 mg, 1.23 mmol) is converted to (S)-cyclopropoxy-[3-cyclopropyl-2-(8-fluoro-5-methyl-chroman-6-yl)-6-methyl-phenyl]-acetic acid (Example 44) (410 mg, 1.00 mmol, 82%).

$^1$H NMR (400 MHz, CDCl$_3$) δ 0.41-0.59 (m, 6H), 0.66-0.71 (m, 2H), 1.32-1.38 (m, 1H), 1.89 (s, 3H), 2.08-2.17 (m, 2H), 2.31 (s, 3H), 2.68-2.72 (m, 2H), 3.27-3.33 (m, 1H), 4.25-4.29 (m, 2H), 4.95 (s, 1H), 6.75 (d, J=11.4 Hz, 1H), 6.79 (d, J=8.0 Hz, 1H), 7.11 (d, J=8.0 Hz, 1H), 8.53-9.56 (bs, 1H).

19F NMR (282 MHz, CDCl3) −142.0 (s, 1F).
MS m/z ([M+Na]+) 433.
MS m/z ([M−H]−) 409.
Example 45
Synthesis of 3-cyclopropyl-2-[3-cyclopropyl-2-(3,4-dihydro-2H-1-benzopyran-6-yl)-6-methylphenyl] propanoic acid
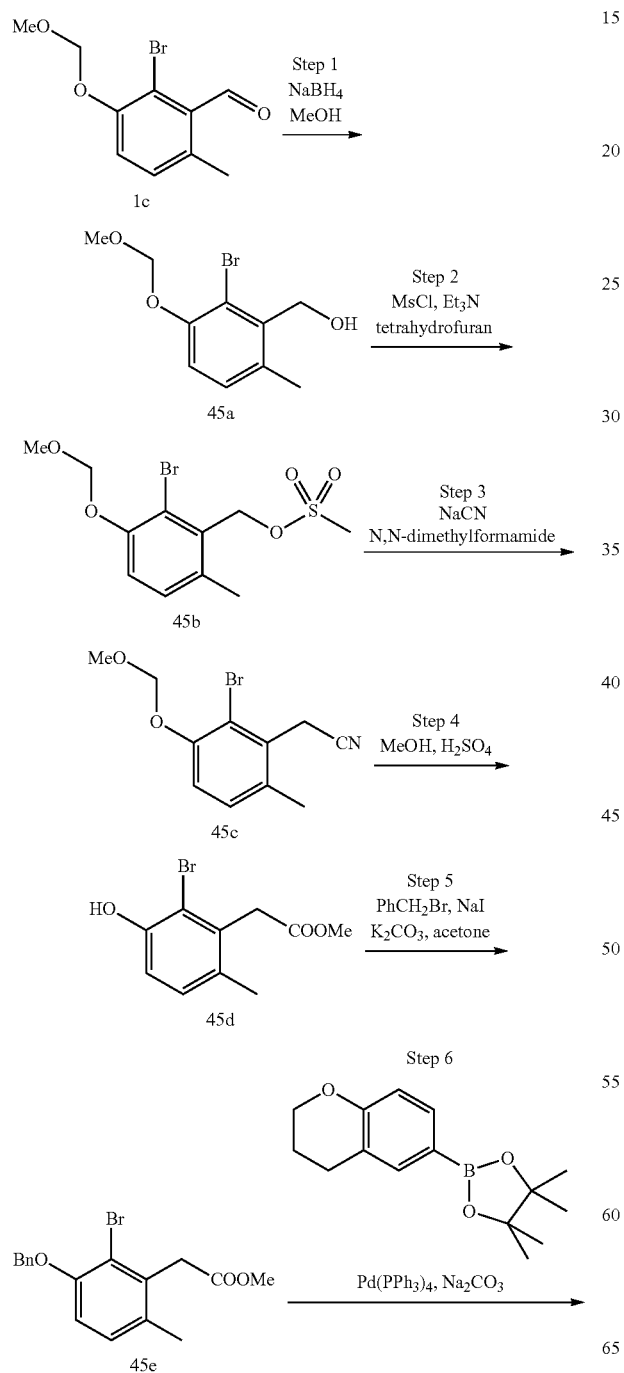
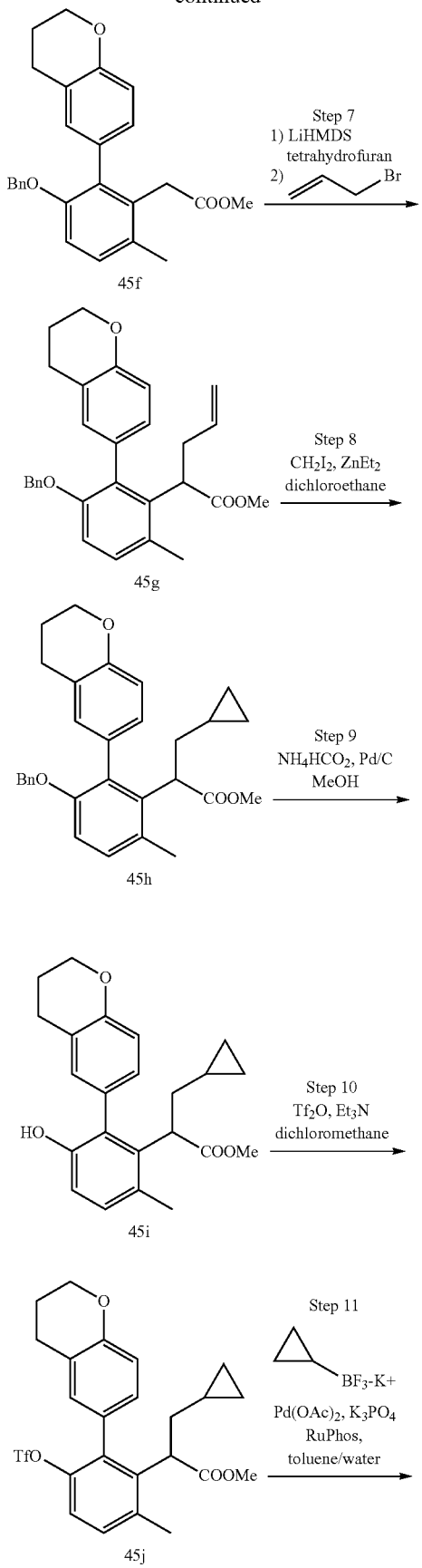

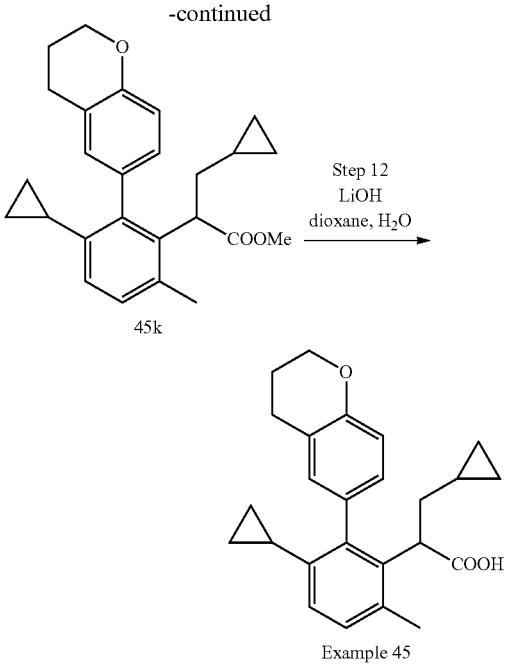

Example 45

Step 1: Preparation of Intermediate (2-bromo-3-(methoxymethoxy)-6-methylphenyl)methanol (45a)

To a solution of compound 2-bromo-3-methoxymethox-6-methyl-benzaldehyde 1c (3.3 g, 12.74 mmol) in anhydrous methanol (127 mL) was added sodium tetraborohydride (482 mg, 12.74 mmol) at 0° C. The mixture was stirred at 0° C. for 1 hour. The reaction mixture was diluted with ethyl acetate and washed with water and brine. The organic layer was dried over sodium sulfate, filtered and concentrated in vacuo to afford the crude product (2-bromo-3-(methoxymethoxy)-6-methylphenyl)methanol (3.40 g, 12.74 mmol, 100%) as a colorless oil which was used in the next step without further purification.

MS m/z ([M+H–H$_2$O]±) 243/245.

Step 2: Preparation of Intermediate (2-bromo-3-(methoxymethoxy)-6-methylphenyl)methyl methanesulfonate (45b)

To a solution of compound (2-bromo-3-(methoxymethoxy)-6-methylphenyl)methanol (45a) (3.32 g, 12.74 mmol) in anhydrous (64 mL) was added at 0° C. methanesulfonyl chloride (1.18 mL, 15.29 mmol) and triethylamine (2.49 mL, 17.84 mmol). The mixture was stirred at room temperature for 3 hours then diluted with ethyl acetate and washed with water and brine. The organic layer was dried over sodium sulfate, filtered and concentrated in vacuo to afford the crude product (2-bromo-3-(methoxymethoxy)-6-methylphenyl)methyl methanesulfonate (45b) (4.32 g, 12.74 mmol, 100%) as a beige gum which was used in the next step without further purification.

Step 3: Preparation of Intermediate 2-(2-bromo-3-(methoxymethoxy)-6-methylphenyl) acetonitrile (45c)

Compound (2-bromo-3-(methoxymethoxy)-6-methylphenyl)methyl methanesulfonate (45b) (4.32 g, 12.74 mmol) was dissolved in anhydrous N,N-dimethylformamide (36 mL) and sodium cyanide (750 mg, 15.29 mmol) was added to it. The reaction mixture was stirred overnight at room temperature and concentrated to dryness to remove N,N-dimethylformamide. The residue was then diluted with ethyl acetate, washed with water and brine and the organic layer was dried over sodium sulfate, filtered and concentrated in vacuo. The residue was purified by flash chromatography on silica gel (cyclohexane/dichloromethane 40/60) to provide 2-(2-bromo-3-(methoxymethoxy)-6-methylphenyl)acetonitrile (45c) (3.16 g, 11.70 mmol, 92% over 3 steps) as a beige solid.

$^1$H NMR (300 MHz, CDCl$_3$) δ 2.41 (s, 3H), 3.51 (s, 3H), 3.92 (s, 2H), 5.23 (s, 1H), 7.06 (d, J=8.5 Hz, 1H), 7.12 (d, J=8.5 Hz, 1H).

Step 4: Preparation of Intermediate methyl 2-(2-bromo-3-hydroxy-6-methylphenyl)acetate (45d)

2-(2-bromo-3-(methoxymethoxy)-6-methylphenyl)acetonitrile (45c) (1.38 g, 5.11 mmol) was dissolved at 0° C. in a 9/1 mixture of methanol/sulfuric acid (27 mL). The mixture was refluxed at 90° C. for 3 days then cooled at room temperature and poured slowly in water (80 mL). The aqueous layer was extracted twice with diethyl ether (2×100 mL) then twice with ethyl acetate (2×100 mL). The combined organic layers were washed with a saturated solution of sodium hydrogenocarbonate (80 mL), brine (80 mL), dried over sodium sulfate and concentrated in vacuo to provide methyl 2-(2-bromo-3-hydroxy-6-methylphenyl)acetate (45d) (1.32 g, 5.11 mmol, 100%) as a beige solid which was used in the next step without further purification.

MS m/z ([M+H]$^+$) 259/261.

Step 5: Preparation of Intermediate methyl 2-(3-(benzyloxy)-2-bromo-6-methylphenyl)acetate (45e)

Using the procedure described in example 42, step 4, methyl 2-(2-bromo-3-hydroxy-6-methylphenyl)acetate (45d) (1.32 g, 5.11 mmol) is converted into methyl 2-(3-(benzyloxy)-2-bromo-6-methylphenyl)acetate (45e) (1.61 g, 4.61 mmol, 90% over 2 steps) as a yellow oil after purification by flash chromatography on silica gel (cyclohexane/ethyl acetate 90/10).

$^1$H NMR (400 MHz, CDCl$_3$) δ 2.29 (s, 3H), 3.71 (s, 3H), 3.95 (s, 2H), 5.13 (s, 2H), 6.79 (d, J=8.4 Hz, 1H), 7.06 (d, J=8.4 Hz, 1H), 7.30-7.34 (m, 1H), 7.36-7.41 (m, 2H), 7.46-7.50 (m, 2H).

MS m/z ([M+H]$^+$) 349/351.
MS m/z ([M–H]$^-$) 347/349.

Step 6: Preparation of Intermediate methyl 2-[3-(benzyloxy)-2-(3,4-dihydro-2H-1-benzopyran-6-yl)-6-methylphenyl]acetate (45f)

Using the procedure described in example 1, step 7, methyl 2-(3-(benzyloxy)-2-bromo-6-methylphenyl)acetate (45e) (1.6 g, 4.58 mmol) is converted into methyl 2-[3-(benzyloxy)-2-(3,4-dihydro-2H-1-benzopyran-6-yl)-6-methylphenyl]acetate (45f) (1.78 g, 4.42 mmol, 96%) as a yellow gum after purification by flash chromatography on silica gel (cyclohexane/ethyl acetate 90/10).

$^1$H NMR (400 MHz, CDCl$_3$) δ 2.01-2.07 (m, 2H), 2.23 (s, 3H), 2.76-2.80 (m, 2H), 3.50 (d, J=1.94 Hz, 2H), 3.64 (s, 3H), 4.22-4.24 (m, 2H), 4.97 (s, 2H), 6.81-6.85 (m, 2H), 6.88-6.90 (m, 1H), 6.93-6.96 (m, 1H), 7.08-7.10 (m, 1H), 7.16-7.18 (m, 2H), 7.20-7.30 (m, 3H).
MS m/z ([M–H]⁻) 401.

Step 7: Preparation of Intermediate methyl 2-[3-(benzyloxy)-2-(3,4-dihydro-2H-1-benzopyran-6-yl)-6-methylphenyl]pent-4-enoate (45g)

To a solution of methyl 2-[3-(benzyloxy)-2-(3,4-dihydro-2H-1-benzopyran-6-yl)-6-methylphenyl]acetate (45f) (134 mg, 0.33 mmol) in anhydrous (3.3 mL) under nitrogen atmosphere at 0° C. was added dropwise a 1 M solution of lithium bis(trimethylsilyl)amide in e (832 L, 0.83 mmol). The mixture was stirred at room temperature for 45 minutes, allyl bromide (288 µL, 3.33 mmol) was then added and the reaction mixture was allowed to stir at room temperature for 2 hours. Ammonium chloride aqueous solution was added and the mixture was extracted with ethyl acetate. The organic layer was dried over sodium sulfate, concentrated in vacuo and the residue was purified by preparative TLC (cyclohexane/ethyl acetate 90/10) to provide methyl 2-[3-(benzyloxy)-2-(3,4-dihydro-2H-1-benzopyran-6-yl)-6-methylphenyl]pent-4-enoate (45g) (117 mg, 0.26 mmol, 74%) as a colorless oil.
$^1$H NMR (400 MHz, CDCl$_3$) δ 2.01-2.08 (m, 2H), 2.21 (s, 3H), 2.27-2.38 (m, 1H), 2.73-2.90 (m, 3H), 3.63 and 3.64 (s, 3H), 3.88-3.93 (m, 1H), 4.22-4.26 (m, 2H), 4.81-5.00 (m, 4H), 5.49-5.61 (m, 1H), 6.80-7.00 (m, 4H), 7.04-7.06 (m, 1H), 7.12-7.15 (m, 2H), 7.20-7.29 (m, 3H)
MS m/z ([M+H]⁺) 443, ([M+Na]⁺) 465.
MS m/z ([M–H]⁻) 441.

Step 8: Preparation of Intermediate methyl 2-[3-(benzyloxy)-2-(3,4-dihydro-2H-1-benzopyran-6-yl)-6-methylphenyl]-3-cyclopropylpropanoate (45h)

Using the procedure described in example 23, step 3, the intermediate methyl 2-[3-(benzyloxy)-2-(3,4-dihydro-2H-1-benzopyran-6-yl)-6-methylphenyl]pent-4-enoate (45g) (157 mg, 0.35 mmol) is converted, after purification by preparative TLC (cyclohexane/ethyl acetate 86/14) to provide methyl 2-[3-(benzyloxy)-2-(3,4-dihydro-2H-1-benzopyran-6-yl)-6-methylphenyl]-3-cyclopropylpropanoate (45h) (89.7 mg, 0.196 mmol, 55%) as a colorless oil.
$^1$H NMR (400 MHz, CDCl$_3$) δ –0.30--0.25 (m, 1H), –0.16-(–) 0.10 (m, 1H), 0.14-0.28 (m, 2H), 0.50-0.61 (m, 1H), 1.35-1.43 (m, 1H), 1.99-2.09 (m, 3H), 2.20 and 2.21 (s, 3H), 2.75-2.84 (m, 2H), 3.64 and 3.66 (s, 3H), 3.97-4.03 (m, 1H), 4.23-4.25 (m, 2H), 4.91-5.00 (m, 2H), 6.80-7.05 (m, 5H), 7.12-7.15 (m, 2H), 7.20-7.28 (m, 3H).
MS m/z ([M+H]⁺) 457, ([M+Na]⁺) 479.
MS m/z ([M–H]⁻) 455.

Step 9: Preparation of Intermediate methyl 3-cyclopropyl-2-[2-(3,4-dihydro-2H-1-benzopyran-6-yl)-3-hydroxy-6-methylphenyl]propanoate (45i)

A degassed suspension of methyl 2-[3-(benzyloxy)-2-(3,4-dihydro-2H-1-benzopyran-6-yl)-6-methylphenyl]-3-cyclopropylpropanoate (45h) (82 mg, 0.18 mmol) with ammonium formate (283 mg, 4.49 mmol) and palladium on carbon (8 mg) in methanol (2 mL) was refluxed 4 hours. More ammonium formate (283 mg, 4.49 mmol) and palladium on carbon (8 mg) were added and the reaction mixture was refluxed overnight until complete conversion of starting material, then filtered on a pad of Celite® and the filtrate was concentrated in vacuo. The residue was diluted with ethyl acetate, washed with water, brine, dried over sodium sulfate, filtered, concentrated in vacuo and purified by preparative TLC (cyclohexane/ethyl acetate 70/30) to provide methyl 3-cyclopropyl-2-[2-(3,4-dihydro-2H-1-benzopyran-6-yl)-3-hydroxy-6-methylphenyl]propanoate (45i) (49.3 mg, 0.13 mmol, 76%).
$^1$H NMR (400 MHz, CDCl$_3$) δ –0.28--0.22 (m, 1H), –0.15--0.10 (m, 1H), 0.17-0.29 (m, 2H), 0.50-0.59 (m, 1H), 1.39-1.47 (m, 1H), 1.94-2.10 (m, 3H), 2.19 and 2.20 (s, 3H), 2.74-2.85 (m, 2H), 3.63 and 3.64 (s, 3H), 3.79-3.85 (m, 1H), 4.23-4.27 (m, 2H), 4.60 and 4.62 (s, 1H), 6.79-6.82 (m, 1H), 6.86-6.93 (m, 2H), 7.01-7.07 (m, 2H).
MS m/z ([M+H]⁺) 367.
MS m/z ([M–H]⁻) 365.

Step 10: Preparation of Intermediate methyl 3-cyclopropyl-2-[2-(3,4-dihydro-2H-1-benzopyran-6-yl)-6-methyl-3-(trifluoromethanesulfonyloxy)phenyl]propanoate (45j)

Using the procedure described in example 1, step 10, the intermediate methyl 3-cyclopropyl-2-[2-(3,4-dihydro-2H-1-benzopyran-6-yl)-3-hydroxy-6-methylphenyl]propanoate (45i) (49 mg, 0.13 mmol) is converted into methyl 3-cyclopropyl-2-[2-(3,4-dihydro-2H-1-benzopyran-6-yl)-6-methyl-3-(trifluoromethanesulfonyloxy)phenyl]propanoate (45j) (67 mg, 0.13 mmol, 100%) as a clear yellow oil which was used in the next step without further purification.
$^1$H NMR (300 MHz, CDCl$_3$) δ –0.28--0.22 (m, 1H), –0.15--0.08 (m, 1H), 0.15-0.31 (m, 2H), 0.43-0.57 (m, 1H), 1.35-1.45 (m, 1H), 1.98-2.10 (m, 3H), 2.27 (s, 3H), 2.73-2.85 (m, 2H), 3.64 and 3.65 (s, 3H), 3.96-4.01 (m, 1H), 4.21-4.25 (m, 2H), 6.78-7.00 (m, 3H), 7.12-7.19 (m, 2H).
MS m/z ([M+H]⁺) 499.
MS m/z ([M–H]⁻) 497.

Step 11: Preparation of Intermediate methyl 3-cyclopropyl-2-[3-cyclopropyl-2-(3,4-dihydro-2H-1-benzopyran-6-yl)-6-methylphenyl]propanoate (45k)

A degassed solution of methyl 3-cyclopropyl-2-[2-(3,4-dihydro-2H-1-benzopyran-6-yl)-6-methyl-3-(trifluoromethanesulfonyloxy)phenyl]propanoate (45j) (67 mg, 0.135 mmol), potassium cyclopropyltrifluoroboronate (26 mg, 0.176 mmol), 2-dicyclohexylphosphino-2',6'-diisopropoxybiphenyl (RuPhos) (3.1 mg, 0.007 mmol), potassium phosphate tribasic monohydrate (193 mg, 0.837 mmol) and palladium(II) acetate (0.8 mg, 0.003 mmol) in a 1/1 mixture of tert-butanol/water (0.27 mL) was heated at 105° C. for 4 hours. More 2-dicyclohexylphosphino-2',6'-diisopropoxybiphenyl (RuPhos) (3.1 mg, 0.007 mmol) and palladium(II) acetate (0.8 mg, 0.003 mmol) were added and the reaction mixture was refluxed an additional 2 hours before being quenched. Water (3 mL) was added. The aqueous layer was extracted with cyclohexane (2×6 mL). The combined organic layers were washed with brine (3 mL), dried over sodium sulfate and concentrated in vacuo. The residue was purified by preparative TLC (cyclohexane/ethyl acetate 90/10) to provide methyl 3-cyclopropyl-2-[3-cyclopropyl-2-(3,4-dihydro-2H-1-benzopyran-6-yl)-6-methyl phenyl]propanoate (45k) (40 mg, 0.102 mmol, 75%) as a colorless gum.
$^1$H NMR (300 MHz, CDCl$_3$) δ –0.15--0.07 (m, 1H), 0.13-0.32 (m, 2H), 0.52-0.72 (m, 5H), 1.24-1.39 (m, 2H), 1.41-1.50 (m, 1H), 2.00-2.14 (m, 3H), 2.22 (s, 3H), 2.76-

2.83 (m, 2H), 3.62 and 3.64 (s, 3H), 3.86-3.95 (m, 1H), 4.22-4.25 (m, 2H), 6.69-6.72 (m, 1H), 6.78-6.90 (m, 2H), 6.94-7.04 (m, 2H).

MS m/z ([M+H]⁺) 391.

Step 12: Preparation of 3-cyclopropyl-2-[3-cyclopropyl-2-(3,4-dihydro-2H-1-benzopyran-6-yl)-6-methylphenyl]propanoic acid (Example 45)

Using the procedure described in example 1, step 12, methyl 3-cyclopropyl-2-[3-cyclopropyl-2-(3,4-dihydro-2H-1-benzopyran-6-yl)-6-methylphenyl]propanoate (40 mg, 0.10 mmol) is converted by reaction with lithium hydroxide (20 mg, 0.82 mmol) into 3-cyclopropyl-2-[3-cyclopropyl-2-(3,4-dihydro-2H-1-benzopyran-6-yl)-6-methylphenyl]propanoic acid (27.1 mg, 0.072 mmol, 69%) (Example 45) as a white amorphous solid after purification by preparative TLC (cyclohexane/ethyl acetate 75/25).

¹H NMR (400 MHz, CDCl₃) δ −0.30−−0.21 (m, 1H), −0.15−−0.09 (m, 1H), 0.15-0.30 (m, 2H), 0.52-0.70 (m, 5H), 1.29-1.49 (m, 2H), 1.98-2.11 (m, 3H), 2.27 and 2.28 (s, 3H), 2.72-2.83 (m, 2H), 3.91-4.01 (m, 1H), 4.20-4.26 (m, 2H), 6.70-6.72 (m, 1H), 6.78-6.90 (m, 2H), 6.95-7.04 (m, 2H).

MS m/z ([M+H]⁺) 377, ([M+Na]⁺) 399.

MS m/z ([M−H]⁻) 375.

Example 46

Synthesis of 2-[3-cyclopropyl-2-(3,4-dihydro-2H-1-benzopyran-6-yl)-6-methylphenyl]-4-methylpentanoic acid

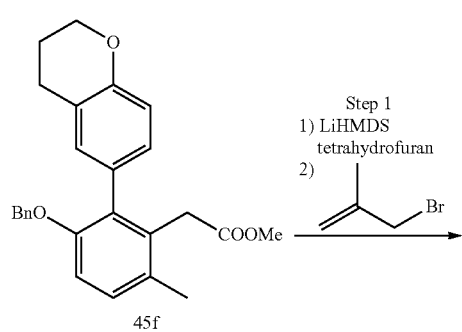

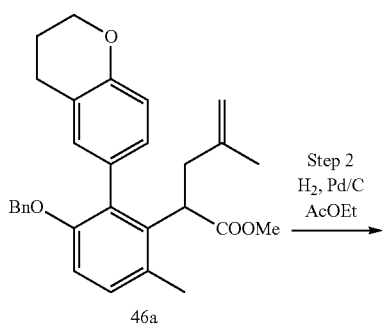

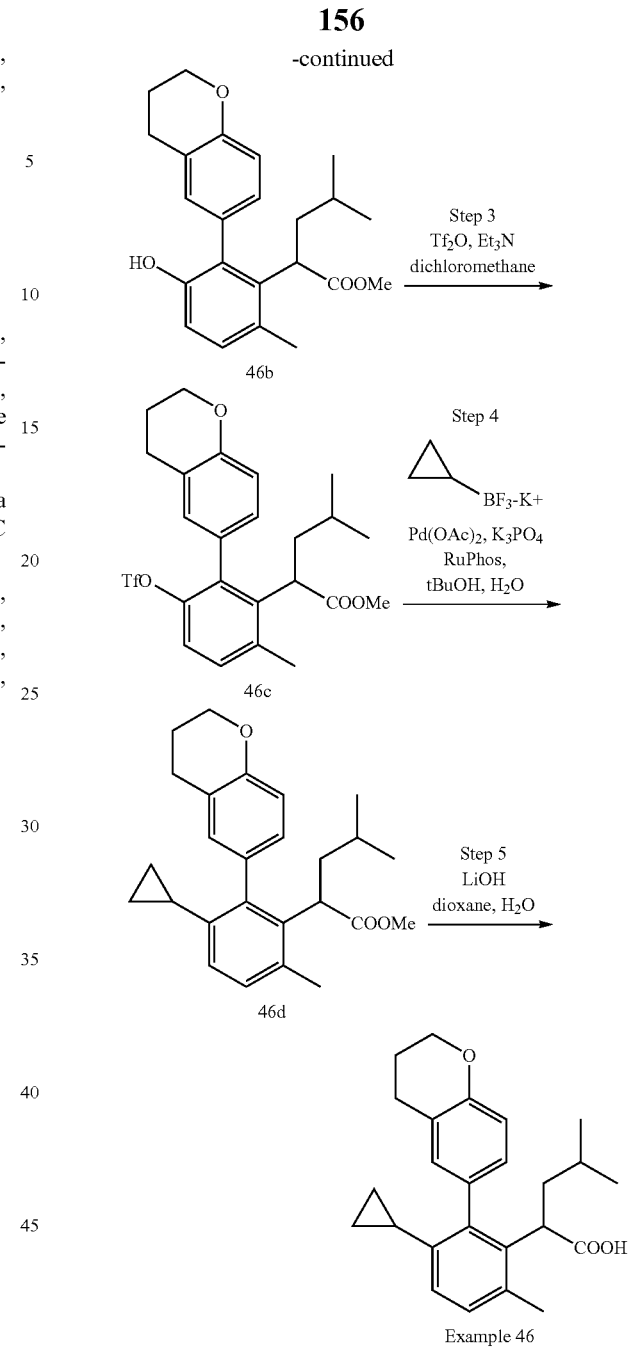

Step 1: Preparation of Intermediate methyl 2-[3-(benzyloxy)-2-(3,4-dihydro-2H-1-benzopyran-6-yl)-6-methylphenyl]-4-methylpent-4-enoate (46a)

Using the procedure described in example 45, step 7, methyl 2-[3-(benzyloxy)-2-(3,4-dihydro-2H-1-benzopyran-6-yl)-6-methylphenyl]acetate (45f) (146 mg, 0.362 mmol) is converted by reaction with 3-bromo-2-methyl-1-propene (365 L, 3.62 mmol) into methyl 2-[3-(benzyloxy)-2-(3,4-dihydro-2H-1-benzopyran-6-yl)-6-methylphenyl]-4-methylpent-4-enoate (46a) (114 mg, 0.25 mmol, 69%) as a colorless oil after purification by preparative TLC (cyclohexane/ethyl acetate 90/10).

¹H NMR (400 MHz, CDCl₃) δ 1.37 and 1.38 (s, 3H), 2.01-2.08 (m, 2H), 2.19-2.24 (m, 4H), 2.68-2.81 (m, 2H), 2.84-2.91 (m, 1H), 3.64 and 3.66 (s, 3H), 4.01-4.08 (m, 1H), 4.19-4.25 (m, 2H), 4.39 (m, 1H), 4.59 (m, 1H), 4.91-5.00 (m, 2H), 6.79-7.06 (m, 5H), 7.13-7.15 (m, 2H), 7.20-7.29 (m, 3H).

MS m/z ([M+H]$^+$) 457.
MS m/z ([M−H]$^−$) 455.

Step 2: Preparation of Intermediate methyl 2-[2-(3,4-dihydro-2H-1-benzopyran-6-yl)-3-hydroxy-6-methylphenyl]-4-methylpentanoate (46b)

A suspension of methyl 2-[3-(benzyloxy)-2-(3,4-dihydro-2H-1-benzopyran-6-yl)-6-methylphenyl]-4-methylpent-4-enoate (46a) (114 mg, 0.25 mmol) and 10% palladium on carbon (12 mg) in ethyl acetate (4.3 mL) was stirred at room temperature under hydrogen atmosphere (5 bars) for 24 hours. The mixture was filtered over Millipore and concentrated in vacuo. to provide methyl 2-[2-(3,4-dihydro-2H-1-benzopyran-6-yl)-3-hydroxy-6-methylphenyl]-4-methylpentanoate (46b) (97 mg, 0.25 mmol, 100%) as a colorless oil used in the next step without further purification.

$^1$H NMR (400 MHz, CDCl$_3$) δ 0.53-060 (m, 3H), 0.69 (d, J=6.6 Hz, 3H), 1.31-1.39 (m, 1H), 1.40-1.51 (m, 1H), 1.95-2.11 (m, 2H), 2.23 and 2.24 (s, 3H), 2.74-2.89 (m, 2H), 3.66 and 3.68 (s, 3H), 3.74-3.81 (m, 1H), 4.24-4.30 (m, 2H), 4.67 and 4.69 (s, 1H), 6.83-6.85 (m, 1H), 6.90-6.98 (m, 2H), 7.04-7.11 (m, 2H).

MS m/z ([M−H]$^−$) 367.

Step 3: Preparation of Intermediate methyl 2-[2-(3,4-dihydro-2H-1-benzopyran-6-yl)-6-methyl-3-(trifluoromethanesulfonyloxy)phenyl]-4-methylpentanoate (46c)

Using the procedure described in example 1, step 10, methyl 2-[2-(3,4-dihydro-2H-1-benzopyran-6-yl)-3-hydroxy-6-methylphenyl]-4-methylpentanoate (46b) (97 mg, 0.25 mmol) is converted into methyl 2-[2-(3,4-dihydro-2H-1-benzopyran-6-yl)-6-methyl-3-(trifluoro methanesulfonyloxy)phenyl]-4-methylpentanoate (46c) (120 mg, 0.24 mmol, 96%) as a colorless oil after purification by preparative TLC (cyclohexane/ethyl acetate 90/10).

$^1$H NMR (400 MHz, CDCl$_3$) δ 0.55-059 (m, 3H), 0.64-0.66 (m, 3H), 1.22-1.43 (m, 3H), 1.98-2.12 (m, 2H), 2.28 and 2.29 (s, 3H), 2.67-2.86 (m, 2H), 3.65 and 3.66 (s, 3H), 3.88-3.93 (m, 1H), 4.20-4.25 (m, 2H), 6.80-6.89 (m, 2H), 6.94-7.00 (m, 1H), 7.12-7.18 (m, 2H). MS m/z ([M−H]$^−$) 499.

Step 4: Preparation of Intermediate methyl 2-[3-cyclopropyl-2-(3,4-dihydro-2H-1-benzopyran-6-yl)-6-methylphenyl]-4-methylpentanoate (46d)

A degassed solution of methyl 2-[2-(3,4-dihydro-2H-1-benzopyran-6-yl)-6-methyl-3-(trifluoromethanesulfonyloxy)phenyl]-4-methylpentanoate (46c) (120 mg, 0.24 mmol), potassium cyclopropyltrifluoroboronate (46 mg, 0.31 mmol), 2-dicyclohexylphosphino-2',6'-diisopropoxybiphenyl (RuPhos) (0.6 mg, 0.012 mmol), potassium phosphate tribasic monohydrate (342 mg, 1.49 mmol) and palladium(II) acetate (0.13 mg, 0.006 mmol) in a 1/1 mixture of tert-butanol/water (0.6 mL) was heated at 105° C. for 4 hours. Water (3 mL) was added. The aqueous layer was extracted with cyclohexane (2×6 mL). The combined organic layers were washed with brine (3 mL), dried over sodium sulfate and concentrated in vacuo. The residue was purified by preparative TLC (dichloromethane 100%) to provide methyl 2-[3-cyclopropyl-2-(3,4-dihydro-2H-1-benzopyran-6-yl)-6-methylphenyl]-4-methyl pentanoate (46d) (75 mg, 0.19 mmol, 80%) as a colorless gum.

$^1$H NMR (400 MHz, CDCl$_3$) δ 0.53-0.71 (m, 10H), 1.18-1.30 (m, 1H), 1.41-1.53 (m, 2H), 1.94-2.15 (m, 3H), 2.22 and 2.23 (s, 3H), 2.69-2.85 (m, 2H), 3.61 and 3.63 (s, 3H), 3.79-3.92 (m, 1H), 4.19-4.24 (m, 2H), 6.69-6.72 (m, 1H), 6.78-6.91 (m, 2H), 6.96-7.03 (m, 2H).

MS m/z ([M+Na]$^+$) 415.

Step 5: Preparation of 2-[3-cyclopropyl-2-(3,4-dihydro-2H-1-benzopyran-6-yl)-6-methylphenyl]-4-methylpentanoic acid (Example 46)

Using the procedure described in example 1, step 12, methyl 2-[3-cyclopropyl-2-(3,4-dihydro-2H-1-benzopyran-6-yl)-6-methylphenyl]-4-methylpentanoate (46d) (75 mg, 0.19 mmol) is converted into 2-[3-cyclopropyl-2-(3,4-dihydro-2H-1-benzopyran-6-yl)-6-methylphenyl]-4-methylpentanoic acid (Example 46) (72 mg, 0.19 mmol, 100%) as a white amorphous solid without further purification.

$^1$H NMR (400 MHz, CDCl$_3$) δ 0.54-0.73 (m, 10H), 1.20-1.33 (m, 1H), 1.41-1.52 (m, 2H), 1.95-2.13 (m, 3H), 2.29 (s, 3H), 2.67-2.83 (m, 2H), 3.86-3.95 (m, 1H), 4.19-4.24 (m, 2H), 6.71-6.73 (m, 1H), 6.77-6.92 (m, 2H), 6.98-7.05 (m, 2H).

MS m/z ([M+H]$^+$) 379.
MS m/z ([M−H]$^−$) 377.

Example 47

Synthesis of (2-chroman-6-yl-3-cyclopropyl-6-methyl-phenyl)-(2,2-difluoro-cyclopropoxy)-acetic acid

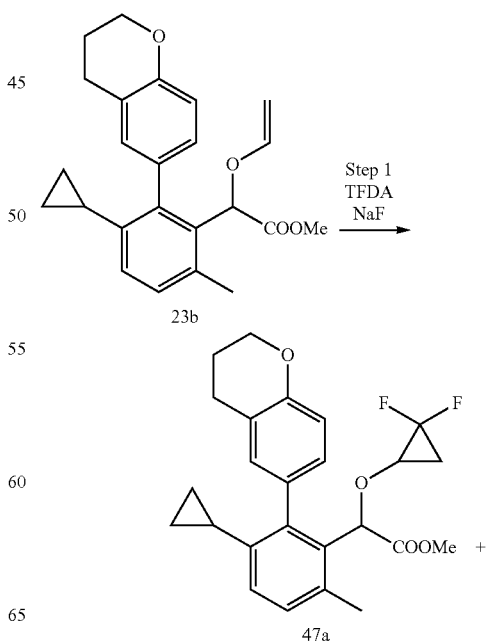

159

-continued

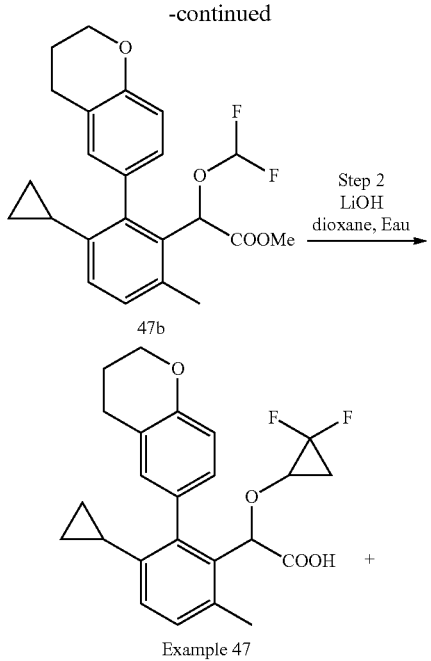

Example 47

Step 1: Preparation of Intermediate (2-chroman-6-yl-3-cyclopropyl-6-methyl-phenyl)-(2,2-difluoro-cyclopropoxy)-acetic acid methyl ester (47a)

In a dry reactor with a magnetic stirrer was charged (2-chroman-6-yl-3-cyclopropyl-6-methyl-phenyl)-vinyloxy-acetic acid methyl ester (23b) (100 mg, 0.264 mmol) and sodium fluoride (1 mg, 0.024 mmol). Mixture was heated at 105° C. under nitrogen atmosphere and Trimethylsilyl fluorosulfonyldifluoroacetate (80 μL, 0.396 mmol) was added slowly over a period of 2 hours. Upon the completion of the addition, the reaction mixture was stirred 2 hours, cooled to room temperature and diluted with ethyl acetate (3 mL). The solution was washed with water and dried over sodium sulfate. Solvent was evaporated and the crude product was purified by preparative TLC on silica gel (cyclohexane/ethyl acetate 80/20) to provide a unseparated mixture (30 mg) of 2-chroman-6-yl-3-cyclopropyl-6-methyl-phenyl)-(2,2-difluoro-cyclopropoxy)-acetic acid methyl ester (47a), the desired product, contaminated by (2-chroman-6-yl-3-cyclopropyl-6-methyl-phenyl)-difluoromethoxy-acetic acid methyl ester (47b) with a 60/40 ratio. This mixture will be used for the next step without further purification.

(47a) MS m/z ([M+Na]$^+$) 451.

(47b) MS m/z ([M+Na]$^+$) 425.

160

Step 2: Preparation of (2-chroman-6-yl-3-cyclopropyl-6-methyl-phenyl)-(2,2-difluoro-cyclopropoxy)-acetic acid (Example 47)

Using the procedure described in example 1, step 12, the unseparated mixture (30 mg) of 2-chroman-6-yl-3-cyclopropyl-6-methyl-phenyl)-(2,2-difluoro-cyclopropoxy)-acetic acid methyl ester (47a) contaminated by (2-chroman-6-yl-3-cyclopropyl-6-methyl-phenyl)-difluoromethoxy-acetic acid methyl ester (47b) with a 60/40 ratio is converted, after purification by preparative TLC (dichloromethane/Methanol 95/5) into an unseparated mixture of 2-chroman-6-yl-3-cyclopropyl-6-methyl-phenyl)-(2,2-difluoro-cyclopropoxy)-acetic acid (Example 47) contaminated by (2-chroman-6-yl-3-cyclopropyl-6-methyl-phenyl)-difluoromethoxy-acetic acid (47c) with a 69/31 ratio (13 mg) as a white solid.

(Example 47) MS m/z ([M+Na]$^+$) 451.

(47c) MS m/z ([M+Na]$^+$) 425.

Example 48

Synthesis of 2-[2-chroman-6-yl-3-cyclopropyl-5-(methanesulfonamido)-6-methyl-phenyl]-2-(cyclopropoxy)acetic acid

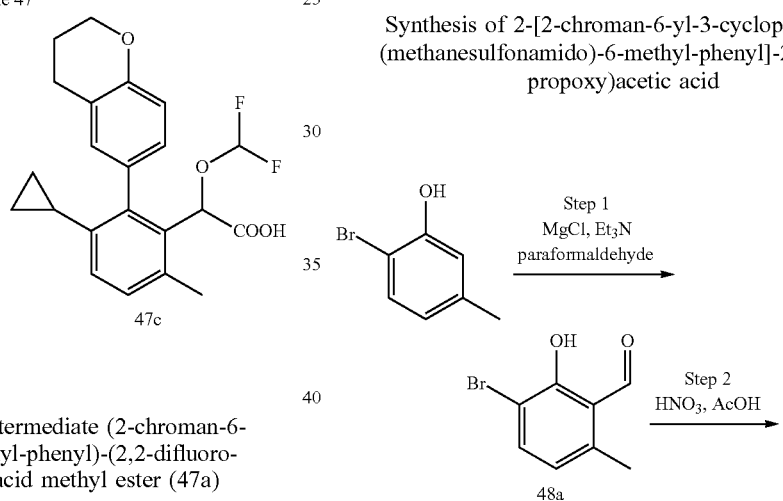

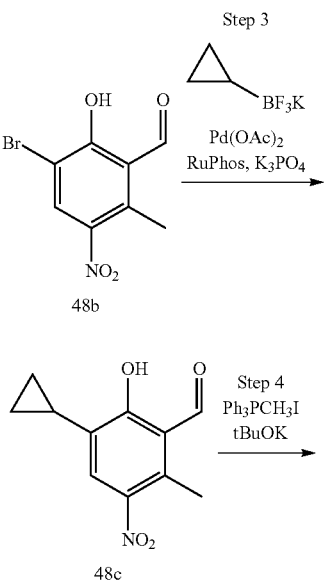

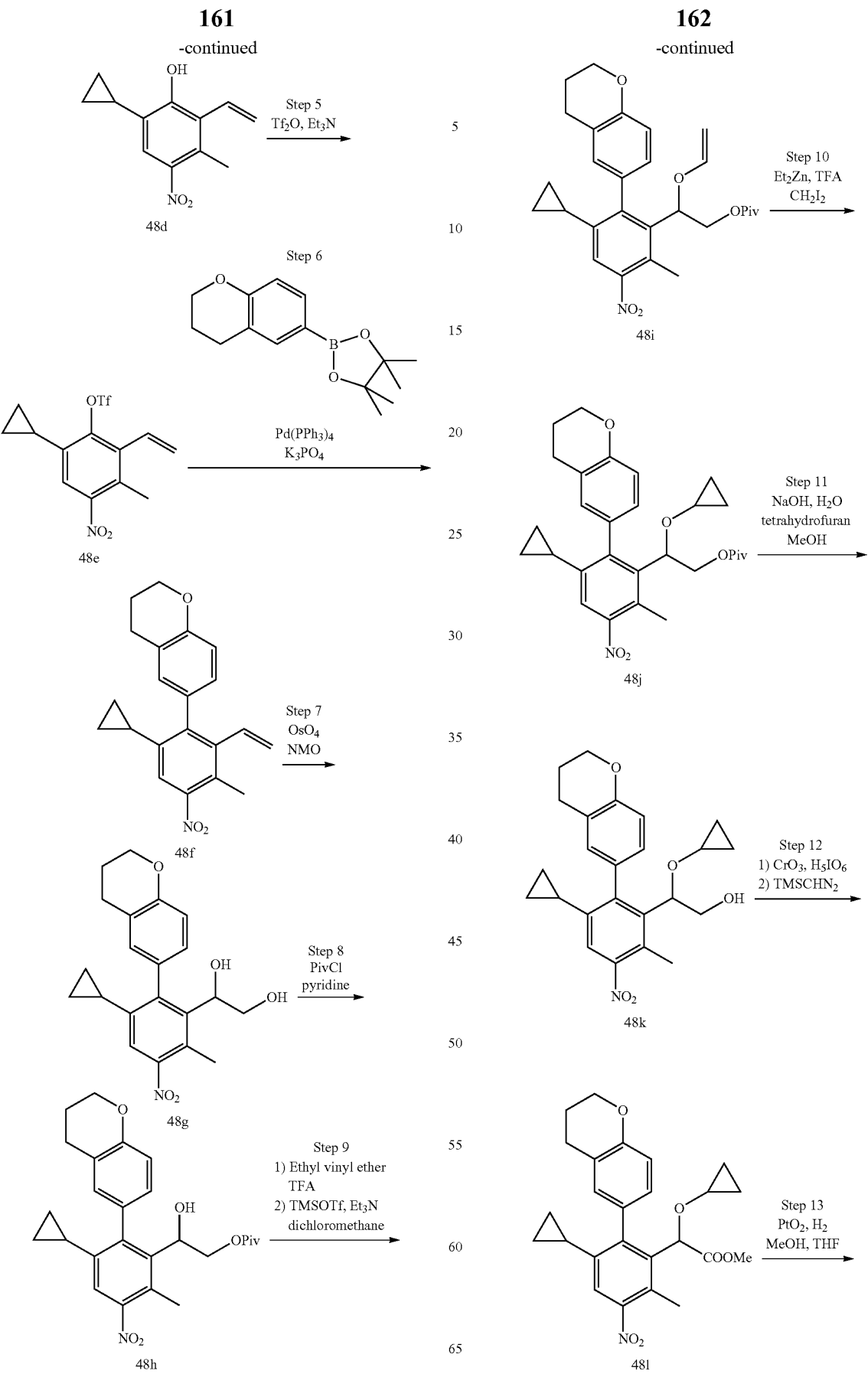

-continued

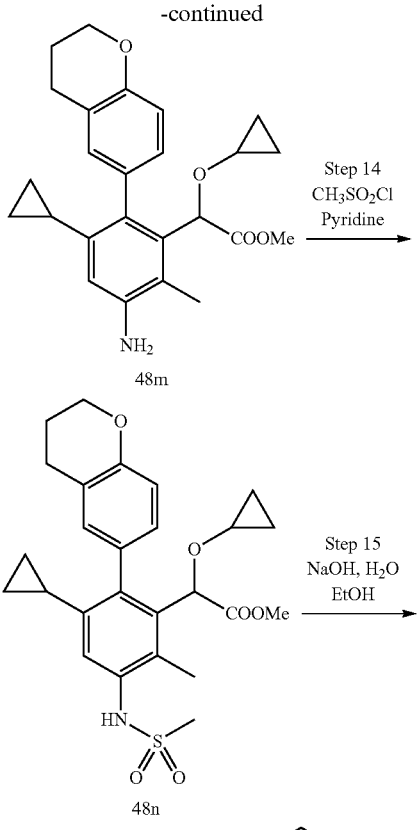

Example 48

Step 1: Preparation of Intermediate 3-bromo-2-hydroxy-6-methylbenzaldehyde (48a)

Triethylamine (27.6 mL, 198 mmol) and magnesium chloride (7.64 g, 80 mmol) were added to a solution of 2-bromo-5-methylphenol (10.0 g, 53 mmol) in acetonitrile (200 mL). After 15 minutes stirring at room temperature, paraformaldehyde (10.76 g, 358 mmol) was added and the reaction mixture was heated at 80° C. for 8 hours and concentrated in vacuo. The residue was dissolved in hydrochloric acid 10% (200 mL) and stirred at room temperature for 30 minutes. Ethyl acetate (200 mL) was added and the layers were separated. The organic layer was dried over sodium sulfate and concentrated in vacuo. The residue was purified through a cake of silica (cyclohexane/ethyl acetate 80/20) to provide 3-bromo-2-hydroxy-6-methylbenzaldehyde (48a) (7.33 g, 34 mmol, 64%).

$^1$H NMR (400 MHz, CDCl$_3$) δ 2.59 (s, 3H), 6.65 (d, J=8.0 Hz, 1H), 7.63 (d, J=8.0 Hz, 1H), 10.27 (s, 1H), 12.53 (s, 1H). MS m/z ([M+H]$^+$) 215/217.

Step 2: Preparation of Intermediate 3-bromo-2-hydroxy-6-methyl-5-nitrobenzaldehyde (48b)

A solution of nitric acid (1.60 mL, 37.49 mmol) in acetic acid (15 mL) was slowly added to a solution of 3-bromo-2-hydroxy-6-methylbenzaldehyde (48a) (7.33 g, 34.08 mmol) in acetic acid (73 mL). The reaction mixture was stirred for 20 minutes at room temperature. Water was added (50 mL), the precipitate was filtered off and rinsed with water. The solid was then dried under reduced pressure in the presence of phosphorus pentoxide to provide 3-bromo-2-hydroxy-6-methyl-5-nitrobenzaldehyde (48b) (5.65 g, 21.73 mmol, 64%), which was used without further purification.

$^1$H NMR (300 MHz, CDCl$_3$) δ 2.80 (s, 3H), 8.37 (s, 1H), 10.42 (s, 1H), 13.31 (s, 1H). MS m/z ([M–H]$^-$) 258/260.

Step 3: Preparation of Intermediate 3-cyclopropyl-2-hydroxy-6-methyl-5-nitro-benzaldehyde (48c)

A solution of 3-bromo-2-hydroxy-6-methyl-5-nitrobenzaldehyde (48b) (2.00 g, 7.7 mmol), potassium cyclopropyltrifluoroborate (2.96 g, 20 mmol), potassium phosphate tribasic monohydrate (5.85 g, 25.4 mmol), and 2-dicyclohexylphosphino-2',6'-diisopropoxy biphenyl (359.3 mg, 0.77 mmol) in a mixture of toluene (24 mL) and water (8 mL) was bubbled with nitrogen for 5 minutes. Palladium (II) acetate (86.4 mg, 0.384 mmol) was added and the reaction mixture was heated at 100° C. overnight. Water (10 mL) was added. The aqueous layer was extracted with ethyl acetate (3×50 mL). The combined organic layers were washed with brine (20 mL), dried over sodium sulfate and concentrated in vacuo. The residue purified by flash chromatography on silica gel (cyclohexane/ethyl acetate 100/0 to 95/5) to provide 3-cyclopropyl-2-hydroxy-6-methyl-5-nitrobenzaldehyde (48c) (1.316 g, 5.95 mmol, 77%) as a pale yellow solid.

$^1$H NMR (400 MHz, CDCl$_3$) δ 0.69-0.75 (m, 2H), 1.02-1.08 (m, 2H), 2.14-2.23 (m, 1H), 2.77 (s, 3H), 7.63 (s, 1H), 10.44 (s, 1H), 13.07 (s, 1H).
MS m/z ([M+H]$^+$) 222.
MS m/z ([M–H]$^-$) 220.

Step 4: Preparation of Intermediate 6-cyclopropyl-3-methyl-4-nitro-2-vinyl-phenol (48d)

To a suspension of methyltriphenylphosphonium iodide (4.05 g, 10 mmol) in anhydrous tetrahydrofuran (10 mL) at 0° C. under nitrogen atmosphere was dropwise added a potassium tert-butoxide solution 1M in tetrahydrofuran (21 mL, 21 mmol). The mixture was stirred at 0° C. for 30 minutes before adding a solution of 3-cyclopropyl-2-hydroxy-6-methyl-5-nitro-benzaldehyde (48c) (2.1 g, 9.49 mmol) in anhydrous tetrahydrofuran (20 mL). The mixture was stirred at 0° C. for 45 minutes before adding water (30 mL) and 1M hydrochloric solution until pH 3. The mixture was extracted with ethyl acetate (2×20 mL). The organic layers were dried over sodium sulfate and concentrated in vacuo. The residue was purified by flash chromatography on silica (cyclohexane/ethyl acetate 90/10) then triturated in cyclohexane to provide 6-cyclopropyl-3-methyl-4-nitro-2-vinyl-phenol (48d) (1.29 g, 5.88 mmol, 62%) as an orange solid.

¹H NMR (400 MHz, CDCl₃) δ 0.56-0.82 (m, 2H), 0.90-1.09 (m, 2H), 1.97-2.04 (m, 1H), 2.44 (s, 3H), 5.61 (dd, J=18.1 Hz, J=1.6 Hz, 1H), 5.85 (dd, J=11.5 Hz, J=1.6 Hz, 1H), 6.24 (s, 1H), 6.67 (dd, J=18.2 Hz, J=11.5 Hz, 1H), 7.53 (s, 1H).
MS m/z ([M+H]⁺) 220.
MS m/z ([M−H]⁻) 218.

Step 5: Preparation of Intermediate (6-cyclopropyl-3-methyl-4-nitro-2-vinyl-phenyl) trifluoromethanesulfonate (48e)

To a solution of 6-cyclopropyl-3-methyl-4-nitro-2-vinyl-phenol (48d) (1.29 g, 5.88 mmol) in anhydrous dichloromethane (15 mL) at 0° C. under nitrogen atmosphere were successively added triethylamine (1.23 mL, 8.82 mmol) and triflic anhydride (1.1 mL, 6.48 mmol). The mixture was stirred at room temperature for 30 minutes. Water (15 mL) was added. The aqueous layer was extracted with dichloromethane (15 mL). The organic layers were washed with a saturated solution of sodium hydrogenocarbonate (15 mL), dried over sodium sulfate and concentrated in vacuo to provide (6-cyclopropyl-3-methyl-4-nitro-2-vinyl-phenyl) trifluoromethanesulfonate (48e) (2.1 g, 5.88 mmol, 100%) as a brown oil which was used without further purification.
¹H NMR (400 MHz, CDCl₃) δ 0.78-0.82 (m, 2H), 1.13-1.19 (m, 2H), 2.10-2.17 (m, 1H), 2.40 (s, 3H), 5.50 (dd, J=18.0 Hz, J=1.2 Hz, 1H), 5.81 (dd, J=11.6 Hz, J=1.2 Hz, 1H), 6.62 (dd, J=18.0 Hz, J=11.6 Hz, 1H), 7.34 (s, 1H).

Step 6: Preparation of Intermediate 6-(6-cyclopropyl-3-methyl-4-nitro-2-vinyl-phenyl)chromane (48f)

In a sealed round bottom flask, a solution of (6-cyclopropyl-3-methyl-4-nitro-2-vinyl-phenyl) trifluoromethanesulfonate (48e) (1.86 g, 5.29 mmol), 6-(4,4,5,5-tetramethyl-1,3,2-dioxaborolan-2-yl)chroman (1.51 g, 5.82 mmol) in toluene (6 mL) and water (2 mL) was degassed by bubbling argon for 10 minutes. Potassium phosphate (2.44 g, 10.59 mmol) and tetrakis(triphenylphosphine)palladium (0) (306 mg, 0.26 mmol) were added and the mixture was heated at 120° C. overnight. The mixture was diluted with toluene (20 mL) and washed with water (10 mL) and brine (10 mL). The organic layer was dried over sodium sulfate and concentrated in vacuo. The residue was purified by flash chromatography on silica gel (cyclohexane/dichloromethane 50/50) to provide 6-(6-cyclopropyl-3-methyl-4-nitro-2-vinyl-phenyl)chromane (48f) (1.63 g, 4.86 mmol, 91%) as a yellow oil.
¹H NMR (400 MHz, CDCl₃) δ 0.60-0.68 (m, 2H), 0.76-0.82 (m, 2H), 1.55-1.62 (m, 1H), 2.01-2.08 (m, 2H), 2.44 (s, 3H), 2.79 (t, J=6.5 Hz, 2H), 4.23 (dd, J=5.9 Hz, J=4.5 Hz, 2H), 5.07 (dd, J=17.9 Hz, J=1.7 Hz, 1H), 5.37 (dd, J=11.5 Hz, J=1.7 Hz, 1H), 6.31 (dd, J=17.9 Hz, J=11.5 Hz, 1H), 6.76-6.87 (m, 3H), 7.21 (s, 1H).
MS m/z ([M+H]⁺) 336.

Step 7: Preparation of Intermediate 1-(2-chroman-6-yl-3-cyclopropyl-6-methyl-5-nitro-phenyl)ethane-1,2-diol (48g)

To a solution of 6-(6-cyclopropyl-3-methyl-4-nitro-2-vinyl-phenyl)chromane (48f) (1.77 g, 5.27 mmol) in acetone (22.5 mL) and water (2.5 mL) were added a solution of osmium tetroxide 4 wt % in water (0.80 mL, 0.13 mmol) and 4-methylmorpholine N-oxide (1.30 g, 11.08 mmol). The mixture was stirred at room temperature for 3 days. A solution of sodium thiosulfate 15% in water was added (20 mL) and the mixture was stirred at room temperature for 30 minutes. The solid was filtered off and washed with water. The solid was dried by co-evaporation of toluene in vacuo. The residue was triturated in tert-butyl methyl ether (5 mL) and filtered to provide 1-(2-chroman-6-yl-3-cyclopropyl-6-methyl-5-nitro-phenyl)ethane-1,2-diol (48g) (1.45 g, 3.92 mmol, 74%) as a white solid.
¹H NMR (300 MHz, DMSO-d₆) δ 0.51-0.78 (m, 4H), 1.29-1.38 (m, 1H), 1.90-2.02 (m, 2H), 2.48 (s, 3H), 2.73-2.82 (m, 2H), 3.34-3.44 (m, 1H), 3.55-3.64 (m, 1H), 4.15-4.22 (m, 2H), 4.60-4.69 (m, 2H), 5.29 (d, J=4.0 Hz, 1H), 6.75-6.93 (m, 3H), 7.16 (s, 1H).
MS m/z ([M+HCOO]⁻) 414.

Step 8: Preparation of Intermediate[2-(2-chroman-6-yl-3-cyclopropyl-6-methyl-5-nitro-phenyl)-2-hydroxy-ethyl]2,2-dimethylpropanoate (48h)

To a suspension of 1-(2-chroman-6-yl-3-cyclopropyl-6-methyl-5-nitro-phenyl)ethane-1,2-diol (48g) (1.45 g, 3.92 mmol) in dichloromethane (20 mL) and pyridine (6.6 mL) was dropwise added pivaloyl chloride (0.73 mL, 5.90 mmol) at room temperature. The mixture was stirred at this temperature for 2 hours and diluted with dichloromethane (20 mL). The mixture was washed with a 1 M hydrochloric acid solution (2×25 mL) and a saturated solution of sodium hydrogenocarbonate (20 mL). The organic layer was dried over sodium sulfate and concentrated in vacuo to provide [2-(2-chroman-6-yl-3-cyclopropyl-6-methyl-5-nitro-phenyl)-2-hydroxy-ethyl]2,2-dimethylpropanoate (48h) (1.92 g, 3.92 mmol, 100%) as a yellow oil containing traces of dichloromethane. The product was used without further purification.
¹H NMR (400 MHz, CDCl₃) δ 0.55-0.65 (m, 2H), 0.71-0.79 (m, 2H), 1.13 and 1.14 (s, 9H), 1.41-1.50 (m, 1H), 2.00-2.10 (m, 2H), 2.31 and 2.39 (d, J=4.2 Hz, 1H), 2.61 (s, 3H), 2.76-2.88 (m, 2H), 4.08-4.26 (m, 3H), 4.38 and 4.47 (dd, J=11.8 Hz, J=8.8 Hz, 1H), 4.97 and 5.02 (dt, J=8.8 Hz, J=3.7 Hz, 1H), 6.79-6.93 (m, 3H), 7.15 (s, 1H).
MS m/z ([M+HCOO]⁻) 498.

Step 9: Preparation of Intermediate[2-(2-chroman-6-yl-3-cyclopropyl-6-methyl-5-nitro-phenyl)-2-vinyloxy-ethyl]2,2-dimethylpropanoate (48i)

To a solution of [2-(2-chroman-6-yl-3-cyclopropyl-6-methyl-5-nitro-phenyl)-2-hydroxy-ethyl]2,2-dimethylpropanoate (48h) (1.78g, 3.92 mmol) in dichloromethane (8 mL) and ethyl vinyl ether (7.5 mL, 78 mmol) was added trifluoroacetic acid (0.09 mL, 1.18 mmol). The mixture was stirred at room temperature for 24 hours before adding a saturated solution of sodium hydrogenocarbonate (10 mL). The mixture was extracted with ethyl acetate (2×20 mL). The organic layer was washed with brine (20 mL), dried over sodium sulfate and concentrated in vacuo. The residue was dissolved in anhydrous dichloromethane (10 mL) cooled at 0° C. and triethylamine (1.64 mL, 11.8 mmol) and trimethylsilyl trifluoromethanesulfonate (1.85 mL, 10.2 mmol) were successively added. The mixture was stirred at room temperature for 2 hours. A 2M solution of sodium hydroxide (10 mL) was added. The mixture was stirred for 10 minutes and the layers were separated. The aqueous layer was extracted with dichloromethane (10 mL). The organic layers were dried over sodium sulfate and concentrated in vacuo. The residue was purified by flash chromatography on silica gel (cyclohexane/dichloromethane 40/60) to provide

[2-(2-chroman-6-yl-3-cyclopropyl-6-methyl-5-nitro-phenyl)-2-vinyloxy-ethyl]2,2-dimethylpropanoate (48i) (1.30 g, 2.71 mmol, 69%) as a yellow oil.

$^1$H NMR (400 MHz, CDCl$_3$) δ 0.58-0.66 (m, 2H), 0.73-0.81 (m, 2H), 1.12 (s, 9H), 1.41-1.51 (m, 1H), 2.00-2.12 (m, 2H), 2.56 (s, 3H), 2.74-2.91 (m, 2H), 3.91-3.97 (m, 1H), 4.13-4.32 (m, 4H), 4.47 and 4.55 (dd, J=12.1 Hz, J=8.9 Hz, 1H), 4.97 and 5.06 (dd, J=8.8 Hz, J=3.1 Hz, 1H), 6.03-6.14 (m, 1H), 6.80-6.89 (m, 3H), 7.15 (s, 1H).

Step 10: Preparation of Intermediate[2-(2-chroman-6-yl-3-cyclopropyl-6-methyl-5-nitro-phenyl)-2-(cyclopropoxy)ethyl]2,2-dimethylpropanoate (48j)

A mixture of dichloromethane (2.6 mL) and a solution of diethylzinc 15 wt % in toluene (4.9 mL, 5.42 mmol) was cooled at 0° C. A solution of trifluoroacetic acid (0.42 mL, 5.42 mmol) in dichloromethane (2.6 mL) was dropwise added. The mixture was stirred at 0° C. for 20 minutes. A solution of diiodomethane (0.44 mL, 5.42 mmol) in dichloromethane (2.6 mL) was dropwise added. The mixture was stirred at 0° C. for 20 minutes then a solution of [2-(2-chroman-6-yl-3-cyclopropyl-6-methyl-5-nitro-phenyl)-2-vinyloxy-ethyl]2,2-dimethylpropanoate (48i) (1.30 g, 2.71 mmol) in dichloromethane (2.6 mL) was dropwise added. The mixture was stirred at room temperature for 45 minutes and a 0.1 M solution of hydrochloric acid (50 mL) was added. The mixture was stirred for 15 minutes. The layers were separated. The aqueous layer was extracted with dichloromethane (2×20 mL). The organic layers were dried over sodium sulfate and concentrated in vacuo. The residue was purified by flash chromatography on silica gel (cyclohexane/ethyl acetate 95/5) to provide[2-(2-chroman-6-yl-3-cyclopropyl-6-methyl-5-nitro-phenyl)-2-(cyclo propoxy)ethyl]2,2-dimethylpropanoate (48j) (1.03 g, 2.08 mmol, 76%) as a yellow oil.

$^1$H NMR (300 MHz, CDCl$_3$) δ 0.21-0.65 (m, 6H), 0.72-0.82 (m, 2H), 1.09 and 1.10 (s, 9H), 1.44-1.55 (m, 1H), 1.99-2.11 (m, 2H), 2.58 (s, 3H), 2.74-2.87 (m, 2H), 3.06-3.17 (m, 1H), 4.02-4.45 (m, 4H), 4.63-4.79 (m, 1H), 6.76-6.92 (m, 3H), 7.14 (s, 1H).

MS m/z ([M+Na]$^+$) 516.

Step 11: Preparation of Intermediate 2-(2-chroman-6-yl-3-cyclopropyl-6-methyl-5-nitro-phenyl)-2-(cyclopropoxy)ethanol (48k)

To a solution of [2-(2-chroman-6-yl-3-cyclopropyl-6-methyl-5-nitro-phenyl)-2-(cyclopropoxy)ethyl]2,2-dimethylpropanoate (48j) (1.03 g, 2.08 mmol) in tetrahydrofuran (9.5 mL) and methanol (1.5 mL) was added a 2 M solution of sodium hydroxide (4.2 mL, 8.4 mmol). The mixture was stirred at 70° C. for 7 hairs. Water (10 mL) was added. Organic solvents were evaporated in vacuo. The solution was extracted with ethyl acetate (2×10 mL). The organic layer was dried over sodium sulfate and concentrated in vacuo. The residue was precipitated in cyclohexane, triturated and filtered to provide 2-(2-chroman-6-yl-3-cyclopropyl-6-methyl-5-nitro-phenyl)-2-(cyclopropoxy)ethanol (48k) (420 mg, 1.02 mmol, 49%). The filtrate was concentrated in vacuo. The residue was triturated in methanol and filtered to provide further 2-(2-chroman-6-yl-3-cyclopropyl-6-methyl-5-nitro-phenyl)-2-(cyclopropoxy)ethanol (48k) (190 mg, 0.46 mmol, 22%).

$^1$H NMR (400 MHz, CDCl$_3$) δ 0.23-0.67 (m, 6H), 0.71-0.81 (m, 2H), 1.40-1.52 (m, 1H), 1.84-2.12 (m, 3H), 2.56 (s, 3H), 2.72-2.90 (m, 2H), 3.11-3.21 (m, 1H), 3.37-3.51 (m, 1H), 3.80-3.92 (m, 1H), 4.20-4.30 (m, 2H), 4.69 and 4.72 (d, J=4.1 Hz, 1H), 6.72-6.92 (m, 3H), 7.12 (s, 1H).

MS m/z ([M+HCOO]$^-$) 454.

Step 12: Preparation of Intermediate methyl 2-(2-chroman-6-yl-3-cyclopropyl-6-methyl-5-nitro-phenyl)-2-(cyclopropoxy)acetate (48l)

To a suspension of 2-(2-chroman-6-yl-3-cyclopropyl-6-methyl-5-nitro-phenyl)-2-(cyclopropoxy)ethanol (48k) (605 mg, 1.48 mmol) in acetonitrile containing 0.75% water (15 mL) at 0° C. was added a solution of periodic acid/chromium trioxide (8.5 mL) in wet acetonitrile [this solution was prepared by dissolving periodic acid (5 g, 21.9 mmol) and chromium trioxide (20 mg, 0.20 mmol) in acetonitrile containing 0.75% water (50 mL)]. The mixture was stirred at 0° C. for 90 minutes. A 1 M hydrochloric acid solution (15 mL) was added. The layers were separated. The aqueous layer was extracted with ethyl acetate (2×15 mL). The unified organic layers were washed with a 15% sodium thiosulfate solution (30 mL), dried over sodium sulfate and concentrated in vacuo. The residue was dissolved in cyclohexane (8 mL) and methanol (2 mL) and cooled at 0° C. A solution of trimethylsilyldiazomethane 2M in diethyl ether (1.5 mL, 3.0 mmol) was dropwise added. The mixture was stirred at 0° C. for 1 hour. A few drops of acetic acid were added. The mixture was diluted with cyclohexane (15 mL) and washed with a saturated solution of sodium hydrogenocarbonate (10 mL). The organic layer was dried over sodium sulfate and concentrated in vacuo. The residue was purified by flash chromatography on silica gel (cyclohexane/ethyl acetate 90/10) to provide methyl 2-(2-chroman-6-yl-3-cyclopropyl-6-methyl-5-nitro-phenyl)-2-(cyclopropoxy)acetate (48l) (496 mg, 1.13 mmol, 76%) as a yellow oil.

$^1$H NMR (400 MHz, CDCl$_3$) δ 0.25-0.41 (m, 3H), 0.48-0.57 (m, 1H), 0.58-0.69 (m, 2H), 0.72-0.84 (m, 2H), 1.47-1.55 (m, 1H), 2.02-2.10 (m, 2H), 2.39 and 2.40 (s, 3H), 2.73-2.89 (m, 2H), 3.32-3.37 and 3.39-3.45 (m, 1H), 3.70 and 3.73 (s, 3H), 4.21-4.30 (m, 2H), 5.10 and 5.15 (s, 1H), 6.83-6.97 (m, 3H), 7.22 and 7.23 (s, 1H).

MS m/z ([M+Na]$^+$) 460.

Step 13: Preparation of Intermediate methyl 2-(5-amino-2-chroman-6-yl-3-cyclopropyl-6-methyl-phenyl)-2-(cyclopropoxy)acetate (48m)

To a solution of methyl 2-(2-chroman-6-yl-3-cyclopropyl-6-methyl-5-nitro-phenyl)-2-(cyclopropoxy)acetate (48l) (496 mg, 1.13 mmol) in methanol (5 mL) and tetrahydrofuran (3 mL) was added platinum oxide (25 mg, 0.06 mmol). The mixture was stirred under hydrogen atmosphere for 3 hours. The mixture was filtered over milipore and the filtrate concentrated in vacuo. The residue was purified by flash chromatography on silica gel (cyclohexane/ethyl acetate 70/30) to provide methyl 2-(5-amino-2-chroman-6-yl-3-cyclopropyl-6-methyl-phenyl)-2-(cyclopropoxy)acetate (48m) (369 mg, 0.90 mmol, 80%) as a white solid after precipitation in methanol.

$^1$H NMR (300 MHz, CDCl$_3$) δ 0.20-0.70 (m, 8H), 1.39-1.51 (m, 1H), 2.00-2.10 (m, 2H), 2.12 and 2.13 (s, 3H), 2.70-2.85 (m, 2H), 3.31-3.45 (m, 1H), 3.60 (bs, 2H), 3.66 and 3.69 (s, 3H), 4.19-4.28 (m, 2H), 5.01 and 5.06 (s, 1H), 6.23 (s, 1H), 6.77-6.83 (m, 1H), 6.88-7.02 (m, 2H).

MS m/z ([M+H]$^+$) 408.

Step 14: Preparation of Intermediate methyl 2-[2-chroman-6-yl-3-cyclopropyl-5-(methanesulfonamido)-6-methyl-phenyl]-2-(cyclopropoxy)acetate (48n)

To a solution of methyl 2-(5-amino-2-chroman-6-yl-3-cyclopropyl-6-methyl-phenyl)-2-(cyclopropoxy)acetate (48m) (55 mg, 0.135 mmol) in anhydrous dichloromethane (1 mL) at 0° C. under nitrogen atmosphere were successively added pyridine (12 μL, 0.148 mmol) and methanesulfonyl chloride (11 μL, 0.140 mmol). The mixture was stirred at room temperature overnight then diluted with dichloromethane (5 mL). The mixture was washed with 1 M hydrochloric acid, dried over sodium sulfate and concentrated in vacuo. The residue was purified by preparative TLC (cyclohexane/ethyl acetate 70/30) to provide methyl 2-[2-chroman-6-yl-3-cyclopropyl-5-(methanesulfonamido)-6-methyl-phenyl]-2-(cyclopropoxy)acetate (48n) (57 mg, 0.117 mmol, 86%) as an yellow oil.

$^1$H NMR (300 MHz, CDCl$_3$) δ 0.21-0.40 (m, 3H), 0.45-0.78 (m, 5H), 1.42-1.54 (m, 1H), 2.00-2.11 (m, 2H), 2.26 (s, 3H), 2.70-2.89 (m, 2H), 3.00 (s, 3H), 3.29-3.43 (m, 1H), 3.67 and 3.70 (s, 3H), 4.18-4.30 (m, 2H), 5.05 and 5.10 (s, 1H), 6.37 (bs, 1H), 6.79-7.01 (m, 4H)

MS m/z ([M–H]$^-$) 484.

Step 15: Preparation of 2-[2-chroman-6-yl-3-cyclopropyl-5-(methanesulfonamido)-6-methyl-phenyl]-2-(cyclopropoxy)acetic acid (Example 48)

To a solution of methyl 2-[2-chroman-6-yl-3-cyclopropyl-5-(methanesulfonamido)-6-methyl-phenyl]-2-(cyclopropoxy)acetate (48n) (57 mg, 0.117 mmol) in ethanol (0.5 mL) was added a 2M sodium hydroxide solution (0.235 mL, 0.47 mmol). The mixture was heated at 100° C. for 3 hours. The mixture was concentrated in vacuo. Water (3 mL) was added to the residue and the solution was extracted with tert-butyl methyl ether (5 mL). The aqueous layer was acidified with 1M hydrochloric acid until pH 3. The mixture was extracted with tert-butyl methyl ether (2×3 mL). The organic layer was dried over sodium sulfate and concentrated in vacuo. The residue was dissolved in ethyl acetate (5 mL) and concentrated in vacuo to provide 2-[2-chroman-6-yl-3-cyclopropyl-5-(methane sulfonamido)-6-methyl-phenyl]-2-(cyclopropoxy)acetic acid (Example 48) (39 mg, 0.082 mmol, 71%) as a beige solid.

$^1$H NMR (300 MHz, CDCl$_3$) δ 0.10-0.42 (m, 4H), 0.46-0.60 (m, 2H), 0.65-0.75 (m, 2H), 1.32-1.46 (m, 1H), 1.90-2.01 (m, 2H), 2.22 (s, 3H), 2.66-2.82 (m, 2H), 2.97 (s, 3H), 3.30-3.41 (m, 1H), 4.14-4.21 (m, 2H), 4.78 and 4.84 (s, 1H), 6.74 and 6.75 (s, 1H), 6.78-6.93 (m, 3H), 8.97 (s, 1H), 12.73 (bs, 1H).

MS m/z ([M+NH$_4$]$^+$) 489.
MS m/z ([M–H]$^-$) 470.

Example 49

Synthesis of 2-(5-acetamido-2-chroman-6-yl-3-cyclopropyl-6-methyl-phenyl)-2-(cyclopropoxy)acetic acid

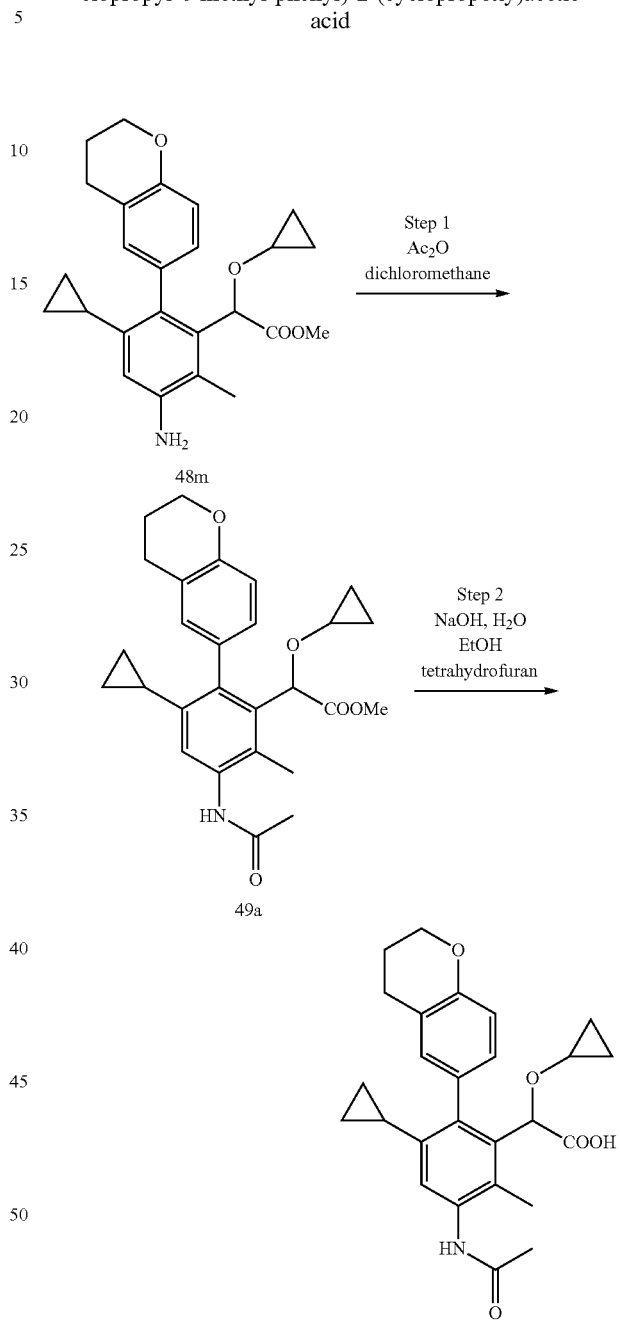

Step 1: Preparation of Intermediate methyl 2-(5-acetamido-2-chroman-6-yl-3-cyclopropyl-6-methyl-phenyl)-2-(cyclopropoxy)acetate (49a)

To a solution of methyl 2-(5-amino-2-chroman-6-yl-3-cyclopropyl-6-methyl-phenyl)-2-(cyclopropoxy)acetate (48a) (50 mg, 0.123 mmol) in anhydrous dichloromethane (1 mL) at 0° C. under nitrogen atmosphere was added acetic anhydride (14 μL, 0.15 mmol). The mixture was stirred at room temperature for 90 minutes before being diluted with dichloromethane (5 mL), washed with a saturated solution of sodium hydrogenocarbonate (5 mL), dried over sodium sulfate and concentrated in vacuo. Cyclohexane (2 mL) was added to the residue to precipitate the product. The mixture was concentrated in vacuo to provide methyl 2-(5-acetamido-2-chroman-6-yl-3-cyclopropyl-6-methyl-phenyl)-2-(cyclo propoxy)acetate (49a) (54 mg, 0.120 mmol, 98%) as a white solid.

$^1$H NMR (300 MHz, CDCl$_3$) δ 0.20-0.80 (m, 8H), 1.39-1.51 (m, 1H), 2.00-2.11 (m, 2H), 2.20 (s, 6H), 2.70-2.88 (m, 2H), 3.28-3.42 (m, 1H), 3.66 and 3.69 (s, 3H), 4.20-4.28 (m, 2H), 5.06 and 5.10 (s, 1H), 6.78-7.00 (m, 4H), 7.30 and 7.31 (s, 1H).

MS m/z ([M+HCOO]$^-$) 494.
MS m/z ([M−H]$^-$) 448.

Step 2: Preparation of 2-(5-acetamido-2-chroman-6-yl-3-cyclopropyl-6-methyl-phenyl)-2-(cyclopropoxy)acetic acid (Example 49)

To a solution of methyl 2-(5-acetamido-2-chroman-6-yl-3-cyclopropyl-6-methyl-phenyl)-2-(cyclopropoxy)acetate (49a) (54 mg, 0.120 mmol) in ethanol (0.8 mL) and tetrahydrofuran (0.2 mL) was added a 2M sodium hydroxide solution (0.48 mL, 0.96 mmol). The mixture was heated at 100° C. for 1 hour. The mixture was concentrated in vacuo. Water (5 mL) was added to the residue and the solution was extracted with ethyl acetate (5 mL). The aqueous layer was acidified with 1M hydrochloric acid until pH 1. The mixture was extracted with tert-butyl methyl ether (5 mL). The organic layer was washed with 1M hydrochloric acid (5 mL), dried over sodium sulfate and concentrated in vacuo. The residue was dissolved in ethyl acetate (5 mL) and filtered over Millipore. Ethyl acetate (1 mL) was added to the residue and heptane was added (5 mL). The precipitate was filtered to provide 2-(5-acetamido-2-chroman-6-yl-3-cyclopropyl-6-methyl-phenyl)-2-(cyclo propoxy)acetic acid (Example 49) (24 mg, 0.055 mmol, 46%) as a beige solid.

$^1$H NMR (400 MHz, DMSO-d$_6$) δ 0.12-0.52 (m, 6H), 0.61-0.72 (m, 2H), 1.32-1.44 (m, 1H), 1.91-2.00 (m, 2H), 2.03 (s, 3H), 2.09 (s, 3H), 2.68-2.83 (m, 2H), 3.32-3.42 (m, 1H), 4.13-4.22 (m, 2H), 4.78 and 4.84 (s, 1H), 6.79-6.83 (m, 2H), 6.85-6.92 (m, 2H), 9.22 (s, 1H), 12.70 (bs, 1H).

MS m/z ([M+NH4]$^+$) 453, MS m/z ([M+H]$^+$) 436.
MS m/z ([M−H]$^-$) 434.

Example 50

Synthesis of 2-[2-chroman-6-yl-3-cyclopropyl-5-(dimethylamino)-6-methyl-phenyl]-2-(cyclopro boxy)acetic acid

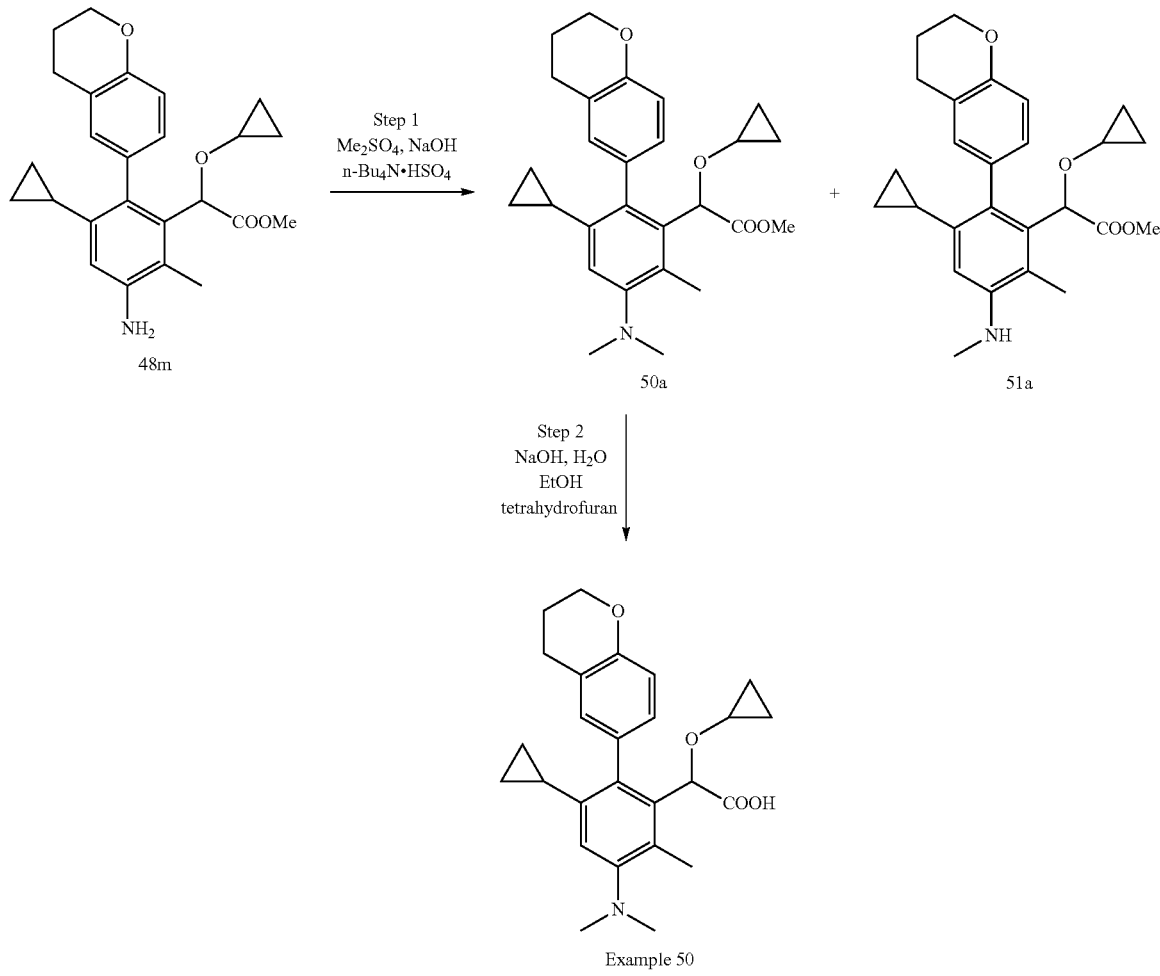 [SMILES: COC(=O)C(OC1CC1)c1c(C)c(N)cc(C2CC2)c1-c1ccc2c(c1)CCCO2 ; COC(=O)C(OC1CC1)c1c(C)c(N(C)C)cc(C2CC2)c1-c1ccc2c(c1)CCCO2 ; CNc1cc(C2CC2)c(-c2ccc3c(c2)CCCO3)c(C(OC2CC2)C(=O)OC)c1C ; Cc1c(N(C)C)cc(C2CC2)c(-c2ccc3c(c2)CCCO3)c1C(OC1CC1)C(=O)O]

Example 50

Step 1: Preparation of Intermediate methyl 2-[2-chroman-6-yl-3-cyclopropyl-5-(dimethylamino)-6-methyl-phenyl]-2-(cyclopropoxy)acetate (50a)

To a solution of methyl 2-(5-amino-2-chroman-6-yl-3-cyclopropyl-6-methyl-phenyl)-2-(cyclopropoxy)acetate (48m) (50 mg, 0.123 mmol) in toluene (1 mL) and sodium hydroxide 30% (1 mL) were added tetrabutylammonium hydrogensulfate (4 mg, 0.01 mmol) and dimethyl sulfate (13 µL, 0.13 mmol). The mixture was stirred at room temperature for 7 hours. Dimethyl sulfate (20 µL, 0.21 mmol) was added and the mixture was stirred overnight. The mixture was diluted with toluene (5 mL), washed with water (5 mL), brine (5 mL), dried over sodium sulfate and concentrated in vacuo. The residue was purified by preparative TLC (cyclohexane/ethyl acetate 70/30) to provide methyl 2-[2-chroman-6-yl-3-cyclopropyl-5-(dimethylamino)-6-methyl-phenyl]-2-(cyclopropoxy)acetate (50a) (8 mg, 0.018 mmol, 15%) and methyl 2-[2-chroman-6-yl-3-cyclopropyl-6-methyl-5-(methylamino)phenyl]-2-(cyclopropoxy)acetate (51a) (30 mg, 0.071 mmol, 57%).

(50a) $^1$H NMR (300 MHz, CDCl$_3$) δ 0.19-0.41 (m, 3H), 0.45-0.73 (m, 5H), 1.44-1.56 (m, 1H), 2.00-2.10 (m, 2H), 2.27 and 2.28 (s, 3H), 2.66 (s, 6H), 2.74-2.83 (m, 2H), 3.29-3.36 and 3.38-3.45 (m, 1H), 3.67 and 3.70 (s, 3H), 4.19-4.28 (m, 2H), 5.06 and 5.11 (s, 1H), 6.62 (s, 1H), 6.78-6.85 (m, 1H), 6.88-7.04 (m, 2H).

MS m/z ([M+H]$^+$) 436.

(51a) $^1$H NMR (300 MHz, CDCl$_3$) 0.20-0.75 (m, 8H), 1.46-1.58 (m, 1H), 2.00-2.12 (m, 5H), 2.70-2.87 (m, 2H), 2.88 (s, 3H), 3.31-3.45 (m, 1H), 3.65 and 3.68 (s, 3H), 4.19-4.28 (m, 2H), 5.03 and 5.08 (s, 1H), 6.18 (s, 1H), 6.67-6.84 (m, 1H), 6.89-7.04 (m, 2H).

MS m/z ([M+H]$^+$) 422.

Step 2: Preparation of 2-[2-chroman-6-yl-3-cyclopropyl-5-(dimethylamino)-6-methyl-phenyl]-2-(cyclopropoxy)acetic acid (Example 50)

To a solution of methyl 2-[2-chroman-6-yl-3-cyclopropyl-5-(dimethylamino)-6-methyl-phenyl]-2-(cyclopropoxy) acetate (50a) (8 mg, 0.018 mmol) in ethanol (0.4 mL) and tetrahydrofuran (0.1 mL) was added a 2M sodium hydroxide solution (75 µL, 0.15 mmol). The mixture was heated at 70° C. for 1 hour. The mixture was concentrated in vacuo. Water (5 mL) was added to the residue and the solution was extracted with ethyl acetate (5 mL). The aqueous layer was acidified with 1M hydrochloric acid until pH 4. The mixture was extracted with ethyl acetate (2×5 mL), dried over sodium sulfate and concentrated in vacuo to provide 2-[2-chroman-6-yl-3-cyclopropyl-5-(dimethylamino)-6-methyl-phenyl]-2-(cyclopropoxy)acetic acid (Example 50) (4.3 mg, 0.010 mmol, 53%) as a beige solid.

$^1$H NMR (400 MHz, CDCl$_3$) δ 0.24-0.31 (m, 1H), 0.33-0.52 (m, 3H), 0.54-0.75 (m, 4H), 1.47-1.56 (m, 1H), 2.00-2.10 (m, 2H), 2.28 and 2.30 (s, 3H), 2.67 (s, 6H), 2.73-2.84 (m, 2H), 3.17-3.30 (m, 1H), 4.19-4.27 (m, 2H), 5.16 and 5.18 (s, 1H), 6.65 (s, 1H), 6.79 and 6.82 (d, J=8.3 Hz, 1H), 6.88-7.07 (m, 2H).

MS m/z ([M+H]$^+$) 422.
MS m/z ([M−H]$^−$) 420.

Example 51

Synthesis of 2-[2-chroman-6-yl-3-cyclopropyl-5-[2-hydroxyethyl(methyl)amino]-6-methyl-phenyl]-2-(cycloproboxy)acetic acid

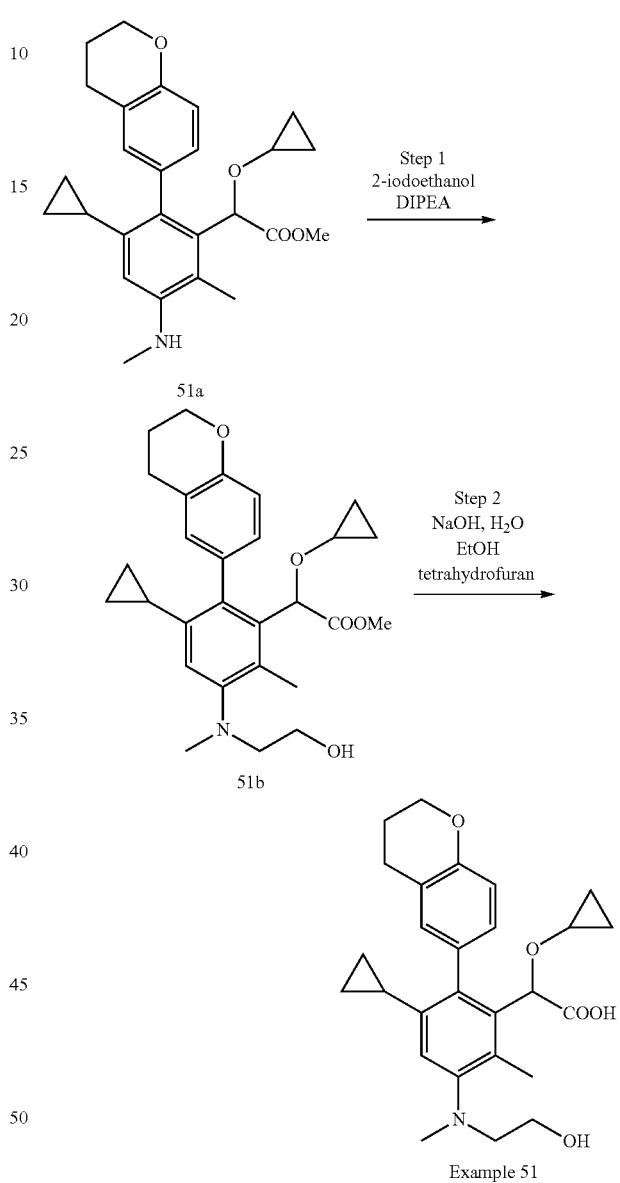

Example 51

Step 1: Preparation of Intermediate methyl 2-[2-chroman-6-yl-3-cyclopropyl-5-[2-hydroxyethyl(methyl)amino]-6-methyl-phenyl]-2-(cyclopropoxy)acetate (51b)

To a solution of methyl 2-[2-chroman-6-yl-3-cyclopropyl-6-methyl-5-(methylamino)phenyl]-2-(cyclopropoxy)acetate (51a) (30 mg, 0.071 mmol) in a mixture of acetonitrile (0.5 mL) and tetrahydrofuran (0.2 mL) was added diisopropylethylamine (12 µL, 0.071 mmol) and 2-iodoethanol (6 µL, 0.071 mmol). The mixture was heated at 100° C. for 6 hours. Diisopropylethylamine (24 µL, 0.142 mmol) and 2-iodoethanol (12 μL, 0.142 mmol) were added. The mixture was heated at 100° C. for 18 hours Diisopropylethylamine (36 μL, 0.213 mmol) and 2-iodoethanol (18 μL, 0.213 mmol) were added and the heating was maintained for 24 hours. The mixture was concentrated in vacuo. The residue was dissolved in ethyl acetate (5 mL), washed with water (5 mL), dried over sodium sulfate and concentrated in vacuo. The residue was purified by preparative TLC (cyclohexane/ethyl acetate 60/40) to provide methyl 2-[2-chroman-6-yl-3-cyclopropyl-5-[2-hydroxyethyl(methyl)amino]-6-methyl-phenyl]-2-(cyclopropoxy)acetate (51b) (21 mg, 0.045 mmol, 63%).

$^1$H NMR (300 MHz, CDCl$_3$) δ 0.18-0.40 (m, 3H), 0.45-0.74 (m, 5H), 1.44-1.56 (m, 1H), 1.98-2.10 (m, 2H), 2.28 and 2.29 (s, 3H), 2.62 (s, 3H), 2.73-2.84 (m, 2H), 3.08 (t, J=5.4 Hz, 2H), 3.28-3.43 (m, 1H), 3.63-3.71 (m, 5H), 4.19-4.27 (m, 2H), 5.06 and 5.11 (s, 1H), 6.66 (s, 1H), 6.78-6.85 (m, 1H), 6.88-7.03 (m, 2H).

MS m/z ([M+H]$^+$) 466.

Step 2: Preparation of 2-[2-chroman-6-yl-3-cyclopropyl-5-[2-hydroxyethyl(methyl)amino]-6-methyl-phenyl]-2-(cyclopropoxy)acetic acid (Example 51)

Using the procedure described in example 50, step 2, the intermediate methyl 2-[2-chroman-6-yl-3-cyclopropyl-5-[2-hydroxyethyl(methyl)amino]-6-methyl-phenyl]-2-(cyclopropoxy)acetate (51b) (21 mg, 0.045 mmol) is converted into 2-[2-chroman-6-yl-3-cyclopropyl-5-[2-hydroxyethyl(methyl)amino]-6-methyl-phenyl]-2-(cyclopropoxy)acetic acid (Example 51) (13 mg, 0.029 mmol, 64%).

$^1$H NMR (300 MHz, CD$_3$OD) δ 0.20-0.41 (m, 4H), 0.51-0.74 (m, 4H), 1.44-1.56 (m, 1H), 1.98-2.08 (m, 2H), 2.31 (s, 3H), 2.70 (s, 3H), 2.76-2.85 (m, 2H), 3.05 and 3.06 (t, J=6.3 Hz, 2H), 3.22-3.30 (m, 1H), 3.65 (t, J=6.3 Hz, 2H), 4.16-4.24 (m, 2H), 5.02 and 5.05 (s, 1H), 6.75 (s, 1H), 6.78 (d, J=8.3 Hz, 1H), 6.88-7.01 (m, 2H).

MS m/z ([M+H]$^+$) 452.
MS m/z ([M−H]$^−$) 450.

Example 52

Synthesis of (2-chroman-6-yl-3-cyclopropyl-4-methanesulfonylamino-6-methyl-phenyl)-cyclopropoxy-acetic acid

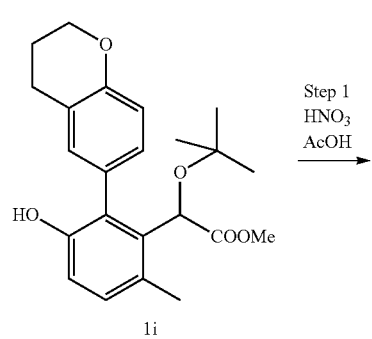

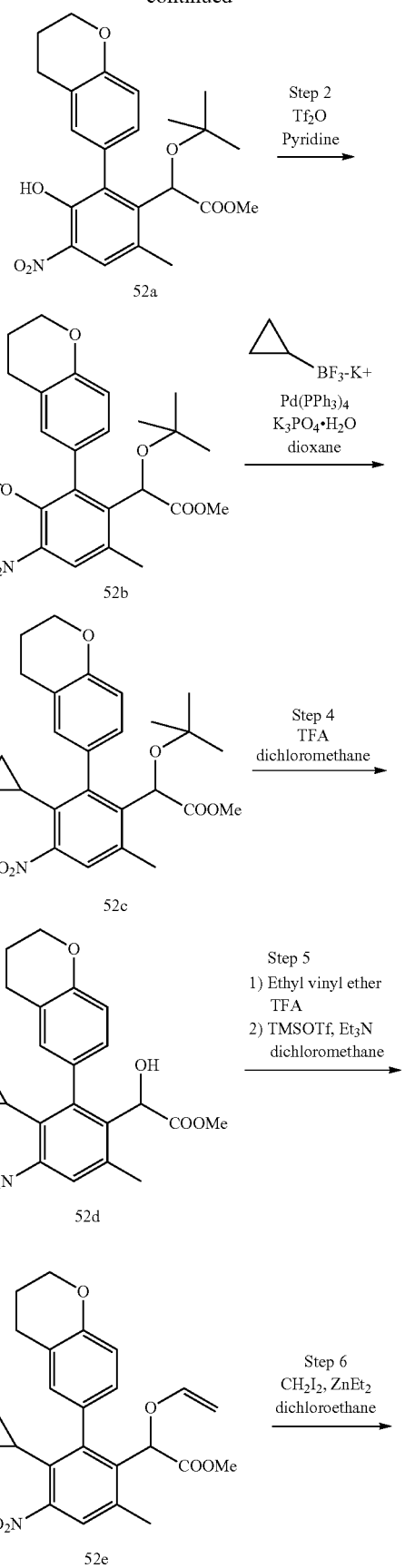

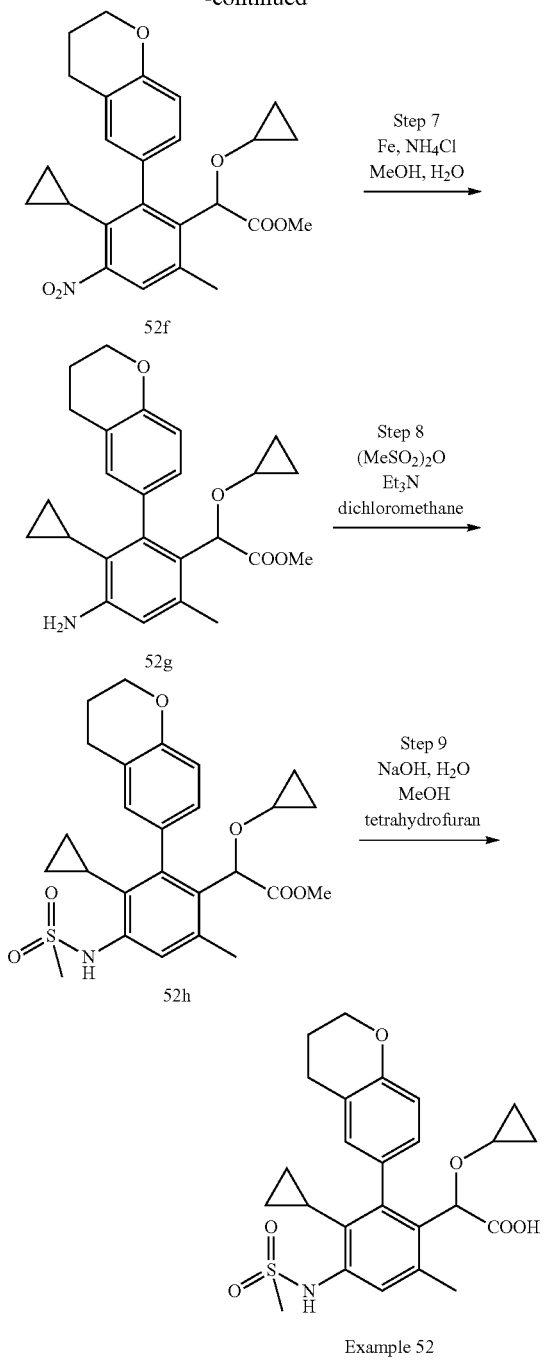

Example 52 filtered and evaporated to give brown oil. The residue was purified by flash chromatography (cyclohexane/ethyl acetate from 100/0 to 97/3) to provide tert-butoxy-(2-chroman-6-yl-3-hydroxy-6-methyl-4-nitro-phenyl)-acetic acid methyl ester (52a) (400 mg, 0.93 mmol, 89%) as a yellow solid.

$^1$H NMR (400 MHz CDCl$_3$) δ 0.96 and 0.97 (s, 9H), 2.02-2.10 (m, 2H), 2.38 and 2.39 (s, 3H), 2.70-2.92 (m, 2H), 3.72 and 3.73 (s, 3H), 4.25 (t, J=5.6 Hz, 2H), 5.11 and 5.12 (s, 1H), 6.89 (d, J=8.4 Hz, 1H), 7.00-7.02 (m, 1H), 7.03-7.07 (m, 1H), 7.89 (s, 1H), 10.81 (s, 1H)

MS m/z ([M−H]$^−$) 428.

Step 2: Preparation of Intermediate tert-butoxy-(2-chroman-6-yl-6-methyl-4-nitro-3-trifluoromethane-sulfonyloxy-phenyl)-acetic acid methyl ester (52b)

To a solution of tert-butoxy-(2-chroman-6-yl-3-hydroxy-6-methyl-4-nitro-phenyl)-acetic acid methyl ester (52a) (400 mg, 0.93 mmol) in 9 mL of pyridine was added, at −20° C., triflic anhydride (235 μL, 1.40 mmol). After stirred at room temperature for 4 hours, the mixture was evaporated. The residue was triturated with dichloromethane and the pyridinium salts was removed by PTFE filtration. Filtrate was evaporated, the residue was triturated with cyclohexane and impurities were eliminated by PTFE filtration. The filtrate was evaporated to provide tert-butoxy-(2-chroman-6-yl-6-methyl-4-nitro-3-trifluoromethanesulfonyloxy-phenyl)-acetic acid methyl ester (52b) (512 mg, 0.91 mmol, 98%) as a beige solid.

$^1$H NMR (400 MHz, CDCl$_3$) δ 0.92 and 0.93 (s, 9H), 2.02-2.08 (m, 2H), 2.50 and 2.51 (s, 3H), 2.69-2.89 (m, 2H), 3.75 (s, 3H), 4.25 (t, J=4.8 Hz, 2H), 5.14 and 5.17 (s, 1H), 6.88 (dd, J=3.6 Hz, J=8.4 Hz, 1H), 7.01-7.14 (m, 2H), 7.80 (s, 1H).

Step 3: Preparation of Intermediate tert-butoxy-(2-chroman-6-yl-3-cyclopropyl-6-methyl-4-nitro-phenyl)-acetic acid methyl ester (52c)

To a solution of tert-butoxy-(2-chroman-6-yl-6-methyl-4-nitro-3-trifluoromethanesulfonyl oxy-phenyl)-acetic acid methyl ester (52b) (300 mg, 0.53 mmol) in 5 mL of dioxane was added potassium cyclopropyltrifluoroborate (158 mg, 1.07 mmol) and potassium phosphate monohydrate (371 mg, 1.75 mmol). The mixture was bubbled with argon for 15 minutes. Palladium tetrakis(triphenylphosphine) (61 mg, 0.05 mmol) was added and the mixture was heated 18 hours at 100° C. Solvent was evaporated and the crude product was purified by preparative TLC on silica gel (cyclohexane/ethyl acetate 80/20) to provide tert-butoxy-(2-chroman-6-yl-3-cyclopropyl-6-methyl-4-nitro-phenyl)-acetic acid methyl ester (52c) (221 mg, 0.49 mmol, 92%).

$^1$H NMR (300 MHz, CDCl$_3$) δ −0.08-0.01 (m, 1H), 0.23-0.31 (m, 1H), 0.34-0.41 (m, 1H), 0.64-0.72 (m, 1H), 0.93 and 0.94 (s, 9H), 1.75-1.83 (m, 1H), 2.01-2.09 (m, 2H), 2.42 and 2.43 (s, 3H), 2.70-2.84 (m, 2H), 3.71 and 3.72 (s, 3H), 4.23-4.27 (m, 2H), 5.15 and 5.16 (s, 1H), 6.82-6.86 (m, 1H), 6.93-7.03 (m, 2H), 7.39 (s, 1H).

MS m/z ([M+H]$^+$) 454.

Step 4: Preparation of Intermediate (2-chroman-6-yl-3-cyclopropyl-6-methyl-4-nitro-phenyl)-hydroxy-acetic acid methyl ester (52d)

Trifluoroacetic acid (0.33 mL, 4.24 mmol) was added to a solution of tert-butoxy-(2-chroman-6-yl-3-cyclopropyl-6-methyl-4-nitro-phenyl)-acetic acid methyl ester (52c) (370

Step 1: Preparation of Intermediate tert-butoxy-(2-chroman-6-yl-3-hydroxy-6-methyl-4-nitro-phenyl)-acetic acid methyl ester (52a)

To a solution of 2-(tert-butoxy)-2-[2-(3,4-dihydro-2H-1-benzopyran-6-yl)-3-hydroxy-6-methylphenyl]acetate (10 (400 mg, 1.04 mmol) in 7 mL of acetic acid was added, at 0° C., nitric acid fuming (66 μL, 1.56 mmol) diluted in 100 μL of acetic acid. After stirred at 0° C. for 30 minutes, water was added and the crude product precipitated. The mixture was extracted with ethyl acetate. The organic layer was washed with sodium bicarbonate, dried with sodium sulfate, mg, 0.82 mmol) in dichloromethane (7.4 mL) cooled to 0° C. The reaction was stirred at room temperature for three days and quenched with a saturated solution of sodium bicarbonate (20 mL). The mixture was extracted with ethyl acetate (3×10 mL), dried over sodium sulfate and concentrated in vacuo. The residue was purified by preparative TLC (cyclohexane/ethyl acetate 70/30) to provide (2-chroman-6-yl-3-cyclopropyl-6-methyl-4-nitro-phenyl)-hydroxy-acetic acid methyl ester (52d) (282 mg, 0.71 mmol, 87%) as a mixture of atropoisomers.

$^1$H NMR (400 MHz, CDCl$_3$) δ 0.07-0.16 (m, 2H), 0.47-0.59 (m, 2H), 1.74-1.78 (m, 1H), 2.02-2.06 (m, 2H), 2.33 and 2.34 (s, 3H), 2.76-2.83 (m, 2H), 3.21-3.22 (m, 1H), 3.69 and 3.71 (s, 3H), 4.21-4.23 (m, 2H), 5.24-5.25 (m, 1H), 6.79-6.84 (m, 1H), 6.91-6.95 (m, 2H), 7.39 (s, 1H).

MS m/z ([M+Na]$^+$) 420.

Step 5: Preparation of Intermediate (2-chroman-6-yl-3-cyclopropyl-6-methyl-4-nitro-phenyl)-vinyloxy-acetic acid methyl ester (52e)

To a stirred solution of (2-chroman-6-yl-3-cyclopropyl-6-methyl-4-nitro-phenyl)-hydroxy-acetic acid methyl ester (52d) (183 mg, 0.46 mmol) in dichloromethane (1.1 mL) and ethyl vinyl ether (0.88 mL), at room temperature was added trifluoroacetic acid (1 drop). The mixture was stirred for 4 hours. Then triethylamine (~50 μL) was added to the mixture before its concentration under nitrogen flux. Under argon atmosphere, the intermediate acetal was directly dissolved in anhydrous dichloromethane (1.1 mL), cooled down to 0° C. and triethylamine (96 μL, 0.69 mmol) and trimethylsilyl trifluoromethanesulfonate (108 μL, 0.60 mmol) were added dropwisely. The mixture was stirred at room temperature for 16 hours and the reaction was quenched with a 1M sodium hydroxide solution. The organic layer was separated, washed with brine, dried over sodium sulfate and concentrated under reduced pressure. The crude material was purified by two preparative TLC (cyclohexane/ethyl acetate 80/20) to give (2-chroman-6-yl-3-cyclopropyl-6-methyl-4-nitro-phenyl)-vinyloxy-acetic acid methyl ester (52e) (125 mg, 0.30 mmol, 64%).

$^1$H NMR (400 MHz, CDCl$_3$) δ 0.06-0.19 (m, 2H), 0.47-0.62 (m, 2H), 1.75-1.82 (m, 1H), 2.01-2.09 (m, 2H), 2.38-2.39 (m, 3H), 2.75-2.83 (m, 2H), 3.72-3.73 (m, 3H), 4.01-4.04 (m, 1H), 4.22-4.27 (m, 3H), 5.39-5.40 (m, 1H), 6.04-6.12 (m, 1H), 6.83-7.01 (m, 3H), 7.40 (s, 1H)

MS m/z ([M+Na]$^+$) 446.

Step 6: Preparation of Intermediate (2-chroman-6-yl-3-cyclopropyl-6-methyl-4-nitro-phenyl)-cyclopropoxy-acetic acid methyl ester (52f)

Using the procedure described in example 23, step 3, the intermediate (2-chroman-6-yl-3-cyclopropyl-6-methyl-4-nitro-phenyl)-vinyloxy-acetic acid methyl ester (52e) (150 mg, 0.35 mmol) was converted, after purification by two preparative TLC (cyclohexane/AcOEt 90/10), into (2-chroman-6-yl-3-cyclopropyl-6-methyl-4-nitro-phenyl)-cyclopropoxy-acetic acid methyl ester (52f) (82 mg, 0.19 mmol, 48%).

$^1$H NMR (400 MHz, CDCl$_3$) δ 0.06-0.14 (m, 1H), 0.22-0.36 (m, 4H), 0.47-0.51 (m, 2H), 0.59-0.67 (m, 1H), 1.74-1.78 (m, 1H), 2.06-2.09 (m, 2H), 2.37 (s, 3H), 2.77-2.81 (m, 2H), 3.27-3.35 (m, 1H), 3.71 and 3.72 (s, 3H), 4.25-4.27 (m, 2H), 5.11 and 5.15 (s, 1H), 6.83-6.96 (m, 3H), 7.39 (s, 1H).

MS m/z ([M+Na]$^+$) 460.

Step 7: Preparation of Intermediate (4-amino-2-chroman-6-yl-3-cyclopropyl-6-methyl-phenyl)-cyclopropoxy-acetic acid methyl ester (52g)

To a solution of (2-chroman-6-yl-3-cyclopropyl-6-methyl-4-nitro-phenyl)-cyclopropoxy-acetic acid methyl ester (52f) (63 mg, 0.14 mmol) in a mixture (2:1) of methanol/water (1.35 mL) was added ammonium chloride (54 mg, 1.01 mmol). The mixture was heated at 50° C. for 10 minutes and iron powder (24 mg, 0.43 mmol) was added. After 1 hour at 60° C., iron was removed by PTFE filtration (many washings with methanol) and the filtrate was evaporated. The residue dissolved in ethyl acetate was washed with saturated solution of sodium bicarbonate and brine (5 mL), dried over sodium sulfate and concentrated in vacuo. The residue was purified by preparative TLC on silica gel (cyclohexane/ethyl acetate 7/3) to provide (4-amino-2-chroman-6-yl-3-cyclopropyl-6-methyl-phenyl)-cyclopropoxy-acetic acid methyl ester (52g) (50 mg, 0.12 mmol, 79%) as a white solid.

$^1$H NMR (400 MHz, CDCl$_3$) δ 0.08-0.48 (m, 7H), 0.61-0.69 (m, 1H), 1.34-1.38 (m, 1H), 2.02-2.09 (m, 2H), 2.25 (s, 3H), 2.75-2.81 (m, 2H), 3.20-3.33 (m, 1H), 3.67 and 3.70 (s, 3H), 4.10 (bs, 2H), 4.22-4.26 (m, 2H), 5.00 and 5.06 (s, 1H), 6.50 (s, 1H), 6.77-7.0 (m, 3H)

MS m/z ([M+H]$^+$) 408.

Step 8: Preparation of Intermediate (2-chroman-6-yl-3-cyclopropyl-4-methanesulfonylamino-6-methyl-phenyl)-cyclopropoxy-acetic acid methyl ester (52h)

A solution of trifluoromethanesulfonic anhydride (39 mg, 0.22 mmol) in dichloromethane (0.5 mL) was dropwisely added to a cooled 0° C. stirred solution of (4-amino-2-chroman-6-yl-3-cyclopropyl-6-methyl-phenyl)-cyclopropoxy-acetic acid methyl ester (52g) (50 mg, 0.12 mmol) in triethylamine (67 μL, 0.48 mmol) and dichloromethane (1 mL). The reaction was completed after 20 minutes of stirring at 0° C. It was quenched with water and extracted twice with dichloromethane. The organic layers were washed with brine, dried over sodium sulfate and concentrated in vacuo. The residue was purified by preparative TLC on silica gel (cyclohexane/ethyl acetate 6/4) to provide (2-chroman-6-yl-3-cyclopropyl-4-methanesulfonylamino-6-methyl-phenyl)-cyclopropoxy-acetic acid methyl ester (52h) (46 mg, 0.09 mmol, 79%) as a white solid.

$^1$H NMR (400 MHz, CDCl$_3$) δ 0.16-0.33 (m, 5H), 0.44-0.62 (m, 2H), 0.80-0.85 (m, 1H), 1.34-1.41 (m, 1H), 2.05-2.09 (m, 2H), 2.34 (s, 3H), 2.77-2.82 (m, 2H), 3.12 (s, 3H), 3.24-3.36 (m, 1H), 3.69 and 3.71 (s, 3H), 4.24-4.27 (m, 2H), 5.06 and 5.11 (s, 1H), 6.79-6.98 (m, 3H), 7.33 (s, 1H).

Step 9: Preparation of (2-chroman-6-yl-3-cyclopropyl-4-methanesulfonylamino-6-methyl-phenyl)-cyclopropoxy-acetic acid (Example 52)

A mixture of (2-chroman-6-yl-3-cyclopropyl-4-methanesulfonylamino-6-methyl-phenyl)-cyclopropoxy-acetic acid methyl ester (52h) (45 mg, 0.09 mmol) and sodium hydroxide 2M in water (93 μL, 0.19 mmol), tetrahydrofuran (0.5 mL) and methanol (0.5 mL) was heated at 90° C. for 15 hours. Water was added to the mixture and the aqueous layer was acidified with a 1M hydrochloric acid until pH 4-5 and extracted twice with ethyl acetate. The combined organic layers were washed with brine, dried over sodium sulfate and concentrated in vacuo. The residue was purified on preparative TLC (dichloromethane/methanol 90/10) to provide (2-chroman-6-yl-3-cyclopropyl-4-methanesulfonylamino-6-methyl-phenyl)-cyclopropoxy-acetic acid (Example 52) (29 mg, 0.05 mmol, 66%) as a white solid.

$^1$H NMR (400 MHz, CDCl$_3$) δ 0.14-0.42 (m, 5H), 0.52-0.56 (m, 1H), 0.81-0.89 (m, 2H), 1.37-1.42 (m, 1H), 2.02-2.06 (m, 3H), 2.29-2.33 (m, 2H), 2.73-2.83 (m, 2H), 3.07-3.13 (m, 4H), 4.24 (m, 2H), 5.13-5.19 (m, 1H), 6.78-7.00 (m, 3H), 7.30-7.36 (m, 2H).

MS m/z ([M–H]$^-$) 470.

Example 53

Synthesis of (4-acetylamino-2-chroman-6-yl-3-cyclopropyl-6-methyl-phenyl)-cyclopropoxy-acetic acid

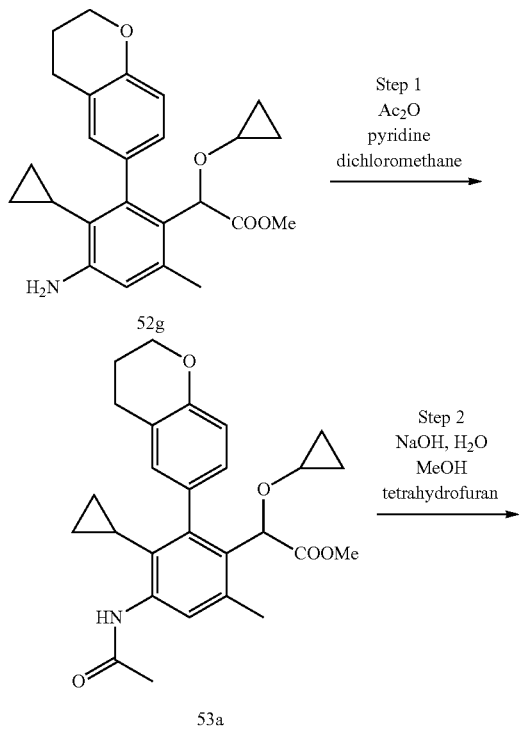

Step 1: Preparation of Intermediate (4-acetylamino-2-chroman-6-yl-3-cyclopropyl-6-methyl-phenyl)-cyclopropoxy-acetic acid methyl ester (53a)

In a dry reactor with a magnetic stirrer was charged (4-amino-2-chroman-6-yl-3-cyclopropyl-6-methyl-phenyl)-cyclopropoxy-acetic acid methyl ester intermediate (52g) (50 mg, 0.123 mmol) in dichloromethane (1 mL). Pyridine (24 μL, 0.293 mmol) then acetic anhydride (14 μL, 0.147 mmol) was added to the solution and the reaction mixture was stirred 2 hours to room temperature and diluted with ethyl acetate (5 mL). The solution was treated with a saturated solution of ammonium chloride and layers were separated. The aqueous layer was extracted with ethyl acetate (2×5 mL). The combined organic layers were washed with a saturated solution of sodium chloride (5 mL), dried over sodium sulfate and concentrated in vacuo. The residue was purified on preparative TLC (cyclohexane/dichloromethane 50/50) to provide (4-acetylamino-2-chroman-6-yl-3-cyclopropyl-6-methyl-phenyl)-cyclopropoxy-acetic acid methyl ester (53a) (36 mg, 0.080 mmol, 65%) as a white solid.

$^1$H NMR (300 MHz, CDCl$_3$) δ 0.13-0.60 (m, 7H), 070-0.80 (m, 1H), 1.38-1.45 (m, 1H), 2.01-2.10 (m, 2H), 2.22 (s, 3H), 2.34 (s, 3H), 2.74-2.81 (m, 2H), 3.19-3.33 (m, 1H), 3.67 and 3.70 (s, 3H), 4.23-4.26 (m, 2H), 5.05 and 511 (s, 1H), 6.78-6.98 (m, 3H), 8.04-8.11 (m, 1H) MS m/z ([M+H]$^+$) 450.

Step 2: Preparation of (4-acetylamino-2-chroman-6-yl-3-cyclopropyl-6-methyl-phenyl)-cyclopropoxy-acetic acid (Example 53)

Using the procedure described in example 23, step 4, the (4-acetylamino-2-chroman-6-yl-3-cyclopropyl-6-methyl-phenyl)-cyclopropoxy-acetic acid methyl ester (53a) (36 mg, 0.073 mmol) is converted into (4-acetylamino-2-chroman-6-yl-3-cyclopropyl-6-methyl-phenyl)-cyclopropoxy-acetic acid (Example 53) (28 mg, 0.064 mmol, 88%).

$^1$H NMR (300 MHz, CDCl$_3$) δ 0.10-0.59 (m, 7H), 0.74-0.83 (m, 1H), 1.40-1.49 (m, 1H), 1.97-2.09 (m, 2H), 2.23 (s, 3H), 2.33 and 2.35 (s, 3H), 2.67-2.88 (m, 2H), 3.06-3.19 (m, 1H), 4.19-4.30 (m, 2H), 5.14 and 5.18 (s, 1H), 6.76-6.87 (m, 2H), 6.96-7.05 (m, 1H), 7.98-8.14 (m, 2H).

MS m/z ([M+H]$^+$) 436. MS m/z ([M–H]$^-$) 434.

Example 54

Synthesis of (3-chroman-6-yl-2-cyclopropyl-5-methyl-biphenyl-4-yl)-cyclopropoxy-acetic acid

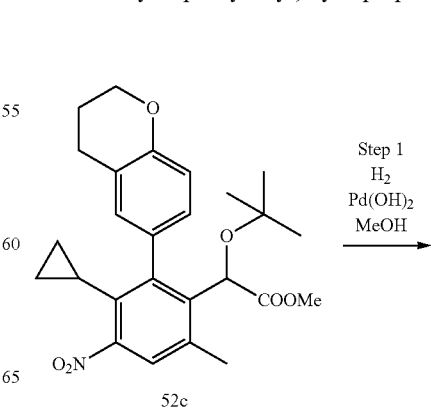

183
-continued

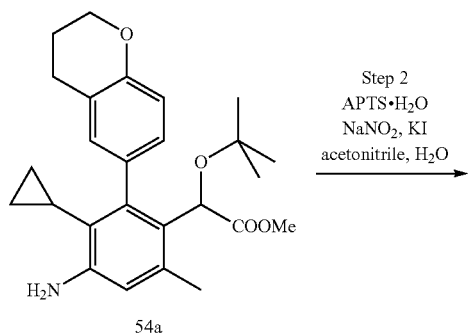
54a

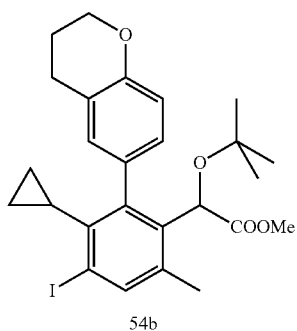
54b

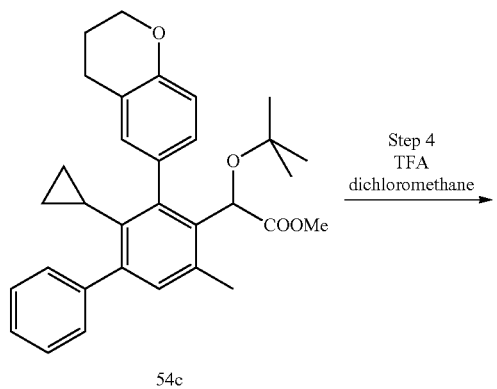
54c

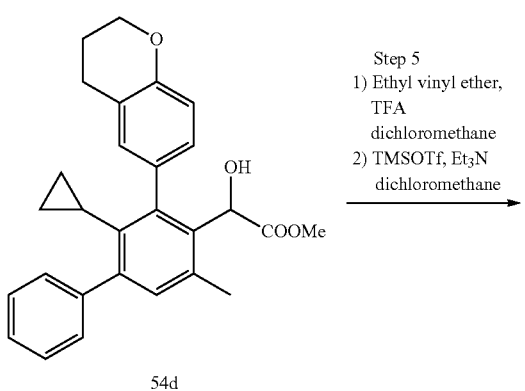
54d

184
-continued

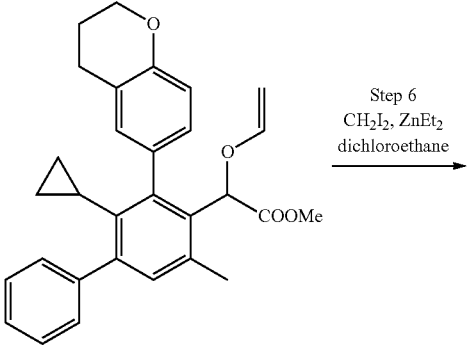
54e

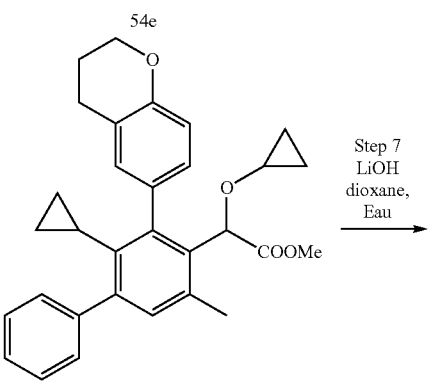
54f

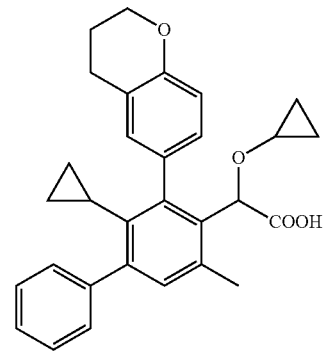
Example 54

Step 1: Preparation of Intermediate (4-amino-2-chroman-6-yl-3-cyclopropyl-6-methyl-phenyl)-tert-butoxy-acetic acid methyl ester (54a)

To a solution of tert-butoxy-(2-chroman-6-yl-3-cyclopropyl-6-methyl-4-nitro-phenyl)-acetic acid methyl ester (52c) (346 mg, 0.76 mmol) in 12 mL of methanol was added Palladium hydroxide on carbon (53 mg, 0.08 mmol). The mixture was placed under hydrogen atmosphere and stirred 6 hours at room temperature. The catalyst was removed by PTFE filtration and the filtrate was evaporated. The residue was purified by preparative TLC on silica gel (cyclohexane/ethyl acetate 7/3) to provide (4-amino-2-chroman-6-yl-3-cyclopropyl-6-methyl-phenyl)-tert-butoxy-acetic acid methyl ester (54a) (282 mg, 0.66 mmol, 87%).

$^1$H NMR (300 MHz, CDCl$_3$) δ −0.04-0.07 (m, 1H), 0.24-0.44 (m, 2H), 0.68-0.75 (m, 1H), 0.90 (s, 9H), 1.34-1.41 (m, 1H), 2.00-2.09 (m, 2H), 2.32 and 2.33 (s, 3H), 2.66-2.83 (m, 2H), 3.67 and 3.69 (s, 3H), 4.05 (bs, 2H), 4.22-4.26 (m, 2H), 5.07 and 5.09 (s, 1H), 6.49 (s, 1H), 6.75-6.81 (m, 1H), 6.88-6.96 (m, 1H), 7.05-7.10 (m, 1H).
MS m/z ([M+H]$^+$) 424.

Step 2: Preparation of Intermediate tert-butoxy-(2-chroman-6-yl-3-cyclopropyl-4-iodo-6-methyl-phenyl)-acetic acid methyl ester (54b)

To a solution of (4-amino-2-chroman-6-yl-3-cyclopropyl-6-methyl-phenyl)-tert-butoxy-acetic acid methyl ester (54a) (129 mg, 0.30 mmol) in anhydrous acetonitrile (3 mL) was added p-toluenesulfonic acid monohydrate (174 mg, 0.91 mmol). The mixture was cooled to 0° C. and a solution of sodium nitrite (42 mg, 0.61 mmol) with potassium iodide (126 mg, 0.76 mmol) in water (0.3 mL) was added slowly. The reaction mixture was stirred for 5 minutes at 0° C. then allowed to warm up to 20° C. After 20 hours at room temperature, the mixture was quenched with a 15% sodium thiosulfate solution (10 mL) and extracted with ethyl acetate (3×5 mL). The organic layers were washed with brine, dried over sodium sulfate and concentrated in vacuo. The residue was purified by preparative TLC on silica gel (cyclohexane/ethyl acetate 8/2) to provide tert-butoxy-(2-chroman-6-yl-3-cyclopropyl-4-iodo-6-methyl-phenyl)-acetic acid methyl ester (54b) (75 mg, 0.14 mmol, 46%) as a colorless oil.
$^1$H NMR (300 MHz, CDCl$_3$) δ −0.06–−0.05 (m, 1H), 0.37-0.49 (m, 2H), 0.89-0.93 (m, 10H), 1.53-1.63 (m, 1H), 2.00-2.08 (m, 2H), 2.32 and 2.33 (s, 3H), 2.70-2.83 (m, 2H), 3.68 and 3.70 (s, 3H), 4.22-4.26 (m, 2H), 5.14 and 5.15 (s, 1H), 6.77-6.93 (m, 2H), 6.99-7.07 (m, 1H), 7.68 and 7.69 (s, 1H).
MS m/z ([M+Na]$^+$) 557.

Step 3: Preparation of Intermediate tert-butoxy-(3-chroman-6-yl-2-cyclopropyl-5-methyl-biphenyl-4-yl)-acetic acid methyl ester (54c)

To a degassed solution of tert-butoxy-(2-chroman-6-yl-3-cyclopropyl-4-iodo-6-methyl-phenyl)-acetic acid methyl ester (54b) (79 mg, 0.15 mmol), potassium carbonate (61 mg, 0.44 mmol), phenylboronic pinacol ester (60 mg, 0.30 mmol) in a mixture of dioxane (1.5 mL) and water (0.35 mL) was added tetrakis(triphenylphosphine)palladium (0) (17 mg, 0.01 mmol). The mixture was heated at 90° C. for 4 hairs. The reaction was quenched with water and extracted twice with ethyl acetate. The organic layer was washed with brine, dried over sodium sulfate and concentrated under reduced pressure. The crude material was purified by preparative TLC (cyclohexane/ethyl acetate 85/15) to give tert-butoxy-(3-chroman-6-yl-2-cyclopropyl-5-methyl-biphenyl-4-yl)-acetic acid methyl ester (54c) (71 mg, 0.15 mmol, 98%).
$^1$H NMR (400 MHz, CDCl$_3$) δ −0.22–−0.17 (m, 2H), 0.16-0.24 (m, 2H), 1.59-1.64 (m, 1H), 0.98 and 0.99 (s, 9H), 2.01-2.08 (m, 2H), 2.43 and 2.44 (s, 3H), 2.73-2.82 (m, 2H), 3.70 and 3.72 (s, 3H), 4.23-4.26 (m, 2H), 5.17 and 5.19 (s, 1H), 6.80-6.85 (m, 1H), 6.98-7.09 (m, 3H), 7.29-7.45 (m, 5H).
MS m/z ([M+Na]$^+$) 507.

Step 4: Preparation of Intermediate (3-chroman-6-yl-2-cyclopropyl-5-methyl-biphenyl-4-yl)-hydroxy-acetic acid methyl ester (54d)

Trifluoroacetic acid (0.13 mL) was added to a solution of tert-butoxy-(3-chroman-6-yl-2-cyclopropyl-5-methyl-biphenyl-4-yl)-acetic acid methyl ester (54c) (83 mg, 0.17 mmol) in dichloromethane (1.3 mL) at room temperature. The reaction was stirred at room temperature for 2 hours and quenched with a saturated solution of sodium bicarbonate. The mixture was extracted twice with dichloromethane, dried over sodium sulfate and concentrated in vacuo. The residue was purified by preparative TLC (cyclohexane/ethyl acetate 80/20) to provide (3-chroman-6-yl-2-cyclopropyl-5-methyl-biphenyl-4-yl)-hydroxy-acetic acid methyl ester (54d) (65 mg, 0.15 mmol, 90%).
$^1$H NMR (400 MHz, CDCl$_3$) δ −0.22–−0.18 (m, 2H), 0.19-0.23 (m, 2H), 1.60-1.64 (m, 1H), 2.04-2.08 (m, 2H), 2.33 and 2.34 (s, 3H), 2.79-2.83 (m, 2H), 3.07 and 3.09 (d, J=2.8 Hz, 1H), 3.73 and 3.74 (s, 3H), 4.23-4.25 (m, 2H), 5.28 and 5.29 (s, 1H), 6.80-6.84 (m, 1H), 6.98-7.03 (m, 2H), 7.10-7.11 (m, 1H), 7.28-7.33 (m, 1H), 7.35-7.43 (m, 4H).
MS m/z ([M+Na]$^+$) 451.

Step 5: Preparation of Intermediate (3-chroman-6-yl-2-cyclopropyl-5-methyl-biphenyl-4-yl)-vinyloxy-acetic acid methyl ester (54e)

Using the procedure described in example 52, step 3, the intermediate (3-chroman-6-yl-2-cyclopropyl-5-methyl-biphenyl-4-yl)-hydroxy-acetic acid methyl ester (54d) (65 mg, 0.15 mmol) was converted, after purification by preparative TLC (cyclohexane/AcOEt 85/15), into (3-chroman-6-yl-2-cyclopropyl-5-methyl-biphenyl-4-yl)-vinyloxy-acetic acid methyl ester (54e) (42 mg, 0.09 mmol, 62%).
$^1$H NMR (400 MHz, CDCl$_3$) δ −0.21–−0.18 (m, 2H), 0.16-0.24 (m, 2H), 1.61-1.68 (m, 1H), 2.04-2.08 (m, 2H), 2.36 and 2.37 (s, 3H), 2.78-2.83 (m, 2H), 3.73 and 3.74 (s, 3H), 4.00-4.03 (m, 1H), 4.23-4.30 (m, 3H), 5.41 and 5.43 (s, 1H), 6.11-6.20 (m, 1H), 6.81-6.85 (m, 1H), 6.90-7.08 (m, 2H), 7.12 (s, 1H), 7.29-7.44 (m, 5H).
MS m/z ([M+Na]$^+$) 477.

Step 6: Preparation of Intermediate (3-chroman-6-yl-2-cyclopropyl-5-methyl-biphenyl-4-yl)-cyclopropoxy-acetic acid methyl ester (54f)

Using the procedure described in example 23, step 3, the intermediate (3-chroman-6-yl-2-cyclopropyl-5-methyl-biphenyl-4-yl)-vinyloxy-acetic acid methyl ester (54e) (42 mg, 0.09 mmol) was converted, after purification by preparative TLC (cyclohexane/AcOEt 90/10), into (3-chroman-6-yl-2-cyclopropyl-5-methyl-biphenyl-4-yl)-cyclopropoxy-acetic acid methyl ester (54f) (23 mg, 0.05 mmol, 53%).
$^1$H NMR (400 MHz, CDCl$_3$) δ −0.19–−0.13 (m, 2H), 0.19-0.42 (m, 5H), 0.50-0.55 (m, 1H), 1.58-1.63 (m, 1H), 2.05-2.10 (m, 2H), 2.36 (s, 3H), 2.78-2.84 (m, 2H), 3.34-3.44 (m, 1H), 3.72 and 3.74 (s, 3H), 4.24-4.26 (m, 2H), 5.11 and 5.17 (s, 1H), 6.81-7.04 (m, 3H), 7.08 (s, 1H), 7.28-7.43 (m, 5H).
MS m/z ([M+Na]$^+$) 491

Step 7: Preparation of (3-chroman-6-yl-2-cyclopropyl-5-methyl-biphenyl-4-yl)-cyclopropoxy-acetic acid (Example 54)

Using the procedure described in example 1, step 12, the intermediate (3-chroman-6-yl-2-cyclopropyl-5-methyl-biphenyl-4-yl)-cyclopropoxy-acetic acid methyl ester (54f) (23 mg, 0.05 mmol) was converted, after purification by preparative TLC (dichloromethane/methanol 95/5), into (3-chroman-6-yl-2-cyclopropyl-5-methyl-biphenyl-4-yl)-cyclopropoxy-acetic acid (Example 54) (13 mg, 0.03 mmol, 57%).

¹H NMR (400 MHz, CDCl₃) δ −0.21-−0.17 (m, 2H), 0.20-0.54 (m, 6H), 1.58-1.66 (m, 1H), 1.97-2.11 (m, 2H), 2.24-2.40 (m, 3H), 2.71-2.86 (m, 2H), 3.18-3.26 (m, 1H), 4.17-4.22 (m, 2H), 5.17-5.22 (m, 1H), 6.77-6.81 (m, 1H), 6.91-7.07 (m, 3H), 7.29-7.40 (m, 5H).

MS m/z ([M−H]⁻) 453.

Example 55

Synthesis of (2-chroman-6-yl-3-cyclopropyl-4-ethyl-6-methyl-phenyl)-cyclopropoxy-acetic acid

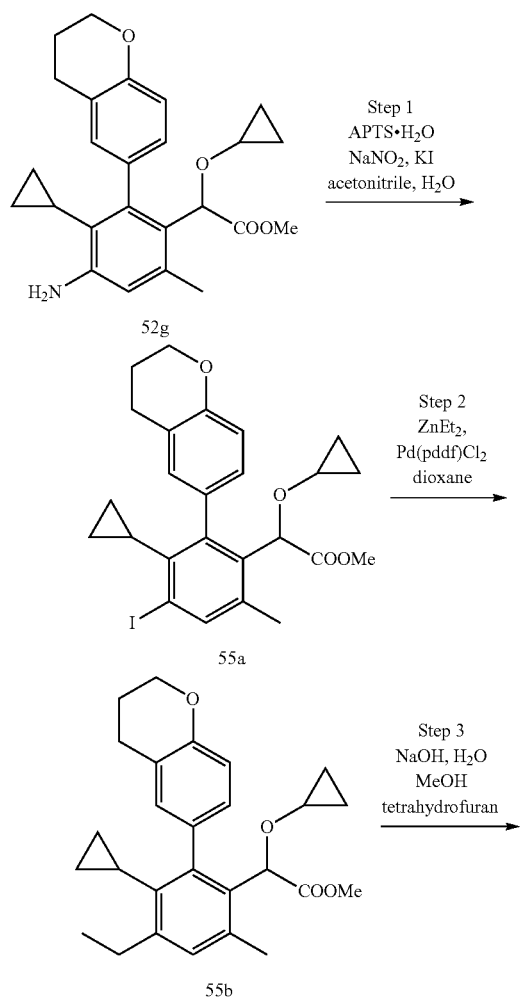

Step 1: Preparation of Intermediate (2-chroman-6-yl-3-cyclopropyl-4-iodo-6-methyl-phenyl)-cyclopropoxy-acetic acid methyl ester (55a)

Using the procedure described in example 54, step 2, the intermediate (4-amino-2-chroman-6-yl-3-cyclopropyl-6-methyl-phenyl)-cyclopropoxy-acetic acid methyl ester (52g) (350 mg, 0.860 mmol) was converted, after purification by preparative TLC (cyclohexane/dichloromethane 70/30), into (2-chroman-6-yl-3-cyclopropyl-4-iodo-6-methyl-phenyl)-cyclopropoxy-acetic acid methyl ester (55a) (313 mg, 0.603 mmol, 70%) as a yellow oil.

¹H NMR (300 MHz, CDCl₃) δ 0.06-0.48 (m, 6H), 0.50-0.60 (m, 1H), 0.77-0.87 (m, 1H), 1.52-1.62 (m, 1H), 2.01-2.10 (m, 2H), 2.26 (s, 3H), 2.68-2.86 (m, 2H), 3.20-3.32 (m, 1H), 3.69 and 3.71 (s, 3H), 4.20-4.29 (m, 2H), 5.08 and 5.13 (s, 1H), 6.78-6.97 (m, 3H), 7.71 (s, 1H).

MS m/z ([M+Na]⁺) 541.

Step 2: Preparation of Intermediate (2-chroman-6-yl-3-cyclopropyl-4-ethyl-6-methyl-phenyl)-cyclopropoxy-acetic acid methyl ester (55b)

To a degassed solution of (2-chroman-6-yl-3-cyclopropyl-4-iodo-6-methyl-phenyl)-cyclopropoxy-acetic acid methyl ester (55a) (47 mg, 0.090 mmol) in dry 1,4-dioxane (0.5 mL) was added [1,1'-bis(diphenylphosphino)ferrocene]dichloropalladium(II), complex with dichloromethane (3.3 mg, 0.004 mmol) and a solution of diethylzinc 15% in toluene (222 µl, 0.246 mmol). The reactor was sealed and the mixture was heated at 80° C. for 1h 30. The mixture was quenched with water (3 mL) and extracted with ethyl acetate (3×2 mL). The combined organic layers were washed with brine (10 mL), dried over sodium sulfate and concentrated in vacuo. The residue was purified on preparative TLC (cyclohexane/dichloromethane 80/20) to provide 2-chroman-6-yl-3-cyclopropyl-4-ethyl-6-methyl-phenyl)-cyclopropoxy-acetic acid methyl ester (55b) (43 mg, 0.090 mmol, quantitative yield) as a yellow oil.

¹H NMR (300 MHz, CDCl₃) δ 0.05-0.50 (m, 7H), 0.64-0.72 (m, 1H), 1.26 (t, J=7.5 Hz, 3H), 1.48-1.56 (m, 1H), 1.99-2.10 (m, 2H), 2.32 (s, 3H), 2.69-2.98 (m, 4H), 3.23-3.36 (m, 1H), 3.69 and 3.71 (s, 3H), 4.23-4.26 (m, 2H), 5.10 and 5.15 (s, 1H), 6.77-6.99 (m, 4H).

MS m/z ([M+Na]⁺) 443.

Step 3: Preparation of (2-chroman-6-yl-3-cyclopropyl-4-ethyl-6-methyl-phenyl)-cyclopropoxy-acetic acid (Example 55)

Using the procedure described in example 23, step 4, the (2-chroman-6-yl-3-cyclopropyl-4-ethyl-6-methyl-phenyl)-cyclopropoxy-acetic acid methyl ester (55b) (43 mg, 0.102 mmol) is converted into (2-chroman-6-yl-3-cyclopropyl-4-ethyl-6-methyl-phenyl)-cyclopropoxy-acetic acid (Example 55) (12 mg, 0.029 mmol, 32%) after purification on preparative TLC (dichloromethane/methanol 95/5).

¹H NMR (400 MHz, CD₃OD) δ 0.00-0.39 (m, 7H), 0.69-0.79 (m, 1H), 1.25 (t, J=7.5 Hz, 3H), 1.53-1.62 (m, 1H), 1.96-2.07 (m, 2H), 2.30 (s, 3H), 2.71-2.99 (m, 4H), 3.08 (bs, 1H), 4.17-4.23 (m, 2H), 5.07 (bs, 1H), 6.69-6.76 (m, 1H), 6.86-6.91 (m, 1H), 6.97 (s, 1H), 7.06 (bs, 1H).

MS m/z ([M+Na]⁺) 429.

MS m/z ([M−H]⁻) 405.

Example 56

Synthesis of (2-chroman-6-yl-3-cyclopropyl-4-methoxy-6-methyl-phenyl)-cyclopropoxy-acetic acid

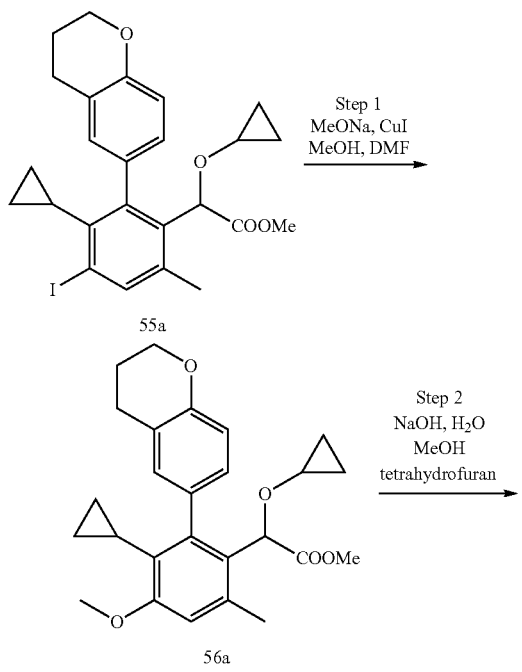

Step 1: Preparation of Intermediate (2-chroman-6-yl-3-cyclopropyl-4-methoxy-6-methyl-phenyl)-cyclopropoxy-acetic acid methyl ester (56a)

To a solution of sodium methoxide 0.5M in methanol (768 μL, 0.384 mmol) in dry dimethylformamide (0.5 mL) was added copper (I) iodide (20 mg, 0.106 mmol). The mixture was heated at 90° C. for 2 hours. A solution of (2-chroman-6-yl-3-cyclopropyl-4-iodo-6-methyl-phenyl)-cyclopropoxy-acetic acid methyl ester (55a) (50 mg, 0.096 mmol) in dry methanol (0.2 mL) was added to the mixture. The reactor was sealed and the reaction was stirred at 90° C. for 6 days. The mixture was quenched with a saturated solution of ammonium chloride (5 mL) and extracted with ethyl acetate (3×3 mL). The combined organic layers were washed with brine (10 mL), dried over sodium sulfate and concentrated in vacuo. The residue was purified on preparative TLC (cyclohexane/dichloromethane 90/10) to provide (2-chroman-6-yl-3-cyclopropyl-4-methoxy-6-methyl-phenyl)-cyclopropoxy-acetic acid methyl ester (56a) (6 mg, 0.014 mmol, 14%) as a yellow oil.

$^1$H NMR (400 MHz, CDCl$_3$) δ 0.19-0.73 (m, 8H), 1.33-1.40 (m, 1H), 1.99-2.10 (m, 2H), 2.33 (s, 3H), 2.70-2.86 (m, 2H), 3.24-3.38 (m, 1H), 3.67 and 3.70 (s, 3H), 3.91 (s, 3H), 4.19-4.28 (m, 2H), 4.97 and 5.02 (s, 1H), 6.64 (s, 1H), 6.76-7.06 (m, 3H).

MS m/z ([M+Na]$^+$) 445.

Step 2: Preparation of (2-chroman-6-yl-3-cyclopropyl-4-methoxy-6-methyl-phenyl)-cyclopropoxy-acetic acid (Example 56)

Using the procedure described in example 23, step 4, the (2-chroman-6-yl-3-cyclopropyl-4-methoxy-6-methyl-phenyl)-cyclopropoxy-acetic acid methyl ester (56a) (6 mg, 0.014 mmol) is converted into (2-chroman-6-yl-3-cyclopropyl-4-methoxy-6-methyl-phenyl)-cyclopropoxy-acetic acid (Example 56) (4.5 mg, 0.011 mmol, 78%).

$^1$H NMR (300 MHz, CD$_3$OD) δ 0.17-0.70 (m, 8H), 1.29-1.41 (m, 1H), 1.99-2.08 (m, 2H), 2.32 (s, 3H), 2.70-2.88 (m, 2H), 3.14-3.25 (m, 1H), 3.80 (s, 3H), 4.19-4.22 (m, 2H), 4.96 and 4.99 (s, 1H), 6.73-7.07 (m, 4H).

MS m/z ([M+Na]$^+$) 431.

MS m/z ([M−H]$^−$) 407.

Example 57

Synthesis of 2-(2-chroman-6-yl-3-cyclopropyl-5-ethyl-6-methyl-phenyl)-2-(cyclopropoxy)acetic acid

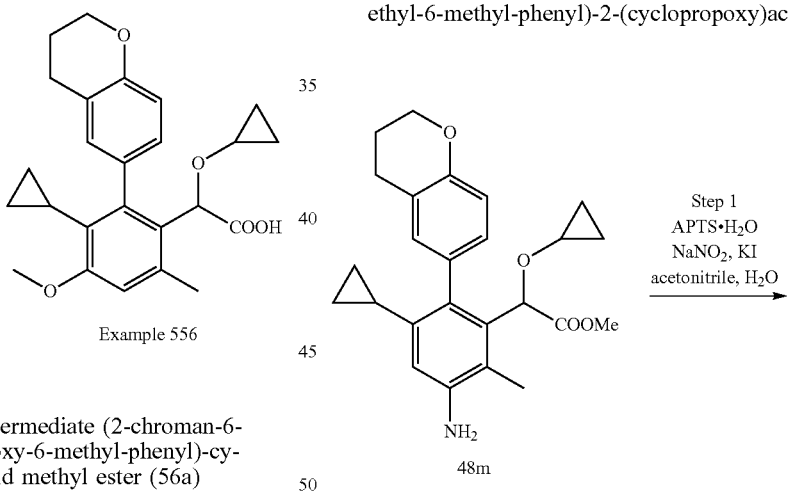

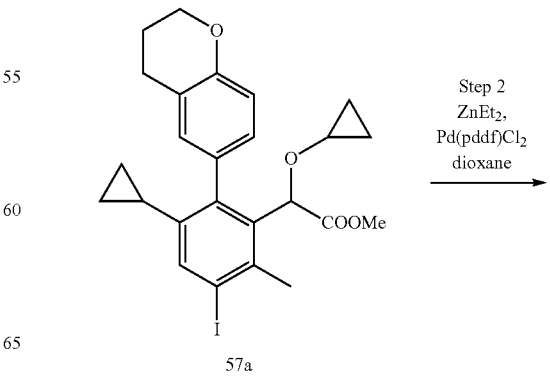

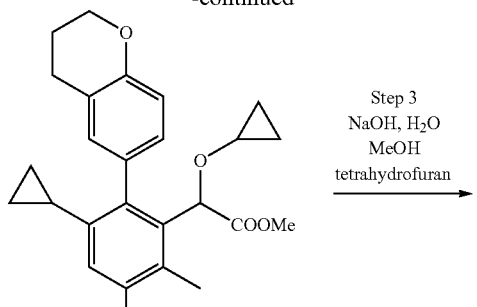

57b

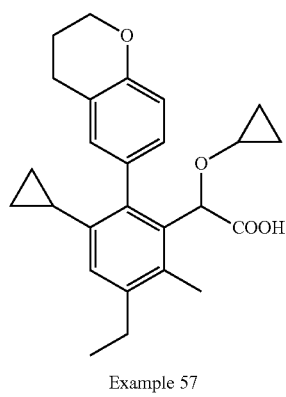

Example 57

Step 1: Preparation of Intermediate methyl 2-(2-chroman-6-yl-3-cyclopropyl-5-iodo-6-methyl-phenyl)-2-(cyclopropoxy)acetate (57a)

Using the procedure described in example 54, step 2, the methyl 2-(5-amino-2-chroman-6-yl-3-cyclopropyl-6-methyl-phenyl)-2-(cyclopropoxy)acetate (48m) (50 mg, 0.123 mmol) is converted into the intermediate methyl 2-(2-chroman-6-yl-3-cyclopropyl-5-iodo-6-methyl-phenyl)-2-(cyclopropoxy)acetate (57a) (32 mg, 0.062 mmol, 50%) after purification on preparative TLC (cyclohexane/ethyl acetate 90/10).

$^1$H NMR (300 MHz, CDCl$_3$) δ 0.21-0.41 (m, 3H), 0.45-0.76 (m, 5H), 1.35-1.48 (m, 1H), 2.00-2.11 (m, 2H), 2.42 and 2.42 (s, 3H), 2.70-2.88 (m, 2H), 3.28-3.43 (m, 1H), 3.68 and 3.71 (s, 3H), 4.18-4.30 (m, 2H), 5.06 and 5.11 (s, 1H), 6.79-7.00 (m, 3H), 7.35 and 7.36 (s, 1H).

MS m/z ([M+Na]$^+$) 541.

Step 2: Preparation of Intermediate methyl 2-(2-chroman-6-yl-3-cyclopropyl-5-ethyl-6-methyl-phenyl)-2-(cyclopropoxy)acetate (57b)

Using the procedure described in example 55, step 2, the intermediate methyl 2-(2-chroman-6-yl-3-cyclopropyl-5-iodo-6-methyl-phenyl)-2-(cyclopropoxy)acetate (57a) (32 mg, 0.062 mmol) was converted, after purification by preparative TLC (cyclohexane/ethyl acetate 90/10), into the intermediate methyl 2-(2-chroman-6-yl-3-cyclopropyl-5-ethyl-6-methyl-phenyl)-2-(cyclopropoxy)acetate (57b) (23 mg, 0.054 mmol, 82%).

$^1$H NMR (400 MHz, CDCl$_3$) δ 0.20-0.42 (m, 3H), 0.47-0.74 (m, 5H), 1.20 (t, J=7.5 Hz, 3H), 1.43-1.53 (m, 1H), 2.00-2.11 (m, 2H), 2.24 and 2.25 (s, 3H), 2.62 (q, J=7.5 Hz, 2H), 2.72-2.87 (m, 2H), 3.31-3.36 and 3.39-3.45 (m, 1H), 3.67 and 3.70 (s, 3H), 4.19-4.29 (m, 2H), 5.06 and 5.12 (s, 1H), 6.70 and 6.71 (s, 1H), 6.80-7.03 (m, 3H).

MS m/z ([M+Na]$^+$) 443.

Step 3: Preparation of 2-(2-chroman-6-yl-3-cyclopropyl-5-ethyl-6-methyl-phenyl)-2-(cyclopropoxy)acetic acid (Example 57)

To a solution of methyl 2-(2-chroman-6-yl-3-cyclopropyl-5-ethyl-6-methyl-phenyl)-2-(cyclopropoxy)acetate (57b) (23 mg, 0.054 mmol) in ethanol (0.8 mL) and tetrahydrofuran (0.2 mL) was added a 2 M solution of sodium hydroxide (0.22 mL, 0.44 mmol). The mixture was heated at 70° C. for 1 hour. The mixture was concentrated in vacuo. Water (2 mL) was added and an 1 M hydrochloric acid solution was added until pH 2. The precipitated was filtered, washed with water (2 mL) and dried in the presence of phosphorus pentoxide to provide 2-(2-chroman-6-yl-3-cyclopropyl-5-ethyl-6-methyl-phenyl)-2-(cyclopropoxy)acetic acid (Example 57) (15.5 mg, 0.038 mmol, 70%) as a white solid.

$^1$H NMR (400 MHz, CDCl$_3$) δ 0.24-0.52 (m, 4H), 0.54-0.74 (m, 4H), 1.20 (t, J=7.5 Hz, 3H), 1.44-1.53 (m, 1H), 1.99-2.09 (m, 2H), 2.23 and 2.25 (s, 3H), 2.63 (q, J=7.5 Hz, 2H), 2.70-2.86 (m, 2H), 3.18-3.30 (m, 1H), 4.19-4.27 (m, 2H), 5.16 and 5.19 (s, 1H), 6.71 and 6.72 (s, 1H), 6.80 and 6.82 (d, J=8.2 Hz, 1H), 6.89-7.05 (m, 2H).

MS m/z ([M+NH$_4$]$^+$) 424.
MS m/z ([M−H]$^−$) 405.

Example 58

Synthesis of (2-chroman-6-yl-3-cyclopropyl-6-methyl-4-thiophen-3-yl-phenyl)-cyclopropoxy-acetic acid

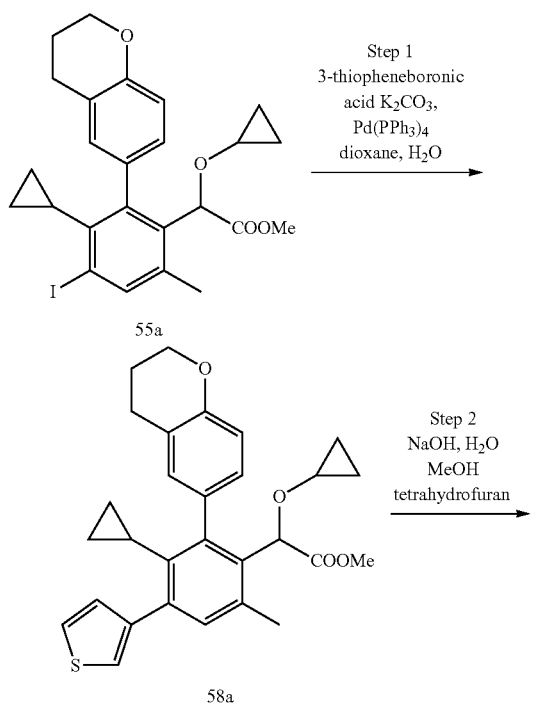

55a

58a

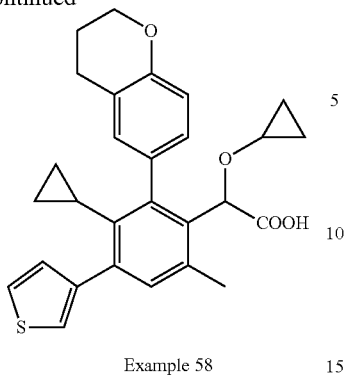

Example 58

Step 1: Preparation of Intermediate (2-chroman-6-yl-3-cyclopropyl-6-methyl-4-thiophen-3-yl-phenyl)-cyclopropoxy-acetic acid methyl ester (58a)

Using the procedure described in example 54, step 3, the (2-chroman-6-yl-3-cyclopropyl-4-iodo-6-methyl-phenyl)-cyclopropoxy-acetic acid methyl ester (55a) (50 mg, 0.096 mmol) is converted, by reaction with 3-thiopheneboronic acid (25.5 mg, 0.200 mmol), into (2-chroman-6-yl-3-cyclopropyl-6-methyl-4-thiophen-3-yl-phenyl)-cyclopropoxy-acetic acid methyl ester (58a) (51 mg, 0.096 mmol, quantitative yield) after purification on preparative TLC (cyclohexane/ethyl acetate 90/10).

$^1$H NMR (400 MHz, CDCl$_3$) δ −0.15-−0.03 (m, 2H), 0.21-0.45 (m, 5H), 0.46-0.55 (m, 1H), 1.55-1.62 (m, 1H), 2.04-2.10 (m, 2H), 2.35 (s, 3H), 2.74-2.88 (m, 2H), 3.31-3.42 (m, 1H), 3.71 and 3.73 (s, 3H), 4.21-4.29 (m, 2H), 5.10 and 5.16 (s, 1H), 6.83 (dd, J=8.6 Hz, J=6.6 Hz, 1H), 6.91-7.06 (m, 2H), 7.15 (s, 1H), 7.22-7.36 (m, 3H).

MS m/z ([M+Na]$^+$) 497.

Step 2: Preparation of (2-chroman-6-yl-3-cyclopropyl-6-methyl-4-thiophen-3-yl-phenyl)-cyclopropoxy-acetic acid (Example 58)

Using the procedure described in example 23, step 4, the (2-chroman-6-yl-3-cyclopropyl-6-methyl-4-thiophen-3-yl-phenyl)-cyclopropoxy-acetic acid methyl ester (58a) (51 mg, 0.108 mmol) is converted into (2-chroman-6-yl-3-cyclopropyl-6-methyl-4-thiophen-3-yl-phenyl)-cyclopropoxy-acetic acid (Example 58) (22 mg, 0.047 mmol, 44%) after purification on preparative TLC (dichloromethane/methanol 90/10).

$^1$H NMR (400 MHz, DMSO-d$_6$) δ −0.28-−0.20 (m, 2H), 0.04-0.35 (m, 6H), 1.65-1.76 (m, 1H), 1.90-2.02 (m, 2H), 2.31 (s, 3H), 2.65-2.85 (m, 2H), 3.39-3.45 (m, 1H), 4.12-4.22 (m, 2H), 4.69 and 4.73 (s, 1H), 6.75 (dd, J=8.2 Hz, J=4.2 Hz, 1H), 6.89-6.95 (m, 1H), 6.99-7.10 (m, 2H), 7.28 (dt, J=5.0 Hz, J=1.5 Hz, 1H), 7.43-7.49 (m, 1H), 7.50-7.56 (m, 1H).

MS m/z ([M+Na]$^+$) 483.
MS m/z ([M−H]$^−$) 459.

Example 59

Synthesis of (2-chroman-6-yl-3-cyclopropyl-4,6-dimethyl-phenyl)-cyclopropoxy-acetic acid

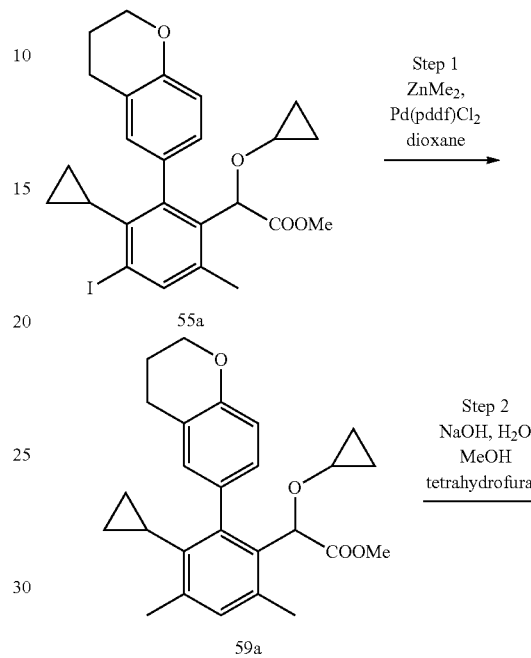

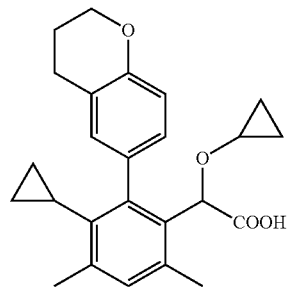

Example 59

Step 1: Preparation of Intermediate (2-chroman-6-yl-3-cyclopropyl-4,6-dimethyl-phenyl)-cyclopropoxy-acetic acid methyl ester (59a)

Using the procedure described in example 55, step 2, and substituting diethylzinc 15% in toluene by dimethylzinc 1.2M in toluene (219 μL, 0.263 mmol), the intermediate (2-chroman-6-yl-3-cyclopropyl-4-iodo-6-methyl-phenyl)-cyclopropoxy-acetic acid methyl ester (55a) (50 mg, 0.096 mmol) is converted into (2-chroman-6-yl-3-cyclopropyl-4,6-dimethyl-phenyl)-cyclopropoxy-acetic acid methyl ester (59a) (32 mg, 0.078 mmol, 81%).

$^1$H NMR (400 MHz, CDCl$_3$) δ 0.04-0.15 (m, 1H), 0.18-0.49 (m, 6H), 0.63-0.71 (m, 1H), 1.48-1.55 (m, 1H), 2.00-2.11 (m, 2H), 2.30 (s, 3H), 2.42 (s, 3H), 2.71-2.86 (m, 2H), 3.23-3.35 (m, 1H), 3.68 and 3.70 (s, 3H), 4.21-4.28 (m, 2H), 5.09 and 5.15 (s, 1H), 6.78-7.00 (m, 4H).

MS m/z ([M+Na]$^+$) 429.

Step 2: Preparation of (2-chroman-6-yl-3-cyclopropyl-4,6-dimethyl-phenyl)-cyclopropoxy-acetic acid (Example 59)

Using the procedure described in example 23, step 4, the (2-chroman-6-yl-3-cyclopropyl-4,6-dimethyl-phenyl)-cyclopropoxy-acetic acid methyl ester (59a) (30 mg, 0.074 mmol) is converted into (2-chroman-6-yl-3-cyclopropyl-4,6-dimethyl-phenyl)-cyclopropoxy-acetic acid (Example 59) (28 mg, 0.071 mmol, 90%).

$^1$H NMR (300 MHz, CD$_3$OD) δ 0.00-0.10 (m, 1H), 0.14-0.43 (m, 6H), 0.64-0.74 (m, 1H), 1.49-1.59 (m, 1H), 1.98-2.05 (m, 2H), 2.28 (s, 3H), 2.41 (s, 3H), 2.69-2.87 (m, 2H), 3.10-3.21 (m, 1H), 4.18-4.21 (m, 2H), 5.09 and 5.12 (s, 1H), 6.76 (dd, J=8.3 Hz, J=1.1 Hz, 1H), 6.85-6.91 (m, 1H), 6.93-7.02 (m, 2H).

MS m/z ([M+Na]$^+$) 415.
MS m/z ([M–H]$^-$) 391.

Example 60

Synthesis of 2-[2-chroman-6-yl-5-(cyclohexylmethylsulfonylamino)-3-cyclopropyl-6-methyl-phenyl]-2-(cyclopropoxy)acetic acid

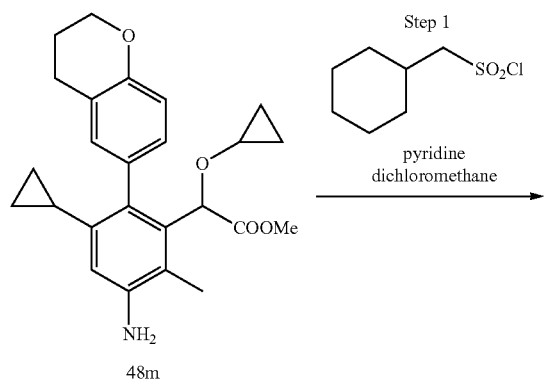

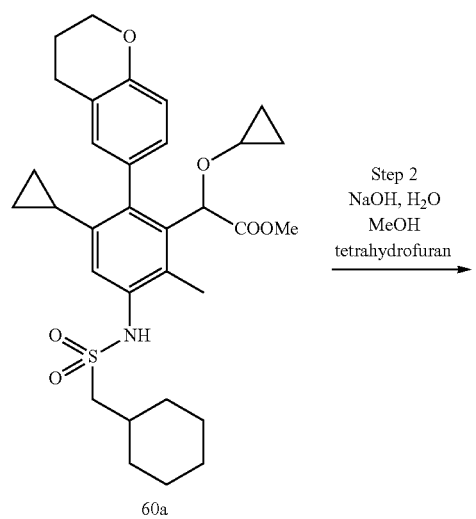

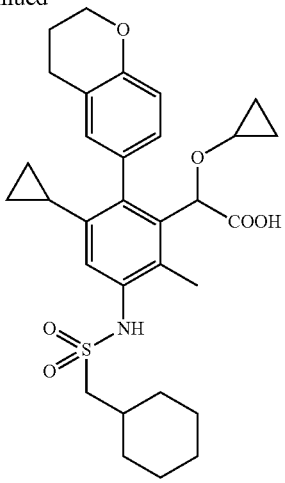

Example 60

Step 1: Preparation of Intermediate methyl 2-[2-chroman-6-yl-5-(cyclohexylmethylsulfonylamino)-3-cyclopropyl-6-methyl-phenyl]-2-(cyclopropoxy)acetate (60a)

Using the procedure described in example 48, step 14, the intermediate methyl 2-(5-amino-2-chroman-6-yl-3-cyclopropyl-6-methyl-phenyl)-2-(cyclopropoxy)acetate (48m) (50 mg, 0.123 mmol) is converted into methyl 2-[2-chroman-6-yl-5-(cyclohexylmethyl sulfonylamino)-3-cyclopropyl-6-methyl-phenyl]-2-(cyclopropoxy)acetate (60a) (59 mg, 0.104 mmol, 84%), by reaction with cyclohexylmethanesulfonyl chloride (25 µL, 0.156 mmol) and after purification by two preparative TLCs (cyclohexane/ethyl acetate 50/50 then dichloromethane/ethyl acetate 97/3).

$^1$H NMR (400 MHz, CDCl$_3$) δ 0.23-0.39 (m, 3H), 0.49-0.65 (m, 3H), 0.69-0.75 (m, 2H), 1.01-1.20 (3H), 1.22-1.34 (m, 3H), 1.43-1.53 (m, 1H), 1.60-1.75 (m, 3H), 1.88-2.10 (m, 4H), 2.22 and 2.24 (s, 3H), 2.72-2.87 (m, 2H), 2.97 (d, J=6.1 Hz, 2H), 3.29-3.34 and 3.36-3.42 (m, 1H), 3.67 and 3.70 (s, 3H), 4.19-4.29 (m, 2H), 5.05 and 5.10 (s, 1H), 6.21 (s, 1H), 6.80-7.03 (m, 4H).

MS m/z ([M+NH$_4$]$^+$) 585.
MS m/z ([M–H]$^-$) 566.

Step 2: Preparation of 2-[2-chroman-6-yl-5-(cyclohexylmethylsulfonylamino)-3-cyclopropyl-6-methyl-phenyl]-2-(cyclopropoxy)acetic acid (Example 60)

To a solution of methyl 2-[2-chroman-6-yl-5-(cyclohexylmethylsulfonylamino)-3-cyclopropyl-6-methyl-phenyl]-2-(cyclopropoxy)acetate (60a) (59 mg, 0.104 mmol) in ethanol (0.8 mL) and tetrahydrofuran (0.4 mL) was added a 2M sodium hydroxide solution (0.42 mL, 0.84 mmol). The mixture was heated at 70° C. for 90 minutes. The mixture was concentrated in vacuo. Water (5 mL) was added to the residue and the solution was extracted with ethyl acetate (5 mL). The aqueous layer was acidified with 1M hydrochloric acid until pH 1. The mixture was extracted with ethyl acetate (2×5 mL). The organic layer was dried over sodium sulfate and concentrated in vacuo to provide 2-[2-chroman-6-yl-5-(cyclohexylmethylsulfonylamino)-3-cyclopropyl-6-methyl-phenyl]-2-(cyclopropoxy)acetic acid (Example 60) (25 mg, 0.045 mmol, 43%).

¹H NMR (400 MHz, CDCl₃) δ 0.26-0.50 (m, 4H), 0.55-0.80 (m, 4H), 1.00-1.36 (m, 6H), 1.44-1.56 (m, 1H), 1.60-1.76 (m, 3H), 1.88-2.08 (m, 4H), 2.22 and 2.24 (s, 3H), 2.70-2.86 (m, 2H), 2.95-3.02 (m, 2H), 3.17-3.29 (m, 1H), 4.20-4.30 (m, 2H), 5.16 and 5.19 (s, 1H), 6.14 (s, 1H), 6.81 and 6.84 (d, J=7.0 Hz, 1H), 6.89-7.01 (m, 2H), 7.03 (s, 1H).
MS m/z ([M+NH₄]⁺) 571.
MS m/z ([M−H]⁻) 552.

Example 61

Synthesis of 2-[3-cyclopropyl-2-(3,4-dihydro-2H-1-benzopyran-6-yl)-6-methylphenyl]pent-4-enoic acid

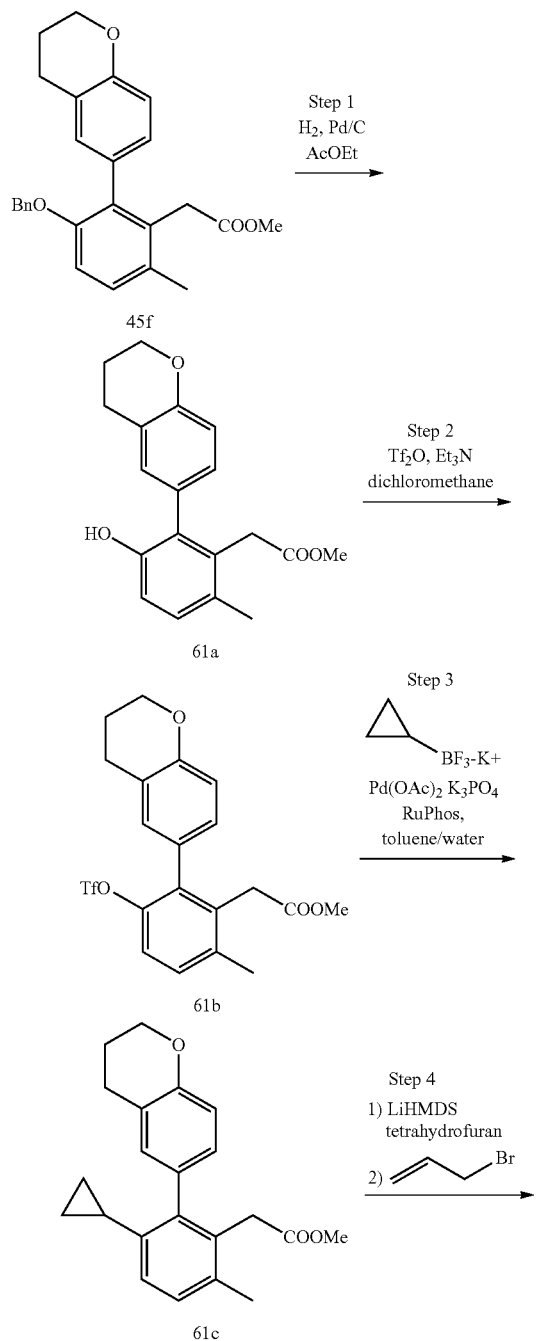

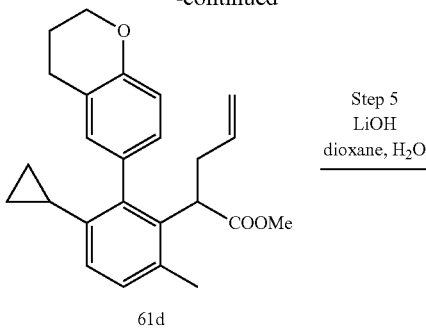

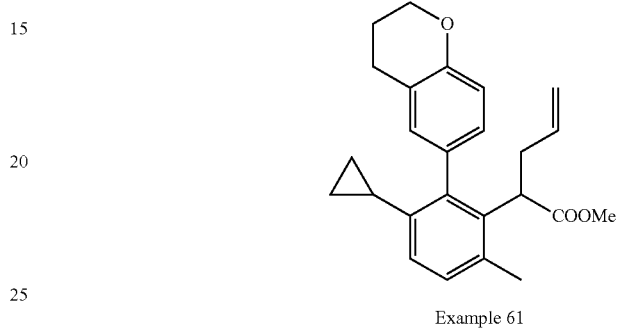

Step 1: Preparation of Intermediate methyl 2-[2-(3,4-dihydro-2H-1-benzopyran-6-yl)-3-hydroxy-6-methylphenyl]acetate (61a)

Using the procedure described in example 1 (step 9), methyl 2-[3-(benzyloxy)-2-(3,4-dihydro-2H-1-benzopyran-6-yl)-6-methylphenyl]acetate (45f) (100 mg, 0.248 mmol) is converted into methyl 2-[2-(3,4-dihydro-2H-1-benzopyran-6-yl)-3-hydroxy-6-methylphenyl]acetate (61a) (80 mg, 0.248 mmol, 100%) as a colorless oil used in the next step without further purification.

¹H NMR (400 MHz, CDCl₃) δ 2.01-2.07 (m, 2H), 2.22 (s, 3H), 2.76-2.83 (m, 2H), 3.43 (s, 2H), 3.62 (s, 3H), 4.22-4.25 (m, 2H), 4.67 (bs, 1H), 6.83-6.89 (m, 2H), 6.92-6.97 (m, 2H), 7.06-7.09 (m, 1H).
MS m/z ([M−H]⁻) 311.

Step 2: Preparation of Intermediate methyl 2-[2-(3,4-dihydro-2H-1-benzopyran-6-yl)-6-methyl-3-(trifluoromethanesulfonyloxy)phenyl]acetate (61b)

Using the procedure described in example 1 (step 10), methyl 2-[2-(3,4-dihydro-2H-1-benzopyran-6-yl)-3-hydroxy-6-methylphenyl]acetate (61a) (80 mg, 0.248 mmol) is converted into methyl 2-[2-(3,4-dihydro-2H-1-benzopyran-6-yl)-6-methyl-3-(trifluoromethanesulfonyloxy)phenyl]acetate (61b) (95 mg, 0.214 mmol, 85%) as a colorless oil after purification by preparative TLC (cyclohexane/ethyl acetate 80/20).

¹H NMR (400 MHz, CDCl₃) δ 2.00-2.07 (m, 2H), 2.31 (s, 3H), 2.70-2.87 (m, 2H), 3.52 (s, 2H), 3.63 (s, 3H), 4.21-4.24 (m, 2H), 6.81-6.90 (m, 3H), 7.17-7.24 (m, 2H).
MS m/z ([M−H]⁻) 443.

Step 3: Preparation of Intermediate methyl 2-[3-cyclopropyl-2-(3,4-dihydro-2H-1-benzopyran-6-yl)-6-methylphenyl]acetate (61c)

Using the procedure described in example 45 (step 11), the intermediate methyl 2-[2-(3,4-dihydro-2H-1-benzopyran-6-yl)-6-methyl-3-(trifluoromethanesulfonyloxy)phenyl] acetate (61b) (598 mg, 1.346 mmol) is converted into methyl 2-[3-cyclopropyl-2-(3,4-dihydro-2H-1-benzopyran-6-yl)-6-methylphenyl]acetate (61c) (394 mg, 1.17 mmol, 87%) after purification by flash chromatography (cyclohexane/ethyl acetate 90/10).

$^1$H NMR (300 MHz, CDCl$_3$) δ 0.54-0.72 (m, 4H), 1.46-1.55 (m, 1H), 2.00-2.08 (m, 2H), 2.26 (s, 3H), 2.76-2.80 (m, 2H), 3.45 (d, J=1.13 Hz, 2H), 3.61 (s, 3H), 4.21-4.24 (m, 2H), 6.73-6.92 (m, 4H), 7.08-7.10 (m, 1H).

MS m/z ([M+H]+) 337.

Step 4: Preparation of Intermediate methyl 2-[3-cyclopropyl-2-(3,4-dihydro-2H-1-benzopyran-6-yl)-6-methylphenyl]pent-4-enoate (61d)

Using the procedure described in example 45 (step 7), methyl 2-[3-cyclopropyl-2-(3,4-dihydro-2H-1-benzopyran-6-yl)-6-methylphenyl]acetate (61c) (35 mg, 0.104 mmol) is converted by reaction with allyl bromide (90 L, 1.04 mmol) into methyl 2-[3-cyclopropyl-2-(3,4-dihydro-2H-1-benzopyran-6-yl)-6-methylphenyl]pent-4-enoate (61 d) (28.5 mg, 0.076 mmol, 73%) as a colorless oil after purification by preparative TLC (cyclohexane/ethyl acetate 92/8).

$^1$H NMR (300 MHz, CDCl$_3$) δ 0.52-0.69 (m, 4H), 1.37-1.48 (m, 1H), 1.98-2.10 (m, 2H), 2.22 (s, 3H), 2.25-2.36 (m, 1H), 2.75-2.90 (m, 3H), 3.60 and 3.62 (s, 3H), 3.78-.3.87 (m, 1H), 4.21-4.25 (m, 2H), 4.83-4.89 (m, 2H), 5.48-5.65 (m, 1H), 6.70-6.73 (m, 1H), 6.78-6.88 (m, 2H), 6.91-6.97 (m, 1H), 7.02-7.05 (m, 1H).

MS m/z ([M+H]$^+$) 377, ([M+Na]$^+$) 399.

Step 5: Preparation of 2-[3-cyclopropyl-2-(3,4-dihydro-2H-1-benzopyran-6-yl)-6-methylphenyl]pent-4-enoic acid (Example 61)

Using the procedure described in example 1 (step 12), methyl 2-[3-cyclopropyl-2-(3,4-dihydro-2H-1-benzopyran-6-yl)-6-methylphenyl]pent-4-enoate (61d) (29 mg, 0.076 mmol) is converted into 2-[3-cyclopropyl-2-(3,4-dihydro-2H-1-benzopyran-6-yl)-6-methylphenyl]pent-4-enoic acid (Example 61) (27 mg, 0.076 mmol, 100%) as a white amorphous solid without further purification.

$^1$H NMR (400 MHz, CDCl$_3$) δ 0.52-0.71 (m, 4H), 1.39-1.49 (m, 1H), 1.98-2.09 (m, 2H), 2.28 (s, 3H), 2.31-2.38 (m, 1H), 2.72-2.84 (m, 3H), 3.86-.3.97 (m, 1H), 4.19-4.24 (m, 2H), 4.84-4.89 (m, 2H), 5.49-5.62 (m, 1H), 6.71-6.73 (m, 1H), 6.77-6.89 (m, 2H), 6.92-6.98 (m, 1H), 7.04-7.06 (m, 1H).

MS m/z ([M+H]$^+$) 363.
MS m/z ([M−H]$^−$) 361.

Comparative Example 62

Synthesis of 2-(tert-butoxy)-2-[2-(3,4-dihydro-2H-1-benzopyran-6-yl)-3,6-dimethylphenyl]acetic acid

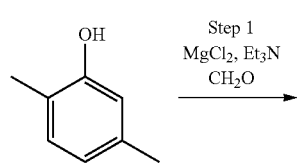

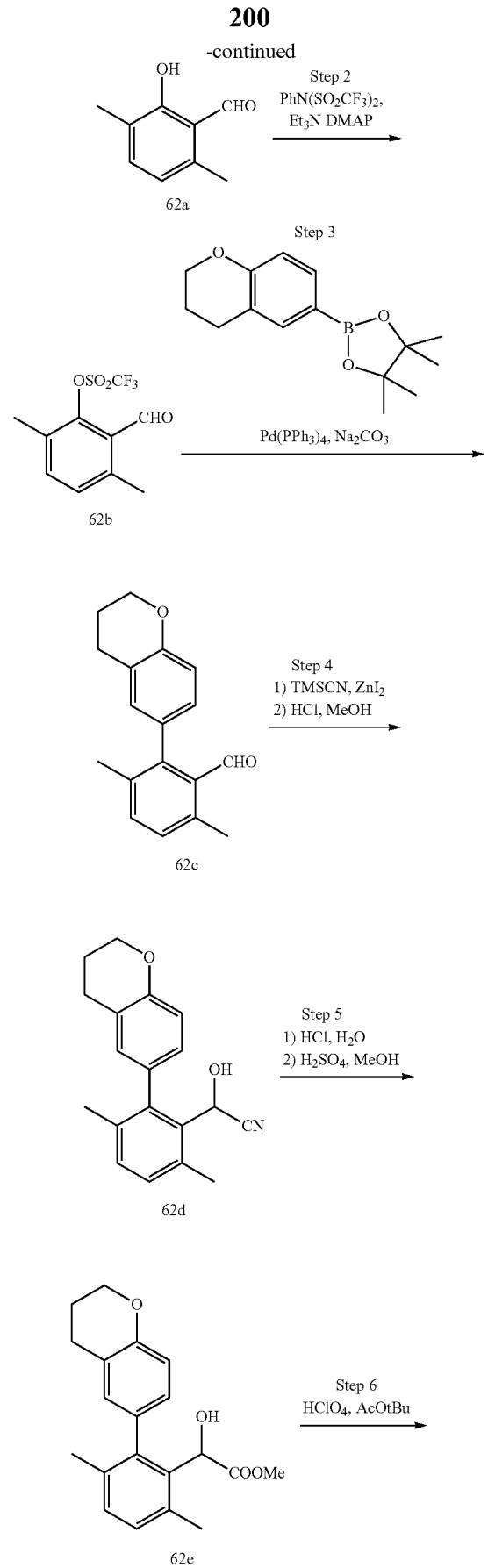

201

-continued

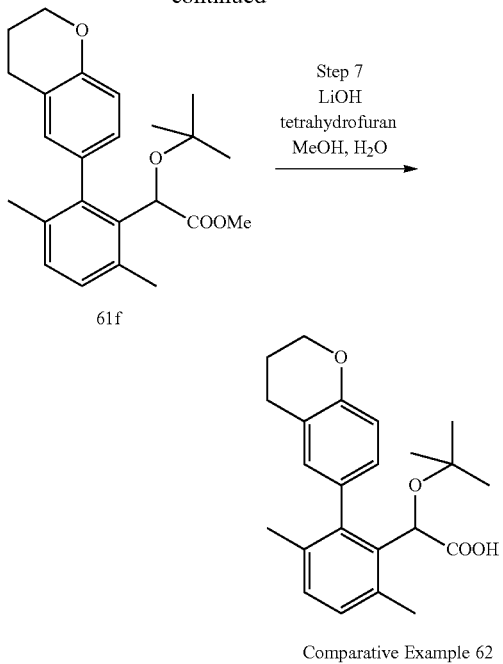

Step 7
LiOH
tetrahydrofuran
MeOH, H₂O
→

61f

Comparative Example 62

Step 1: Preparation of Intermediate 3,6-dimethyl-2-hydroxybenzaldehyde (62a)

To a solution of 2,5-dimethylphenol (7.0 g, 57.3 mmol) in acetonitrile (250 mL) were added triethylamine (30.1 mL, 0.212 mol) and magnesium chloride (8.17 g, 86 mmol). The mixture was stirred at room temperature for 15 minutes before adding paraformaldehyde (11.5 g, 0.38 mol). The mixture was heated at 80° C. for 20 hours. Acetonitrile was removed by evaporation in vacuo and a 10% hydrochloric acid solution was added to the residue. The mixture was stirred at room temperature for 30 minutes and extracted with dichloromethane (2×40 mL). The organic layers were dried over sodium sulfate and concentrated in vacuo. The residue was purified by flash chromatography on silica gel (dichloromethane) to provide 3,6-dimethyl-2-hydroxybenzaldehyde (62a) (3.56 g, 23.7 mmol, 42%).

$^1$H NMR (400 MHz, CDCl$_3$) δ 2.21 (s, 3H), 2.57 (s, 3H), 6.62 (d, J=8.0 Hz, 1H), 7.24 (d, J=8.0 Hz, 1H), 10.30 (s, 1H), 12.18 (s, 1H).

Step 2: Preparation of Intermediate 2-formyl-3,6-dimethylphenyltrifluoromethanesulfonate (62b)

A mixture of 3,6-dimethyl-2-hydroxybenzaldehyde (62a) (1.0 g, 6.6 mmol) in anhydrous dichloromethane (30 mL) at 0° C. under nitrogen atmosphere were added N-phenyl-bis(trifluoromethanesulfonimide) (3.56 g, 9.9 mmol), 4-(dimethylamino)pyridine (80 mg, 0.66 mmol) and triethylamine (1.9 mL, 13.2 mmol). The mixture was stirred at room temperature for 5h. Water (30 mL) was added. The aqueous layer was extracted with dichloromethane (2×20 mL). The organic layers were dried over sodium sulfate and concentrated in vacuo. The residue was purified by flash chromatography on silica gel (cyclohexane/dichloromethane 50/50) to provide 2-formyl-3,6-dimethylphenyltrifluoromethanesulfonate (62b) (1.66 g, 5.88 mmol, 89%).

202

$^1$H NMR (400 MHz, CDCl$_3$) δ 2.42 (s, 3H), 2.60 (s, 3H), 7.21 (d, J=8.0 Hz, 1H), 7.41 (d, J=8.0 Hz, 1H), 10.41 (s, 1H).

Step 3: Preparation of Intermediate 2-(3,4-dihydro-2H-1-benzopyran-6-yl)-3,6-dimethyl benzaldehyde (62c)

A mixture of 2-formyl-3,6-dimethylphenyltrifluoromethanesulfonate (62b) (300 mg, 1.06 mmol), sodium carbonate (449 mg, 4.2 mmol), 6-(4,4,5,5-tetramethyl-1,3,2-dioxaborolan-2-yl)chroman (359 mg, 1.38 mmol) and palladium tetrakis(triphenylphosphine) (62 mg, 0.053 mmol) in a mixture of toluene (3 mL), ethanol (1 mL) and water (1.5 mL) was irradiated (200 W, 80° C.) for 1 hour. The mixture was poured into water (10 mL). The aqueous layer was extracted with ethyl acetate (2×10 mL). The organic layer was washed with brine (10 mL), dried over sodium sulfate and concentrated in vacuo. The residue was purified by flash chromatography on silica gel (cyclohexane/ethyl acetate 95/5) to provide 2-(3,4-dihydro-2H-1-benzopyran-6-yl)-3,6-dimethylbenzaldehyde (62c) (160 mg, 0.60 mmol, 57%) as a yellow oil.

$^1$H NMR (400 MHz, CDCl$_3$) δ 1.98-2.05 (m, 2H), 2.10 (s, 3H), 2.58 (s, 3H), 2.78-2.82 (m, 2H), 4.20-4.24 (m, 2H), 6.83-6.90 (m, 3H), 7.14 (d, J=8.0 Hz, 1H), 7.31 (d, J=8.0 Hz, 1H), 9.80 (s, 1H).

Step 4: Preparation of Intermediate 2-[2-(3,4-dihydro-2H-1-benzopyran-6-yl)-3,6-dimethylphenyl]-2-hydroxyacetonitrile (62d)

To a solution of 2-(3,4-dihydro-2H-1-benzopyran-6-yl)-3,6-dimethylbenzaldehyde (62c) (800 mg, 3.00 mmol) in anhydrous dichloromethane (10 mL) at 0° C. under nitrogen atmosphere were successively added zinc iodide (96 mg, 0.30 mmol) and trimethylsilyl cyanide (372 mg, 3.75 mmol). The mixture was stirred at room temperature overnight. A saturated solution of sodium hydrogenocarbonate (10 mL) was added. Layers were separated and the aqueous layer was extracted with dichloromethane (10 mL). The organic layers were dried over sodium sulfate and concentrated in vacuo. The residue was dissolved in 3N hydrochloric acid in methanol (4 mL) and stirred overnight at room temperature then concentrated in vacuo. The residue was purified by flash chromatography on silica gel (cyclohexane/ethyl acetate 80/20) to provide 2-[2-(3,4-dihydro-2H-1-benzopyran-6-yl)-3,6-dimethylphenyl]-2-hydroxy acetonitrile (62d) (700 mg, 2.38 mmol, 79%) as a yellow oil.

$^1$H NMR (400 MHz, CDCl$_3$) δ 2.00 (s, 3H), 2.02-2.06 (m, 2H), 2.63 and 2.65 (s, 3H), 2.78-2.82 (m, 2H), 4.23-4.26 (m, 2H), 5.56 (d, J=1.0 Hz, 1H), 6.80-6.88 (m, 3H), 7.15 (d, J=8.0 Hz, 1H), 7.19 (d, J=8.0 Hz, 1H).

Step 5: Preparation of Intermediate methyl 2-[2-(3,4-dihydro-2H-1-benzopyran-6-yl)-3,6-dimethylphenyl]-2-hydroxyacetate (62e)

A solution of 2-[2-(3,4-dihydro-2H-1-benzopyran-6-yl)-3,6-dimethylphenyl]-2-hydroxy acetonitrile (62d) (700 mg, 2.39 mmol) in 12N hydrochloric acid (10 mL) was heated at 80° C. for 16 hours. The mixture was extracted with dichloromethane (2×10 mL). The organic layers were dried over sodium sulfate and concentrated in vacuo. The residue was dissolved methanol (20 mL), sulfuric acid (0.5 mL) was added and the mixture was refluxed for 16 hours. Methanol was evaporated in vacuo. The residue was dissolved in dichloromethane (20 mL) and washed with a saturated solution of sodium hydrogenocarbonate (20 mL), brine (20 mL), dried over sodium sulfate and concentrated in vacuo. The residue was purified by flash chromatography on silica gel (cyclohexane/ethyl acetate 80/20) to provide methyl 2-[2-(3,4-dihydro-2H-1-benzopyran-6-yl)-3,6-dimethylphenyl]-2-hydroxyacetate (62e) (160 mg, 0.49 mmol, 20%) as a brown solid.

$^1$H NMR (400 MHz, CDCl$_3$) δ 1.99 (s, 3H), 2.02-2.06 (m, 2H), 2.29 and 2.31 (s, 3H), 2.78-2.80 (m, 2H), 3.70 and 3.71 (s, 3H), 4.21-4.25 (m, 2H), 5.18 (d, J=1.0 Hz, 1H), 6.82-6.90 (m, 3H), 7.06 (d, J=8.0 Hz, 1H), 7.13 (d, J=8.0 Hz, 1H).

Step 6: Preparation of Intermediate methyl 2-(tert-butoxy)-2-[2-(3,4-dihydro-2H-1-benzopyran-6-yl)-3,6-dimethylphenyl]acetate (62f)

To a solution of methyl 2-[2-(3,4-dihydro-2H-1-benzopyran-6-yl)-3,6-dimethylphenyl]-2-hydroxyacetate (62e) (160 mg, 0.49 mmol) in tert-butyl acetate (10 mL) at −15° C. was added perchloric acid (1.45 mL). The mixture was stirred at −15° C. for 2 hours before being poured into a saturated aqueous solution of sodium bicarbonate (30 mL). The layers were separated and the aqueous layer was extracted with ethyl acetate (20 mL). The organic layers were dried over sodium sulfate and concentrated in vacuo. The residue was purified by flash chromatography on silica gel (cyclohexane/ethyl acetate 97/3 then (90/10) to provide methyl 2-(tert-butoxy)-2-[2-(3,4-dihydro-2H-1-benzopyran-6-yl)-3,6-dimethylphenyl]acetate (62f) (16 mg, 0.042 mmol, 8%).

$^1$H NMR (400 MHz, CDCl$_3$) δ 0.99 (s, 9H), 1.98 and 1.99 (s, 3H), 2.02-2.08 (m, 2H), 2.40 (s, 3H), 2.75-2.82 (m, 2H), 3.65 and 3.67 (s, 3H), 4.24-4.26 (m, 2H), 5.05 and 5.07 (s, 1H), 6.79-6.90 (m, 2H), 6.97-7.04 (m, 2H), 7.08 (d, J=8.0 Hz, 1H).

Step 7: Preparation of 2-(tert-butoxy)-2-[2-(3,4-dihydro-2H-1-benzopyran-6-yl)-3,6-dimethylphenyl]acetic acid A solution of methyl 2-(tert-butoxy)-2-[2-(3,4-dihydro-2H-1-benzopyran-6-yl)-3,6-dimethylphenyl]acetate (62f) (16 mg, 0.042 mmol) in a mixture of tetrahydrofuran (2 mL), methanol (0.7 mL), water (2 mL) and 1 M lithium hydroxide solution (0.44 mL, 0.44 mmol) was stirred at 60° C. for 20 hours. 2M hydrochloric mid was added until pH 3. The solid was filtered and washed with water to provide the comparative compound 62 (13 mg, 0.035 mmol, 84%) as a yellow solid.

$^1$H NMR (400 MHz, CDCl$_3$) δ 1.00 (s, 9H), 2.00-2.05 (m, 5H), 2.36 (s, 3H), 2.75-2.85 (m, 2H), 4.22-4.24 (m, 2H), 5.19 (s, 1H), 6.79-6.90 (m, 2H), 7.03 (d, J=8.0 Hz, 1H), 7.11 (d, J=8.0 Hz, 1H), 7.18 (s, 1H).
MS m/z ([M−H]$^-$) 367.

Comparative Example 63

Synthesis of 2-[3-(benzyloxy)-2-(3,4-dihydro-2H-1-benzopyran-6-yl)-6-(trifluoromethyl)phenyl]-2-(tert-butoxy)acetic acid

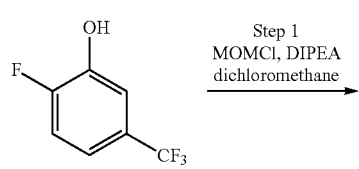

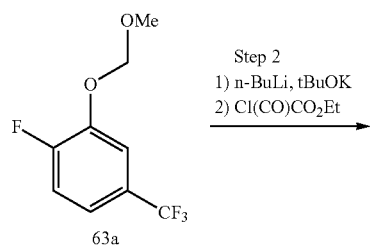

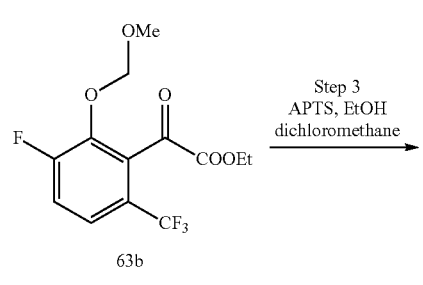

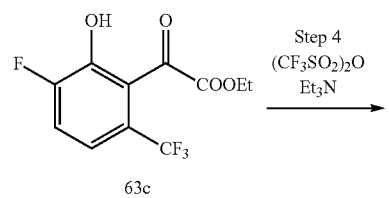

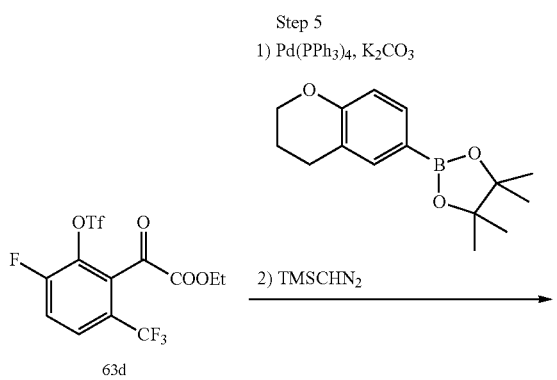

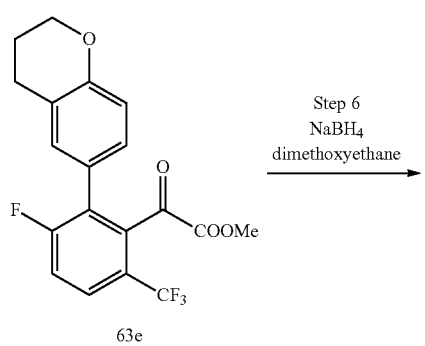

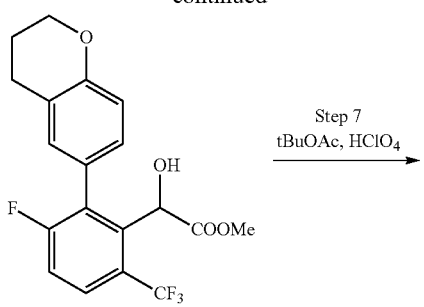

63f

Step 7
tBuOAc, HClO₄
→

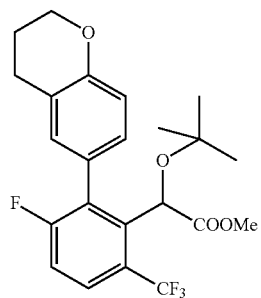

63g

Step 8
KOH, H₂O
EtOH
→

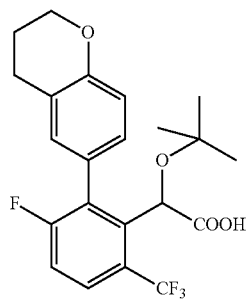

63h

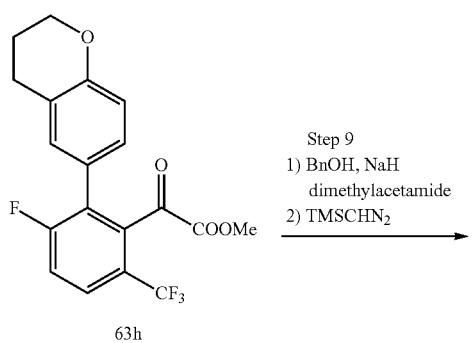

63h

Step 9
1) BnOH, NaH
dimethylacetamide
2) TMSCHN₂
→

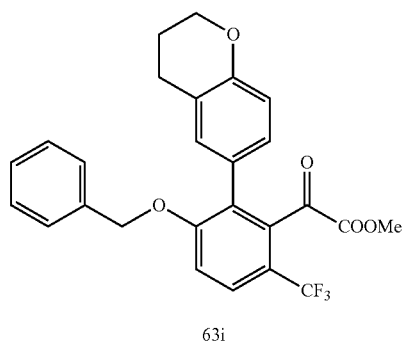

63i

Step 10
NaBH₄, MeOH
→

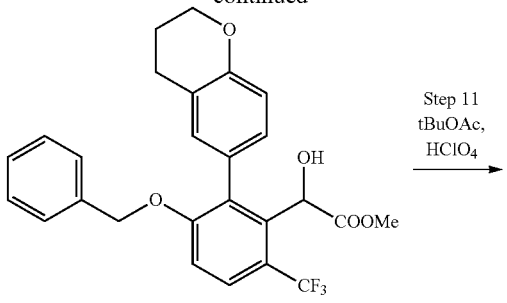

63j

Step 11
tBuOAc,
HClO₄
→

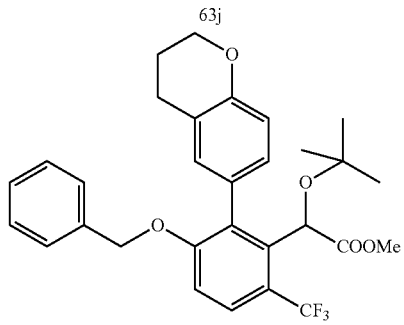

63k

Step 12
KOH,
EtOH
H₂O
→

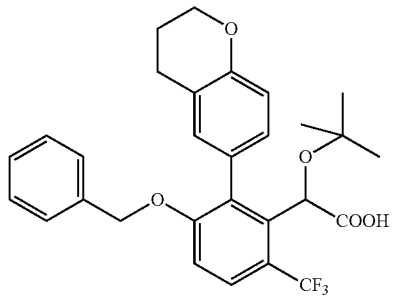

Comparative example 63

Step 1: Preparation of Intermediate 1-fluoro-2-(methoxymethoxy)-4-(trifluoromethyl)benzene (63a)

To a solution of 2-fluoro-5-(trifluoromethyl)phenol (2.0 g, 11.1 mmol) in anhydrous dichloromethane (20 mL) under nitrogen atmosphere at 0° C. were successively added diisopropylethylamine (3.87 mL, 22.2 mmol) and chloromethyl methyl ether (1.26 mL, 16.6 mmol). The mixture was stirred at 0° C. for 45 minutes before adding water (20 mL). Layers were separated and the aqueous one was extracted with dichloromethane (30 mL). The combined organic layers were washed with a 2 M sodium hydroxide solution (20 mL), dried over sodium sulfate and concentrated in vacuo to provide 1-fluoro-2-(methoxymethoxy)-4-(trifluoromethyl)benzene (63a) (2.49 g, 11.1 mmol, 100%) as a lightly yellow oil.

$^1$H NMR (400 MHz, CDCl$_3$) δ 3.53 (s, 3H), 5.25 (s, 2H), 7.16-7.20 (m, 1H), 7.24-7.27 (m, 1H), 7.46 (dd, J=1.8 Hz, J=7.4 Hz, 1H).

Step 2: Preparation of Intermediate ethyl 2-[3-fluoro-2-(methoxymethoxy)-6-(trifluoromethyl)phenyl]-2-oxoacetate (63b)

Under nitrogen atmosphere, a 1.6 M n-butyllithium solution in hexanes (3.5 mL, 5.6 mmol) and a 1M potassium tert-butoxide solution in tetrahydrofuran (5.6 mL, 5.6 mmol) were added to anhydrous tetrahydrofuran (30 mL) at −78° C. The mixture was stirred for 15 minutes before adding dropwise a solution of 1-fluoro-2-(methoxymethoxy)-4-(trifluoromethyl)benzene (63a) (1.0 g, 4.46 mmol) in tetrahydrofuran (10 mL). The mixture was stirred at −78° C. for 2 hours and was added via cannulation to a solution of ethyl oxalyl chloride (1.4 mL, 9.0 mmol) in tetrahydrofuran (20 mL) at −78° C. The mixture was stirred at −78° C. for 45 minutes and water (50 mL) was added Layers were separated and the aqueous layer was extracted with ethyl acetate (2×30 mL). The combined organic layers were washed with a saturated solution of sodium hydrogenocarbonate (30 mL), brine (30 mL), dried over sodium sulfate and concentrated in vacuo. The residue was purified by flash chromatography on silica gel (cyclohexane/ethyl acetate 90/10) to provide ethyl 2-[3-fluoro-2-(methoxymethoxy)-6-(trifluoromethyl) phenyl]-2-oxoacetate (63b) (840 mg, 2.59 mmol, 58%) as a yellow oil.

$^1$H NMR (300 MHz, CDCl$_3$) δ 1.36 (t, J=7.2 Hz, 3H), 3.45 (s, 3H), 4.38 (q, J=7.2 Hz, 2H), 5.16 (s, 2H), 7.28-7.34 (m, 1H), 7.43 (dd, J=4.4 Hz, J=8.8 Hz, 1H).

Step 3: Preparation of Intermediate ethyl 2-[3-fluoro-2-hydroxy-6-(trifluoromethyl)phenyl]-2-oxoacetate (63c)

To a solution of ethyl 2-[3-fluoro-2-(methoxymethoxy)-6-(trifluoromethyl)phenyl]-2-oxoacetate (63b) (500 mg, 1.54 mmol) and p-toluenesulfonic acid (59 mg, 0.31 mmol) in dichloromethane (7.5 mL) and ethanol (1.5 mL) was heated at 50° C. overnight. The mixture was concentrated in vacuo. The residue was purified by flash chromatography on silica gel (cyclohexane/ethyl acetate 60/40) to provide ethyl 2-[3-fluoro-2-hydroxy-6-(trifluoromethyl)phenyl]-2-oxoacetate (63c) (394 mg, 1.40 mmol, 91%) as a yellow oil.

$^1$H NMR (300 MHz, CDCl$_3$) δ 1.38 (t, J=7.2 Hz, 3H), 4.38 (q, J=7.2 Hz, 2H), 6.91 (d, J=2.7 Hz), 7.26-7.35 (m, 2H).

Step 4: Preparation of Intermediate ethyl 2-{3-fluoro-2-[(trifluoromethane)sulfonyloxy]-6-(trifluoromethyl)phenyl}-2-oxoacetate (63d)

To a solution of ethyl 2-[3-fluoro-2-hydroxy-6-(trifluoromethyl)phenyl]-2-oxoacetate (63c) (394 mg, 1.41 mmol) in anhydrous dichloromethane (5 mL) under nitrogen atmosphere at −78° C. were successively added triethylamine (0.24 mL, 1.69 mmol) and triflic anhydride (0.26 mL, 1.55 mmol). The mixture was stirred at −78° C. for 45 minutes before adding water (10 mL). Layers were separated. The aqueous layer was extracted with dichloromethane (10 mL). The combined organic layers were washed with a saturated solution of sodium hydrogenocarbonate (10 mL), dried over sodium sulfate and concentrated in vacuo to ethyl 2-{3-fluoro-2-[(trifluoromethane)sulfonyloxy]-6-(trifluoromethyl)phenyl}-2-oxoacetate (63d) (548 mg, 1.32 mmol, 94%) as a yellow oil which was used without further purification.

$^1$H NMR (300 MHz, CDCl$_3$) δ 1.37 (t, J=7.2 Hz, 3H), 4.42 (q, J=7.2 Hz, 2H), 7.55 (t, J=8.7 Hz), 7.78 (dd, J=4.5 Hz, J=8.7 Hz, 1H).

Step 5: Preparation of Intermediate methyl 2-[2-(3,4-dihydro-2H-1-benzopyran-6-yl)-3-fluoro-6-(trifluoromethyl)phenyl]-2-oxoacetate (63e)

A degassed solution of ethyl 2-{3-fluoro-2-[(trifluoromethane)sulfonyloxy]-6-(trifluoromethyl)phenyl}-2-oxoacetate (63d) (478 mg, 1.16 mmol), potassium carbonate (641 mg, 4.64 mmol), 6-(4,4,5,5-tetramethyl-1,3,2-dioxaborolan-2-yl)chroman (392 mg, 1.51 mmol) and palladium tetrakis(triphenylphosphine) (134 mg, 0.12 mmol) in dioxane (10 mL) and water (2 mL) was heated at 85° C. overnight. Water (10 mL) was added and dioxane was evaporated in vacuo. Diethyl ether (10 mL) was added and the layers were separated. The organic layer was washed with a saturated solution of sodium hydrogenocarbonate (10 mL). The combined aqueous layers were acidified with 37% hydrochloric acid until pH 2 then extracted with diethyl ether (2×20 mL). The organic layer was dried over sodium sulfate and concentrated in vacuo. The residue was dissolved in cyclohexane (5 mL) and methanol (2.5 mL) at 0° C. and a 2M solution of trimethylsilyldiazomethane in diethyl ether (4 mL, 8 mmol) was added. The mixture was stirred at room temperature for 15 minutes, cooled at 0° C. and acetic acid was added until the end of bubbling. The mixture was concentrated in vacuo. The residue was dissolved in ethyl acetate (10 mL), washed with a saturated solution of sodium hydrogenocarbonate (10 mL), brine (10 mL), dried over sodium sulfate and concentrated in vacuo to provide methyl 2-[2-(3,4-dihydro-2H-1-benzopyran-6-yl)-3-fluoro-6-(trifluoromethyl)phenyl]-2-oxoacetate (63e) (343 mg, 0.90 mmol, 77%) as a yellow solid which was used without further purification.

$^1$H NMR (400 MHz, CDCl$_3$) δ 1.98-2.04 (m, 2H), 2.77 (t, J=6.4 Hz, 2H), 3.57 (s, 3H), 4.19-4.22 (m, 2H), 6.81 (d, J=8.4 Hz, 1H), 6.86 (d, J=1.0 Hz, 1H), 6.95 (dd, J=1.0 Hz, J=8.4 Hz, 1H), 7.35 (t, J=8.6 Hz, 1H), 7.73 (dd, J=4.8 Hz, J=8.6 Hz, 1H).

Step 6: Preparation of Intermediate methyl 2-[2-(3,4-dihydro-2H-1-benzopyran-6-yl)-3-fluoro-6-(trifluoromethyl)phenyl]-2-hydroxyacetate (63f)

To a solution of methyl 2-[2-(3,4-dihydro-2H-1-benzopyran-6-yl)-3-fluoro-6-(trifluoromethyl)phenyl]-2-oxoacetate (63e) (100 mg, 0.26 mmol) in anhydrous 1,2-dimethoxyethane (2 mL) at 0° C. was portionwise added sodium borohydride (12 mg, 0.31 mmol). The mixture was stirred at room temperature for 1 hour. Water (5 mL) was added. 1,2-Dimethoxyethane was evaporated in vacuo. The resulting solution was extracted with ethyl acetate (2×5 mL). The organic layer was washed with brine (5 mL) and dried over sodium sulfate to provide methyl 2-[2-(3,4-dihydro-2H-1-benzopyran-6-yl)-3-fluoro-6-(trifluoromethyl)phenyl]-2-hydroxyacetate (63f) (84 mg, 0.22 mmol, 83%) as a white solid.

$^1$H NMR (300 MHz, CDCl$_3$) 2.00-2.08 (m, 2H), 2.75-2.82 (m, 2H), 3.57 and 3.60 (s, 3H), 4.22-4.25 (m, 2H), 5.40 (s, 1H), 6.80-6.85 (m, 2H), 7.06-7.10 (m, 1H), 7.22 (t, J=8.6 Hz, 1H), 7.73 (dd, J=5.2 Hz, J=8.6 Hz, 1H).

Step 7: Preparation of Intermediate methyl 2-(tert-butoxy)-2-[2-(3,4-dihydro-2H-1-benzopyran-6-yl)-3-fluoro-6-(trifluoromethyl)phenyl]acetate (63g)

Using the procedure described in example 28, step 5, the intermediate methyl 2-[2-(3,4-dihydro-2H-1-benzopyran-6-yl)-3-fluoro-6-(trifluoromethyl)phenyl]-2-hydroxyacetate (63f) (84 mg, 0.22 mmol) is converted, after purification by preparative TLC (cyclohexane/ethyl acetate 80/20), to methyl 2-(tert-butoxy)-2-[2-(3,4-dihydro-2H-1-benzopyran-6-yl)-3-fluoro-6-(trifluoro methyl)phenyl]acetate (63g) (28 mg, 0.06 mmol, 29%) as a colorless oil.

¹H NMR (400 MHz, CDCl₃) δ 0.97 and 0.98 (s, 9H), 2.03-2.07 (m, 2H), 2.72-2.89 (m, 2H), 3.70 (s, 3H), 4.22-4.26 (m, 2H), 5.14 (s, 1H), 6.83-6.87 (m, 1H), 6.94-6.98 (m, 1H), 7.04-7.09 (m, 1H), 7.17 (t, J=8.6 Hz, 1H), 7.70 (dd, J=5.6 Hz, J=8.6 Hz, 1H).

Step 8: Preparation of 2-(tert-butoxy)-2-[2-(3,4-dihydro-2H-1-benzopyran-6-yl)-3-fluoro-6-(trifluoromethyl)phenyl]acetic acid A solution of methyl 2-(tert-butoxy)-2-[2-(3,4-dihydro-2H-1-benzopyran-6-yl)-3-fluoro-6-(trifluoromethyl)phenyl]acetate (63g) (28 mg, 0.063 mmol) and potassium hydroxide (36 mg, 0.64 mmol) in a mixture of ethanol (3 mL) and water (1 mL) was stirred at 90° C. for 18 hours. Ethanol was evaporated in vacuo. The residue was diluted with water (2 mL) and acidified with 1M hydrochloric acid was added until pH 2 and extracted with diethyl ether (2×5 mL). The organic layer was dried over sodium sulfate and concentrated in vacuo. The residue was triturated in pentane and concentrated in vacuo to provide the desired acid (63h) (21 mg, 0.049 mmol, 78%) as a white solid.

¹H NMR (400 MHz, CDCl₃) δ 1.00 (s, 9H), 2.01-2.07 (m, 2H), 2.75-2.85 (m, 2H), 4.23-4.26 (m, 2H), 5.24 and 5.28 (s, 1H), 6.86-6.99 (m, 2H), 7.22 (t, J=8.6 Hz, 1H), 7.35 (broad s, 1H), 7.72 (dd, J=5.6 Hz, J=8.6 Hz, 1H).

MS m/z ([M–H]⁻) 425.

Step 9: Preparation of Intermediate methyl 2-[3-(benzyloxy)-2-(3,4-dihydro-2H-1-benzopyran-6-yl)-6-(trifluoromethyl)phenyl]-2-oxoacetate (63h)

To a suspension of sodium hydride 60% in oil (21 mg, 0.52 mmol) in anhydrous dimethylacetamide (1 mL) at 0° C. under nitrogen atmosphere, was dropwise added anhydrous benzyl alcohol (54 µL, 0.52 mmol). The mixture was stirred at room temperature for 30 minutes before adding dropwise a solution of methyl 2-[2-(3,4-dihydro-2H-1-benzopyran-6-yl)-3-fluoro-6-(trifluoromethyl)phenyl]-2-oxoacetate (63h) (100 mg, 0.26 mmol) in anhydrous dimethylacetamide (1 mL). The mixture was stirred for 1 hour at room temperature then sodium hydride 60% in oil (10 mg, 0.25 mmol) and benzyl alcohol (25 µL, 0.24 mmol) were added. The stirring was maintained for 3 hours. The mixture was poured in brine (5 mL) and 1M hydrochloric acid was added until pH 2. The mixture was extracted with ethyl acetate (2×10 mL). The organic layer was washed with brine (5 mL), dried over sodium sulfate and concentrated in vacuo. The residue was dissolved in cyclohexane (3 mL) and methanol (1.5 mL) at 0° C. and a 2 M solution of trimethylsilyldiazomethane in diethyl ether (0.3 mL, 0.6 mmol) was added. The mixture was stirred at room temperature for 20 minutes before adding a few drops of acetic acid. The residue was dissolved in ethyl acetate (10 mL), washed with a saturated solution of sodium hydrogenocarbonate (10 mL), brine (10 mL), dried over sodium sulfate and concentrated in vacuo The residue was purified by flash chromatography on silica gel (cyclohexane/ethyl acetate 75/25) to provide methyl 2-[3-(benzyloxy)-2-(3,4-dihydro-2H-1-benzopyran-6-yl)-6-(trifluoromethyl)phenyl]-2-oxoacetate (63i) (76 mg, 0.16 mmol, 62%) as a colorless oil.

¹H NMR (300 MHz, CDCl₃) δ 1.97-2.05 (m, 2H), 2.75 (t, J=6.4 Hz, 2H), 3.55 (s, 3H), 4.19-4.22 (m, 2H), 5.15 (s, 2H), 6.80 (d, J=8.4 Hz, 1H), 6.85 (d, J=2.1 Hz, 1H), 6.99 (dd, J=2.1 Hz, J=8.4 Hz, 1H), 7.11 (d, J=8.7 Hz, 1H), 7.23-7.36 (m, 5H), 7.65 (d, J=8.7 Hz, 1H).

Step 10: Preparation of Intermediate methyl 2-[3-(benzyloxy)-2-(3,4-dihydro-2H-1-benzopyran-6-yl)-6-(trifluoromethyl)phenyl]-2-hydroxyacetate (63j)

To a solution of methyl 2-[3-(benzyloxy)-2-(3,4-dihydro-2H-1-benzopyran-6-yl)-6-(trifluoromethyl)phenyl]-2-oxoacetate (63i) (76 mg, 0.16 mmol) in anhydrous methanol (2 mL) at 0° C. was portionwise added sodium borohydride (12 mg, 0.32 mmol). The mixture was stirred at room temperature for 30 minutes before adding another portion of sodium borohydride (12 mg, 0.32 mmol). After 30 minutes stirring, water (5 mL) was added. Methanol was evaporated in vacuo. The resulting solution was extracted with ethyl acetate (2×5 mL). The organic layer was washed with brine (5 mL) and dried over sodium sulfate to provide methyl 2-[3-(benzyloxy)-2-(3,4-dihydro-2H-1-benzopyran-6-yl)-6-(trifluoromethyl)phenyl]-2-hydroxyacetate (63j) (76 mg, 0.16 mmol, 100%) as a white solid.

¹H NMR (300 MHz, CDCl₃) δ 2.01-2.09 (m, 2H), 2.75-2.82 (m, 2H), 3.58 and 3.61 (s, 3H), 4.22-4.26 (m, 2H), 5.07 (s, 2H), 5.38 and 5.39 (s, 1H), 6.79-6.85 (m, 2H), 6.97-7.14 (m, 4H), 7.24-7.31 (m, 3H), 7.65 (d, J=9.0 Hz, 1H).

Step 11: Preparation of Intermediate methyl 2-[3-(benzyloxy)-2-(3,4-dihydro-2H-1-benzopyran-6-yl)-6-(trifluoromethyl)phenyl]-2-(tert-butoxy)acetate (63k)

To a solution of methyl 2-[3-(benzyloxy)-2-(3,4-dihydro-2H-1-benzopyran-6-yl)-6-(trifluoromethyl)phenyl]-2-hydroxyacetate (63j) (76 mg, 0.12 mmol) in tert-butyl acetate (3 mL) at 0° C. was added perchloric acid (0.4 mL). The mixture was stirred at 0° C. for 30 minutes hours then for 30 minutes at room temperature before being poured into a saturated aqueous solution of sodium hydrogenocarbonate (20 mL). The layers were separated and the aqueous layer was extracted with ethyl acetate (2×10 mL). The organic layers were washed with brine, dried over sodium sulfate and concentrated in vacuo. The residue was purified by preparative TLC (cyclohexane/ethyl acetate 80/20) to provide methyl 2-[3-(benzyloxy)-2-(3,4-dihydro-2H-1-benzopyran-6-yl)-6-(trifluoromethyl)phenyl]-2-(tert-butoxy)acetate (63k) (17 mg, 0.032 mmol, 20%) as a colorless oil.

¹H NMR (300 MHz, CDCl₃) δ 0.99 and 1.36 and 1.37 (s, 9H), 2.00-2.09 (m, 2H), 2.70-2.85 (m, 2H), 3.59 and 3.61 and 3.69 and 3.70 (s, 3H), 4.22-4.27 (m, 2H), 5.00-5.41 (m, 3H), 6.81-7.32 (m, 9H), 7.63-7.70 (m, 1H).

Step 12: Preparation of 2-[3-(benzyloxy)-2-(3,4-dihydro-2H-1-benzopyran-6-yl)-6-(trifluoromethyl)phenyl]-2-(tert-butoxy)acetic acid Using the procedure described in example 33, step 8, the intermediate methyl 2-[3-(benzyloxy)-2-(3,4-dihydro-2H-1-benzopyran-6-yl)-6-(trifluoromethyl)phenyl]-2-(tert-butoxy)acetate (63k) (17 mg, 0.032 mmol) is converted to 2-[3-(benzyloxy)-2-(3,4-dihydro-2H-1-benzopyran-6-yl)-6-(trifluoromethyl)phenyl]-2-(tert-butoxy)acetic acid (comparative example 63) (12 mg, 0.023 mmol, 70%) as a white solid.

¹H NMR (400 MHz, CDCl₃) δ 1.01 and 1.33 and 1.35 (s, 9H), 1.96-2.08 (m, 2H), 2.69-2.83 (m, 2H), 4.17-4.25 (m, 2H), 5.00-5.12 (m, 2H), 5.24 and 5.29 and 5.46 and 5.48 (s, 1H), 6.72-7.06 (m, 3H), 7.10-7.16 (m, 2H), 7.23-7.32 (m, 4H), 7.64-7.69 (m, 1H).

MS m/z ([M–H]⁻) 513.

Antiviral Activity

The antiviral activity, particularly against HIV, of compounds according to the invention is evaluated by the protocol described below.

Preparation of Virus stock of the NL4-3 strain of HIV-1 (Adachi et al, J Virol, 1986, 59(2):284-91).

The virus was prepared as described in Lopez et al (Lopez et al, Proc Natl Acad Sci USA., 2006, 103(40):14947-52, by transfecting $2 \times 10^6$ 293 T cells (CRL-1573, ATCC) with following modifications: 6 μg of NL4-3 proviral DNA molecular clone were mixed with X-tremeGENE 9 DNA transfection reagent from Roche, and used according to manufacturer's instructions. Twenty four hours later, cells were washed and fresh medium added. Forty eight hours after transfection, cell supernatants were harvested, filtered through 0.45-μm-pore-size filters, quantified for HIV-1 p24 antigen by using an Innotest HIV antigen mAb assay (Ingen) according to manufacturer's instructions, and used in infection experiments.

Preparation of Compounds:

Serial dilutions of compounds to be tested were prepared in complete RPMI medium from 10 mM DMSO stock solutions, and distributed in a volume of 20 μl in 96 well tissue-culture treated plates (Costar 3917), in order to get 0.5% DMSO final concentration in each well, after the addition of infected cells. Control wells contained also 0.5% DMSO final concentration but no compound.

Infection of Cells:

MT4 cells (from the NIH AIDS Research and Reference Reagent Program) in RPMI complete medium were counted ($10 \times 10^6$ cells per well in Falcon 353047 Multiwell™ 24 well) and infected for 2 hours at 37°, at a multiplicity of infection (moi) of 0.0001-0.00001. Cells were then centrifuged for 3 min at 3000 rpm, and washed two times in 1 ml PBS to remove viruses that have not entered the cells. Infected cells were resuspended in complete RPMI at 1.25× $10^6$ cells/ml, and 80 μl of infected cells were distributed in each well containing compounds to be tested or control wells. The plates were then incubated at 37° C. for 5 days.

Assay used to measure the inhibition of HIV replication by the compounds (according to Gregg S. Jones et al., Antimicrobial Agents and Chemotherapy, 2009, 53 (3): 1194-1203).

After 5 days of incubation, microplates were equilibrated to room temperature for 30 min and then 50 μl of CellTiter-Glo reagent (Promega Biosciences, Inc., Madison Wis., USA) were added to each well. Cell lysis was carried out at room temperature during 10 min and luminescence was read on a Fluoroskan (Thermo Scientific).

The EC50, or effective concentration 50, is the concentration of compound leading to 50% of cyto-protection in a CellTiter-Glo® viability assay based on MT4 cells infected with NL4-3 virus (table 1).

TABLE 1

| Example number | EC50 (μM) |
|---|---|
| 1 | 0.017 |
| 2 | 0.090 |
| 4 | 0.034 |
| 5 | 0.023 |
| 6 | 0.270 |
| 7 | 0.062 |
| 8 | 0.190 |
| 9 | 0.500 |
| 10 | 0.084 |
| 11 | 0.360 |

TABLE 1-continued

| Example number | EC50 (μM) |
|---|---|
| 12 | 0.078 |
| 13 | 0.008 |
| 14 | 0.051 |
| 15 | 0.340 |
| 16 | 0.009 |
| 17 | 0.330 |
| 18 | 0.019 |
| 19 | 0.400 |
| 20 | 0.054 |
| 21 | 0.014 |
| 22 | 0.091 |
| 23 | 0.100 |
| 24 | 0.042 |
| 25 | 0.200 |
| 26 | 0.300 |
| 27 | 0.280 |
| 28 | 0.500 |
| 29 | 0.500 |
| 30 | 0.860 |
| 31 | 1.000 |
| 32 | 0.032 |
| 33 | 0.450 |
| 34 | 0.440 |
| 35 | 0.830 |
| 36 | 0.100 |
| 37 | 0.024 |
| 38 | 0.003 |
| 39 | 0.024 |
| 40 | 0.014 |
| 41 | 0.006 |
| 42 | 0.190 |
| 43 | 0.094 |
| 44 | 0.017 |
| 45 | 0.290 |
| 46 | 0.650 |
| 47 | 0.450 |
| 56 | 0.500 |
| 57 | 0.580 |
| 62 | 1.6 |
| 63 | 3.2 |

The results show that the compounds according to the invention have a stronger inhibition activity of HIV replication than the compounds 62 and 63. The compounds according to the invention thus can be used as powerful anti-HIV compounds with an enhanced inhibition activity.

The invention claimed is:

1. A compound according to formula (I):

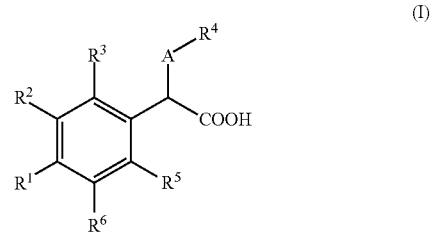

wherein:
R$^1$ and R$^6$ represent a hydrogen atom;
R$^2$, non-substituted or substituted by at least one T$^1$, represents a cyclopropyl;
R$^3$, non-substituted or substituted by at least one T$^2$, represents a saturated, partially or totally unsaturated or aromatic 5-, 6- or 7-membered carbocycle; a saturated, partially or totally unsaturated or aromatic 5-, 6- or 7-membered carbocycle fused with a saturated, partially or totally unsaturated or aromatic 4-, 5-, 6- or 7-membered heterocycle;

A represents —O—;

R⁴, substituted or non-substituted by at least one T³, represents a linear or branched $C_2$-$C_6$ alkyl; a linear or branched $C_2$-$C_6$ alkenyl; a linear or branched $C_1$-$C_6$ fluoroalkyl; a $C_3$-$C_6$ cycloalkyl; or a $C_1$-$C_3$ alkyl-($C_3$-$C_6$ cycloalkyl);

R⁵ represents a halogen atom; —CF₃; a linear or branched $C_1$-$C_6$ alkyl; a linear or branched $C_2$-$C_6$ alkenyl; a linear or branched $C_2$-$C_6$ alkynyl; a linear or branched fluoroalkyl; a $C_3$-$C_6$ cycloalkyl; —CH₂OH; or —CH₂—O—CH₃;

T¹ independently represents an alkyl or —(X)$_x$—$C_3$-$C_6$ cycloalkyl

T² independently represents a halogen atom; a linear or branched —O—($C_1$-$C_3$ alkyl); a linear or branched $C_1$-$C_3$ fluoroalkyl; a linear or branched —O—($C_1$-$C_3$ fluoroalkyl); a linear or branched $C_1$-$C_3$ alkyl; a $C_3$-$C_6$ cycloalkyl; or —CN;

two geminal T² may form with the carbon atom to which they are bonded, a $C_3$-$C_7$ cycloalkyl;

T³ independently represents a $C_1$-$C_2$ alkyl ; or a fluor atom;

T⁸ independently represents a hydrogen atom, a linear or branched $C_1$-$C_3$ alkyl; or a $C_3$-$C_6$ cycloalkyl;

X independently represents an oxygen atom; a sulphur atom; NT⁸; S=O; or S(O)₂;

x represents 0 or 1;

or a racemate, enantiomer, stereoisomer, atropisomer diastereoisomer or pharmaceutically acceptable salt thereof.

2. A compound according to claim 1 that is of formula (A) or (D):

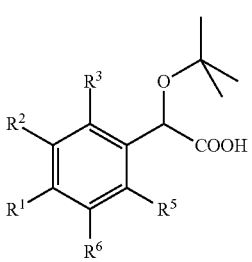
(A)

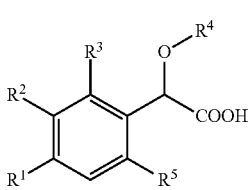
(B)

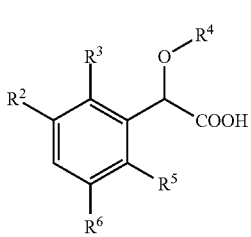
(C)

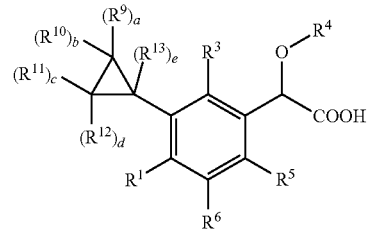
(D)

wherein,
R⁹, R¹⁰, R¹¹, R¹², R¹³, identical or different, represent a hydrogen atom; a halogen atom; an alkyl; or a $C_3$-$C_6$ cycloalkyl; and a, b, c, d, e, identical or different, represent 0 or 1.

3. A compound according to claim 1 that is of formula (D):

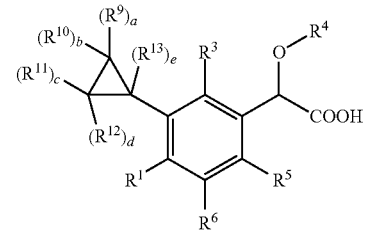
(D)

wherein,
R⁹, R¹⁰, R¹¹, R¹², R¹³, identical or different, represent a hydrogen atom; a halogen atom; an alkyl; or a $C_3$-$C_6$ cycloalkyl; and a, b, c, d, e, identical or different, represent 0 or 1.

4. A compound according to claim 1 that is of formula (DA):

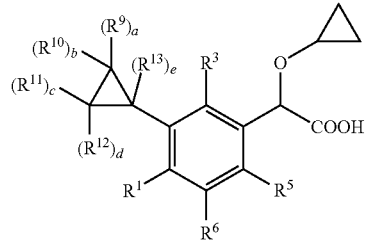
(DA)

wherein,
R⁹, R¹⁰, R¹¹, R¹², R¹³, identical or different, represent a hydrogen atom; a halogen atom; an alkyl; or a $C_3$-$C_6$ cycloalkyl; and a, b, c, d, e, identical or different, represent 0 or 1.

5. A compound according to claim 1 that is of formula (AB), (AC), (AD), (BD), or (CD):

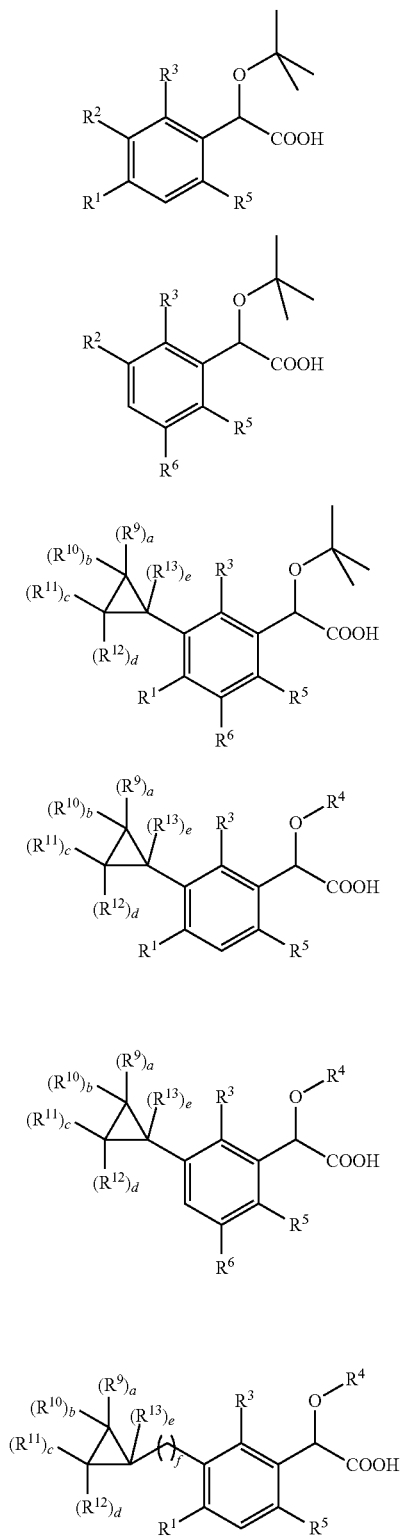

(AB)
(AC)
(AD)
(BD)
(CD)
(BE)

wherein, $R^9$, $R^{10}$, $R^{11}$, $R^{12}$, $R^{13}$, identical or different, represent a hydrogen atom; a halogen atom; an alkyl; or a $C_3$-$C_6$ cycloalkyl; and a, b, c, d, e, identical or different, represent 0 or 1.

6. A compound according to claim 1 that is of formula (ABC), (ABD), or (BCD):

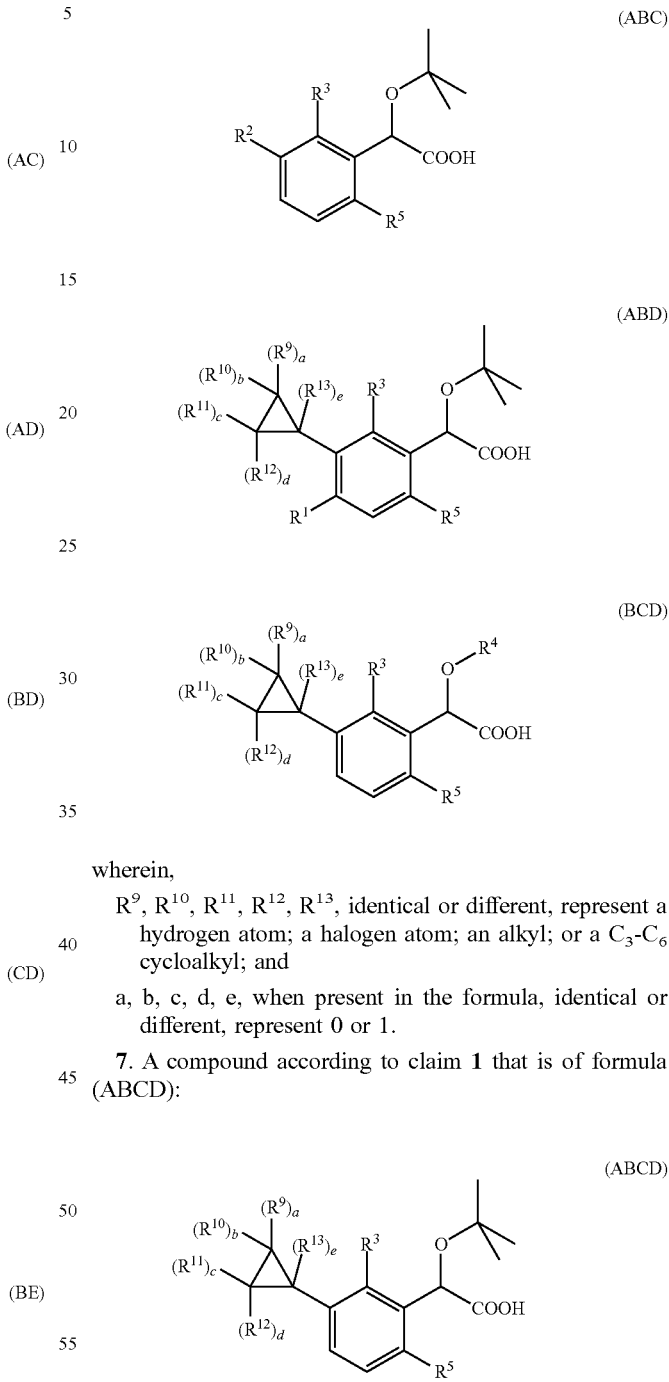

(ABC)
(ABD)
(BCD)

wherein, $R^9$, $R^{10}$, $R^{11}$, $R^{12}$, $R^{13}$, identical or different, represent a hydrogen atom; a halogen atom; an alkyl; or a $C_3$-$C_6$ cycloalkyl; and a, b, c, d, e, when present in the formula, identical or different, represent 0 or 1.

7. A compound according to claim 1 that is of formula (ABCD):

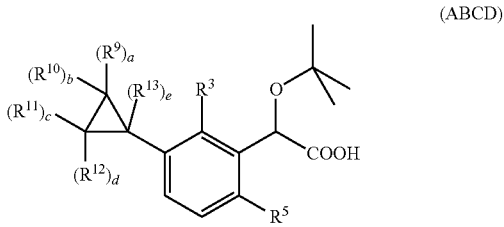

(ABCD)

wherein, $R^9$, $R^{10}$, $R^{11}$, $R^{12}$, $R^{13}$, identical or different, independently represent a hydrogen atom; a halogen atom; an alkyl; or a $C_3$-$C_6$ cycloalkyl; and a, b, c, d, e, identical or different, represent 0 or 1.

8. A compound according to claim 1 that is of formula (A), (D), (AB), (AC), (AD), (BD), (CD), (DA), (ABC), (ABD), (BCD) or (ABCD):

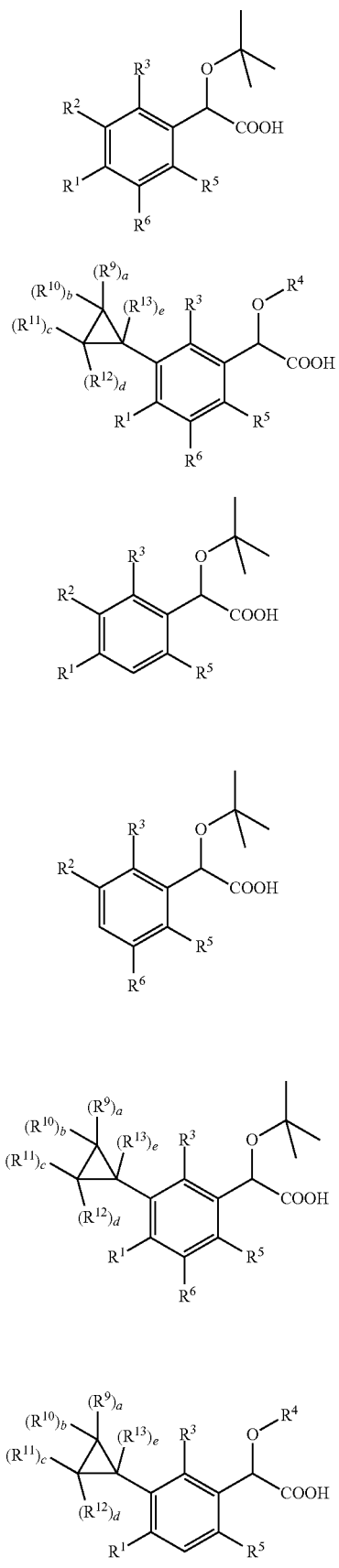
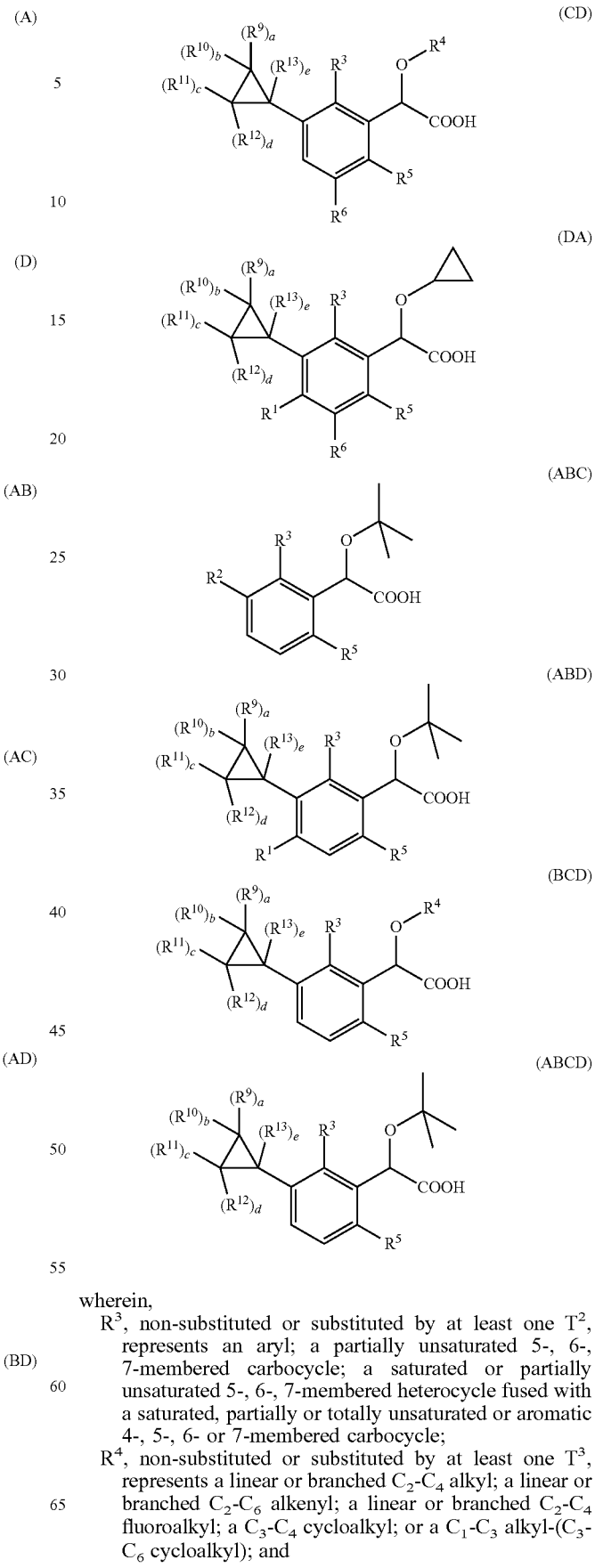

wherein,
R³, non-substituted or substituted by at least one T², represents an aryl; a partially unsaturated 5-, 6-, 7-membered carbocycle; a saturated or partially unsaturated 5-, 6-, 7-membered heterocycle fused with a saturated, partially or totally unsaturated or aromatic 4-, 5-, 6- or 7-membered carbocycle;

R⁴, non-substituted or substituted by at least one T³, represents a linear or branched $C_2$-$C_4$ alkyl; a linear or branched $C_2$-$C_6$ alkenyl; a linear or branched $C_2$-$C_4$ fluoroalkyl; a $C_3$-$C_4$ cycloalkyl; or a $C_1$-$C_3$ alkyl-($C_3$-$C_6$ cycloalkyl); and R⁵ represents —CH₃; —CH₂F; —CHF₂; —CF₃; —CH₂OH; or —CH₂OCH₃.

9. A compound according to claim 1 wherein R⁴ represents a tert-butyl; and R¹ and R⁶ represent a hydrogen atom.

10. A compound according to claim 1 wherein: R⁴ represents a cyclopropyl.

11. A compound according to claim 1 that is selected from the group consisting of:
2-(tert-butoxy)-2-[3-cyclopropyl-2-(3,4-dihydro-2H-1-benzopyran-6-yl)-6-methylphenyl]acetic acid;
2-(tert-butoxy)-2-[3-cyclopropyl-2-(3,4-dihydro-2H-1-benzopyran-6-yl)-6-(trifluoromethyl)phenyl]acetic acid;
2-(tert-butoxy)-2-(6-cyclopropyl-4'-methoxy-3-methyl-biphenyl-2-yl]acetic acid;
(S)-2-(tert-butoxy)-2-[3-cyclopropyl-2-(3,4-dihydro-2H-1-benzopyran-6-yl)-6-methylphenyl]acetic acid;
2-(tert-butoxy)-2-(6-cyclopropyl-3,4'-dimethyl-biphenyl-2-yl)-acetic acid;
2-(tert-butoxy)-2-(6-cyclopropyl-4'-fluoro-3-methyl-biphenyl-2-yl)-acetic acid;
2-(tert-butoxy)-2-[3-cyclopropyl-6-methyl-2-(5-methyl-chroman-6-yl)-phenyl]acetic acid;
(trans-3-bicyclopropyl-2-yl-2-chroman-6-yl-6-methyl-phenyl)-tert-butoxy-acetic acid;
2-(tert-butoxy)-2-[3-cyclopropyl-2-(4,4-dimethyl-cyclohex-1-enyl)-6-methyl-phenyl]acetic acid;
2-(tert-butoxy)-2-(4'-chloro-6-cyclopropyl-3-methyl-biphenyl-2-yl)acetic acid;
tert-butoxy-[3-cyclopropyl-2-(8-fluoro-5-methyl-chroman-6-yl)-6-methyl-phenyl]-acetic acid;
tert-butoxy-[2-chroman-6-yl-6-methyl-3-(1-methyl-cyclopropyl)-phenyl]-acetic acid;
tert-Butoxy-[2-chroman-6-yl-6-methyl-3-(cis-2-methyl-cyclopropyl)-phenyl]-acetic acid;
(S)-tert-butoxy-[3-cyclopropyl-6-methyl-2-(5-methyl-chroman-6-yl)-phenyl]-acetic acid;
(S)-tert-butoxy-[3-cyclopropyl-2-(8-fluoro-5-methyl-chroman-6-yl)-6-methyl-phenyl]-acetic acid;
2-(2-chroman-6-yl-3-cyclopropyl-6-methyl-phenyl)-2-ethoxy-acetic acid;
2-[3-cyclopropyl-2-(3,4-dihydro-2H-1-benzopyran-6-yl)-6-methylphenyl]-2-cyclopropoxyacetic acid;
(S)-2-[3-cyclopropyl-2-(3,4-dihydro-2H-1-benzopyran-6-yl)-6-methylphenyl]-2-cyclopropoxyacetic acid;
(2-chroman-6-yl-3-cyclopropyl-6-methyl-phenyl)-propoxy-acetic acid;
(2-chroman-6-yl-3-cyclopropyl-6-methyl-phenyl)-cyclopropyl methoxy-acetic acid;
(2-chroman-6-yl-3-cyclopropyl-6-methyl-phenyl)-(2,2,2-trifluoro-ethoxy)-acetic acid;
(2-chroman-6-yl-3-cyclopropyl-6-methyl-phenyl)-cyclobutoxy-acetic acid;
(2-chroman-6-yl-3-cyclopropyl-6-methyl-phenyl)-(2,2-difluoro-ethoxy)-acetic acid;
(2-chroman-6-yl-3-cyclopropyl-6-methyl-phenyl)-(2-fluoro-ethoxy)-acetic acid;
(2-chroman-6-yl-3-cyclopropyl-6-methyl-phenyl)-isopropoxy-acetic acid;
cyclopropoxy-[3-cyclopropyl-2-(8-fluoro-5-methyl-chroman-6-yl)-6-methyl-phenyl]-acetic acid;
(2-chroman-6-yl-3-cyclopropyl-6-methyl-phenyl)-(1-methyl-cyclopropoxy)-acetic acid;
(S)-cyclopropoxy-[3-cyclopropyl-6-methyl-2-(5-methyl-chroman-6-yl)-phenyl]-acetic acid;
(2-chroman-6-yl-3-cyclopropyl-6-trifluoromethyl-phenyl)-cyclopropoxy-acetic acid;
cyclopropoxy-[3-cyclopropyl-6-methyl-2-(5-methyl-chroman-6-yl)-phenyl]-acetic acid;
(S)-cyclopropoxy-[3-cyclopropyl-2-(8-fluoro-5-methyl-chroman-6-yl)-6-methyl-phenyl]-acetic acid;
(2-chroman-6-yl-3-cyclopropyl-6-methyl-phenyl)-(2,2-difluoro-cyclopropoxy)-acetic acid;
3-cyclopropyl-2-[3-cyclopropyl-2-(3,4-dihydro-2H-1-benzopyran-6-yl)-6-methylphenyl]propanoic acid;
2-[3-cyclopropyl-2-(3,4-dihydro-2H-1-benzopyran-6-yl)-6-methylphenyl]-4-methylpentanoic acid; and
2-[3-cyclopropyl-2-(3,4-dihydro-2H-1-benzopyran-6-yl)-6-methylphenyl]pent-4-enoic acid.

12. A pharmaceutical composition comprising a compound according to claim 1 as an active ingredient and at least one pharmaceutically acceptable carrier.

13. A pharmaceutical composition according to claim 12 comprising at least one further antiviral agent.

14. A pharmaceutical composition comprising a compound according to claim 8 as an active ingredient and at least one pharmaceutically acceptable carrier.

15. The pharmaceutical composition according to claim 14 and at least one antiviral agent.

16. A method for treating a HIV infection comprising administering to a person in need thereof a therapeutically effective amount of a compound according to claim 1.

17. A method for treating a HIV infection comprising administering to a person in need thereof a therapeutically effective amount of a compound according to claim 8.

* * * * *